US009777070B2

(12) United States Patent
Damelin et al.

(10) Patent No.: US 9,777,070 B2
(45) Date of Patent: Oct. 3, 2017

(54) ANTI-PTK7 ANTIBODY-DRUG CONJUGATES

(71) Applicants: Pfizer Inc., New York, NY (US); AbbVie Stemcentrx LLC, North Chicago, IL (US)

(72) Inventors: Marc Isaac Damelin, Park Ridge, NJ (US); Puja Sapra, River Edge, NJ (US); Alexander John Bankovich, San Francisco, CA (US); Scott J. Dylla, Emerald Hills, CA (US)

(73) Assignees: PFIZER INC, New York, NY (US); ABBVIE STEMCENTRX LLC, North Chicago, IL (US)

( * ) Notice: Subject to any disclaimer, the term of this patent is extended or adjusted under 35 U.S.C. 154(b) by 42 days.

(21) Appl. No.: 14/696,663

(22) Filed: Apr. 27, 2015

(65) Prior Publication Data
US 2015/0315293 A1   Nov. 5, 2015

Related U.S. Application Data

(60) Provisional application No. 61/986,520, filed on Apr. 30, 2014.

(51) Int. Cl.
*C07K 16/30* (2006.01)
*A61K 47/48* (2006.01)
*C07K 16/40* (2006.01)

(52) U.S. Cl.
CPC ........ *C07K 16/40* (2013.01); *A61K 47/48438* (2013.01); *A61K 47/48553* (2013.01); *A61K 47/48646* (2013.01); *A61K 47/48715* (2013.01); *C07K 16/30* (2013.01); *C07K 2317/24* (2013.01); *C07K 2317/33* (2013.01); *C07K 2317/55* (2013.01); *C07K 2317/565* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,422,739 B2 | 9/2008 | Anderson et al. | |
| 7,619,068 B2 | 11/2009 | Pilkington et al. | |
| 7,659,374 B2 | 2/2010 | Wu et al. | |
| 7,744,877 B2 | 6/2010 | Anderson et al. | |
| 8,058,252 B2 | 11/2011 | Chouaib et al. | |
| 8,222,253 B2 | 7/2012 | Wang et al. | |
| 8,222,375 B2 | 7/2012 | Terrett et al. | |
| 8,273,862 B2 | 9/2012 | Moran et al. | |
| 8,461,119 B2 | 6/2013 | Pasquale et al. | |
| 2007/0292414 A1 | 12/2007 | Duntsch et al. | |
| 2008/0138313 A1 | 6/2008 | Frankel | |
| 2009/0123371 A1 | 5/2009 | Debinski et al. | |
| 2009/0155255 A1 | 6/2009 | Glaser et al. | |
| 2010/0034826 A1 | 2/2010 | Terrett et al. | |
| 2010/0184119 A1 | 7/2010 | Bright et al. | |
| 2010/0273160 A1 | 10/2010 | Donahoe et al. | |
| 2011/0020221 A1 | 1/2011 | Berman et al. | |
| 2011/0280892 A1 | 11/2011 | Kinch et al. | |
| 2012/0027782 A1 | 2/2012 | Terrett et al. | |
| 2012/0083454 A1 | 4/2012 | Vescovi et al. | |
| 2012/0219557 A1 | 8/2012 | Terrett et al. | |
| 2013/0061340 A1 | 3/2013 | Dylla et al. | |
| 2013/0061342 A1 | 3/2013 | Dylla et al. | |
| 2013/0122020 A1 | 5/2013 | Liu et al. | |
| 2013/0129753 A1 | 5/2013 | Doroski et al. | |
| 2013/0260385 A1 | 10/2013 | Dylla et al. | |
| 2014/0170063 A1* | 6/2014 | Govindan | ............ A61K 31/454 424/1.49 |
| 2015/0030636 A1 | 1/2015 | Dylla et al. | |

FOREIGN PATENT DOCUMENTS

| | | |
|---|---|---|
| CN | 101678075 A | 3/2010 |
| CN | 101939028 A | 1/2011 |
| EP | 0216846 A1 | 4/1987 |
| EP | 0256055 A1 | 2/1988 |
| EP | 0323997 A1 | 7/1989 |
| EP | 0338841 A1 | 10/1989 |
| EP | 2380909 A1 | 10/2011 |
| EP | 2446895 A1 | 5/2012 |
| EP | 1957539 B1 | 4/2013 |
| KR | 2009 0099471 | 9/2009 |
| WO | WO 03/075957 A1 | 9/2003 |
| WO | WO 2004/017992 A2 | 3/2004 |
| WO | WO 2005/040413 | 5/2005 |
| WO | WO 2007/067730 A2 | 6/2007 |
| WO | WO 2008/149803 A1 | 12/2008 |
| WO | WO 2009/070767 A2 | 6/2009 |
| WO | WO 2009/073546 A2 | 6/2009 |
| WO | WO 2009/116764 A2 | 9/2009 |
| WO | WO 2009/157623 A1 | 12/2009 |

(Continued)

OTHER PUBLICATIONS

Alley et al (Current Opinion in Chemical Biology, 2010, vol. 14, pp. 529-537).*
Gartner et al (PLoS One, Jan. 2014, vol. 9, No. 1, p. e84472).*
Doronina et al (Bioconjugate Chemistry, 2006, vol. 17, pp. 114-124).*
abstract of Mueller et al (Biology of Blood and Bone Marrow Transplantation, 2011, vol. 17, No. 2, suppl. 1, p. S198, Abstract No. 122 ).*
Al-Hajj et al., "Self-renewal and solid tumor stem cells" *Oncogene* (2004) 23, 7274-7282.
Almagro et al.,"Humanization of antibodies" Frontiers in Bioscience(2008) 13:1619-33.
Botchkina et al., "Phenotypic Subpopulations of Metastatic Colon Cancer Stem Cells: Genomic Analysis", *Cancer Genomics & Proteomics* (2009) 6:19-30.
Caddy et al., "Epidermal wound repair is regulated by the planar cell polarity signaling pathway." *Dev Cell.* Jul. 20, 2010;19(1):138-47.

(Continued)

*Primary Examiner* — Karen Canella
(74) *Attorney, Agent, or Firm* — Womble Carlyle Sandridge & Rice, LLP

(57) ABSTRACT

The present invention provides anti-PTK7 antibody-drug conjugates and methods for preparing and using the same.

60 Claims, 24 Drawing Sheets

(56) References Cited

FOREIGN PATENT DOCUMENTS

| WO | WO 2012/031280 A2 | 3/2012 |
|---|---|---|
| WO | WO 2012/042021 A1 | 4/2012 |
| WO | WO 2012/112943 A1 | 8/2012 |
| WO | WO 2012/162482 | 11/2012 |
| WO | WO 2013/072813 A2 | 5/2013 |
| WO | WO 2013/119964 A2 | 8/2013 |
| WO | WO 2015/031698 | 3/2015 |
| WO | WO 2016/064749 | 4/2016 |

OTHER PUBLICATIONS

Carter "Potent antibody therapeutics by design" *Nat. Rev. Immunol*, (2006) 6:343-357.
Cavard et al., "Gene expression profiling provides insights into the pathways involved in solid pseudopapillary neoplasm of the pancreas", *J Pathol* (2009) 218: 201-209.
Dalerba et al., "Phenotypic characterization of human colorectal cancer stem cells" *Proc Natl Acad Sci U S A*. Jun. 12, 2007;104(24).
De Genst et al., "Antibody repertoire development in camelids" Dev. Comp. Immunol (2006) 30:187-98.
Dylla et al., "Colorectal Cancer Stem Cells Are Enriched in Xenogeneic Tumors Following Chemotherapy" *PLoS ONE*. 2008; 3(6): e2428. 2008.
Easty et al., "Loss of Expression of Receptor Tyrosine Kinase Family Genes Ptk7 and Sek in Metastatic Melanoma" *Int J Cancer*. (Jun. 11, 1997) 71(6):1061-5.
Endoh et al., "Prognostic Model of Pulmonary Adenocarcinoma by Expression Profiling of Eight Genes As Determined by Quantitative Real-Time Reverse Transcriptase Polymerase Chain Reaction" *J Clin Oncol*. Mar. 1, 2004; 22(5):811-9.
Forrest et al.,"Genome-wide review of transcriptional complexity in mouse protein kinases and phosphatases." *Genome Biol.* 2006;7(1):R5.
Golubkov et al., (2012) "The Wnt/Planar Cell Polarity Protein-tyrosine Kinase-7 (PTK7) Is a Highly Efficient Proteolytic Target of Membrane Type-1 Matrix Metalloproteinase." *J Biol Chem*. Nov. 12, 2010; 285(46): 35740-35749.
Gorringe et al.,"Novel regions of chromosomal amplification at 6p21, 5p13, and 12q14 in gastric cancer identified by array comparative genomic hybridization" *Genes Chromosomes Cancer*. Mar. 2005; 42(3):247-59.
Haines et al "Human CD4+ T cell recent thymic emigrants are identified by protein tyrosine kinase 7 and have reduced immune function" *J Exp Med*, (2009) 206(2) pp. 275-285.
Hanks et al.,"Protein kinase catalytic domain sequence database: identification of conserved features of primary structure and classification of family members." *Methods Enzymol*. (1991) 200: 38-62.
Hoey et al., "DLL4 Blockade Inhibits Tumor Growth and Reduces Tumor-Initiating Cell Frequency" *Cell Stem Cell*. Aug. 7, 2009; 5(2):168-77.
Huff et al.,"Strategies to eliminate cancer stem cells: Clinical implications" *European Journal of Cancer* (2006) 42: 1293-1297.
Jung et al., "Organization of the human PTK7 gene encoding a receptor protein tyrosine kinase-like molecule and alternative splicing of its mRNA." *Biochim Biophys Acta*. Dec. 12, 2002;1579(2-3):153-63.
Katoh et al.,"Comparative integromics on non-canonical WNT or planar cell polarity signaling molecules: transcriptional mechanism of PTK7 in colorectal cancer and that of SEMA6A in undifferentiated ES cells." *Int J Mol Med*. Sep. 2007; 20(3): 405-9.
Kobus "The GxxxG-containing transmembrane domain of the CCK4 oncogene does not encode preferential self-interactions." *Biochemistry*. Feb. 8, 2005;44(5):1464-70.
Kroiher et al. "Deceiving appearances: signaling by "dead" and "fractured" receptor protein-tyrosine kinases." *Bioessays*. Jan. 2001;23(1):69-76.

Lee et al., "A survey of protein tyrosine kinase mRNAs expressed in normal human melanocytes." *Oncogene* Dec. 1993; 8(12):3403-10.
Lu et al., "PTK7/CCK-4 is a novel regulator of planar cell polarity in vertebrates." *Nature*. Jul. 1, 2004;430(6995):93-8.
Lu et al., "Cell cycle regulator gene CDC5L, a potential target for 6p12-p21 amplicon in osteosarcoma." *Mol Cancer Res*. Jun. 2008; 6(6):937-46.
Meng et al "Silencing of PTK7 in Colon Cancer Cells: Caspase-lO-Dependent Apoptosis via Mitochondrial Pathway." *PLoS One*. Nov. 16, 2010; 5(11):e14018.
Mossie et al., "Colon carcinoma kinase-4 defines a new subclass of the receptor tyrosine kinase family." *Oncogene* Nov. 16, 1995; 11(10): 2179-84.
Muller-Tidow, et al.,"High-Throughput Analysis of Genome-Wide Receptor Tyrosine Kinase Expression in Human Cancers Identifies Potential Novel Drug Targets." *Clin Cancer Res*. Feb. 15, 2004;10(4):1241-9.
Orsulic et al.,"Expression of Eph receptors and ephrins is differentially regulated by E-cadherin", *Journal of Cell Science* 113, 1793-1802 (2000).
Paudyal et al., "The novel mouse mutant, chuzhoi, has disruption of Ptk7 protein and exhibits defects in neural tube, heart and lung development and abnormal planar cell polarity in the ear." *BMC Dev Biol*. Aug. 12, 2010;10:87.
Peradziryi et al., "The many roles of PTK7: A versatile regulator of cell-cell communication", Archives of Biochemistry and Biophysics 524:71-76 (2012).
Piao et al., "Identification of novel deletion regions on chromosome arms 2q and 6p in breast carcinomas by amplotype analysis." *Genes Chromosomes Cancer*. Feb. 2001;30(2):113-22.
Prebet et al., "The cell polarity PTK7 receptor acts as a modulator of the chemotherapeutic response in acute myeloid leukemia and impairs clinical outcome." *Blood* (2010) 116(13):2315-23.
Puppo et al., "Protein tyrosine kinase 7 has a conserved role in Wnt/β-catenin canonical signalling." *EMBO Rep*. Jan. 2011;12(1):43-9.
Retter et al., "VBASE2, an integrative V gene database" *Nucleic Acids Res*. Jan. 1, 2005;33(Database issue):D671-4.
Saha et al.,"A phosphatase associated with metastasis of colorectal cancer." *Science*. Nov. 9, 2001; 294(5545): 1343-6.
Schmalhofer et al., "E-cadherin, β-catenin, and ZEB1 in malignant progression of cancer." *Cancer Metastasis Rev*. Jun. 2009; 28 (1-2):151-66.
Schulenburg et al., "Neoplastic stem cells: Current concepts and clinical perspectives" *Crit Rev Oncol Hematol*. 76 (2010) 79-98.
Shangguan et al., "Cell-Specific Aptamer Probes for Membrane Protein Elucidation in Cancer Cells" *J Proteome Res*. May 2008; 7(5):2133-9.
Shin et al., "Soluble PTK7 inhibits tube formation, migration, and invasion of endothelial cells and angiogenesis", *Biochem Biophys Res Commun*. Jul. 11, 2008; 371(4) :793-8.
Shnitsar et al., "PTK7 recruits dsh to regulate neural crest migration", *Development*. Dec. 2008;135(24):4015-24.
Soyuer et al., "Prognostic significance of CD9 expression in locally advanced gastric cancer treated with surgery and adjuvant chemoradiotherapy", *Pathology—Research and Practice* (2010) 206; 607-610.
Su et al., "Undetectable and Decreased Expression of KIAA1949 (Phostensin) Encoded on Chromosome 6p21.33 in Human Breast Cancers Revealed by Transcriptome Analysis." *J Cancer*. Jun. 21, 2010; 1:38-50.
Todaro et al., "Colon Cancer Stem Cells: Promise of Targeted Therapy", *Gastroenterology* (2010) 138:2151-2162.
Toyofuku et al., "Dual roles of Sema6D in cardiac morphogenesis through region-specific association of its receptor, Plexin-A1, with off-track and vascular endothelial growth factor receptor type 2" *Genes Dev*. Feb. 15, 2004;18(4):435-47.
Visvader et al., "Cancer stem cells in solid tumours: accumulating evidence and unresolved questions" *Nature Reviews Cancer* 8, 755-768 (Oct. 2008) PMID 18784658.

(56) References Cited

OTHER PUBLICATIONS

Wagner et al., "PlexinA1 interacts with PTK7 and is required for neural crest migration" *Biochem Biophys Res Commun.* Nov. 12, 2010;402(2):402-7.
Winberg et al.,"The Transmembrane Protein Off-Track Associates with Plexins and Functions Downstream of Semaphorin Signaling during Axon Guidance" Neuron. Oct. 11, 2001;32(1):53-62.
Xiao et al., "Structure elucidation and theoretical investigation of key steps in the biogenetic pathway of schisanartane nortriterpenoids by using DFT methods." *Chemistry.* 2008;14(36):11584-92.
Zantek et al.,"E-cadherin regulates the function of the EphA2 receptor tyrosine kinase." *Cell Growth Differ.* Sep. 1999; 10(9):629-38.
Zhou et al.,"Tumour-initiating cells: challenges and opportunities for anticancer drug discovery." *Nat Rev Drug Discov.* Oct. 2009;8(10):806-23.
Office Action dated Apr. 8, 2015 issued in Australian patent application (No. 2012219313).
Official Action dated Dec. 1, 2014 issued in Chinese application (No. 201280019016.6).
Office Action dated May 25, 2015 issued in Colombian patent application (No. 13-216.891) with English translation.
Office Action dated Jul. 26, 2015 issued in Colombian patent application (No. 13-216.891) translation.
Official Action dated Sep. 29, 2014 issued in European application (No. 12705776.8).
Official Action dated Feb. 28, 2014 issued in New Zealand application (No. 615285).
Official Action dated Jun. 16, 2015 issued in New Zealand application (No. 615285).
Office Action dated Jun. 16, 2015 issued in New Zealand application (No. 708615).
Official Action dated Jun. 4, 2016 issued in Saudi Arabian t application (No. 112330278).
Second Office action issued in Saudi Arabian counterpart application (No. 112330278.2).
Official Action dated Jan. 30, 2015 issued in U.S. Appl. No. 14/000,289).
Official Action dated May 13, 2015 issued in U.S. Appl. No. 14/000,289).
Search Report dated May 25, 2012 issued in International application (No. PCT/US2012/025726).
Written Opinion dated May 25, 2012 issued in International Application (No. PCT/US2012/025726).
Search report and written opinion dated Nov. 2, 2015 issued in International Application No. PCT/US2015/027791.
Office action dated Oct. 13, 2015 issued in European patent application (No. 12705776.8).
Office action dated Oct. 23, 2015 issued in Chinese patent application (No. 21280019016.6).
Official Action dated Feb. 28, 2016, issued in Australian Patent Application No. 2012219313).
Official Action dated May 3, 3016, issued in Chinese Patent Application No. 201280019016.6).
Official Action dated Dec. 9, 2015, issued in Japanese Patent Application No. 2013-554656).
Official Action dated Feb. 9, 2016, issued in Mexican Patent Application No. MX/a/2013/009541).
Official Action dated Jun. 16, 2015, issued in New Zealand Patent Application No. 708615).
Official Action dated Apr. 6, 2016, issued in Russian Patent Application No. 2013141976.
Official Action dated Jun. 13, 2016, issued in Taiwan Patent Application No. 101105374).
International Preliminary Report on Patentability (IPRP) dated Nov. 1, 2016, issued in International Patent Application No. PCT/US2015/027791.
Genbank accession No. NM_002821 (dated Dec. 1, 2013) *Homo sapiens* protein tyrosine kinase 7 (PTK7), transcript variant PTK7-1, mRNA.
Genbank accession No. NP_002812 (dated Dec. 1, 2013) inactive tyrosine-protein kinase 7 isoform a precursor [*Homo sapiens*].
Genbank accession No. NP_690619 (dated Dec. 1, 2013) inactive tyrosine-protein kinase 7 isoform b precursor [*Homo sapiens*].
Genbank accession No. NP_690620 (dated Dec. 1, 2013) inactive tyrosine-protein kinase 7 isoform c precursor [*Homo sapiens*].
Genbank accession No. NP_690621 (dated Dec. 1, 2013) inactive tyrosine-protein kinase 7 isoform d precursor [*Homo sapiens*].
Official action dated Nov. 18, 2016, issued in Colombian Patent Application (No. NC2016/0003575).
Official action dated Nov. 28, 2016, issued in Israeli Patent Application (No. 228018)—Hebrew.
Official action dated Apr. 3, 2016, issued in Israeli Patent Application (No. 228018).
Official action dated Sep. 20, 2016, issued in Japanese Patent Application (No. 2013-554656).
Official action dated Sep. 30, 2016, issued in Mexican Patent Application (No. MX/a/2013/009541).
Official action dated Oct. 14, 2016, issued in New Zealand Patent Application (No. 708615).
Official action dated Feb. 13, 2017, issued in New Zealand Patent Application (No. 728364).
Official action dated Sep. 7, 2016, issued in Russian Patent Application (No. 2013141976).
Decision to grant dated Mar. 24, 2017 issued in Russian patent application (No. 2013141976).

\* cited by examiner

>gi|47938093|gb|AAH71557.1| PTK7 protein tyrosine kinase 7 [Homo sapiens]

```
   1 MGAARGSPAR PRRLPLLSVL LLPLLGGTQT AIVFIKQPSS QDALQGRRAL LRCEVEAPGP
  61 VHVYWLLDGA PVQDTERRFA QGSSLSFAAV DRPQDSGTFQ CVARDDVTGE EARSANASFN
 121 IKWIEAGPVV LKHPASEAEI QPQTQVTLRC HIDGHPRPTY QWFRDGTPLS DGQSNHTVSS
 181 KERNLTLRPA GPEHSGLYSC CAHSAFGQAC SSQNFTLSIA DESFARVVLA PQDVVVARYE
 241 EAMFHCQFSA QPPPSLQWLF EDETPITNRS RPPHLRRATV FANGSLLLTQ VRPNAGIYR
 301 CIGQGQRGPP IILEATLHLA EIEDMPLFEP RVFTAGSEER VTCLPPKGLP EPSVWWEHAG
 361 VRLPTHGRVY QKGHELVLAN IAESDAGVYT CHAANLAGQR RQDVNITVAT VPSWLKKPQD
 421 SQLEEGKPGY LDCLTQATPK PTVVWYRNQM LISEDSRFEV FKNGTLRINS VEVYDGTWYR
 481 CMSSTPAGSI EAQARVQVLE KLKFTPPPQP QQCMEFDKEA TVPCSATGRE KPTIKWERAD
 541 GSSLPEWVTD NAGTLHFARV TRDDAGNYTC IASNGPQGQI RAHVQLTVAV FITFKVEPER
 601 TTVYQGHTAL LQCEAQGDPK PLIQWKGKDR ILDPTKLGPR MHIFQNGSLV IHDVAPEDSG
 661 RYTCIAGNSC NIKHTEAPLY VVDKPVPEES EGPGSPPPYK MIQTIGLSVG AAVAYIIAVL
 721 GLMFYCKKRC KAKRLQKQPE GEEPEMECLN GGPLQNGQPS AEIQEEVALT SLGSGPAATN
 781 KRHSTSDKMH FPRSSLQPIT TLGKSEFGEV FLAKAQGLEE GVAETLVLVK SLQSKDEQQQ
 841 LDFRRELEMF GKLNHANVVR LLGLCREAEP HYMVLEYVDL GDLKQFLRIS KSKDEKLKSQ
 901 PLSTKQKVAL CTQVALGMEH LSNNRFVHKD LAARNCLVSA QRQVKVSALG LSKDVYNSEY
 961 YHFRQAWVPL RWMSPEAILE GDFSTKSDVW AFGVLMWEVF THGEMPHGGQ ADDEVLADLQ
1021 AGKARLPQPE GCPSKLYRLM QRCWALSPKD RPSFSEIASA LGDSTVDSKP
```
(SEQ ID NO 73)

FIG. 1

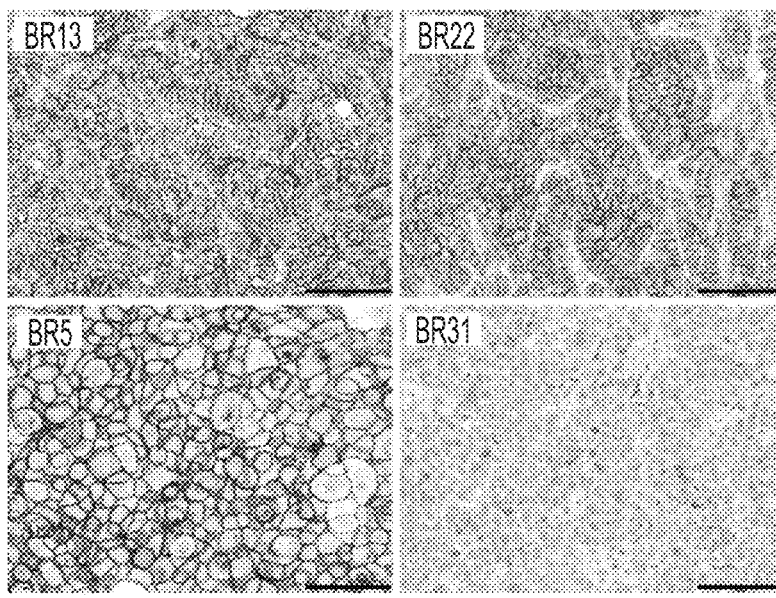
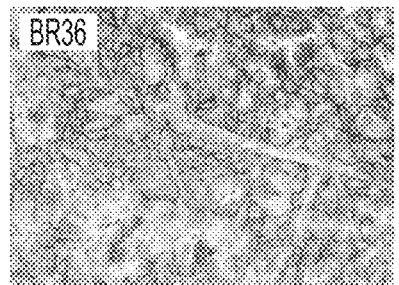
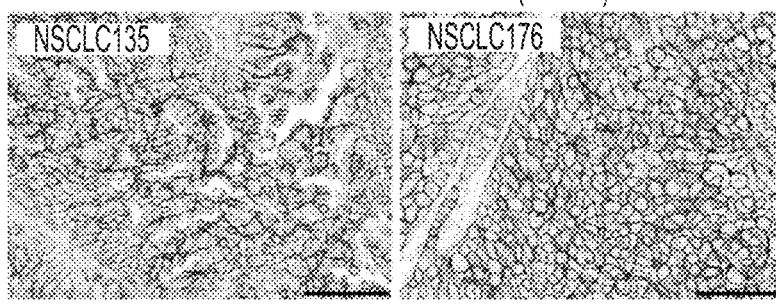
FIG. 3

EFFICACY OF anti-PTK7 ADCs IN THE BR13 TNBC PDX.

| DAY | VEHICLE | 10mg/kg hu24-vc0101 | 10mg/kg hu23-mc8261 | 3mg/kg hu23-mc8261 | 10mg/kg hu24-mc8261 | 3mg/kg hu24-mc8261 | 10mg/kg hu58-mc8261 | 3mg/kg hu58-mc8261 |
|---|---|---|---|---|---|---|---|---|
| 0 | 144 ± 13 | 192 ± 23 | 157 ± 11 | 162 ± 8 | 196 ± 26 | 160 ± 12 | 163 ± 14 | 153 ± 8 |
| 7 | 255 ± 22 | 203 ± 30 | 205 ± 12 | 188 ± 11 | 248 ± 23 | 196 ± 21 | 233 ± 15 | 230 ± 20 |
| 14 | 349 ± 40 | 136 ± 14 | 142 ± 12 | 203 ± 13 | 243 ± 30 | 188 ± 23 | 249 ± 20 | 277 ± 29 |
| 21 | 428 ± 48 | 36 ± 6 | 148 ± 21 | 125 ± 12 | 166 ± 19 | 150 ± 15 | 301 ± 24 | 366 ± 26 |
| 28 | 650 ± 62 | 20 ± 5 | 169 ± 19 | 159 ± 15 | 158 ± 23 | 187 ± 25 | 525 ± 77 | 463 ± 51 |
| 35 | 734 ± 74 | 4 ± 2 | 286 ± 41 | 207 ± 26 | 216 ± 41 | 237 ± 37 | 717 ± 78 | 599 ± 55 |
| 42 | 940 ± 105 | 6 ± 3 | 404 ± 53 | 286 ± 40 | 276 ± 53 | 310 ± 46 | GT | 688 ± 64 |
| 49 | GT | 5 ± 2 | 629 ± 83 | 394 ± 54 | 419 ± 97 | 435 ± 76 | GT | GT |
| 56 | GT | 3 ± 3 | 776 ± 54 | 611 ± 63 | 582 ± 130 | 587 ± 95 | GT | GT |
| 63 | GT | 3 ± 2 | 935 ± 115 | 700 ± 76 | 798 ± 53 | 650 ± 102 | GT | GT |
| 70 | GT | 0 ± 0 | 1166 ± 81 | 1024 ± 100 | 1107 ± 240 | 924 ± 117 | GT | GT |
| 77 | GT | 4 ± 2 | GT | GT | 1215 ± 207 | GT | GT | GT |
| 84 | GT | 3 ± 2 | GT | GT | GT | GT | GT | GT |
| 91 | GT | 3 ± 3 | GT | GT | GT | GT | GT | GT |
| 98 | GT | 5 ± 5 | GT | GT | GT | GT | GT | GT |
| 105 | GT | 5 ± 5 | GT | GT | GT | GT | GT | GT |
| 112 | GT | 9 ± 9 | GT | GT | GT | GT | GT | GT |
| 119 | GT | 10 ± 10 | GT | GT | GT | GT | GT | GT |
| 126 | GT | 11 ± 11 | GT | GT | GT | GT | GT | GT |
| 133 | GT | 1 ± 1 | GT | GT | GT | GT | GT | GT |
| 140 | GT | 0 ± 0 | GT | GT | GT | GT | GT | GT |
| 147 | GT | 0 ± 0 | GT | GT | GT | GT | GT | GT |
| 154 | GT | 0 ± 0 | GT | GT | GT | GT | GT | GT |
| 161 | GT | 0 ± 0 | GT | GT | GT | GT | GT | GT |
| 168 | GT | 5 ± 5 | GT | GT | GT | GT | GT | GT |
| 175 | GT | 9 ± 9 | GT | GT | GT | GT | GT | GT |
| 182 | GT | 10 ± 10 | GT | GT | GT | GT | GT | GT |
| 189 | GT | 15 ± 15 | GT | GT | GT | GT | GT | GT |
| 196 | GT | 19 ± 19 | GT | GT | GT | GT | GT | GT |
| 203 | GT | 28 ± 28 | GT | GT | GT | GT | GT | GT |
| 210 | GT | 30 ± 30 | GT | GT | GT | GT | GT | GT |
| 217 | GT | 34 ± 34 | GT | GT | GT | GT | GT | GT |
| 224 | GT | 65 ± 65 | GT | GT | GT | GT | GT | GT |
| 231 | GT | 0 ± 0 | GT | GT | GT | GT | GT | GT |

FIG. 9

EFFICACY OF anti-PTK7 ADCs IN THE BR22 TNBC PDX.

| DAY | VEHICLE | 10mg/kg hu23-vc0101 | 10mg/kg hu23-mc8261 | 3mg/kg hu23-mc8261 | 10mg/kg hu24-mc8261 | 3mg/kg hu24-mc8261 | 1mg/kg hu24-mc8261 | 10mg/kg hu58-mc8261 | 3mg/kg hu58-mc8261 |
|---|---|---|---|---|---|---|---|---|---|
| 0 | 195 ± 17 | 166 ± 24 | 164 ± 19 | 156 ± 12 | 188 ± 13 | 185 ± 10 | 184 ± 13 | 164 ± 17 | 149 ± 12 |
| 7 | 376 ± 43 | 69 ± 14 | 258 ± 50 | 335 ± 41 | 359 ± 24 | 315 ± 17 | 413 ± 44 | 289 ± 35 | 370 ± 19 |
| 14 | 564 ± 54 | 12 ± 3 | 364 ± 40 | 360 ± 59 | 588 ± 42 | 633 ± 55 | 750 ± 69 | 563 ± 69 | 672 ± 39 |
| 21 | 819 ± 97 | 0 ± 0 | 701 ± 106 | 916 ± 93 | 878 ± 79 | 1265 ± 218 | 1134 ± 112 | 1133 ± 133 | 984 ± 65 |
| 28 | GT | 0 ± 0 | 1189 ± 176 | 1534 ± 112 | GT | GT | GT | GT | 1555 ± 121 |
| 35 | GT | 0 ± 0 | GT | GT | GT | GT | GT | GT | GT |
| 42 | GT | 0 ± 0 | GT | GT | GT | GT | GT | GT | GT |
| 49 | GT | 0 ± 0 | GT | GT | GT | GT | GT | GT | GT |
| 56 | GT | 0 ± 0 | GT | GT | GT | GT | GT | GT | GT |
| 63 | GT | 0 ± 0 | GT | GT | GT | GT | GT | GT | GT |
| 70 | GT | 0 ± 0 | GT | GT | GT | GT | GT | GT | GT |
| 77 | GT | 0 ± 0 | GT | GT | GT | GT | GT | GT | GT |
| 84 | GT | 0 ± 0 | GT | GT | GT | GT | GT | GT | GT |
| 91 | GT | 0 ± 0 | GT | GT | GT | GT | GT | GT | GT |
| 98 | GT | 0 ± 0 | GT | GT | GT | GT | GT | GT | GT |
| 105 | GT | 0 ± 0 | GT | GT | GT | GT | GT | GT | GT |
| 112 | GT | 0 ± 0 | GT | GT | GT | GT | GT | GT | GT |
| 119 | GT | 0 ± 0 | GT | GT | GT | GT | GT | GT | GT |
| 126 | GT | 0 ± 0 | GT | GT | GT | GT | GT | GT | GT |
| 133 | GT | 0 ± 0 | GT | GT | GT | GT | GT | GT | GT |
| 140 | GT | 0 ± 0 | GT | GT | GT | GT | GT | GT | GT |
| 147 | GT | 0 ± 0 | GT | GT | GT | GT | GT | GT | GT |
| 154 | GT | 0 ± 0 | GT | GT | GT | GT | GT | GT | GT |
| 161 | GT | 0 ± 0 | GT | GT | GT | GT | GT | GT | GT |
| 168 | GT | 0 ± 0 | GT | GT | GT | GT | GT | GT | GT |
| 175 | GT | 0 ± 0 | GT | GT | GT | GT | GT | GT | GT |
| 182 | GT | 0 ± 0 | GT | GT | GT | GT | GT | GT | GT |
| 189 | GT | 0 ± 0 | GT | GT | GT | GT | GT | GT | GT |
| 196 | GT | 0 ± 0 | GT | GT | GT | GT | GT | GT | GT |

FIG. 12

ANTI-PTK7 ANTIBODY-DRUG CONJUGATES

RELATED APPLICATION

Priority is claimed to provisional U.S. Application No. 61/986,520, filed Apr. 30, 2014, which is incorporated by reference herein in its entirety.

SEQUENCE LISTING

This application is being filed electronically via EFS-Web and includes an electronically submitted sequence listing in .txt format. The .txt file contains a sequence listing entitled "PC072045_Sequence_Listing.txt" created on Apr. 30, 2014, and having a size of 57.7 KB. The sequence listing contained in this .txt file is part of the specification and which is incorporated herein by reference in its entirety.

FIELD OF THE INVENTION

The present invention relates to protein tyrosine kinase 7 (PTK7) antibodies and antibody-drug conjugates. The present invention further relates to the methods of using such antibodies and antibody-drug conjugates for the treatment of cancer.

BACKGROUND OF THE INVENTION

Protein tyrosine kinase 7 (PTK7), also known as colon carcinoma kinase 4 (CCK4), is a receptor tyrosine kinase originally cloned from normal human melanocytes and separately from colon carcinoma tissue. High levels of PTK7 have been identified in a number of tumor cells, including bladder, breast, colorectal, kidney, and lung cancers and melanoma. PTK7 expression has also been observed on adult myeloid leukemia (AML) and acute lymphoblastic leukemia (ALL) cells.

The treatment of cancer has improved over the past decade with surgery, radiation therapy, and chemotherapy as the primary treatment options. Such treatments can extend survival and/or relieve symptoms in many patients but are not likely to produce a cure for many patients. Consequently, there remains a significant need for additional therapeutic options for cancers.

To this end, the present invention provides novel antibody-drug conjugates that target PTK7-positive cancers. The disclosed anti-PTK7 antibody-drug conjugates can exert a clinically useful cytotoxic effect on PTK7 expressing tumor cells without exerting undesirable effects on non-PTK7 expressing cells.

SUMMARY OF THE INVENTION

The present invention provides PTK7 antibody-drug conjugates and their use in detection, prophylaxis, and therapy of PTK7 associated disorders. A PTK7 antibody-drug conjugate of the invention is generally of the formula: Ab-(L-D), wherein Ab is an antibody, or antigen-binding fragment thereof, that binds to PTK7, or a PTK7-binding fragment thereof; and L-D is a linker-drug moiety, wherein L is a linker, and D is a drug.

The Ab of the disclosed antibody-drug conjugate can be any PTK7-binding antibody. In some aspects of the invention, the Ab is a chimeric, CDR-grafted, humanized, or a recombinant human antibody, or PTK7-binding fragment thereof. In some aspects of the invention, the Ab is an internalizing antibody and/or a neutralizing antibody.

The present invention also provides PTK7 antibody-drug conjugates and their use in detection, prophylaxis and therapy of PTK7 associated disorders. A PTK7 antibody-drug conjugate of the invention is generally of the formula: Ab-(L-D), wherein Ab is an antibody, or antigen-binding fragment thereof, that binds to PTK7, or a PTK7-binding fragment thereof; and L-D is a linker-drug moiety, wherein L is a linker, and D is an auristatin.

In particular aspects of the invention, the Ab is a hu23, hu24, or hu58 antibody, or an antibody that competes for binding to human PTK7 with hu23, hu24, or hu58, and/or an antibody that binds to the same epitope as a hu23, hu24, or hu58 antibody. For example, the Ab may compete for binding to human PTK7 with, and/or bind the same epitope as, an antibody comprising (a) a heavy chain variable region set forth as SEQ ID NO: 1 and a light chain variable region set forth as SEQ ID NO: 15; (b) a heavy chain variable region set forth as SEQ ID NO: 25 and a light chain variable region set forth as SEQ ID NO: 39; or (c) a heavy chain variable region set forth as SEQ ID NO: 49 and a light chain variable region set forth as SEQ ID NO: 63.

Among Abs that compete for binding to human PTK7 with hu23, and/or bind to the same epitope as hu23, representative Abs useful for preparing PTK7 antibody-drug conjugates of the invention include antibodies comprising at least one heavy chain variable region and at least one light chain variable region, wherein the at least one heavy chain variable region comprises three CDRs defined by SEQ ID NOs: 3, 7, and 11. Additional Abs include antibodies comprising at least one heavy chain variable region and at least one light chain variable region, wherein the at least one light chain variable region comprises three CDRs defined as SEQ ID NOs: 17, 19, and 21. Additional Abs include antibodies comprising (a) a heavy chain variable region comprising three CDRs set forth as SEQ ID NOs: 3, 7, and 11; and (b) a light chain variable region comprising three CDRs set forth as SEQ ID NOs: 17, 19, and 21.

In other PTK7 antibody-drug conjugates of the invention, the Ab comprises a heavy chain variable region having an amino acid sequence that is at least 90% identical to SEQ ID NO: 1 and a light chain variable having an amino acid sequence that is at least 90% identical to SEQ ID NO: 15, for example, a heavy chain variable region set forth as SEQ ID NO: 1 and a light chain variable region set forth as SEQ ID NO: 15.

Among Abs that compete for binding to human PTK7 with hu24, and/or bind to the same epitope as hu24, representative Abs useful for preparing PTK7 antibody-drug conjugates of the invention include antibodies comprising at least one heavy chain variable region and at least one light chain variable region, wherein the at least one heavy chain variable region comprises three CDRs defined by SEQ ID NOs: 27, 31, and 35. Additional Abs include antibodies comprising at least one heavy chain variable region and at least one light chain variable region, wherein the at least one light chain variable region comprises three CDRs defined as SEQ ID NOs: 41, 43, and 45. Additional Abs include antibodies comprising (a) a heavy chain variable region comprising three CDRs set forth as SEQ ID NOs: 27, 31, and 35; and (b) a light chain variable region comprising three CDRs set forth as SEQ ID NOs: 41, 43, and 45.

In other PTK7 antibody-drug conjugates of the invention, the Ab comprises a heavy chain variable region having an amino acid sequence that is at least 90% identical to SEQ ID NO: 25 and a light chain variable having an amino acid sequence that is at least 90% identical to SEQ ID NO: 39, for example, a heavy chain variable region set forth as SEQ ID NO: 25 and a light chain variable region set forth as SEQ ID NO: 39.

Among Abs that compete for binding to human PTK7 with hu58, and/or bind to the same epitope as hu58, representative Abs useful for preparing PTK7 antibody-drug conjugates of the invention include antibodies comprising at least one heavy chain variable region and at least one light chain variable region, wherein the at least one heavy chain variable region comprises three CDRs defined by SEQ ID NOs: 51, 55, and 59. Additional Abs include antibodies comprising at least one heavy chain variable region and at least one light chain variable region, wherein the at least one light chain variable region comprises three CDRs defined as SEQ ID NOs: 65, 67, and 69. Additional Abs include antibodies comprising (a) a heavy chain variable region comprising three CDRs set forth as SEQ ID NOs: 51, 55, and 59; and (b) a light chain variable region comprising three CDRs set forth as SEQ ID NOs65, 67, and 69.

In other PTK7 antibody-drug conjugates of the invention, the Ab comprises a heavy chain variable region having an amino acid sequence that is at least 90% identical to SEQ ID NO: 49 and a light chain variable region having an amino acid sequence that is at least 90% identical to SEQ ID NO: 63, for example, a heavy chain variable region set forth as SEQ ID NO: 49 and a light chain variable region set forth as SEQ ID NO: 63.

In some aspects of the invention, PTK7 antibody-drug conjugates comprise an Ab comprising an IgG1 heavy chain constant region, a kappa light chain constant region, or an IgG1 heavy chain constant region and a kappa light chain constant region. For example, Abs useful for preparing PTK7 antibody-drug conjugates of the invention include antibodies comprising a heavy chain set forth as SEQ ID NO: 13, a light chain set forth as SEQ ID NO: 23, or a heavy chain set forth as SEQ ID NO: 13 and a light chain set forth as SEQ ID NO: 23. Additional examples include antibodies comprising a heavy chain set forth as SEQ ID NO: 37, a light chain set forth as SEQ ID NO: 47, or a heavy chain set forth as SEQ ID NO: 37 and a light chain set forth as SEQ ID NO: 47. Still further examples include antibodies comprising a heavy chain set forth as SEQ ID NO: 61, a light chain set forth as SEQ ID NO: 71, or a heavy chain set forth as SEQ ID NO: 61 and a light chain set forth as SEQ ID NO: 71.

In other aspects of the invention, a PTK7 antibody-drug conjugate of the invention comprises an antibody having a heavy chain variable region set forth as SEQ ID NO: 1, 25, or 49. In other aspects of the invention, a PTK7 antibody-drug conjugate of the invention comprises an antibody having light chain variable region set forth as SEQ ID NO: 15, 39, or 63.

In particular aspects of the invention, the Ab is a hu23, hu24 or hu58 antibody, or an antibody that competes for binding to human PTK7 with hu23, hu24 or hu58 antibody and/or an antibody that binds to the same epitope as hu23, hu24 or hu58 antibody. For example, the Ab may compete for binding to human PTK7 with and/or bind to the same epitope as an antibody comprising (a) a heavy chain variable region of SEQ ID NO:13 and a light chain variable region of SEQ ID NO:23; (b) a heavy chain variable region of SEQ ID NO:25 and a light chain variable region of SEQ ID NO:39; or (c) a heavy chain variable region of SEQ ID NO:49 and a light chain variable region of SEQ ID NO:63.

In another aspect of the invention, the Ab is a humanized monoclonal antibody such as hu23, hu24 or hu58 antibody.

Any of the PTK7 antibody-drug conjugates disclosed herein may be prepared with a linker that is cleavable or non-cleavable. In one aspect the cleavable linker may be maleimidocaproyl-valine-citrulline-p-aminobenzyloxycarbonyl (vc). In another aspect the cleavable linker may be 4 (4'acetylphenoxy)butanoic acid (AcBut). In another aspect the non-cleavable linker may be maleimidocaproyl (mc).

Any of the PTK7 antibody drug conjugates disclosed herein may be prepared with a drug that is auristatin. In one aspect, the auristatin may be 0101 (2-Methylalanyl-N-[(3R, 4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide). In another aspect, the auristatin may be 8261 2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide.

Any of the PTK7 antibody drug conjugates disclosed herein may be prepared with a drug that is calicheamicin, including N acetyl derivatives of calicheamicin such as N-acetyl-γ-calicheamicin and N-acetyl-γ-calicheamicin dimethyl hydrazide (CM).

Any of the PTK7 antibodies disclosed herein may be used in an antibody-drug conjugate by conjugation with a linker-drug moiety (L-D). In one aspect, the L-D may be vc0101 (N-[6-(2,5-dioxo-2,5-dihydro-1H-pyrrol-1-yl)hexanoyl]-L-valyl-N-{4-[(21S,24S,25R)-24-[(2S)-butan-2-yl]-25-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-18,18,23-trimethyl-3,16,19,22-tetraoxo-21-(propan-2-yl)-2,7,10,13,26-pentaoxa-4,17,20,23-tetraazaheptacos-1-yl]phenyl}-N~5~-carbamoyl-L-ornithinamide). In another aspect, the L-D may be mc8261 (N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide). In yet another aspect, the L-D may be AcButCM (4(4'acetylphenoxy)butanoic acid N-acetyl-γ-calicheamicin dimethyl hydrazide). Any of the PTK7 antibody-drug conjugates disclosed herein may have a drug-to-antibody ratio (DAR) from 1 to 8.

In a particular aspect of the invention, a PTK7 antibody-drug conjugate of the formula Ab-(L-D) comprises (a) an antibody, or antigen-binding fragment thereof, Ab, comprising a heavy chain set forth as SEQ ID NO: 13 and a light chain set forth as SEQ ID NO: 23; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 37 and a light chain set forth as SEQ ID NO: 47; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 61 and a light chain set forth as SEQ ID NO: 71; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 13 and a light chain set forth as SEQ ID NO: 23; and (b) a linker-drug moiety, L-D, wherein L is a linker, and D is a drug, wherein the linker is maleimidocaproyl (mc), and wherein the drug is 8261.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 37 and a light chain set forth as SEQ ID NO: 47; and (b) a linker-drug moiety, L-D, wherein L is a linker, and D is a drug, wherein the linker is maleimidocaproyl (mc), and wherein the drug is 8261.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 61 and a light chain set forth as SEQ ID NO: 71; and (b) a linker-drug moiety, L-D, wherein L is a linker, and D is a drug, wherein the linker is maleimidocaproyl (mc), and wherein the drug is 8261.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 13 and a light chain set forth as SEQ ID NO: 23; and (b) a linker-drug moiety, L-D, wherein L is a linker, and D is a drug, wherein the linker is AcBut (4'acetylphenoxy)butanoic acid) and wherein the drug is CM (N-acetyl-γ-calicheamicin dimethyl hydrazide).

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 37 and a light chain set forth as SEQ ID NO: 47; and (b) a linker-drug moiety, L-D, wherein L is a linker, and D is a drug, wherein the linker is AcBut (4'acetylphenoxy)butanoic acid) and wherein the drug is CM (N-acetyl-γ-calicheamicin dimethyl hydrazide).

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 61 and a light chain set forth as SEQ ID NO: 71; and (b) a linker-drug moiety, L-D, wherein Lisa linker, and D is a drug, wherein the linker is AcBut (4'acetylphenoxy)butanoic acid) and wherein the drug is CM (N-acetyl-γ-calicheamicin dimethyl hydrazide).

The present invention provides for compositions comprising a plurality of antibody-drug conjugates disclosed herein and optionally a pharmaceutical carrier, wherein the composition has an average DAR within the range of 1 to 8. In a particular aspect of the invention, the composition may have an average DAR within the range of 3 to 5. In another aspect of the invention, the composition may have an average DAR within the range of 3 to 4. In another aspect of the invention, the composition may have an average DAR of about 4.

The present invention further provides for a composition comprising a plurality of an antibody-drug conjugate disclosed herein and optionally a pharmaceutical carrier, wherein the composition has at least 50% antibody-drug conjugates having a DAR from 3 to 5. In another aspect of the invention, the composition has at least 60% antibody-drug conjugates having a DAR from 3 to 5.

The present invention further provides for a PTK7 antibody-drug conjugate that is generally of the formula: Ab-(L-D), wherein Ab is an antibody or antigen-binding fragment thereof that binds to PTK7 or a PTK7-binding fragment thereof; and L-D is a linker-drug moiety, wherein L is vc or mc or AcBut, and D is a drug.

The present invention further provides for a PTK7 antibody-drug conjugate that is generally of the formula: Ab-(L-D), wherein Ab is an antibody, or antigen-binding fragment thereof that binds to PTK7, or a PTK7-binding fragment thereof; and L-D is a linker-drug moiety, wherein L is a linker, and D is an auristatin (such as 0101 or 8261) or CM.

The present invention further provides methods for preparing a PTK7 antibody-drug conjugate disclosed herein. For example, a process for producing an antibody-drug conjugate can include the steps of (a) linking the linker to the drug; (b) conjugating the linker-drug moiety to the antibody; and (c) purifying the antibody-drug conjugate.

Another aspect of the invention includes methods of making, methods of preparing, methods of synthesis, methods of conjugation and methods of purification of the antibody-drug conjugates disclosed herein and the intermediates for the preparation, synthesis and conjugation of the antibody-drug conjugates disclosed herein.

Further provided are pharmaceutical compositions comprising a PTK7 antibody-drug conjugate disclosed herein and a pharmaceutically acceptable carrier.

In other aspects are provided methods of treating a PTK7 associated disorder by administering a therapeutically effective amount of a composition comprising a PTK7 antibody-drug conjugate disclosed herein. Representative PTK7 associated disorders include hyperproliferative disorders, such as neoplastic disorders, such as solid tumors (e.g., breast cancer, such as triple-negative breast cancer (TNBC), progesterone-receptor positive breast cancer (PR+), estrogen-receptor positive breast cancer (ER+) and double positive breast cancer; ovarian cancer; colorectal cancer; esophageal cancer; gastric cancer; melanoma; sarcoma; kidney cancer; pancreatic cancer; prostate cancer; liver cancer, such as hepatocellular carcinoma (HCC); and lung cancer, such as non-small cell lung cancer (NSCLC) and small cell lung cancer (SCLC), etc.) and hematologic malignancies (e.g., leukemia, such as adult myeloid leukemia (AML) or acute lymphoblastic leukemia (ALL), etc.). Also provided are uses of the disclosed PTK7 antibody-drug conjugates for the manufacture of a medicament for treating a PTK7 associated disorder in a subject. Also provided are PTK7 antibody-drug conjugates for use in the treatment of a PTK7 associated disorder.

In other aspects, the present invention provides for methods of treating a PTK7 associated disorder in a subject by administering a therapeutically effective amount of a composition comprising a PTK7 antibody-drug conjugate disclosed herein and a chemotherapeutic agent.

Another aspect of the invention includes methods of treating a disorder characterized by the overexpression of PTK7 in a patient with an antibody-drug conjugate disclosed herein. In other aspects, the present invention provides for methods of treating cancer characterized by the overexpression of PTK7 in a patient with an antibody-drug conjugate disclosed herein.

In still other aspects, the present invention provides a method of reducing tumor initiating cells in a tumor cell population. For example, the method can comprise contacting a tumor cell population, wherein the population comprises tumor initiating cells and tumor cells other than tumor initiating cells, with a PTK7 antibody-drug conjugate; whereby the frequency of tumor initiating cells in the tumor cell population is reduced. The contacting step may be performed in vitro or in vivo.

Another aspect of the invention includes diagnostic and therapeutic uses for the compounds and compositions disclosed herein.

Other aspects of the invention include articles of manufacture, i.e. kits, comprising an antibody-drug conjugate disclosed herein, a container, and a package insert or label indicating a treatment.

These and other aspects of the invention will be appreciated by a review of the application as a whole.

BRIEF DESCRIPTION OF THE DRAWINGS

FIG. 1 provides the amino acid sequence of a representative full-length PTK7 protein (SEQ ID NO. 73)

FIG. 3 shows PTK7 expression on tissue samples from seven PDX models by immunohistochemistry. Staining indicates PTK7. Representative micrographs are shown for each model. Scale bar, 100 µM.

FIG. 9 is a data table showing the efficacy of hu24-vc0101 and anti-PTK7-mc8261 ADCs in the BR13 TNBC PDX.

FIG. 12 is a data table showing the efficacy of hu23-vc0101 and anti-PTK7-mc8261 ADCs in the BR22 TNBC PDX.

DETAILED DESCRIPTION OF THE INVENTION

Figure 2A:
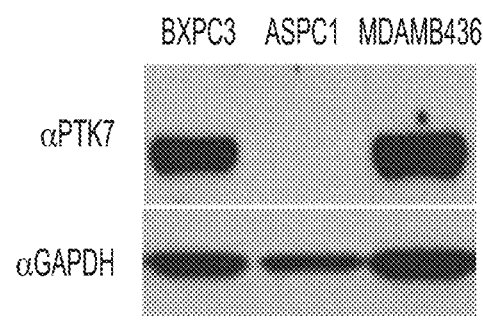
FIGS. 2A-B show that hu24 binding correlates with cell expression of PTK7. (A) Immunoblot of whole cell lysates with anti-PTK7 and anti-GAPDH antibodies. The immunoblot signal had been previously validated by demonstrating loss of signal when PTK7 gene expression was inhibited by siRNA. (B) Mean fluorescence intensity values from flow cytometry with anti-PTK7 (hu24) on the same cancer cell lines as in the immunoblot. The dotted line represents the signal when the primary antibody was a negative control antibody rather than hu24.

The present invention provides antibody-drug conjugates that bind to PTK7, processes for preparing the conjugates using PTK7 antibodies, linkers, and drugs. The antibody-drug conjugates of the invention are useful for the preparation and manufacture of compositions, such as medicaments that may be used in the diagnosis, prophylaxis, and/or treatment of hyperproliferative disorders characterized by PTK7 expression. In some aspects of the invention, the disclosed antibody-drug conjugates may reduce the frequency of tumor initiating cells (TIC), which encompass both tumor perpetuating cells (TPC) and highly proliferative tumor progenitor cells (TProg).

I. PTK7 Physiology

Protein tyrosine kinase (PTK7), also known as colon carcinoma kinase 4 (CCK4), is a receptor tyrosine kinase originally cloned from normal human melanocytes (Lee et al., Oncogene 8(12):3403-3410, 1993) and separately from colon carcinoma tissue (Mossie et al., Oncogene 11(10): 2179-2184, 1995). The PTK7 gene is located at 6p21.1-p12.2. Five splice isoforms of human PTK7 have been cloned from testis cDNA (Jung, et al., Biochim Biophys Acta 1579, 2002). The relative abundance of the isoforms with respect to one another differs between testis and hepatoma or colon carcinoma lines, but the functional significance of these isoforms, if any, is unknown. Bioinformatics analyses have suggested that the mouse may express a soluble PTK7 isoform from alternatively spliced mRNAs (Forrest, Taylor et al., Genome Biol 7, 2006).

Full length PTK7 protein is a type I transmembrane protein, with a 674 amino acid extracellular domain (ECD), followed by a short TM spanning portion and a 345 amino acid cytoplasmic domain. A representative a full-length amino acid sequence of PTK7 is shown in FIG. 1 (SEQ ID NO. 73). The amino acid sequences of representative PTK7 isoforms are found in GenBank Accession Nos. EAX04154.1 (isoform a), EAX04155.1 (isoform b), EAX04156.1 (isoform c), EAX04157.1 (isoform d), EAX04158.1 (isoform e), EAX04159.1 (isoform f), and EAX04160.1 (isoform g). All isoforms encode the same intracellular domain. A complete nucleic acid sequence of a representative isoform of human PTK7 (i.e. transcript variant PTK7-1), has Genbank Accession No. NM_002821.

The mature full length PTK7 ECD comprises seven immunoglobulin-like domains while the various splice variants encode PTK7 isoforms that differ in their ECD structure. All isoforms contain a cytoplasmic domain with substantial homology to that found in the general class of tyrosine kinases. However, PTK7 lacks detectable tyrosine kinase activity and, as such, belongs to a subfamily of pseudokinases in which several amino acid changes in various conserved kinase subdomains lead to impaired binding of ATP (Boudeau, et al., Trends Cell Biol. 16, 2006). Specifically, key residues in subdomains I and VII are altered in PTK7 such that direct interactions with the non-transferable phosphates of ATP, as well as, chelation of the $Mg^{2+}$ cofactor bridging these phosphates, would be impaired.

The biological importance of PTK7 function can be inferred from the presence of conserved orthologs from Hydra through *Drosophila* to chicken and human, each of which by sequence analysis is predicted to lack kinase activity. Based upon the high conservation of a specific TM domain motif associated with a propensity for helix-helix association, it has been suggested that the TM domain may mediate PTK7 dimerization. The PTK7 pseudokinase domain itself is not expected to directly transmit the signal, but it may interact as a scaffold for other molecules in the signaling pathway, or may recruit other tyrosine kinase(s). It has been shown that PTK7 may function in cell adhesion, cell migration, cell polarity, proliferation, actin cytoskeleton reorganization, and apoptosis to regulate embryogenesis, epithelial tissue organization, neuronal tube closure, neuronal crest formation, and axon guidance (Peradziryi, H. et al. Arch Biochem Biophys. 524, 2012).

Normal tissues and cells reported to express PTK7 include lung, thyroid, ovary, CD4+ recent thymic emigrant T-cells, and normal myeloid progenitors and CD34+CD38− bone marrow cells. With respect to cancerous tissues, PTK7 expression has also been found in colon carcinoma cells, adult myeloid leukemia (AML) samples, CD34− pre-TALL cells, and gastric carcinoma. PTK7 may be lost in certain breast cancers containing deletions of chromosome 6p21, although expression is variable in breast cancer cell lines. PTK7 is also expressed in lung adenocarcinoma. Fine mapping of the amplifications of 6p1 2-p21 region in osteosarcomas has shown that increases in gene copy number do not necessarily result in overexpression of PTK7, as determined by qRT-PCR.

The ligand or ligands for PTK7 are not known, although PTK7 has been linked to a variety of biological signaling pathways and developmental processes. For example, PTK7 acts as a co-receptor in both the non-canonical (also known as the Wnt/planar cell polarity signaling) and the canonical Wnt signaling pathways. In the non-canonical Wnt pathway, PTK7 activates downstream signaling by direct interaction with RACK1 and recruitment of DSH into the membrane localized receptor complex. PTK7 exerts an inhibitory effect on canonical Wnt pathway signal transduction through competition for frizzled receptor binding at the membrane surface. PTK7 gene expression is regulated by Cdx, while protein stability is regulated by membrane associated proteinase degradation. PTK7 is targeted for proteolytic degradation and extracellular domain shedding by the metalloproteinases MMP14 and Adam17, leading to enhanced cell proliferation, migration, and facilitated cancer cell invasion (Peradziryi, et al. Arch Biochem Biophys. 524, 2012). Soluble PTK7 (sPTK7) was used to show a role for PTK7 in VEGF-induced angiogenesis, as well as, in vitro tube formation, migration and invasion of human endothelial cells.

Within cancerous tissues, in addition to its potential for modulating the Wnt pathways, PTK appears to convey pro-proliferation and anti-apoptotic signals in the HCT116 colon carcinoma line, phenotypes which could be reversed by RNAi mediated knock-down of PTK7 (Meng, et al., 2010, PLoS One 5(11):e14018). PTK7 anti-apoptotic signals conveyed resistance to anthracycline-mediated cell killing in adult myeloid leukemia (AML) blasts, which could be reversed using a soluble PTK7-Fc protein (Prebet, et al., 2010, Blood 116(13):2315-23). Overexpression of PTK7 by specific cancer cells has been exploited in a strategy to target delivery of daunorubicin to T-ALL cells in culture using aptamers that bind PTK7 and are subsequently internalized.

II. PTK7 Antibody-Drug Conjugates

The present invention provides antibody-drug conjugates of the formula Ab-(L-D), wherein (a) Ab is an antibody, or antigen-binding fragment thereof, that binds to PTK7, and (b) L-D is a linker-drug moiety, wherein L is a linker, and D is a drug. Also provided are methods of preparing and manufacturing such antibody-drug conjugates, and use of the same in clinical applications. "Antibody-drug conjugate" or "ADC" refers to antibodies, or antigen-binding fragments thereof, including antibody derivatives that bind to PTK7 and are conjugated to a drug such as a cytotoxic, cytostatic, and/or therapeutic agent, as described further herein below. For example, a cytotoxic agent can be linked or conjugated to an anti-PTK7 antibody as described herein for targeted local delivery of the cytotoxic agent to tumors (e.g., PTK7 expressing tumors).

As used herein, the term "PTK7" includes variants, isoforms, homologs, orthologs and paralogs. PTK7 is also known in the art as colon carcinoma kinase 4 (CCK4 or CCK-4). For the purposes of the instant application it will be appreciated that the terms "PTK7" and "CCK4" are used interchangeably and include splice variants, isoforms, species orthologs and homologs of human PTK7 or human CCK4. It will further be appreciated that the terms may also refer to any derivative or fragment of a native or variant form of PTK7 or CCK4 containing an epitope to which a PTK7 antibody can specifically bind.

In some aspects of the invention, antibodies and antibody-drug conjugates cross-react with PTK7 from species other than human, such as PTK7 of mouse, rat, or primate, as well as different forms of PTK7 (e.g., glycosylated PTK7). In other aspects, the antibodies and antibody-drug conjugates may be completely specific for human PTK7 and may not exhibit species or other types of cross-reactivity. As used herein the term PTK7 refers to naturally occurring human PTK7 unless contextually dictated otherwise. Therefore, a "PTK7 antibody" or "anti-PTK7 antibody" or other similar designation, means any antibody (as defined herein) that associates, binds or reacts with human PTK7, or fragment or derivative thereof. Further, a "PTK7 antibody-drug conjugate" or "anti-PTK7 antibody-drug conjugate" means any antibody-drug conjugate or ADC (as defined herein) that associates, binds or reacts with human PTK7, or fragment or derivative thereof.

"Linker (L)" describes the direct or indirect linkage of the antibody to the drug. Attachment of a linker to an antibody can be accomplished in a variety of ways, such as through surface lysines, reductive-coupling to oxidized carbohydrates, cysteine residues liberated by reducing interchain disulfide linkages, reactive cysteine residues engineered at specific sites, and acyl donor glutamine-containing tag or an endogenous glutamine made reactive by polypeptide engineering in the presence of transglutaminase and an amine. A variety of ADC linkage systems are known in the art, including hydrazone-, disulfide- and peptide-based linkages.

"Drug (D)" is any substance having biological or detectable activity, for example, therapeutic agents, detectable labels, binding agents, etc., and prodrugs, which are metabolized to an active agent in vivo. The terms drug, payload, and compound are used interchangeably.

"L-D" is a linker-drug moiety resulting from a drug (D) linked to a linker (L).

Additional scientific and technical terms used in connection with the present invention, unless indicated otherwise herein, shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

In a particular aspect of the invention, a PTK7 antibody-drug conjugate of the formula Ab-(L-D) comprises (a) an antibody, or antigen-binding fragment thereof, Ab, comprising a heavy chain variable region set forth as SEQ ID NO: 1 and a light chain variable region set forth as SEQ ID NO: 15; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 13 and a light chain set forth as SEQ ID NO: 23; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain variable region set forth as SEQ ID NO: 25 and a light chain variable region set forth as SEQ ID NO: 39; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 37 and a light chain set forth as SEQ ID NO: 47; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain variable region set forth as SEQ ID NO: 49 and a light chain variable region set forth as SEQ ID NO: 63; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

In another aspect of the invention, a PTK7 antibody-drug conjugate of the formula Ab-(L-D) comprises (a) an antibody, or antigen-binding fragment thereof, Ab, comprising a heavy chain set forth as SEQ ID NO: 61 and a light chain set forth as SEQ ID NO: 71; and (b) a linker-drug moiety, L-D, wherein L is a linker, and D is a drug, wherein the linker is maleimidocaproyl-valine-citrulline-p-aminobenzyloxycarbonyl (vc), and wherein the drug is 0101.

The DAR (drug-to-antibody ratio) or drug loading, indicating the number of drug molecules conjugated per antibody, may be from 1 to 8. Compositions, batches, and/or formulations of a plurality of antibody-drug conjugates may be characterized by an average DAR. DAR and average DAR can be determined by various conventional means such as UV spectroscopy, mass spectroscopy, ELISA assay, radiometric methods, hydrophobic interaction chromatography (HIC), electrophoresis and HPLC.

In particular aspects of the invention, purified anti-PTK7 ADCs may have no unconjugated antibodies (free antibodies) present. In other aspects of the invention, the purified anti-PTK7 ADCs may be monomeric ADCs, and the aggregates and dimers are absent. In other aspects of the invention, the purified anti-PTK7 ADCs may have no free drug present. In further aspects of the invention, the purified anti-PTK7 ADCs may be monomeric ADCs and have no free drug present.

IIA. PTK7 Antibodies

For preparation of PTK7 antibody-drug conjugates of the invention, the antibody, or antigen-binding fragment thereof, can be any antibody, or antigen-binding fragment thereof, that specifically binds to PTK7. The antibodies the present invention are further disclosed and characterized in PCT International Publication No. WO 2012/112943, which is incorporated herein by reference in its entirety. More particularly, the sequences of PTK7 antibodies disclosed therein, including complete heavy and light chains, variable regions thereof, and CDRs thereof, are incorporated herein by reference. For use in preparation of PTK7 antibody-drug conjugates, the antibody, or antigen-binding fragment thereof, may be isolated, purified, or derivatized.

An "antibody" or "Ab" is an immunoglobulin molecule capable of recognizing and binding to a specific target or antigen, such as a carbohydrate, polynucleotide, lipid, polypeptide, etc., through at least one antigen recognition site, located in the variable region of the immunoglobulin molecule. As used herein, the term "antibody" can encompass any type of antibody, including but not limited to monoclonal antibodies, polyclonal antibodies, "antigen-binding fragments" (or portion), such as Fab, Fab', F(ab')$_2$, Fd, Fv, Fc, etc., of intact antibodies that retain the ability to specifically bind to a given antigen (e.g. PTK7), an isolated complementarity determining region (CDR), bispecific antibodies, heteroconjugate antibodies, mutants thereof, fusion proteins having an antibody, or antigen-binding fragment thereof, (e.g., a domain antibody), single chain (ScFv) and single domain antibodies (e.g., shark and camelid antibodies), maxibodies, minibodies, intrabodies, diabodies, triabodies, tetrabodies, v-NAR and bis-scFv (see, e.g., Holliger and Hudson, 2005, Nature Biotechnology 23(9): 1126-1136), humanized antibodies, chimeric antibodies and any other modified configuration of the immunoglobulin molecule that includes an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some aspects of the invention, the antibody, or antigen-binding fragment thereof, of the disclosed PTK7 antibody-drug conjugates is a chimeric, humanized, or a recombinant human antibody, or PTK7-binding fragment thereof.

An antibody, an antibody-drug conjugate, or a polypeptide that "specifically binds" or "preferentially binds" (used interchangeably herein) to a target or antigen (e.g., PTK7 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target or antigen if it binds with greater affinity, avidity, more readily, and/or with greater duration than it binds to other substances. For example, an antibody that specifically or preferentially binds to a PTK7 epitope is an antibody that binds this epitope with greater affinity, avidity, more readily, and/or with greater duration than it binds to other PTK7 epitopes or non-PTK7 epitopes.

The term "binding affinity" or "$K_D$" as used herein, is intended to refer to the equilibrium dissociation constant of a particular antigen-antibody interaction. The $K_D$ is the ratio of the rate of dissociation, also called the "off-rate" or "$K_d$", to the rate of association, or "on-rate" or "$K_a$". Thus, $K_D$ equals $K_d/K_a$ and is expressed as a molar concentration (M). It follows that the smaller the $K_D$, the stronger the binding affinity. Therefore, a $K_D$ of 1 µM indicates weak binding affinity compared to a $K_D$ of 1 nM. $K_D$ values for antibodies can be determined using methods well established in the art. One method for determining the $K_D$ of an antibody is by using surface plasmon resonance, typically using a biosensor system such as a BIACORE® system.

Specific binding of the disclosed PTK7 antibody-drug conjugates refers to a preferential binding of an antibody-drug conjugate to human PTK7 antigen in a heterogeneous sample having multiple different antigens. Typically, specific binding occurs if the binding affinity of the antibody-drug conjugate, or antibody portion (Ab) thereof, is at least about $10^{-7}$ M or higher, such as at least about $10^{-8}$ M or higher, including at least about $10^{-9}$ M or higher, at least about $10^{-10}$ M or higher, at least about $10^{-11}$ M or higher, or at least about $10^{-12}$ M or higher. For example, specific binding of an antibody-drug conjugate, or antibody portion (Ab) thereof, of the invention to a human PTK7 antigen includes binding in the range of at least about $1\times10^{-7}$ M to about $1\times10^{-12}$ M, such as within the range of about $1\times10^{-8}$ M to about $1\times10^{-12}$ M, or within the range of about $1\times10^{-8}$ M to about $1\times10^{-11}$ M, or within the range of about $1\times10^{-8}$ M to about $1\times10^{-10}$ M, or within the range of about $1\times10^{-9}$ M to about $1\times10^{-10}$ M. Specific binding also refers to selective targeting of a PTK7 antibody-drug conjugate, or antibody portion (Ab) thereof, to PTK7-expressing cells following administration of the antibody to a subject.

It is also understood that an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be 'linear' or 'conformational.' In a linear epitope, all of the points of interaction between the protein and the interacting molecule (such as an antibody) occur linearly along the primary amino acid sequence of the protein. In a conformational epitope, the points of interaction include amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, i.e. the antibodies compete for binding to the antigen. A high throughput process for 'binning' antibodies based upon their cross-competition is described in PCT International Publication No. WO 03/48731. As used herein, the term 'binning' refers to a method to group antibodies based on their antigen binding characteristics and competition with each other.

An "isolated antibody", as used herein, refers to an antibody that is substantially free of other antibodies having different antigenic specificities (e.g., an isolated antibody that specifically binds PTK7 is substantially free of antibodies that specifically bind antigens other than PTK7). Moreover, an isolated antibody may be substantially free of other cellular material and/or chemicals. An isolated antibody that specifically binds PTK7 may, however, have cross-reactivity to other antigens, such as PTK7 molecules from other species (i.e. an ortholog) or with more than one isoform of PTK7.

In some aspects of the invention, a PTK7 antibody-drug conjugate includes an antibody that competes for binding to human PTK7 with, and/or binds the same epitope as, an antibody, or antigen-binding fragment thereof, having (a) a heavy chain variable region set forth as SEQ ID NO: 1 and a light chain variable region set forth as SEQ ID NO: 15; or (c) a heavy chain variable region set forth as SEQ ID NO: 25 and a light chain variable region set forth as SEQ ID NO: 39; or (c) a heavy chain variable region set forth as SEQ ID NO: 49 and a light chain variable region set forth as SEQ ID NO: 63.

The term "compete", as used herein with regard to an antibody, means that a first antibody, or an antigen-binding fragment thereof, binds to an epitope in a manner sufficiently similar to the binding of a second antibody, or an antigen-binding fragment thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Native or naturally occurring antibodies, and native immunoglobulins, are typically heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains. The term "variable" refers to the fact that certain portions of the variable domains differ extensively in sequence among antibodies.

Antibodies and the above-noted antibody domains may be described as "polypeptides", "oligopeptides", "peptides" and "proteins", i.e., chains of amino acids of any length, preferably, relatively short (e.g., 10-100 amino acids). The chain may be linear or branched, it may comprise modified amino acids, and/or may be interrupted by non-amino acids. It is further understood that the polypeptides can occur as single chains or associated chains. Amino acids may be referred to herein by either their commonly known three letter symbols or by the one-letter symbols recommended by the IUPAC-IUB Biochemical. The terms "polypeptides", "oligopeptides", "peptides" and "proteins" also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, 1982, Nucl. Acids Res. 10:6487-6500; and Kunkel, 1985, Proc. Natl. Acad. Sci USA 82:488).

A "constant region" of an antibody refers to the constant region of the antibody light chain or the constant region of the antibody heavy chain, either alone or in combination. The constant regions of chimeric and humanized PTK7 antibodies may be derived from constant regions of any one of IgA, IgD, IgE, IgG, IgM, any isotypes thereof (e.g., IgG1, IgG2, IgG3, or IgG4 isotypes of IgG), as well as subclasses and mutated versions thereof. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy chain constant regions that correspond to the different classes of immunoglobulins are called alpha, delta, epsilon, gamma, and mu, respectively. The subunit structures and three-dimensional configurations of different classes of immunoglobulins are well known.

The constant domains are not involved directly in binding an antibody to an antigen, but exhibit various effector functions, such as Fc receptor (FcR) binding, participation of the antibody in antibody-dependent cellular toxicity, opsonization, initiation of complement dependent cytotoxicity, and mast cell degranulation. As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally having two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587-593 (1976); and Kim et al., European J. Immunol., 24:2429-2434 (1994)).

It has been previously reported that certain residues presumably present on the surface of the CH2 or CH3 domain of the heavy chain of antibodies, or on the constant domain of the light chain, or otherwise accessible, are suitable for the substitution of the naturally-occurring wild type amino acid with, for example, cysteine, and are therefore useful to engineer a site capable of conjugation to various agents.

By "engineered Fc polypeptide", "engineered Fc region" and "engineered Fc" as the terms are interchangeably used herein, is meant as an Fc polypeptide, or portion thereof, comprising at least one mutation, e.g., an amino acid substitution, introducing a site for conjugation. The mutation introduces a cysteine in place of the naturally-occurring amino acid residue at that position, where the mutation creates a reactive site (e.g., a reactive sulfhydryl group) for conjugation of a moiety to the Fc.

The term "acyl donor glutamine-containing tag" or "glutamine tag" as used herein refers to a polypeptide or a protein containing one or more Gln residue(s) that acts as a transglutaminase amine acceptor.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-Lazikani et al., J. Molec. Biol. 273:927-948 (1997). As used herein, a CDR may refer to CDRs defined by either approach or by a combination of both approaches.

A CDR of a variable domain are amino acid residues within the variable region that are identified in accordance with the definitions of the Kabat, Chothia, the accumulation of both Kabat and Chothia, VBASE2, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, (1989). The CDR positions may also be derived from an analysis of the VBASE2 database. (See, e.g. Retter et al., 2005, Nucleic Acids Res. 33(Database Issue):D671-D674).

Other approaches to CDR identification include the "AbM definition," which is a compromise between Kabat and Chothia and is derived using Oxford Molecular's AbM antibody modeling software (now ACCELRYS®), or the "contact definition" of CDRs based on observed antigen contacts, set forth in MacCallum et al., J. Mol. Biol., 262:732-745, (1996). In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For PTK7 antibody-drug conjugates described herein, CDRs may be defined in accordance with any of Kabat, Chothia, extended, VBASE2, AbM, contact, and/or conformational definitions.

In other aspects of the invention, the PTK7 antibody, or antigen-binding fragment thereof, includes one or more CDR(s) of the antibody (such as one, two, three, four, five, or all six CDRs).

For the instant invention, the CDRs of hu23, hu24, and hu58 set forth in Table 1 below (SEQ ID NOS: 1-72) were derived using Kabat and Chothia. The CDRs as set forth in FIG. 6 of PCT International Publication No. WO 2012/112943 which is incorporated by references herein, were derived from an analysis of the VBASE2 database. Accordingly, antibodies having CDRs defined by all such nomenclature are expressly included within the scope of the instant invention. More broadly, the term "variable region CDR amino acid residue" includes amino acids in a CDR as identified using any sequence or structure based method as set forth above.

In some aspects of the invention, a PTK7 antibody-drug conjugate includes an antibody, or antigen-binding fragment thereof, having CDRs of a hu23 antibody. For example, a PTK7 antibody-drug conjugate may include an antibody, or antigen-binding fragment thereof, including at least one heavy chain variable region and at least one light chain variable region, wherein the at least one heavy chain variable region has three CDRs set forth as SEQ ID NOs: 3, 7, and 11. In some aspects of the invention, a PTK7 antibody-drug conjugate includes an antibody, or antigen-binding fragment thereof, having at least one heavy chain variable region and at least one light chain variable region, wherein the at least one light chain variable region has three CDRs set forth as SEQ ID NOs: 17, 19, and 21. A PTK7 antibody-drug conjugate of the invention can also include an antibody, or antigen-binding fragment thereof, including (a) a heavy chain variable region having three CDRs set forth as SEQ ID NOs: 3, 7, and 11; and (b) a light chain variable region having three CDRs set forth as SEQ ID NOs: 17, 19, and 21.

In still other aspects of the invention, a PTK7 antibody-drug conjugate includes an antibody, or antigen-binding fragment thereof, having one or more hu23 CDRs defined according to Chothia or derived from an analysis of the VBASE2 database. For example, a PTK7 antibody-drug conjugate can include an antibody, or antigen-binding fragment thereof, having at least one heavy chain variable region and at least one light chain variable region, wherein the at least one heavy chain variable region includes three hu23 CDRs defined by Chothia (see Table 1) or three hu23 CDRs derived from an analysis of the VBASE2 database (see PCT International Publication No. WO 2012/112943). As another example, a PTK7 antibody-drug conjugate can include an antibody, or antigen-binding fragment thereof, having at least one heavy chain variable region and at least one light chain variable region, wherein the at least one light chain variable region includes three hu23 CDRs defined by Chothia (see Table 1) or three hu23 CDRs derived from an analysis of the VBASE2 database (see PCT International Publication No. WO 2012/112943). In some aspects of the invention, a PTK7 antibody-drug conjugate of the invention can include an antibody, or antigen-binding fragment thereof, having (a) a heavy chain variable region having three hu23 CDRs defined according to Chothia (see Table 1); and (b) a light chain variable region having three hu23 CDRs defined according to Chothia (see Table 1). In some aspects of the invention, a PTK7 antibody-drug conjugate of the invention can include an antibody, or antigen-binding fragment thereof, having (a) a heavy chain variable region including three hu23 CDRs derived from an analysis of the VBASE2 database (see PCT International Publication No. WO 2012/112943); and (b) a light chain variable region including three hu23 CDRs derived from an analysis of the VBASE2 database (see PCT International Publication No. WO 2012/112943).

In other aspects of the invention, a PTK7 antibody-drug conjugate includes an antibody, or antigen-binding fragment thereof, having CDRs of a hu24 antibody. For example, a PTK7 antibody-drug conjugate may include an antibody, or antigen-binding fragment thereof, having at least one heavy chain variable region and at least one light chain variable region, wherein the at least one heavy chain variable region includes three CDRs set forth as SEQ ID NOs: 27, 31, and 35. In some aspects of the invention, a PTK7 antibody-drug conjugate includes an antibody, or antigen-binding fragment thereof, having at least one heavy chain variable region and at least one light chain variable region, wherein the at least one light chain variable region includes three CDRs set forth as SEQ ID NOs: 41, 43, and 45. A PTK7 antibody-drug conjugate of the invention can also include (a) a heavy chain variable region having three CDRs set forth as SEQ ID NOs: 27, 31, and 35; and (b) a light chain variable region having three CDRs set forth as SEQ ID NOs: 41, 43, and 45.

In other aspects of the invention, a PTK7 antibody-drug conjugate includes an antibody, or antigen-binding fragment thereof, having one or more hu24 CDRs defined according to Chothia or derived from an analysis of the VBASE2 database. For example, a PTK7 antibody-drug conjugate can include an antibody, or antigen-binding fragment thereof, having at least one heavy chain variable region and at least one light chain variable region, wherein the at least one heavy chain variable region includes three hu24 CDRs defined by Chothia (see Table 1) or three hu24 CDRs derived from an analysis of the VBASE2 database (see PCT International Publication No. WO 2012/112943). As another example, a PTK7 antibody-drug conjugate can include an antibody, or antigen-binding fragment thereof, having at least one heavy chain variable region and at least one light chain variable region, wherein the at least one light chain variable region includes three hu24 CDRs defined by Chothia (see Table 1) or three hu24 CDRs derived from an analysis of the VBASE2 database (see PCT International Publication No. WO 2012/112943). In some aspects of the invention, a PTK7 antibody-drug conjugate of the invention can include an antibody, or antigen-binding fragment thereof, having (a) a heavy chain variable region having three hu24 CDRs defined according to Chothia (see Table 1); and (b) a light chain variable region having three hu24 CDRs defined according to Chothia (see Table 1). In some aspects of the invention, a PTK7 antibody-drug conjugate of the invention can include an antibody, or antigen-binding fragment thereof, having (a) a heavy chain variable region including three hu24 CDRs derived from an analysis of the VBASE2 database (see PCT International Publication No. WO 2012/112943); and (b) a light chain variable region including three hu24 CDRs derived from an analysis of the VBASE2 database (see PCT International Publication No. WO 2012/112943).

In other aspects of the invention, a PTK7 antibody-drug conjugate includes an antibody, or antigen-binding fragment thereof, having CDRs of a hu58 antibody. For example, a PTK7 antibody-drug conjugate may include an antibody, or antigen-binding fragment thereof, having at least one heavy chain variable region and at least one light chain variable region, wherein the at least one heavy chain variable region includes three CDRs set forth as SEQ ID NOs: 51, 55, and 59. In some aspects of the invention, a PTK7 antibody-drug conjugate includes an antibody, or antigen-binding fragment thereof, having at least one heavy chain variable region and at least one light chain variable region, wherein the at least one light chain variable region includes three CDRs set forth as SEQ ID NOs: 65, 67, and 69. A PTK7 antibody-drug conjugate of the invention can also include (a) a heavy chain variable region having three CDRs set forth as SEQ ID NOs: 51, 55, and 59; and (b) a light chain variable region having three CDRs set forth as SEQ ID NOs: 65, 67, and 69.

In other aspects of the invention, a PTK7 antibody-drug conjugate includes an antibody, or antigen-binding fragment thereof, having one or more hu58 CDRs defined according to Chothia or derived from an analysis of the VBASE2 database. For example, a PTK7 antibody-drug conjugate can include an antibody, or antigen-binding fragment thereof, having at least one heavy chain variable region and at least one light chain variable region, wherein the at least one heavy chain variable region includes three hu58 CDRs defined by Chothia or three hu58 CDRs derived from an analysis of the VBASE2 database. As another example, a PTK7 antibody-drug conjugate can include an antibody, or antigen-binding fragment thereof, having at least one heavy chain variable region and at least one light chain variable region, wherein the at least one light chain variable region includes three hu58 CDRs defined by Chothia or three hu58 CDRs derived from an analysis of the VBASE2 database. In some aspects of the invention, a PTK7 antibody-drug conjugate of the invention can include an antibody, or antigen-binding fragment thereof, having (a) a heavy chain variable region having three hu58 CDRs defined according to Chothia; and (b) a light chain variable region having three hu58 CDRs defined according to Chothia. In some aspects of the invention, a PTK7 antibody-drug conjugate of the invention can include an antibody, or antigen-binding fragment thereof, having (a) a heavy chain variable region including three hu58 CDRs derived from an analysis of the VBASE2 database; and (b) a light chain variable region including three hu24 CDRs derived from an analysis of the VBASE2 database.

In some aspects of the invention, antibodies used to prepare PTK7 antibody-drug conjugates of the invention will be monoclonal antibodies. The term "monoclonal antibody" or "mAb" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495-497 (1975), or may be made by recombinant DNA methods such as described in U.S. Pat. No. 4,816,567. The monoclonal antibodies may also be isolated from phage libraries generated using the techniques described in McCafferty et al., Nature 348:552-554 (1990) for example.

In some aspects of the invention, antibodies used to prepare antibody-drug conjugates of the invention will be monovalent, i.e., having one antigen binding site per molecule (e.g., IgG or Fab). In some instances, a monovalent antibody can have more than one antigen binding sites, but the binding sites are from different antigens. In some aspects of the invention, the antibody, or antigen-binding fragment thereof, of an antibody-drug conjugate of the invention may include a "bivalent antibody", i.e., having two antigen binding sites per molecule (e.g., IgG). In some instances, the two binding sites have the same antigen specificities. Alternatively, bivalent antibodies may be bispecific. A "bispecific," "dual-specific" or "bifunctional" antibody is a hybrid antibody having two different antigen binding sites. The two antigen binding sites of a bispecific antibody bind to two different epitopes, which may reside on the same or different protein targets.

The term "chimeric antibody" is intended to refer to antibodies in which part or all of the variable region sequences are derived from one species and the constant region sequences are derived from another species, such as an antibody in which the variable region sequences are derived from a mouse antibody and the constant region sequences are derived from a human antibody.

As used herein, "humanized" or "CDR grafted" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from a non-human immunoglobulin. Preferably, humanized antibodies are human immunoglobulins (recipient antibody) in which residues from one or more complementary determining regions (CDRs) of the recipient are replaced by residues from one or more CDRs of a non-human species (donor antibody) such as mouse, rat, or rabbit having the desired specificity, affinity, and capacity.

In some instances, Fv framework region (FR) residues of the human immunoglobulin are replaced by corresponding non-human residues. Furthermore, the humanized antibody may include residues that are found neither in the recipient antibody nor in the imported CDR or framework sequences, but are included to further refine and optimize antibody performance. In general, the humanized antibody will include substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region or domain (Fc), typically that of a human immunoglobulin. In some aspects of the invention the antibodies have Fc regions modified as described in PCT International Publication No. WO 99/58572. Other forms of humanized antibodies have one or more CDRs (CDR L1, CDR L2, CDR L3, CDR H1, CDR H2, or CDR H3) which may be altered with respect to the original antibody, which are also termed one or more CDRs "derived from" one or more CDRs from the original antibody.

Humanization can be essentially performed following the method of Winter and co-workers (Jones et al. Nature 321:522-525 (1986); Riechmann et al. Nature 332:323-327 (1988); Verhoeyen et al. Science 239:1534-1536 (1988)), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; which are incorporated herein by reference in its entirety. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may include residues that are not found in the recipient antibody or in the donor antibody. These modifications are made to further refine antibody performance (e.g., to obtain desired affinity). In general, the humanized antibody will include substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will include at least a portion of an immunoglobulin constant region (Fc), typically that of a human immunoglobulin. For further details see Jones et al. Nature 321:522-525 (1986); Riechmann et al. Nature 332:323-327 (1988); and Presta Curr. Op. Struct. Biol. 2:593-596 (1992); which are incorporated herein by reference in their entirety. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and PCT International Publication No. WO 01/27160, where humanized antibodies and techniques for producing humanized antibodies having improved affinity for a predetermined antigen are disclosed.

"Recombinant human antibody" or "fully human antibody" refers to those antibodies having an amino acid sequence corresponding to that of an antibody produced by a human and/or which has been made using any of the techniques for making human antibodies known to those skilled in the art or disclosed herein. This definition of a human antibody includes antibodies having at least one human heavy chain polypeptide or at least one human light chain polypeptide. One such example is an antibody having murine light chain and human heavy chain polypeptides. Human antibodies can be produced using various techniques known in the art. For example, a human antibody is selected from a phage library, where that phage library expresses human antibodies (Vaughan et al., Nature Biotechnology, 14:309-314, (1996); Sheets et al., Proc. Natl. Acad. Sci. (USA) 95:6157-6162, (1998); Hoogenboom and Winter, J. Mol. Biol., 227(2):381-388 (1992); Marks et al., J. Mol. Biol., 222(3):581-597 (1991)). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, (1985); Boerner et al., J. Immunol., 147 (1):86-95, (1991); and U.S. Pat. No. 5,750,373.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50 (1999) and Fellouse, F. A., et al, J. Mol. Biol., 373(4):924-40 (2007)). Additional guidance may be found in Sambrook J. & Russell D. Molecular Cloning: A Laboratory Manual, 3rd ed., Cold Spring Harbor Laboratory Press, Cold Spring Harbor, N.Y. (2000); Ausubel et al., Short

*Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Representative methods are also described in Example 1 herein below.

In general, for the production of hybridoma cell lines, the route and schedule of immunization of the host animal are generally in keeping with established and conventional techniques for antibody stimulation and production. It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the PTK7 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay). Hybridomas that may be used as source of antibodies encompass all derivatives, progeny cells of the parent hybridomas that produce monoclonal antibodies specific for PTK7, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human PTK7, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N\!=\!C\!=\!NR$, where R and $R^1$ are different alkyl groups, can yield a population of antibodies (e.g., monoclonal antibodies).

If desired, the PTK7 antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329:112-124 (2008); U.S. Pat. No. 7,314,622.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

The term "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

Alternatively, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to PTK7 and greater efficacy in inhibiting PTK7.

There are four general steps that may be used to humanize a monoclonal antibody: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

Humanized antibodies may be prepared using any one of a variety of methods including veneering, grafting of complementarity determining regions (CDRs), grafting of abbreviated CDRs, grafting of specificity determining regions (SDRs), and Frankenstein assembly, as described below. Humanized antibodies also include superhumanized antibodies, in which one or more changes have been introduced in the CDRs. For example, human residues may be substituted for non-human residues in the CDRs. These general approaches may be combined with standard mutagenesis and synthesis techniques to produce an anti-PTK7 antibody of any desired sequence.

Veneering is based on the concept of reducing potentially immunogenic amino acid sequences in a rodent or other non-human antibody by resurfacing the solvent accessible exterior of the antibody with human amino acid sequences. Thus, veneered antibodies appear less foreign to human cells than the unmodified non-human antibody. See Padlan (1991) *Mol. Immunol.* 28:489-98. A non-human antibody is veneered by identifying exposed exterior framework region residues in the non-human antibody, which are different from those at the same positions in framework regions of a human antibody, and replacement of the identified residues with amino acids that typically occupy these same positions in human antibodies.

Grafting of CDRs is performed by replacing one or more CDRs of an acceptor antibody (e.g., a human antibody or other antibody having desired framework residues) with CDRs of a donor antibody (e.g., a non-human antibody). Acceptor antibodies may be selected based on similarity of framework residues between a candidate acceptor antibody and a donor antibody. For example, according to the Frankenstein approach, human framework regions are identified as having substantial sequence homology to each framework region of the relevant non-human antibody, and CDRs of the non-human antibody are grafted onto the composite of the different human framework regions. A related method also useful for preparation of antibodies of the invention is described in U.S. Pat. No. 7,321,026.

Grafting of abbreviated CDRs is a related approach. Abbreviated CDRs include the specificity-determining residues and adjacent amino acids, including those at positions 27d-34, 50-55 and 89-96 in the light chain, and at positions 31-35b, 50-58, and 95-101 in the heavy chain (numbering convention of (Kabat et al. (1987)). See (Padlan et al. (1995) *FASEB J.* 9: 133-9). Grafting of specificity-determining residues (SDRs) is premised on the understanding that the binding specificity and affinity of an antibody combining site is determined by the most highly variable residues within each of the complementarity determining regions (CDRs). Analysis of the three-dimensional structures of antibody-antigen complexes, combined with analysis of the available amino acid sequence data may be used to model sequence variability based on structural dissimilarity of amino acid residues that occur at each position within the CDR. SDRs are identified as minimally immunogenic polypeptide sequences consisting of contact residues. See Padlan et al. (1995) *FASEB J.* 9: 133-139.

In general, human acceptor frameworks are selected on the basis that they are substantially similar to the framework regions of the donor antibodies, or which are most similar to the consensus sequence of the variable region subfamily. Following grafting, additional changes may be made in the donor and/or acceptor sequences to optimize antibody binding, functionality, codon usage, expression levels, etc., including introduction of non-human residues into the framework regions. See e.g., PCT International Publication No. WO 91/09967.

For grafting of CDRs onto a heavy chain variable framework region, useful framework sequences may be derived from a DP-21 (VH7), DP-54 (VH3-07), DP-47 (VH3-23), DP-53 (VH-74), DP-49 (VH3-30), DP-48 (VH3-13), DP-75, DP-8(VH1-2), DP-25, VI-2b and VI-3 (VH1-03), DP-15 and V1-8 (VH1-08), DP-14 and V1-18 (VH1-18), DP-5 and V1-24P (VH1-24), DP-4 (VH1-45), DP-7 (VH1-46), DP-10, DA-6 and YAC-7 (VH1-69), DP-88 (VH1-e), DP-3 and DA-8 (VH1-f). For grafting of CDRs onto a light chain variable framework region, useful framework sequences may be derived from a DPK24 subgroup IV germ line clone, a Will subgroup (DPK23, DPK22, DPK20, DPK21), or a VκI subgroup germ line clone (DPK9, DPK1, O2, DPK7).

Antigen-binding fragments or antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody or antibody fragment could be produced by an automated polypeptide synthesizer employing the solid phase method. See also, U.S. Pat. Nos. 5,807,715; 4,816,567; and 6,331,415.

In other aspects of the invention, the PTK7 antibody-drug conjugates include an antibody, or antigen-binding fragment thereof, having a hu23, hu24, or hu58 heavy chain and/or light chain variable region, or a variable region substantially similar to a hu23, hu24, or hu58 heavy chain or light chain variable region.

As applied to polypeptides, the term "substantial identity" or "substantial similarity" means that two amino acid sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In some substantially similar amino acid sequences, residue positions that are not identical differ by conservative amino acid substitutions.

Substantially similar polypeptides also include conservatively substituted variants in which one or more residues have been conservatively substituted with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

A further indication that two proteins are substantially identical is that they share an overall three-dimensional structure, or are biologically functional equivalents.

In some aspects of the invention, an antibody-drug conjugate, which binds to PTK7, includes an antibody, or antigen-binding fragment thereof, having a heavy chain variable region set forth as any one of SEQ ID NOs: 1, 25, or 49 and/or a light chain variable region set forth as any one of SEQ ID NOs: 15, 39, or 63. For example, a PTK7 antibody-drug conjugate of the invention can include an antibody, or antigen-binding fragment thereof, having a heavy chain variable region having an amino acid sequence that is at least 90% identical to SEQ ID NO: 1 and a light chain variable region having an amino acid sequence that is at least 90% identical to SEQ ID NO: 15; or an antibody, or antigen-binding fragment thereof, having a heavy chain variable region set forth as SEQ ID NO: 1 and a light chain variable region having an amino acid sequence set forth as SEQ ID NO: 15. As another example, a PTK7 antibody-drug conjugate of the invention can include an antibody, or antigen-binding fragment thereof, having a heavy chain variable region having an amino acid sequence that is at least 90% identical to SEQ ID NO: 25 and a light chain variable region having an amino acid sequence that is at least 90% identical to SEQ ID NO: 39; or an antibody, or antigen-binding fragment thereof, having a heavy chain variable region set forth as SEQ ID NO: 25 and a light chain variable region having an amino acid sequence set forth as SEQ ID NO: 39. As another example, a PTK7 antibody-drug conjugate of the invention can include an antibody, or antigen-binding fragment thereof, having a heavy chain variable region having an amino acid sequence that is at least 90% identical to SEQ ID NO: 49 and a light chain variable region having an amino acid sequence that is at least 90% identical to SEQ ID NO: 63; or an antibody, or antigen-binding fragment thereof, having a heavy chain variable region set forth as SEQ ID NO: 49 and a light chain variable region having an amino acid sequence set forth as SEQ ID NO: 63.

The antibodies may also be modified, e.g. in the variable domains of the heavy and/or light chains, e.g., to alter a binding property of the antibody. For example, a mutation may be made in one or more of the CDR regions to increase or decrease the $K_D$ of the antibody for PTK7, to increase or decrease $K_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of a PTK7 antibody. See, e.g. PCT international Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., J. Mol. Biol. 227:776-798, 1992; and Cox et al., Eur. J. Immunol. 24:827-836, 1994.

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of a PTK7 antibody of the invention can be cleaved. In various aspects of the invention, the heavy and light chains of the PTK7 antibodies may optionally include a signal sequence.

To express the PTK7 antibodies of the present invention, DNA fragments encoding VH and VL regions can first be obtained using any of the methods described above. As known in the art, "polynucleotide," "nucleic acid/nucleotide," and "oligonucleotide" are used interchangeably herein, and include polymeric forms of nucleotides of any length, either deoxyribonucleotides or ribonucleotides, analogs thereof, or any substrate that can be incorporated into a chain by DNA or RNA polymerase. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof. A polynucleotide may include modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, features wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

Representative DNAs encoding anti-PTK7 antibody heavy chain and light chain variable regions are set forth as SEQ ID NO: 2 (hu23 VH DNA), SEQ ID NO: 16 (hu23 VL DNA), SEQ ID NO: 26 (hu24 VH DNA), SEQ ID NO: 40 (hu24 VL DNA), SEQ ID NO: 50 (hu58 VH DNA) and SEQ ID NO: 64 (hu58 VL DNA). Representative DNAs encoding anti-PTK7 antibody heavy chains and light chains are set forth as SEQ ID NO: 14 (hu23 HC DNA), SEQ ID NO: 24 (hu23 LC DNA), SEQ ID NO: 38 (hu24 HC DNA), SEQ ID NO: 48 (hu24 LC DNA), SEQ ID NO: 62 (hu58 HC DNA), and SEQ ID NO: 72 (hu58 LC DNA)

Various modifications, e.g. mutations, substitutions, deletions, and/or additions can also be introduced into the hu23, hu24, and hu58 DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

Accordingly, based upon the disclosure of the instant application, one skilled in the art would readily recognize the sequences of DNAs substantially similar hu23, hu24, and hu58 DNAs. The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132:185-219 (2000); Pearson, Methods Enzymol. 266:227-258 (1996); Pearson, J. Mol. Biol. 276:71-84 (1998); which are incorporated herein by reference in its entirety). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, which is incorporated herein by reference in its entirety.

A further indication that two nucleic acid sequences are substantially identical is that proteins encoded by the nucleic acids are substantially identical, share an overall three-dimensional structure, or are biologically functional equivalents. These terms are defined further herein below. Nucleic acid molecules that do not hybridize to each other under stringent conditions are still substantially identical if the corresponding proteins are substantially identical. This may occur, for example, when two nucleotide sequences comprise conservatively substituted variants as permitted by the genetic code.

Conservatively substituted variants are nucleic acid sequences having degenerate codon substitutions wherein the third position of one or more selected (or all) codons are substituted with mixed-base and/or deoxyinosine residues. See Batzer et al. (1991) Nucleic Acids Res. 19:5081; Ohtsuka et al. (1985) J. Biol. Chem. 260:2605-2608; and Rossolini et al. (1994) Mol. Cell Probes 8:91-98.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. As another example, the cysteine may be canonical.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. The single chain antibody may be monovalent, if only a single VH and VL are used, bivalent, if two VH and VL are used, or polyvalent, if more than two VH and VL are used. Bispecific or polyvalent antibodies may be generated that bind specifically to PTK7 and to another molecule.

In another aspect of the invention, a fusion antibody or immunoadhesin may be made that includes all or a portion of a PTK7 antibody of the invention linked to another polypeptide. In another aspect, only the variable domains of the PTK7 antibody are linked to the polypeptide. In another aspect, the VH domain of a PTK7 antibody is linked to a first polypeptide, while the VL domain of a PTK7 antibody is linked to a second polypeptide that associates with the first polypeptide in a manner such that the VH and VL domains can interact with one another to form an antigen binding site. In another aspect, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

Other modified antibodies may be prepared using PTK7 antibody encoding nucleic acid molecules. For instance, "Kappa bodies" (Ill et al., Protein Eng. 10:949-57, 1997), "Minibodies" (Martin et al., EMBO J., 13:5303-9, 1994), "Diabodies" (Holliger et al., Proc. Natl. Acad. Sci. USA 90:6444-6448, 1993), or "Janusins" (Traunecker et al., EMBO J. 10:3655-3659, 1991 and Traunecker et al., Int. J. Cancer (Suppl.) 7:51-52, 1992) may be prepared using standard molecular biological techniques following the teachings of the specification.

Bispecific antibodies or antigen binding fragments can be produced by a variety of methods including fusion of hybridomas or linking of Fab' fragments. See, e.g., Songsivilai & Lachmann, Clin. Exp. Immunol. 79:315-321, 1990, Kostelny et al., J. Immunol. 148:1547-1553, 1992. In addition, bispecific antibodies may be formed as "diabodies" or "Janusins." In some aspects of the invention, a bispecific antibody binds to two different epitopes of PTK7. In other aspects, modified antibodies described above are prepared using one or more of the variable domains or CDR regions from the PTK7 antibodies provided herein.

For use in preparation of antibody-drug conjugates, PTK7 antibodies described herein may be substantially pure, i.e., at least 50% pure (i.e., free from contaminants), more preferably, at least 90% pure, more preferably, at least 95% pure, yet more preferably, at least 98% pure, and most preferably, at least 99% pure.

Table 1 provides the amino acid (protein) sequences and associated nucleic acid (DNA) sequences of humanized anti-PTK7 antibodies of the present invention. The CDRs of hu23 VH, hu23 VL, hu24 VH, hu24 VL, hu58 VH, and hu58 VL as defined by Kabat and by Chothia, are set forth as separate sequences.

TABLE 1

Sequences of humanized anti-PTK7 antibodies.

| SEQ ID NO. | Description | Sequences |
|---|---|---|
| 1 | hu23 VH Protein | QITLKESGPTLVKPTQTLTLTC TFSGFSLSTSNMGVGWIRQPPG KALEWLAHIWWDDDKYYSPSLK SRLTITKDTSKNQVVLTMTNMD PVDTATYYCVRSNYGYAWFAYW GQGTLVTSS |
| 2 | hu23 VH DNA | CAGATCACCTTGAAGGAGTCTG GTCCTACGCTGGTGAAACCCAC ACAGACCCTCACGCTGACCTGC ACCTTCTCTGGGTTCTCACTCA GCACTAGTAACATGGGTGTGGG CTGGATCCGTCAGCCCCCAGGA AAGGCCCTGGAGTGGCTTGCAC ACATTTGGTGGGATGATGATAA GTACTACAGCCCATCTCTGAAG AGCAGGCTCACCATCACCAAGG ACACCTCCAAAAACCAGGTGGT CCTTACAATGACCAACATGGAC CCTGTGGACACAGCCACATATT ACTGTGTTCGAAGTAACTATGG TTACGCCTGGTTTGCTTACTGG GGCCAAGGGACTCTGGTCACTG TCTCTTCA |
| 3 | hu23 VH CDR1 Protein- Kabat | TSNMGVG |
| 4 | hu23 VH CDR1 Protein- Chothia | GFSLSTSNM |
| 5 | hu23 VH CDR1 DNA- Kabat | ACTAGTAACATGGGTGTGGGC |
| 6 | hu23 VH CDR1 DNA- Chothia | GGGTTCTCACTCAGCACTAGTA ACATG |
| 7 | hu23 VH CDR2 Protein- Kabat | HIWWDDDKYYSPSLKS |
| 8 | hu23 VH CDR2 Protein- Chothia | WWDDD |
| 9 | hu23 VH CDR2 DNA- Kabat | CACATTTGGTGGGATGATGATA AGTACTACAGCCCATCTCTGAA GAGC |
| 10 | hu23 VH CDR2 DNA- Chothia | TGGTGGGATGATGAT |
| 11 | hu23 VH CDR3 Protein- Kabat and Chothia | SNYGYAWFAY |
| 12 | hu23 VH CDR3 DNA- Kabat and Chothia | AGTAACTATGGTTACGCCTGGT TTGCTTAC |

TABLE 1-continued

Sequences of humanized anti-PTK7 antibodies.

| SEQ ID NO. | Description | Sequences |
|---|---|---|
| 13 | hu23 HC Protein- HuIgG1 | QITLKESGPTLVKPTQTLTLTC TFSGFSLSTSNMGVGWIRQPPG KALEWLAHIWWDDDKYYSPSLK SRLTITKDTSKNQVVLTMTNMD PVDTATYYCVRSNYGYAWFAYW GQGTLVTVSSASTKGPSVFPLA PSSKSTSGGTAALGCLVKDYFP EPVTVSWNSGALTSGVHTFPAV LQSSGLYSLSSVVTVPSSSLGT QTYICNVNHKPSNTKVDKKVEP KSCDKTHTCPPCPAPELLGGPS VFLFPPKPKDTLMISRTPEVTC VVVDVSHEDPEVKFNWYVDGVE VHNAKTKPREEQYNSTYRVVSV LTVLHQDWLNGKEYKCKVSNKA LPAPIEKTISKAKGQPREPQVY TLPPSRDELTKNQVSLTCLVKG FYPSDIAVEWESNGQPENNYKT TPPVLDSDGSFFLYSKLTVDKS RWQQGNVFSCSVMHEALHNHYT QKSLSLSPG |
| 14 | hu23 HC DNA- HuIgG1 | CAGATCACCTTGAAGGAGTCTG GTCCTACGGGTGGTGAAACCCAC ACAGACCCTCACGCTGACCTGC ACCTTCTCTGGGTTCTCACTCA GCACTAGTAACATGGGTGTGGG CTGGATCCGTCAGCCCCCAGGA AAGGCCCTGGAGTGGCTTGCAC ACATTTGGTGGGATGATGATAA GTACTACAGCCCATCTCTGAAG AGCAGGCTCACCATCACCAAGG ACACCTCCAAAAACCAGGTGGT CCTTACAATGACCAACATGGAC CCTGTGGACACAGCCACATATT ACTGTGTTCGAAGTAACTATGG TTACGCCTGGTTTGCTTACTGG GGCCAAGGGACTCTGGTCACTG TCTCTTCAGCCTCCACCAAGGG CCCATCGGTCTTCCCCCTGGCA CCCTCGAGCAAGAGCACCTCTG GGGGCACAGCGGCCCTGGGCTG CCTGGTCAAGGACTACTTCCCC GAGCCGGTGACGGTGTCGTGGA ACTCAGGCGCCCTGACCAGCGG CGTGCACACCTTCCCGGCTGTC CTACAGTCCTCAGGACTCTACT CCCTCAGCAGCGTGGTGACCGT GCCCTCCAGCAGCTTGGGCACC CAGACCTACATCTGCAACGTGA ATCACAAGCCCAGCAACACCAA GGTGGACAAGAAAGTTGAGCCC AAATCTTGTGACAAAACTCACA CATGCCCACCGTGCCCAGCACC TGAACTCCTGGGGGGACCGTCA GTCTTCCTCTTCCCCCCAAAAC CCAAGGACACCCTCATGATCTC CCGGACCCCTGAGGTCACATGC GTGGTGGTGGACGTGAGCCACG AAGACCCTGAGGTCAAGTTCAA CTGGTACGTGGACGGCGTGGAG GTGCATAATGCCAAGACAAAGC CGCGGGAGGAGCAGTACAACAG CACGTACCGTGTGGTCAGCGTC CTCACCGTCCTGCACCAGGACT GGCTGAATGGCAAGGAGTACAA GTGCAAGGTCTCCAACAAAGCC CTCCCAGCCCCCATCGAGAAAA CCATCTCCAAAGCCAAAGGGCA GCCCCGAGAACCACAGGTGTAC ACCCTGCCCCCATCCCGGGATG AGCTGACCAAGAACCAGGTCAG CCTGACCTGCCTGGTCAAAGGC TTCTATCCCAGCGACATCGCCG TGGAGTGGGAGAGCAATGGGCA GCCGGAGAACAACTACAAGACC ACGCCTCCCGTGCTGGACTCCG ACGGCTCCTTCTTCCTCTACAG CAAGCTCACCGTGGACAAGAGC AGGTGGCAGCAGGGGAACGTCT TCTCATGCTCCGTGATGCATGA GGCTCTGCACAACCACTACACG CAGAAGAGCCTCTCCCTGTCTC CGGGT |
| 15 | hu23 VL Protein | DIQMTQSPSSLSASVGDRVTIT CKASQDIYPYLNWFQQKPGKAP KTLIYRTNRLLDGVPSRFSGSG SGTDFTFTISSLQPEDIATYYC LQYDEFPLTFGAGTKLEIK |
| 16 | hu23 VL DNA | GACATCCAGATGACCCAGTCTC CATCTTCCCTGTCTGCATCTGT AGGAGATAGAGTCACTATCACT TGCAAGGCGAGTCAGGACATTT ATCCCTATTTAAACTGGTTCCA ACAAAAACCAGGGAAAGCTCCT AAGACCCTGATCTATCGTACAA ATAGATTGCTAGATGGGGTCCC ATCAAGGTTCAGTGGCAGTGGA TCTGGAACAGATTTTACTTTCA CCATCAGCAGCCTGCAACCTGA AGATATTGCAACTTATTATTGT CTACAGTATGATGAGTTTCCGC TCACGTTCGGTGCTGGGACCAA GCTGGAAATCAAA |
| 17 | hu23 VL CDR1 Protein- Kabat and Chothia | KASQDIYPYLN |
| 18 | hu23 VL CDR1 DNA- Kabat and Chothia | AAGGCGAGTCAGGACATTTATC CCTATTTAAAC |
| 19 | hu23 VL CDR2 Protein- Kabat and Chothia | RTNRLLD |
| 20 | hu23 VL CDR2 DNA- Kabat and Chothia | CGTACAAATAGATTGCTAGAT |
| 21 | hu23 VL CDR3 Protein- Kabat and Chothia | LQYDEFPLT |
| 22 | hu23 VL CDR3 DNA- Kabat and Chothia | CTACAGTATGATGAGTTTCCGC TCACG |
| 23 | hu23 LC Protein- Kappa | DIQMTQSPSSLSASVGDRVTIT CKASQDIYPYLNWFQQKPGKAP KTLIYRTNRLLDGVPSRFSGSG SGTDFTFTISSLQPEDIATYYC LQYDEFPLTFGAGTKLEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC |
| 24 | hu23 LC DNA- Kappa | GACATCCAGATGACCCAGTCTC CATCTTCCCTGTCTGCATCTGT AGGAGATAGAGTCACTATCACT TGCAAGGCGAGTCAGGACATTT ATCCCTATTTAAACTGGTTCCA ACAAAAACCAGGGAAAGCTCCT AAGACCCTGATCTATCGTACAA ATAGATTGCTAGATGGGGTCCC |

TABLE 1-continued

Sequences of humanized anti-PTK7 antibodies.

| SEQ ID NO. | Description | Sequences |
|---|---|---|
|  |  | ATCAAGGTTCAGTGGCAGTGGA TCTGGAACAGATTTTACTTTCA CCATCAGCAGCCTGCAACCTGA AGATATTGCAACTTATTATTGT CTACAGTATGATGAGTTTCCGC TCACGTTCGGTGCTGGGACCAA GCTGGAAATCAAACGGACTGTG GCTGCACCAAGTGTCTTCATCT TCCCGCCATCTGATGAGCAGTT GAAATCTGGAACTGCCTCTGTT GTGTGCCTGCTGAATAACTTCT ATCCCAGAGAGGCCAAAGTACA GTGGAAGGTGGATAACGCCCTC CAATCGGGTAACTCCCAGGAGA GTGTCACAGAGCAGGACAGCAA GGACAGCACCTACAGCCTCAGC AGCACCCTGACGCTGAGCAAAG CAGACTACGAGAAACACAAAGT CTACGCCTGCGAAGTCACCCAT CAGGGCCTGAGCTCGCCCGTCA CAAAGAGCTTCAACAGGGGAGA GTGT |
| 25 | hu24 VH Protein | QVQLVQSGPEVKKPGASVKVSC KASGYTFTDYAVHWVRQAPGKR LEWIGVISTYNDYTYNNQDFKG RVTMTRDTSASTAYMELSRLRS EDTAVYYCARGNSYFYALDYWG QGTSVTVSS |
| 26 | hu24 VH DNA | CAGGTCCAGCTTGTGCAGTCTG GGCCTGAGGTGAAGAAGCCTGG GGCCTCAGTGAAGGTTTCCTGC AAGGCTTCTGGATACACCTTCA CTGACTATGCTGTGCATTGGGT GCGCCAGGCCCCCGGAAAAAGG CTTGAGTGGATTGGAGTGATCA GCACTTACAATGATTACACATA CAATAACCAGGACTTCAAGGGC AGAGTCACCATGACCAGGGACA CATCCGCGAGCACAGCCTACAT GGAGCTGAGCAGACTGAGATCT GAAGACACGGCTGTGTATTACT GTGCGAGAGGTAACTCCTACTT CTATGCTTTGGACTACTGGGGT CAAGGAACCTCAGTCACCGTCT CCTCA |
| 27 | hu24 VH CDR1 Protein- Kabat | DYAVH |
| 28 | hu24 VH CDR1 Protein- Chothia | GYTFTDY |
| 29 | hu24 VH CDR1 DNA- Kabat | GACTATGCTGTGCAT |
| 30 | hu24 VH CDR1 DNA- Chothia | GGATACACCTTCACTGACTAT |
| 31 | hu24 VH CDR2 Protein- Kabat | VISTYNDYTYNNQDFKG |
| 32 | hu24 VH CDR2 Protein- Chothia | STYNDY |
| 33 | hu24 VH CDR2 DNA- Kabat | GTGATCAGCACTTACAATGATT ACACATACAATAACCAGGACTT CAAGGGC |
| 34 | hu24 VH CDR2 DNA- Chothia | AGCACTTACAATGATTAC |
| 35 | hu24 VH CDR3 Protein- Kabat and Chothia | GNSYFYALDY |
| 36 | hu24 VH CDR3 DNA- Kabat and Chothia | GGTAACTCCTACTTCTATGCTT TGGACTAC |
| 37 | hu24 HC Protein- HuIgG1 | QVQLVQSGPEVKKPGASVKVSC KASGYTFTDYAVHWVRQAPGKR LEWIGVISTYNDYTYNNQDFKG RVTMTRDTSASTAYMELSRLRS EDTAVYYCARGNSYFYALDYWG QGTSVTVSSASTKGPSVFPLAP SSKSTSGGTAALGCLVKDYFPE PVTVSWNSGALTSGVHTFPAVL QSSGLYSLSSVVTVPSSSLGTQ TYICNVNHKPSNTKVDKKVEPK SCDKTHTCPPCPAPELLGGPSV FLFPPKPKDTLMISRTPEVTCV VVDVSHEDPEVKFNWYVDGVEV HNAKTKPREEQYNSTYRVVSVL TVLHQDWLNGKEYKCKVSNKAL PAPIEKTISKAKGQPREPQVYT LPPSRDELTKNQVSLTCLVKGF YPSDIAVEWESNGQPENNYKTT PPVLDSDGSFFLYSKLTVDKSR WQQGNVFSCSVMHEALHNHYTQ KSLSLSPG |
| 38 | hu24 HC DNA- HuIgG1 | CAGGTCCAGCTTGTGCAGTCTG GGCCTGAGGTGAAGAAGCCTGG GGCCTCAGTGAAGGTTTCCTGC AAGGCTTCTGGATACACCTTCA CTGACTATGCTGTGCATTGGGT GCGCCAGGCCCCCGGAAAAAGG CTTGAGTGGATTGGAGTGATCA GCACTTACAATGATTACACATA CAATAACCAGGACTTCAAGGGC AGAGTCACCATGACCAGGGACA CATCCGCGAGCACAGCCTACAT GGAGCTGAGCAGACTGAGATCT GAAGACACGGCTGTGTATTACT GTGCGAGAGGTAACTCCTACTT CTATGCTTTGGACTACTGGGGT CAAGGAACCTCAGTCACCGTCT CCTCAGCCTCCACCAAGGGCCC ATCGGTCTTCCCCCTGGCACCC TCGAGCAAGAGCACCTCTGGGG GCACAGCGGCCCTGGGCTGCCT GGTCAAGGACTACTTCCCCGAG CCGGTGACGGTGTCGTGGAACT CAGGCGCCCTGACCAGCGGCGT GCACACCTTCCCGGCTGTCCTA CAGTCCTCAGGACTCTACTCCC TCAGCAGCGTGGTGACCGTGCC CTCCAGCAGCTTGGGCACCCAG ACCTACATCTGCAACGTGAATC ACAAGCCCAGCAACACCAAGGT GGACAAGAAAGTTGAGCCCAAA TCTTGTGACAAAACTCACACAT GCCCACCGTGCCCAGCACCTGA ACTCCTGGGGGGACCGTCAGTC TTCCTCTTCCCCCCAAAACCCA AGGACACCCTCATGATCTCCCG GACCCCTGAGGTCACATGCGTG GTGGTGGACGTGAGCCACGAAG ACCCTGAGGTCAAGTTCAACTG GTACGTGGACGGCGTGGAGGTG CATAATGCCAAGACAAAGCCGC GGGAGGAGCAGTACAACAGCAC GTACCGTGTGGTCAGCGTCCTC ACCGTCCTGCACCAGGACTGGC TGAATGGCAAGGAGTACAAGTG CAAGGTCTCCAACAAAGCCCTC |

TABLE 1-continued

Sequences of humanized anti-PTK7 antibodies.

| SEQ ID NO. | Description | Sequences |
|---|---|---|
| | | CCAGCCCCCATCGAGAAACCATCTCCAAAGCCAAAGGGCAGCCCCGAGAACCACAGGTGTACACCCTGCCCCCATCCCGGGATGAGCTGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGA |
| 39 | hu24 VL Protein | EIVLTQSPATLSLSPGERATLSCRASESVDSYGKSFMHWYQQKPGQAPRLLIYRASNLESGIPARFSGSGSGTDFTLTISSLEPEDFAVYYCQQSNEDPWTFGGGTKLEIK |
| 40 | hu24 VL DNA | GAAATTGTGTTGACACAGTCTCCAGCCACCCTGTCTTTGTCTCCAGGGGAAAGAGCCACCCTCTCCTGCAGGGCCAGTGAGAGTGTTGACAGCTATGGCAAAAGTTTTATGCACTGGTACCAACAGAAACCTGGCCAGGCTCCCAGGCTCCTCATCTATAGGGCATCCAACCTGGAATCTGGCATCCCAGCCAGGTTCAGTGGCAGTGGGTCTGGGACAGACTTCACTCTCACCATCAGCAGCCTAGAGCCTGAAGATTTTGCAGTTTATTACTGTCAGCAGAGTAATGAGGATCCGTGGACGTTCGGTGGAGGCACCAAGCTGGAAATCAAA |
| 41 | hu24 VL CDR1 Protein- Kabat and Chothia | RASESVDSYGKSFMH |
| 42 | hu24 VL CDR1 DNA- Kabat and Chothia | AGGGCCAGTGAGAGTGTTGACAGCTATGGCAAAAGTTTTATGCAC |
| 43 | hu24 VL CDR2 Protein- Kabat and Chothia | RASNLES |
| 44 | hu24 VL CDR2 DNA- Kabat and Chothia | AGGGCATCCAACCTGGAATCT |
| 45 | hu24 VL CDR3 Protein- Kabat and Chothia | QQSNEDPWT |
| 46 | hu24 VL CDR3 DNA- Kabat and Chothia | CAGCAGAGTAATGAGGATCCGTGGACG |
| 47 | hu24 LC Protein- Kappa | EIVLTQSPATLSLSPGERATLSCRASESVDSYGKSFMHWYQQKPGQAPRLLIYRASNLESGIPARFSGSGSGTDFTLTISSLEPEDFAVYYCQQSNEDPWTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 48 | hu24 LC DNA- Kappa | GAAATTGTGTTGACACAGTCTCCAGCCACCCTGTCTTTGTCTCCAGGGGAAAGAGCCACCCTCTCCTGCAGGGCCAGTGAGAGTGTTGACAGCTATGGCAAAAGTTTTATGCACTGGTACCAACAGAAACCTGGCCAGGCTCCCAGGCTCCTCATCTATAGGGCATCCAACCTGGAATCTGGCATCCCAGCCAGGTTCAGTGGCAGTGGGTCTGGGACAGACTTCACTCTCACCATCAGCAGCCTAGAGCCTGAAGATTTTGCAGTTTATTACTGTCAGCAGAGTAATGAGGATCCGTGGACGTTCGGTGGAGGCACCAAGCTGGAAATCAAACGGACTGTGGCTGCACCAAGTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT |
| 49 | hu58 VH Protein | EVQLVESGGGLVQPGGSLRLSCAASGFDFSRYWMSWVRQAPGKGLEWIGDLNPDSSAINYVDSVKGRFTISRDNAKNSLYLQMNSLRAEDTAVYYCTLITTLVPYTMDFWGQGTSVTVSS |
| 50 | hu58 VH DNA | GAGGTGCAGCTGGTGGAGTCTGGGGGAGGCTTGGTCCAGCCTGGGGGGTCCCTGAGACTCTCCTGTGCAGCCTCTGGATTCGACTTTAGTAGATATTGGATGAGCTGGGTCCGCCAGGCTCCAGGGAAGGGGCTGGAGTGGATCGGCGACCTAAACCCAGATTCAAGTGCGATAAACTATGTGGACTCTGTGAAGGGCCGATTCACCATCTCCAGAGACAACGCCAAGAACTCACTGTATCTGCAAATGAACAGCCTGAGAGCCGAGGACACGGCTGTGTATTACTGTACACTCATTACTACGTTAGTACCCTATACTATGGACTTCTGGGGTCAAGGAACCTCAGTCACCGTCTCCTCA |
| 51 | hu58 VH CDR1 Protein- Kabat | RYWMS |
| 52 | hu58 VH CDR1 Protein- Chothia | GFDFSRY |
| 53 | hu58 VH CDR1 DNA- Kabat | AGATATTGGATGAGC |
| 54 | hu58 VH CDR1 DNA- Chothia | GGATTCGACTTTAGTAGATAT |
| 55 | hu58 VH CDR2 Protein- Kabat | DLNPDSSAINYVDSVKG |

TABLE 1-continued

Sequences of humanized anti-PTK7 antibodies.

| SEQ ID NO. | Description | Sequences |
|---|---|---|
| 56 | hu58 VH CDR2 Protein- Chothia | NPDSSA |
| 57 | hu58 VH CDR2 DNA- Kabat | GACCTAAACCCAGATTCAAGTGCGATAAACTATGTGGACTCTGTGAAGGGC |
| 58 | hu58 VH CDR2 DNA- Chothia | AACCCAGATTCAAGTGCG |
| 59 | hu58 VH CDR3 Protein- Kabat and Chothia | ITTLVPYTMDF |
| 60 | hu58 VH CDR3 DNA- Kabat and Chothia | ATTACTACGTTAGTACCCTATACTATGGACTTC |
| 61 | hu58 HC Protein- HuIgG1 | EVQLVESGGGLVQPGGSLRLSCAASGFDFSRYWMSWVRQAPGKGLEWIGDLNPDSSAINYVDSVKGRFTISRDNAKNSLYLQMNSLRAEDTAVYYCTLITTLVPYTMDFWGQGTSVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| 62 | hu58 HC DNA- HuIgG1 | GAGGTGCAGCTGGTGGAGTCTGGGGGAGGCTTGGTCCAGCCTGGGGGGTCCCTGAGACTCTCCTGTGCAGCCTCTGGATTCGACTTTAGTAGATATTGGATGAGCTGGGTCCGCCAGGCTCCAGGGAAGGGGCTGGAGTGGATCGGCGACCTAAACCCAGATTCAAGTGCGATAAACTATGTGGACTCTGTGAAGGGCCGATTCACCATCTCCAGAGACAACGCCAAGAACTCACTGTATCTGCAAATGAACAGCCTGAGAGCCGAGGACACGGCTGTGTATTACTGTACACTCATTACTACGTTAGTACCCTATACTATGGACTTCTGGGGTCAAGGAACCCTCAGTCACCGTCTCCTCAGCCTCCACCAAGGGCCCATCGGTCTTCCCCCTGGCACCCTCGAGCAAGAGCACCTCTGGGGGCACAGCGGCCCTGGGCTGCCTGGTCAAGGACTACTTCCCCGAGCCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAACCATCTCCAAAGCCAAAGGGCAGCCCCGAGAACCACAGGTGTACACCCTGCCCCCATCCCGGGATGAGCTGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGT |
| 63 | hu58 VL Protein | ETTLTQSPAFMSATPGDKVNISCITNTDIDDDMNWYQQKPGEAAILLISEGNGLRPGIPPRFSGSGYGTDFTLTINNIESEDAAYYFCLQSDNLPLTFGSGTKLEIK |
| 64 | hu58 VL DNA | GAAACGACACTCACGCAGTCTCCAGCATTCATGTCAGCGACTCCAGGAGACAAAGTCAACATCTCCTGCATAACCAACACAGACATTGATGATGATATGAACTGGTACCAACAGAAACCAGGAGAAGCTGCTATTCTCCTTATTTCAGAAGGTAATGGTCTCCGTCCTGGAATCCCACCTCGATTCAGTGGCAGCGGGTATGGAACAGATTTTACCCTCACAATTAATAACATAGAATCTGAGGATGCTGCATATTACTTCTGTCTACAAAGTGATAACTTGCCTCTCACGTTCGGCTCGGGGACAAAGTTGGAAATAAAA |
| 65 | hu58 VL CDR1 Protein- Kabat and Chothia | ITNTDIDDDMN |
| 66 | hu58 VL CDR1 DNA- Kabat and Chothia | ATAACCAACACAGACATTGATGATGATATGAAC |
| 67 | hu58 VL CDR2 Protein- Kabat and Chothia | EGNGLRP |
| 68 | hu58 VL CDR2 DNA- Kabat and Chothia | GAAGGTAATGGTCTCCGTCCT |
| 69 | hu58 VL CDR3 Protein- Kabat and Chothia | LQSDNLPLT |
| 70 | hu58 VL CDR3 DNA- Kabat and Chothia | CTACAAAGTGATAACTTGCCTCTCACG |

TABLE 1-continued

Sequences of humanized anti-PTK7 antibodies.

| SEQ ID NO. | Description | Sequences |
|---|---|---|
| 71 | hu58 LC Protein- Kappa | ETTLTQSPAFMSATPGDKVNIS CITNTDIDDDMNWYQQKPGEAA ILLISEGNGLRPGIPPRFSGSG YGTDFTLTINNIESEDAAYYFC LQSDNLPLTFGSGTKLEIKRTV AAPSVFIFPPSDEQLKSGTASV VCLLNNFYPREAKVQWKVDNAL QSGNSQESVTEQDSKDSTYSLS STLTLSKADYEKHKVYACEVTH QGLSSPVTKSFNRGEC |
| 72 | hu58 LC DNA- Kappa | GAAACGACACTCACGCAGTCTC CAGCATTCATGTCAGCGACTCC AGGAGACAAAGTCAACATCTCC TGCATAACCAACACAGACATTG ATGATGATATGAACTGGTACCA ACAGAAACCAGGAGAAGCTGCT ATTCTCCTTATTTCAGAAGGTA ATGGTCTCCGTCCTGGAATCCC ACCTCGATTCAGTGGCAGCGGG TATGGAACAGATTTTACCCTCA CAATTAATAACATAGAATCTGA GGATGCTGCATATTACTTCTGT CTACAAAGTGATAACTTGCCTC TCACGTTCGGCTCGGGACAAA GTTGGAAATAAAACGGACTGTG GCTGCACCAAGTGTCTTCATCT TCCCGCCATCTGATGAGCAGTT GAAATCTGGAACTGCCTCTGTT GTGTGCCTGCTGAATAACTTCT ATCCCAGAGAGGCCAAAGTACA GTGGAAGGTGGATAACGCCCTC CAATCGGGTAACTCCCAGGAGA GTGTCACAGAGCAGGACAGCAA GGACAGCACCTACAGCCTCAGC AGCACCCTGACGCTGAGCAAAG CAGACTACGAGAAACACAAAGT CTACGCCTGCGAAGTCACCCAT CAGGGCCTGAGCTCGCCCGTCA CAAAGAGCTTCAACAGGGGAGA GTGT |

II.B. Linkers

Anti-PTK7 antibody-drug conjugates of the present invention can be prepared using a linker to link or conjugate a drug to an anti-PTK7 antibody. A linker is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells. Suitable linkers include, for example, cleavable and non-cleavable linkers. A cleavable linker is typically susceptible to cleavage under intracellular conditions. Major mechanisms by which a conjugated drug is cleaved from an antibody include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. As a result of these varying mechanisms for cleavage, mechanisms of linking the drug to the antibody also vary widely and any suitable linker can be used.

Suitable cleavable linkers include, for example, a peptide linker cleavable by an intracellular protease, such as lysosomal protease or an endosomal protease. In aspects of the invention, the linker can be a dipeptide linker, such as a valine-citrulline (val-cit), a phenylalanine-lysine (phe-lys) linker, or maleimidocaproyl-valine-citrulline-p-aminobenzyloxycarbonyl (vc) linker. In another aspect, the linker may be Sulfosuccinimidyl-4-[Nmaleimidomethyl] cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Further, the linker may be maleimidocaproyl (mc).

Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

In particular aspects of the invention, the linker of PTK7 antibody-drug conjugates of the invention may be or maleimidocaproyl-valine-citrulline-p-aminobenzyloxycarbonyl (vc), maleimidocaproyl (mc) or AcBut.

An example of a suitable conjugation procedure relies on the conjugation of hydrazides and other nucleophiles to the aldehydes generated by oxidation of the carbohydrates that naturally occur on antibodies. Hydrazone-containing conjugates can be made with introduced carbonyl groups that provide the desired drug-release properties. Conjugates can also be made with a linker that has a disulfide at one end, an alkyl chain in the middle, and a hydrazine derivative at the other end. The anthracyclines are one example of cytotoxins that can be conjugated to antibodies using this technology.

Linkers containing functional groups other than hydrazones have the potential to be cleaved in the acidic milieu of the lysosomes. For example, conjugates can be made from thiol-reactive linkers that contain a site other than a hydrazone that is cleavable intracellularly, such as esters, amides, and acetals/ketals. Camptothecin is one cytotoxic agent that can be conjugated using these linkers. Ketals made from a 5 to 7-member ring ketone and that has one of the oxygens attached to the cytotoxic agent and the other to a linker for antibody attachment also can be used. The anthracyclines are also an example of a suitable cytotoxin for use with these linkers.

Another example of a class of pH sensitive linkers are the cis-aconitates, which have a carboxylic acid juxtaposed to an amide bond. The carboxylic acid accelerates amide hydrolysis in the acidic lysosomes. Linkers that achieve a similar type of hydrolysis rate acceleration with several other types of structures can also be used. The maytansinoids are an example of a cytotoxin that can be conjugated with linkers attached at C-9.

Another potential release method for drug conjugates is the enzymatic hydrolysis of peptides by the lysosomal enzymes. In one example, a peptide is attached via an amide bond to para-aminobenzyl alcohol and then a carbamate or carbonate is made between the benzyl alcohol and the cytotoxic agent. Cleavage of the peptide leads to the collapse, or self-immolation, of the aminobenzyl carbamate or carbonate. The cytotoxic agents exemplified with this strategy include anthracyclines, taxanes, mitomycin C, and the auristatins. In one example, a phenol can also be released by collapse of the linker instead of the carbamate. In another variation, disulfide reduction is used to initiate the collapse of a para-mercaptobenzyl carbamate or carbonate.

Many of the cytotoxic agents conjugated to antibodies have little, if any, solubility in water and that can limit drug loading on the conjugate due to aggregation of the conjugate. One approach to overcoming this is to add solubilizing groups to the linker. Conjugates made with a linker consisting of PEG and a dipeptide can been used, including those having a PEG di-acid, thiol-acid, or maleimide-acid attached to the antibody, a dipeptide spacer, and an amide bond to the amine of an anthracycline or a duocarmycin analogue. Another example is a conjugate prepared with a PEG-containing linker disulfide bonded to a cytotoxic agent and amide bonded to an antibody. Approaches that incorporate PEG groups may be beneficial in overcoming aggregation and limits in drug loading.

U.S. Pat. No. 5,773,001, which is incorporated herein by reference in its entirety, discloses linkers that may be used with nucleophilic drugs, particularly hydrazides and related nucleophiles, prepared from the calicheamicins. These linkers are especially useful in those cases where better activity is obtained when the linkage formed between the drug and the linker is hydrolysable. These linkers contain two functional groups, including (1) a group for reaction with an antibody (e.g., carboxylic acid), and (2) a carbonyl group (e.g., an aldehyde or a ketone) for reaction with a drug. The carbonyl groups may react with a hydrazide group on the drug to form a hydrazone linkage. This linkage is cleavable hydrolysable, allowing for release of the therapeutic agent from the conjugate after binding to the target cells. In particular aspects of the invention, the linker of PTK7 antibody-drug conjugates of the invention may 4-(4-acetylphenoxy) butanoic acid (AcBut). In other aspects of the invention, antibody-drug conjugates can be prepared using (3-Acetylphenyl) acetic acid (AcPAc) or 4-mercapto-4-methyl-pentanoic acid (Amide) as the linker molecule.

N-hydroxysuccinimide (OSu) esters or other comparably activated esters can be used to generate the activated hydrolyzable linker-drug moiety. Examples of other suitable activating esters include NHS (N-hydroxysuccinimide), sulfo-NHS (sulfonated NHS), PFP (pentafluorophenyl), TFP (tetrafluorophenyl), and DNP (dinitrophenyl).

In some aspects of the invention, the antibody-drug conjugates are prepared by reacting calicheamicin or derivatives thereof, the AcBut linker and an anti-PTK7 antibody of the present invention. See e.g., U.S. Pat. No. 5,773,001. The AcBut linker produces conjugates that are substantially stable in circulation, releasing an estimated 2% of the calicheamicin per day when assayed at 37° C. in human plasma in vitro. The conjugates release the calicheamicin in the acidic lysosomes.

In some aspects of the invention, the AcButCM moiety can be generated using methods and processes described in the art, such as PCT International Publication No. WO 08/147765 and in U.S. Pat. No. 8,273,862, which are incorporated herein by reference in their entirety. In some aspects of the invention, the AcButCM moiety can be generated using an improved synthesis process, as described in U.S. Provisional Application No. 61/899,682, which is incorporated herein by reference in its entirety.

Representative linkers useful for conjugation of radioisotopes include diethylenetriamine pentaacetate (DTPA)-isothiocyanate, succinimidyl 6-hydrazinium nicotinate hydrochloride (SHNH), and hexamethylpropylene amine oxime (HMPAO) (Bakker et al. (1990) *J. Nucl. Med.* 31: 1501-1509, Chattopadhyay et al. (2001) *Nucl. Med. Biol.* 28: 741-744, Dewanjee et al. (1994) *J. Nucl. Med.* 35: 1054-63, Krenning et al. (1989) *Lancet* 1: 242-244, Sagiuchi et al. (2001) *Ann. Nucl. Med.* 15: 267-270); U.S. Pat. No. 6,024,938). Alternatively, a targeting molecule may be derivatized so that a radioisotope may be bound directly to it (Yoo et al. (1997) *J. Nucl. Med.* 38: 294-300). Iodination methods are also known in the art, and representative protocols may be found, for example, in Krenning et al. (1989) *Lancet* 1:242-4 and in Bakker et al. (1990) *J. Nucl. Med.* 31:1501-9.

II.C. Drugs

Drugs useful in preparation of the disclosed PTK7 antibody-drug conjugates include any substance having biological or detectable activity, for example, therapeutic agents, detectable labels, binding agents, etc., and prodrugs, which are metabolized to an active agent in vivo. A drug may also be a drug derivative, wherein a drug has been functionalized to enable conjugation with an antibody of the invention. In accordance with the disclosed methods, the drugs are used to prepare antibody-drug conjugates of the formula Ab-(L-D), wherein (a) Ab is an antibody, or antigen-binding fragment thereof, that binds to PTK7; and (b) L-D is a linker-drug moiety, wherein L is a linker, and D is a drug. The drug-to-antibody ratio (DAR) or drug loading indicates the number of drug (D) molecules that are conjugated per antibody. The antibody-drug conjugates of the present invention have a DAR that is within the range of 1 to 8. Thus, in aspects of the invention, a PTK7 antibody-drug conjugate may include 1 drug molecule (DAR of 1), or 2 drug molecules (DAR of 2), or 3 drug molecules (DAR of 3), or 4 drug molecules (DAR of 4), or 5 drug molecules (DAR of 5), or 6 drug molecules (DAR of 6), or 7 drug molecules (DAR of 7), or 8 drug molecules (DAR of 8). DAR can be determined by various conventional means such as UV spectroscopy, mass spectroscopy, ELISA assay, radiometric methods, hydrophobic interaction chromatography (HIC), electrophoresis and HPLC.

Compositions, batches and/or formulations of antibody-drug conjugate (ADC), of the formula Ab-(L-D), may include a plurality of antibodies, each antibody conjugated to a particular number of drug molecules (from DAR 1 to 8). The compositions, batches and/or formulations have an average DAR.

In particular aspects of the invention, a composition, batch, and/or formulation of antibody-drug conjugates may be characterized by an average DAR in the range of about 1 to about 8, for example, an average DAR in the range of about 2 to about 7, or an average DAR in the range of about 3 to about 6, or an average DAR in the range of about 4 to about 5, or an average DAR in the range of about 5 to about 7, or an average DAR in the range of about 6 to about 8. In some aspects the compositions, batches and/or formulations of antibody-drug conjugate may have an average DAR of about 1, or an average DAR of about 2, or an average DAR of about 3, or an average DAR of about 4, or an average DAR of about 5, or an average DAR of about 6, or an average DAR of about 7, or an average DAR of about 8. As used in the foregoing ranges of average DAR, the term "about" means+/−0.5%.

Moreover, a composition, batch, and/or formulation of antibody-drug conjugates may be characterized by a preferred range of average DAR, e.g., an average DAR in the range of about 3 to about 5, an average DAR in the range of about 3 to about 4, or an average DAR in the range of about 4 to about 5. Further, a composition, batch, and/or formulation of antibody-drug conjugates may be characterized by a preferred range of average DAR, e.g., an average DAR in the range of 3 to 5, an average DAR in the range of 3 to 4, or an average DAR in the range of 4 to 5.

Compositions, batches and/or formulations of ADCs of the formula Ab-(L-D), may be characterized by a DAR distribution. The DAR distribution provides the percent or fraction of various ADC species, e.g. DAR 1 to 8 that may be present in a composition, batch, and/or formulation of ADCs. The DAR distribution of a composition, batch, and/or formulation of ADCs may be determined by methods known in the art, such as capillary iso-electric focusing (cIEF).

In one aspect of the invention, the DAR distribution of a composition, batch, and/or formulation of ADCs, of the formula Ab-(L-D), may be characterized as a highly heterogeneous mixture of ADCs with a broad DAR distribution, generally containing a broad range of ADC species with DAR 1 to 8.

In another aspect of the invention, the DAR distribution of a composition, batch, and/or formulation of ADCs may be characterized as a highly homogeneous mixture with a narrow DAR distribution, generally containing a narrow range of ADC species having a particular DAR, such as DAR 3 to 5.

For example, a therapeutic agent is an agent that exerts a cytotoxic, cytostatic, and/or immunomodulatory effect on cancer cells or activated immune cells. Examples of therapeutic agents include cytotoxic agents, chemotherapeutic agents, cytostatic agents, and immunomodulatory agents. Chemotherapeutic agents are chemical compounds useful in the treatment of cancer.

Therapeutic agents are compositions that may be used to treat or prevent a disorder in a subject in need thereof. Therapeutic agents useful in the invention include anti-cancer agents, i.e., agents having anti-cancer activity in PTK7-expressing cells such as cancer cells from breast cancer, such as triple-negative breast cancer (TNBC), progesterone-receptor positive breast cancer (PR+), estrogen-receptor positive breast cancer (ER+) and double positive breast cancer; ovarian cancer; colorectal cancer; leukemias, such as acute myeloid leukemia (AML) and acute lymphoblastic leukemia (ALL); esophageal cancer; gastric cancer; melanoma; sarcoma; kidney cancer; pancreatic cancer; prostate cancer; liver cancer, such as hepatocellular carcinoma (HCC); and lung cancer, such as non-small cell lung cancer (NSCLC) and small cell lung cancer (SCLC).

Representative therapeutic agents include cytotoxins, cytotoxic agents, and cytostatic agents. A cytotoxic effect refers to the depletion, elimination and/or the killing of a target cell(s). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells.

Additional representative therapeutic agents include radioisotopes, chemotherapeutic agents, immunomodulatory agents, anti-angiogenic agents, anti-proliferative agents, pro-apoptotic agents, and cytolytic enzymes (e.g., RNAses). An agent may also include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above-noted terms. For example, selected radioisotopes are also cytotoxins. Therapeutic agents may be prepared as pharmaceutically acceptable salts, acids or derivatives of any of the above. Generally, conjugates having a radioisotope as the drug are referred to as radioimmunoconjugates and those having a chemotherapeutic agent as the drug are referred to as chemoimmunoconjugates.

Examples of a cytotoxic agents include, but are not limited to an anthracycline, an auristatin, CC-1065, a dolastatin, a duocarmycin, an enediyne, a geldanamycin, a maytansine, a puromycin, a taxane, a vinca alkaloid, a SN-38, a tubulysin, a hemiasterlin, and stereoisomers, isosteres, analogs or derivatives thereof. Chemotherapeutic agents, plant toxins, other bioactive proteins, enzymes (i.e., ADEPT), radioisotopes, photosensitizers (i.e., for photodynamic therapy) can also be used. In one embodiment, the cytotoxic agent is not a ribosome inactivating protein. In a more specific embodiment, the cytotoxic agent is not saporin.

The anthracyclines are derived from bacteria *Strepomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, (1998). Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB).

In some aspects of the invention, auristatins described in PCT International Publication No. WO 2013/072813, which is incorporated herein by reference in its entirety, and methods of producing those auristatins are used herein.

For example, the auristatin is 0101, (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), having the following structure:

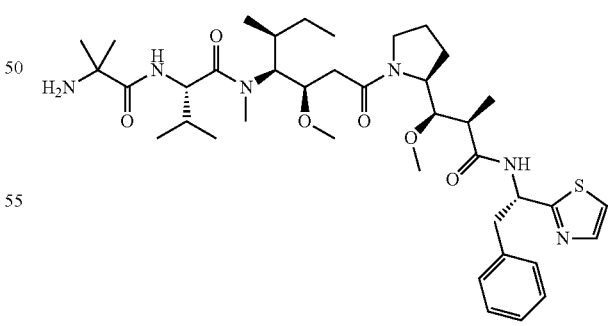

In another example, the auristatin is 8261, (8261 2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide), having the following structure:

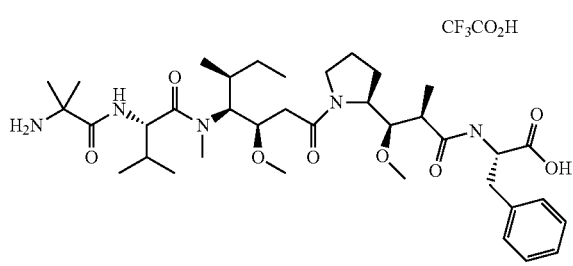 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)N)C(C)C ; "CF3CO2H"]

Duocarmycin and CC-1065 are DNA alkylating agents with cytotoxic potency. See Boger and Johnson, *PNAS* 92:3642-3649, 1995. Exemplary dolastatins and auristatins include, but are not limited to, (+)-docarmycin A and (+)-duocarmycin SA, and (+)-CC-1065.

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin.

In some aspects of the invention, the cytotoxic agent is an antibiotic, such as calicheamicin, also called the LL-E33288 complex, for example, β-calicheamicin, γ-calicheamicin or N-acetyl-γ-calicheamicin (gamma-calicheamicin ($\gamma_1$)). Examples of calicheamicins suitable for use in the present invention are disclosed, for example, in U.S. Pat. Nos. 4,671,958 4,970,198, 5,053,394, 5,037,651, 5,079,233 and 5,108,912, which are incorporated herein by reference in its entirety. These compounds contain a methyltrisulfide that may be reacted with appropriate thiols to form disulfides, at the same time introducing a functional group such as a hydrazide or other functional group that is useful for conjugating calicheamicin to an anti-PTK7 antibody. Disulfide analogs of calicheamicin can also be used, for example, analogs described in U.S. Pat. Nos. 5,606,040 and 5,770,710, which are incorporated herein by reference in its entirety. In some aspects of the invention, the disulfide analog is N-acetyl-γ-calicheamicin dimethyl hydrazide (hereinafter "CM").

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethyl-aminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., *Science* 189:1002-1005, 1975. Exemplary maytansines and maytansinoids include, but are not limited to, mertansine (DM1) and its derivatives as well as ansamitocin.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some aspects of the invention, the agent is an immunomodulating agent. Examples of an immunomodulating agent include, but are not limited to, gancyclovier, etanercept, tacrolimus, sirolimus, voclosporin, cyclosporine, rapamycin, cyclophosphramide, azathioprine, mycophenolgate mofetil, methotrextate, glucocorticoid and its analogs, cytokines, xanthines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

Immunomodulatory agents useful in the invention also include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Representative immunosuppressive agents include 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNFα antibodies, anti-IL2 antibodies), streptokinase, TGFβ, rapamycin, T-cell receptor, T-cell receptor fragments, and T cell receptor antibodies.

In some aspects of the invention, the drug is a therapeutic protein including, but is not limited to, a toxin, a hormone, an enzyme, and a growth factor.

Examples of a toxin protein (or polypeptide) include, but are not limited to, dipththeria (e.g., diphtheria A chain), *Pseudomonas* exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAR, PAPII, and PAP-S), *momordica charantia* inhibitor, curcin, crotin, *sapaonaria officinalis* inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

Examples of hormones include, but are not limited to, estrogens, androgens, progestins and corticosteroids.

In some aspects of the invention, the cytotoxic agent can be made using a liposome or biocompatible polymer. The anti-PTK7 antibodies as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some aspects of the invention, the drug is an oligonucleotide, such as anti-sense oligonucleotides.

Additional drugs useful in the invention include anti-angiogenic agents that inhibit blood vessel formation, for example, farnesyltransferase inhibitors, COX-2 inhibitors, VEGF inhibitors, bFGF inhibitors, steroid sulphatase inhibitors (e.g., 2-methoxyoestradiol bis-sulphamate (2-MeOE2bisMATE)), interleukin-24, thrombospondin, metallospondin proteins, class I interferons, interleukin 12, protamine, angiostatin, laminin, endostatin, and prolactin fragments.

Anti-proliferative agents and pro-apoptotic agents include activators of PPAR-gamma (e.g., cyclopentenone prostaglandins (cyPGs)), retinoids, triterpinoids (e.g., cycloartane, lupane, ursane, oleanane, friedelane, dammarane, cucurbitacin, and limonoid triterpenoids), inhibitors of EGF receptor (e.g., HER4), rampamycin, CALCITRIOL® (1,25-dihydroxycholecalciferol (vitamin D)), aromatase inhibitors (FEMARA® (letrozone)), telomerase inhibitors, iron chelators (e.g., 3-aminopyridine-2-carboxaldehyde thiosemicarbazone (Triapine)), apoptin (viral protein 3-VP3 from chicken aneamia virus), inhibitors of Bcl-2 and Bcl-X(L), TNF-alpha, FAS ligand, TNF-related apoptosis-inducing ligand (TRAIL/Apo2L), activators of TNF-alpha/FAS ligand/TNF-related apoptosis-inducing ligand (TRAIL/Apo2L) signaling, and inhibitors of PI3K-Akt survival pathway signaling (e.g., UCN-01 and geldanamycin).

Representative chemotherapeutic agents include alkylating agents such as thiotepa and cyclosphosphamide; alkyl sulfonates such as busulfan, improsulfan and piposulfan; aziidines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechiorethamine, mechiorethamine oxide hydrochloride, melphalan, novembichin, phenesterine, prednimustine, trofosfarnide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-EU; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2'-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g. paclitaxel (TAXOL®, Bristol-Myers Squibb Oncology of Princeton, N.J.) and doxetaxel (TAXOTERE®, Rhone-Poulenc Rorer of Antony, France); chiorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aininopterin; xeloda; ibandronate; CPT-11; topoisomerase inhibitor RFS 2000; difluoromethylornithine (DMFO); retinoic acid; esperamicins; and capecitabine.

Additional therapeutic agents that may be used in accordance with the present invention include photosensitizing agents, such as U.S. Pat. Nos. 7,498,029 and 5,952,329, which are incorporated herein by reference in its entirety, for photodynamic therapy; magnetic particles for thermotherapy, such as U.S. Pat. No. 6,997,863, which is incorporated herein by reference in its entirety; binding agents, such as peptides, ligands, cell adhesion ligands, etc., and prodrugs such as phosphate-containing prodrugs, thiophosphate-containing prodrugs, sulfate containing prodrugs, peptide containing prodrugs, β-lactam-containing prodrugs, substituted phenoxyacetamide-containing prodrugs or substituted phenylacetamide-containing prodrugs, 5-fluorocytosine and other 5-fluorouridine prodrugs that may be converted to the more active cytotoxic free drug.

For diagnostic methods using anti-PTK7 antibodies, a drug may include a detectable label used to detect the presence of PTK7-expressing cells in vitro or in vivo. Radioisotopes that are detectable in vivo, such as those labels that are detectable using scintigraphy, magnetic resonance imaging, or ultrasound, may be used in clinical diagnostic applications. Useful scintigraphic labels include positron emitters and γ-emitters. Representative contrast agents for magnetic source imaging are paramagnetic or superparamagnetic ions (e.g., iron, copper, manganese, chromium, erbium, europium, dysprosium, holmium and gadolinium), iron oxide particles, and water soluble contrast agents. For ultrasonic detection, gases or liquids may be entrapped in porous inorganic particles that are released as microbubble contrast agents. For in vitro detection, useful detectable labels include fluorophores, detectable epitopes or binding agents, and radioactive labels.

Thus, in some aspects of the invention, the drug is an imaging agent (e.g., a fluorophore or a PET (Positron Emission Tomography) label, SPECT (Single-Photon Emission Computed Tomorgraphy) label), or MRI (Magnetic Resonance Imaging) label.

The term "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Radionuclides that can serve as detectable labels include, for example, I-131, I-123, I-125, Y-90, Re-188, Re-186, At-211, Cu-67, Bi-212, and Pd-109. The label might also be a non-detectable entity such as a toxin.

Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101).

Therapeutic or diagnostic radioisotopes or other labels (e.g., PET or SPECT labels) can be incorporated in the agent for conjugation to the anti-PTK7 antibodies as described herein. The isotope may be directly bound to the antibody, for example, at a cysteine residue present in the antibody, or a chelator may be used to mediate the binding of the antibody and the radioisotope. Radioisotopes suitable for radiotherapy include but are not limited to α-emitters, β-emitters, and auger electrons. For diagnostic applications, useful radioisotopes include positron emitters and γ-emitters. An anti-PTK7 antibody of the invention may further be iodinated, for example, on a tyrosine residue of the antibody, to facilitate detection or therapeutic effect of the antibody.

Examples of a radioisotope or other labels include, but are not limited to, $^{3}$H, $^{11}$C, $^{13}$N, $^{14}$C, $^{15}$N, $^{15}$O, $^{35}$S, $^{18}$F, $^{32}$P, $^{33}$P, $^{47}$Sc, $^{51}$Cr, $^{57}$Co, $^{58}$Co, $^{59}$Fe, $^{62}$Cu, $^{64}$Cu, $^{67}$Cu, $^{67}$Ga, $^{68}$Ga, $^{75}$Se, $^{76}$Br, $^{77}$Br, $^{86}$Y, $^{89}$Zr, $^{90}$Y, $^{94}$Tc, $^{95}$Ru, $^{97}$Ru, $^{99}$Tc, $^{103}$Ru, $^{105}$Rh, $^{105}$Ru, $^{107}$Hg, $^{109}$Pd, $^{111}$Ag, $^{111}$In, $^{113}$In, $^{121}$Te, $^{122}$Te, $^{123}$I, $^{124}$I, $^{125}$I, $^{125}$Te, $^{126}$I, $^{131}$I, $^{131}$In, $^{133}$I, $^{142}$Pr, $^{143}$Pr, $^{153}$Pb, $^{153}$Sm, $^{161}$Tb, $^{165}$Tm, $^{166}$Dy, $^{166}$H, $^{167}$Tm, $^{168}$Tm, $^{169}$Yb, $^{177}$Lu, $^{186}$Re, $^{188}$Re, $^{189}$Re, $^{197}$Pt, $^{198}$Au, $^{199}$Au, $^{201}$Tl, $^{203}$Hg, $^{211}$At, $^{212}$Bi, $^{212}$Pb, $^{213}$Bi, $^{223}$Ra, $^{224}$Ac, and $^{225}$Ac.

II.D. Methods of Preparing PTK7 Antibody-Drug Conjugate

Also provided are methods for preparing antibody-drug conjugates of the present invention. For example, a process for producing a PTK7 antibody-drug conjugate as disclosed herein can include (a) linking the linker to the drug; (b) conjugating the linker-drug moiety to the antibody; and (c) purifying the antibody-drug conjugate. Representative methods for synthesis of vc0101 and mc8261 are described in Example 9, and representative methods for conjugation of anti-PTK7-vc0101, anti-PTK7-mc8621 ADCs and anti-PTK7-AcButCM ADCs are described in Example 10.

In one aspect, an antibody-drug conjugate of the formula Ab-(L-D) may be prepared by (a) adding the linker-drug moiety (e.g. vc0101 or mc8261) to an anti-PTK7 antibody, or antigen-binding fragment thereof, wherein anti-PTK7 antibodies may be partially reduced in a solution containing: 2-10 molar excess of tris(2-carboxyethyl)phosphine (TCEP), 100 mM of 4-(2-hydroxyethyl)-1-piperazineethanesulfonic acid buffer (HEPES) having a pH of 6-9 and 1 mM diethylenetriaminepentaacetic acid (DTPA) for a period of time ranging from about 30 minutes to 16 hours at a temperature ranging from about 0-37° C. The vc0101 or mc8261 linker-payload may then be added at a linker-payload/antibody molar ratio from about 4-10 with dimethylacetamide (DMA) for an incubation period of time ranging from about 30 minutes to 16 hours at a temperature ranging from about 0-37° C. Subsequently, the unreacted thiols may be capped with N-ethylmaleimide and the unreacted linker-payload may be quenched with L-Cys.

In another aspect, an antibody-drug conjugate of the formula Ab-(L-D) may be prepared by (a) adding the linker-drug moiety (e.g. AcButCM) to an anti-PTK7 antibody, or antigen-binding fragment thereof, wherein the concentration of antibody may range from 1 to 25 mg/ml and the linker-drug moiety is at a molar ratio ranging from about 1-15 to 1 of the anti-PTK7 antibody; (b) incubating the linker-drug moiety and anti-PTK7 antibody in a non-nucleophilic, protein-compatible, buffered solution having a pH in a range from about 7 to 9 to produce an monomeric antibody-drug conjugate, wherein the solution further compromises (i) a suitable organic cosolvent, and (ii) an additive having at least one $C_{6}$-$C_{18}$ carboxylic acid or its salt, and wherein the incubation is conducted at a temperature ranging from about 0° C. to about 45° C., for a period of time ranging from about 1 minute to about 24 hours; and (c) subjecting the conjugate produced in step (b) to a chromatographic separation process to separate antibody-drug conjugates with a DAR from 1 to 8; and provides low conjugated fraction (LCF) of below 10% from unconjugated anti-PTK7 antibody, linker-drug moiety, and aggregated conjugates.

Optimal reaction conditions for formation of a conjugate may be empirically determined by variation of reaction variables such as temperature, pH, linker-payload moiety input, and additive concentration. Conditions suitable for conjugation of other drugs may be determined by those skilled in the art without undue experimentation.

In some aspects the drug may be modified to include a group reactive with a conjugation point on an antibody. For example, a drug may be attached by alkylation (e.g., at the epsilonamino group lysines or the N-terminus of antibodies), reductive amination of oxidized carbohydrate, transesterification between hydroxyl and carboxyl groups, amidation at amino groups or carboxyl groups, and conjugation to thiols. In some embodiments, the number of drug (D) molecules conjugated per antibody molecule ranges from 1 to 8; 1 to 7, 1 to 6, 1 to 5, 1 to 4, 1 to 3, or 1 to 2. In other embodiments, the number of drug (D) molecules conjugated per antibody is 1, 2, 3, 4, 5, 6, 7 or 8. In some embodiments, compositions, batches, and/or formulations of a plurality of antibody-drug conjugates may be characterized by an average DAR. The average DAR ranges from about 1 to about 8, about 1 to about 7, about 1 to about 6, about 1 to about 5, about 1 to about 4; about 1 to about 3, about 1 to about 2. In some embodiments, the average DAR for a composition, batch, and/or formulation of a plurality of antibody-drug conjugates ranges from about 2 to about 8, about 2 to about 7, about 2 to about 6, about 2 to about 5, about 2 to about 4, about 2 to about 3 or about 3 to about 5. As used in the foregoing ranges of average DAR, the term "about" means+/−0.5%. For examples of chemistries that can be used for conjugation, see, e.g., Current Protocols in Protein Science (John Wiley & Sons, Inc.), Chapter 15 (Chemical Modifications of Proteins).

Other methods for preparing antibody-drug conjugates have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Further, reactive cysteine residues engineered at specific sites of antibodies for specific drug conjugation with defined stoichiometry have also been described. See, e.g., Junutula et al., Nature Biotechnology, 26:925-932, 2008.

Further as described in International Publication No. WO 2013/093809, certain residues presumably present on the surface of the CH2 or CH3 domain of the heavy chain of antibodies, or on the constant domain of the light chain, or otherwise accessible, are suitable for the substitution of the naturally-occurring wild type amino acid with, for example, cysteine, and are therefore useful to engineer a site capable of conjugation to various agents, In some aspects, an engineered Fc polypeptide of the invention may be used to prepare a PTK7 antibody or antibody-drug conjugate, such that the antibody or fragment thereof thereby comprises an engineered Fc region which can be used to conjugate, at the engineered residue (i.e., the amino acid substituted compared to wild type unmodified Fc), a wide variety of agents.

The PTK7 antibodies and antibody-drug conjugates of the present invention may encompass an engineered Fc polypeptide where 1, 2, or more amino acids chosen from positions: 347, 392, 398, 422 and 443 of the antibody heavy chain (HC) of a parent, native, or wild type antibody, substituted with another amino acid (including natural and non-natural/synthetic amino acids), wherein the numbering system of the constant region is that of the EU index according to Kabat.

It should be noted that a single substitution in an Fc polypeptide, for example of a cysteine residue, normally results in the display of two corresponding residues in the resultant IgG antibody due to the homodimeric nature of IgG antibody molecules. Thus, the resultant engineered IgG antibodies of the invention may display at least 1, 2, 3, 4, or more reactive groups for the purpose of conjugation to a drug or compound. In an aspect, one or more of the substitutions is with a cysteine residue, and the resulting engineered antibodies may display at least 1, 2, 3, 4, or more thiol groups for the purpose of conjugation to a drug or compound.

In another aspect, an engineered Fc polypeptide of the disclosure may comprise one or more substitutions selected from the positions 347, 392, 398, 422 and 443, of the heavy chain (HC) of an antibody, wherein the numbering system of the constant region is that of the EU index as set forth in Kabat, and wherein the amino acid sequence of the heavy chain is selected from the group consisting of SEQ ID NO: 13, SEQ ID NO: 37, and SEQ ID NO: 61.

The PTK7 antibodies and antibody-drug conjugates of the present invention may encompass an engineered antibody light chain constant region (LC), or a portion thereof, where 1, 2, or 3 amino acids chosen from positions 111, 183, or 188, of the antibody light chain, wherein the numbering system of the light chain constant region is that of the Kabat, of a parent, native, or wild type antibody, substituted with another amino acid (including natural and non-natural/synthetic amino acids).

In some aspects, the engineered LC polypeptide of the disclosure comprises one or more substitutions from positions 111, 183, or 188, of the antibody light chain wherein the amino acid sequence of the light chain is selected from the group consisting of SEQ ID NO: 23, SEQ ID NO: 47, and SEQ ID NO: 71

In other aspects, due to the dimeric nature of many antibodies (e.g., IgGs comprise two light chains and two heavy chains, each heavy chain comprising an Fc polypeptide), an antibody of the invention may comprise at least one engineered Fc polypeptide and may further comprise at least one engineered light chain constant polypeptide thereby providing at least two site-specific conjugation sites—one in the Fc polypeptide and another in the LC polypeptide.

In some aspects of the invention, the antibody, or antigen-binding fragment thereof, of the disclosed PTK7 antibody-drug conjugates includes an IgG1 heavy chain constant region, for example a hu23 heavy chain set forth as SEQ ID NO: 13, a hu24 heavy chain set forth as SEQ ID NO: 37, or a hu58 heavy chain set forth as SEQ ID NO: 61. In other aspects, the antibody, or antigen-binding fragment thereof, of the disclosed PTK7 antibody-drug conjugates includes a kappa light chain constant region, for example a hu23 light chain set forth as SEQ ID NO: 23, a hu24 light chain set forth as SEQ ID NO: 47, or a hu58 light chain set forth as SEQ ID NO: 71. In particular aspects of the invention, a PTK7 antibody-drug conjugate can include an IgG1 heavy chain constant region and a kappa light chain constant region, for example, a heavy chain set forth as SEQ ID NO: 13 and a light chain set forth as SEQ ID NO: 23; or as another example, a heavy chain set forth as SEQ ID NO: 37 and a light chain set forth as SEQ ID NO: 47; or as another example, a heavy chain set forth as SEQ ID NO: 61 and a light chain set forth as SEQ ID NO: 71.

Also, as described in International Publication No. WO2012/059882, conjugation methods include use of an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent comprising or attached to a reactive amine).

In some aspects, the PTK7 antibody or antibody-drug conjugate may comprise an acyl donor glutamine-containing tag engineered at a specific site of the antibody (e.g., a carboxyl terminus, an amino terminus, or at another site) of the PTK7 antibody. In some aspects, the tag comprises an amino acid glutamine (Q) or an amino acid sequence GGLLQGG (SEQ ID NO:74), LLQGA (SEQ ID NO:75), GGLLQGA (SEQ ID NO:76), LLQ, LLQGPGK (SEQ ID NO: 77), LLQGPG (SEQ ID NO: 78), LLQGPA (SEQ ID NO: 79), LLQGP (SEQ ID NO: 80), LLQP (SEQ ID NO: 81), LLQPGK (SEQ ID NO: 82), LLQGAPGK (SEQ ID NO: 83), LLQGAPG (SEQ ID NO: 84), LLQGAP (SEQ ID NO: 85), LLQ$X_1X_2X_3X_4X_5$, wherein $X_1$ is G or P, wherein $X_2$ is A, G, P, or absent, wherein $X_3$ is A, G, K, P, or absent, wherein $X_4$ is G, K or absent, and wherein $X_5$ is K or absent (SEQ ID NO: 86), or LLQ$X_1X_2X_3X_4X_5$, wherein $X_1$ is any naturally occurring amino acid and wherein $X_2$, $X_3$, $X_4$, and $X_5$ are any naturally occurring amino acids or absent (SEQ ID NO: 87). In some embodiments, the PTK7 antibody or antibody-drug conjugate may comprise an amino acid substitution from asparagine (N) to glutamine (Q) at position 297 of the PTK7 antibody.

In another aspect, the PTK7 antibody or antibody-drug conjugate may comprise an acyl donor glutamine-containing tag and an amino acid modification at position 222, 340, or 370 of the antibody (EU numbering scheme), wherein the modification is an amino acid deletion, insertion, substitution, mutation, or any combination thereof. Accordingly, in some aspects, the PTK7 antibody or antibody-drug conjugate may comprise the acyl donor glutamine-containing tag (e.g., Q, GGLLQGG (SEQ ID NO:74), LLQGA (SEQ ID NO:75), GGLLQGA (SEQ ID NO:76), LLQ, LLQGPGK (SEQ ID NO: 77), LLQGPG (SEQ ID NO: 78), LLQGPA (SEQ ID NO: 79), LLQGP (SEQ ID NO: 80), LLQP (SEQ ID NO: 81), LLQPGK (SEQ ID NO: 82), LLQGAPGK (SEQ ID NO: 83), LLQGAPG (SEQ ID NO: 84), LLQGAP (SEQ ID NO: 85), LLQ$X_1X_2X_3X_4X_5$, wherein $X_1$ is G or P, wherein $X_2$ is A, G, P, or absent, wherein $X_3$ is A, G, K, P, or absent, wherein $X_4$ is G, K or absent, and wherein $X_5$ is K or absent (SEQ ID NO: 86), or LLQ$X_1X_2X_3X_4X_5$, wherein $X_1$ is any naturally occurring amino acid and wherein $X_2$, $X_3$, $X_4$, and $X_5$ are any naturally occurring amino acids or absent (SEQ ID NO: 87) conjugated at a specific site (e.g., at a carboxyl terminus of the heavy or light chain or at another site) of the PTK7 antibody and an amino acid modification at position 222, 340, or 370 of the antibody (EU numbering scheme).

To further increase the number of drug molecules per antibody-drug conjugate, the drug may be conjugated to polyethylene glycol (PEG), including straight or branched polyethylene glycol polymers and monomers. A PEG monomer is of the formula: —$(CH_2CH_2O)$—. Drugs and/or peptide analogs may be bound to PEG directly or indirectly, i.e. through appropriate spacer groups such as sugars. A PEG-antibody-drug composition may also include additional lipophilic and/or hydrophilic moieties to facilitate drug stability and delivery to a target site in vivo. Representative methods for preparing PEG-containing compositions may be found in U.S. Pat. Nos. 6,461,603; 6,309,633; and 5,648,095, among other places.

For example, to increase the amount of auristatin or calicheamicin in PTK7 antibody-drug conjugates disclosed herein, the antibody may be conjugated to PEG prior to conjugation with the drug, for example, using PEG-SPA, PEG-SBA, or PEG-bis-maleimide. Antibody-drug conjugates prepared using PEG may show reduced binding affinity for the target antigen, but are still effective as a result of increased drug load.

Following conjugation, the conjugates may be separated and purified from unconjugated reactants and/or aggregated forms of the conjugates by conventional methods. This can include processes such as size exclusion chromatography (SEC), ultrafiltration/diafiltration, ion exchange chromatography (IEC), chromatofocusing (CF) HPLC, FPLC, or Sephacryl S-200 chromatography. The separation may also be accomplished by hydrophobic interaction chromatography (HIC). Suitable HIC media includes Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium.

In some aspects of the invention, the separation may be performed using Butyl Sepharose 4 Fast Flow chromatographic medium. When using a customized gradient, higher DAR species that remain bound to the column are removed. In some aspects, the purification process may include a centrifuge cell removal step, optionally a Protein A affinity capture step followed by one or two orthogonal chromatographic polishing steps, a virus filtration step, and a tangential flow filtration step for concentration and formulation.

III. Functional Assays for Characterization of PTK7 Antibody-Drug Conjugates

The present invention further discloses in vitro and in vivo assays to characterize activities of a PTK7 antibody-drug conjugate, including PTK7 binding activity, cellular internalization following binding to PTK7 antigen presented on a cell surface, and targeting to PTK7-expressing cells in a subject. In some aspects of the invention, PTK7 antibody-drug conjugates are characterized by the neutralizing or depleting aspects of the antibody, or antigen-binding fragment thereof. In some aspects of the invention, PTK7 antibody-drug conjugates are characterized by unexpected efficacy of a particular drug as compared to lack of efficacy of an alternate drug. In some aspects of the invention, PTK7 antibody-drug conjugates are characterized as outperforming a standard-of-care therapeutic agent having a same mode of action as the drug.

Techniques for detecting binding of PTK7 antibody-drug conjugates to a PTK7 antigen, or other PTK7 antigen, are known in the art, including for example, BIACORE® assays. Additional representative techniques include centrifugation, affinity chromatography and other immunochemical methods. See e.g., Manson (1992) Immunochemical Protocols, Humana Press, Totowa, N.J., United States of America; Ishikawa (1999) Ultrasensitive and Rapid Enzyme Immunoassay, Elsevier, Amsterdam/New York. Antigen binding assays may be performed using isolated PTK7 antigen or PTK7-expressing cells.

The binding specificity of PTK7 antibody-drug conjugates may be further described by definition of a binding epitope, i.e., identification of residues, including nonadjacent residues that participate in antigen binding, and/or definition of residues that influence antigen binding.

Internalization of PTK7 antibody-drug conjugates by PTK7-expressing cells may be assayed by observing the amount of antibodies or conjugates bound to the surface of the PTK7-expressing cells over time. See e.g., Example 7. Selected PTK7 ligands or their isoforms may be present in a soluble form, and at least some PTK7 likely remains associated with the cell surface thereby allowing for internalization of the antibodies disclosed herein. Accordingly, anti-PTK7 antibody-drug conjugates of the present invention may be internalized by cells that express PTK7. For example, an anti-PTK7 antibody-drug conjugate that binds to PTK7 on the surface of a tumor initiating cell may be internalized by the tumor initiating cell. The number of ADC molecules internalized may be sufficient or adequate to kill a PTK7 expressing cell, especially a PTK7 expressing tumor cell. Depending on the potency of the ADC, in some instances, the uptake of a single ADC molecule into the cell is sufficient to kill the target cell to which the ADC binds. For example, certain toxins are highly potent in killing such that internalization of one molecule of the toxin conjugated to the antibody is sufficient to kill the tumor cell.

Internalization of PTK7 antibodies may be assessed using a functional assay in which cells are incubated with the PTK7 antibody and a secondary antibody Fab fragment that is conjugated to the saporin toxin. Cell viability is then measured by any suitable method, with cellular cytotoxicity indicative of antibody internalization. See Example 7.

In some aspects of the invention, the antibody, or antigen-binding fragment thereof, of the disclosed PTK7 antibody-drug conjugates is an "antagonist" as used in the broadest sense, i.e., any molecule that partially or fully blocks, inhibits, or neutralizes a biological activity of a native target disclosed herein or the transcription or translation thereof. The terms "inhibit" or "neutralize" as used herein with respect to bioactivity of an antibody of the invention mean the ability of the antibody to substantially antagonize, prohibit, prevent, restrain, slow, disrupt, eliminate, stop, reduce or reverse e.g. progression or severity of that which is being inhibited including, but not limited to, a biological activity. For example, in some aspects of the invention, anti-PTK7 antibody-drug conjugate facilitate cell killing upon internalization of the antibody-drug conjugate. For example, a neutralizing antibody or antagonist will preferably diminish a PTK7 function by at least about 20%, 30%, 40%, 50%, 60%, 70%, 80%, 85%, 90%, 95%, 97%, 99% or more.

In other aspects of the invention the anti-PTK7 antibody-drug conjugates of the present invention may be depleting antibodies. The term depleting antibody refers to an antibody that binds to or associates with PTK7 on or near the cell surface and induces, promotes or causes the death or elimination of the cell (e.g., by complement-dependent cytotoxicity or antibody-dependent cellular cytotoxicity). Preferably a depleting antibody will be able to remove, eliminate or kill at least 20%, 30%, 40%, 50%, 60%, 70%, 80%, 85%, 90%, 95%, 97%, or 99% of tumor perpetuating cells in a defined cell population.

Functional assays also include methods for assessing anti-cancer activity of antibody-drug conjugates, for example, an ability to destroy existing cancer cells, or to delay or prevent growth of cancer cells. Cancers targeted by antibody-drug conjugates of the invention include both primary and metastasized tumors and carcinomas of any tissue in a subject, including carcinomas and hematopoietic malignancies such as leukemias and lymphomas.

PTK7 antibody-drug conjugates having growth inhibitory activity can eliminate PTK7-expressing cells or to prevent or reduce proliferation of PTK7-expressing cancer cells. Representative methods for rapid in vitro assessment of cell growth inhibition are described in Jones et al. (2001) J. Immunol. Methods 254:85-98.

PTK7 antibody-drug conjugates may also include an ability to induce cell death, for example, programmed cell death characterized by nuclear DNA degradation, nuclear degeneration and condensation, loss of membrane integrity, and phagocytosis. Representative assays to assess cell are described in Hoves et al. (2003) Methods 31:127-34; Peng et al. (2002) Chin. Med. Sci. J. 17:17-21; Yasuhara et al. (2003) J. Histochem. Cytochem. 51:873-885.

For example, to assess the cytotoxicity of PTK7 antibody-drug conjugates in vitro, PTK7-expressing cancer cells and control cells are cultured in the presence PTK7 antibody-drug conjugates and separately with free drug. The cytotoxicity of each agent is reported as ED50 (ng/ml), which is the amount of drug given as conjugate or as free drug that causes 50% reduction of a cell culture relative to an untreated control. The number of cells in culture is determined using a vital dye (MTS) following drug exposure. See Example 12.

To assess the cytotoxicity of PTK7 antibody-drug conjugates in vivo, tumors are prepared in NOD/SCID, nude (nu/nu) or other strain of immune-compromised mice by subcutaneous injection of various cancer cells. PTK7 antibody-drug conjugates and control compounds may be administered to tumor-bearing mice, for example, by intraperitoneal injection twice a week for two weeks (q4dx4). Measurable therapeutic outcomes include inhibition of tumor cell growth. See Example 13.

Further, the present invention provides for PTK7 antibody-drug conjugates that may deplete, silence, neutralize, eliminate or inhibit growth, propagation or survival of tumor cells, including tumor initiating cells (TIC), and/or associated neoplasia through a variety of mechanisms, including agonizing or antagonizing selected pathways or eliminating specific cells depending, for example, on the anti-PTK7 antibody, or dosing and method of delivery.

As used herein, the term tumor initiating cell (TIC) encompasses both tumor perpetuating cells (TPC; i.e., cancer stem cells or CSC) and highly proliferative tumor progenitor cells (TProg), which together generally include a unique subpopulation (i.e. 0.1-40%) of a bulk tumor or mass. For the purposes of the instant disclosure the terms tumor perpetuating cells and cancer stem cells are equivalent and may be used interchangeably herein. Conversely, TPC differ from TProg in that they can completely recapitulate the composition of tumor cells existing within a tumor and have unlimited self-renewal capacity as demonstrated by serial transplantation (two or more passages through mice) of low numbers of isolated cells. As used herein, the term "tumor initiating cell" also refers to cancer stem cells of various hematologic malignancies, which are not characterized by a tumor per se.

The present invention provides PTK7 antibody-drug conjugates that target tumor initiating cells (TIC), and especially tumor perpetuating cells (TPC), thereby facilitating the treatment, management or prevention of neoplastic disorders and hyperproliferative disorders. More specifically, specific tumor cell subpopulations express PTK7 and likely modify localized coordination of morphogen signaling important to cancer stem cell self-renewal and cell survival. Thus, PTK7 antibody-drug conjugates may be used to reduce the frequency of TICs upon administration to a subject. The reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some aspects of the invention, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to exert effects on the tumor environment or other cells, in turn allows for the more effective treatment of PTK7-associated disorders by inhibiting tumorigenesis, tumor maintenance and/or metastasis and recurrence.

Among the methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. It is also possible to determine reduction of frequency values through well-known flow cytometric or immunohistochemical means. As to all the aforementioned methods see, for example, Dylla et al. 2008, PMCID: PMC2413402 & Hoey et al. 2009, PMID: 19664991, each of which is incorporated herein by reference in its entirety. Other methods compatible with the instant invention that may be used to calculate tumor initiating cell frequency, include quantifiable flow cytometric techniques and immunohistochemical staining procedures.

Using any of the above-referenced methods it is then possible to quantify the reduction in frequency of TIC (or the TPC therein) provided by the disclosed PTK7 antibody-drug conjugates in accordance with the teachings herein. In some instances, the PTK7 antibody-drug conjugates of the instant invention may reduce the frequency of TIC (by a variety of mechanisms noted above, including elimination, induced differentiation, niche disruption, silencing, etc.) by 10%, 15%, 20%, 25%, 30% or even by 35%. In other aspects of the invention, the reduction in frequency of TIC may be on the order of 40%, 45%, 50%, 55%, 60% or 65%. In certain aspects of the invention, the disclosed compounds my reduce the frequency of TIC by 70%, 75%, 80%, 85%, 90% or even 95%. It will be appreciated that any reduction of the frequency of the TIC likely results in a corresponding reduction in the tumorigenicity, persistence, recurrence and aggressiveness of the neoplasia.

Amassing evidence supports the hypothesis that tumor growth, resistance to therapy, and disorder relapse are controlled by TPC. The frequency of TPC may vary in a tumor type or between patients with the same tumor type as a product of disorder stage and/or degree of differentiation within the tumor. TPC can be identified and enriched using panels of cell surface markers that often overlap in their expression among patients with certain types of cancer. TPC are best defined by their functional ability to initiate tumors upon serial transplantation, whereas non-tumorigenic (NTG) cells are devoid of this capacity. Solid tumor cells enriched for their unique tumor initiating capacity were first identified in breast cancer; however, breast cancer includes a spectrum of malignancies. To date, the scientific community has failed to associate specific TPC identities with particular disorder subtypes, which may underlie discrepant results both across and within groups and may also increase the likelihood of failed translation to the clinic.

The present invention provides a combination of new cell surface makers that improve the enrichment of TPC. In a particular aspect, the invention provides a combination of new cell surface makers that facilitate the enrichment of triple negative breast cancer (TNBC) TPC. The present invention further provides for the identification of PTK7 as a novel TPC-associated therapeutic target in TNBC; the expression level of which is significantly higher than in other breast cancer subtypes and normal tissue.

The pharmacokinetics of PTK7 antibody-drug conjugates can be evaluated and compared to the pharmacokinetics of unconjugated antibody in various animals. For example, this can be done following a single intravenous bolus administration in female NOD/SCID, nude (nu/nu) or other strain of immune-compromised mice, male Sprague-Dawley rats, and female cynomolgus monkeys. Pharmacokinetics of PTK7 antibody-drug conjugates are generally characterized by low clearance, low volume of distribution, and long apparent terminal half-life in various species. The serum concentrations of unconjugated auristatin derivatives are expected to be below the quantification limit. The toxicity profile for these conjugates in single-dose toxicity ranging studies is expected to be similar to that obtained for other antibody-drug conjugates at comparable doses.

An antibody, antibody-drug conjugate or other agent which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., breast, ovarian, colorectal, prostate, liver and lung. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or U.S. Pat. No. 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., PNAS (USA), 95:652-656 (1998).

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163-171 (1997), may be performed.

"Human effector cells" are leukocytes that express one or more FcRs and perform effector functions. The cells may express FcγRIII and carry out antigen-dependent cell-mediated cytotoxicity (ADCC) effector function. Examples of human leukocytes that mediate ADCC include but are not limited to peripheral blood mononuclear cells (PBMC), natural killer (NK) cells, monocytes, macrophages, eosinophils, and neutrophils, with PBMCs and NK cells being preferred. Antibodies that have ADCC activity are typically of the IgG1 or IgG3 isotype. Such ADCC-mediating antibodies can also be made by engineering a variable region from a non-ADCC antibody or variable region fragment to an IgG1 or IgG3 isotype constant region.

IV. Uses of PTK7 Antibody-Drug Conjugates

The antibodies and the antibody drug-conjugates of the present invention are useful in various applications including, but are not limited to, therapeutic treatment methods and diagnostic treatment methods.

IV.A. In Vitro Applications

The present invention provides in vitro methods using PTK7 antibody-drug conjugates. For example, the disclosed antibodies may be used, either alone or in combination with cytotoxic agents or other drugs to specifically bind PTK7-positive cancer cells to deplete such cells from a cell sample. Methods are also provided for inducing apoptosis and/or inhibition of cell proliferation via contacting PTK7-expressing cells with a PTK7 antibody-drug conjugate. Representative in vitro methods are described herein above under the heading of "Functional Assays for Characterization of PTK7 antibody-drug conjugates."

PTK7 antibody-drug conjugates of the invention also have utility in the detection of PTK7-positive cells in vitro based on their ability to specifically bind PTK7 antigen. A method for detecting PTK7-expressing cells may include: (a) preparing a biological sample having cells; (b) contacting a PTK7 antibody-drug conjugates with the biological sample in vitro, wherein the drug is a detectable label; and (c) detecting binding the PTK7 antibody-drug conjugates.

PTK7 antibody-drug conjugates disclosed herein are also useful for reducing the frequency of tumor initiating cells in a tumor sample. For example, the method can include the steps contacting in vitro a tumor cell population, wherein the population comprises tumor initiating cells and tumor cells other than tumor initiating cells, with a PTK7 antibody-drug conjugate; whereby the percentage of tumor initiating cells in the cell population is reduced. As used herein, the term "tumor initiating cell" also refers to cancer stem cells of various hematologic malignancies, which are not characterized by a tumor per se. Representative tumor samples include any biological or clinical sample which contains tumor cells, for example, a tissue sample, a biopsy, a blood sample, plasma, saliva, urine, seminal fluid, etc.

IV.B. Therapeutic Applications

PTK7 associated disorders or conditions include but are not limited to mesothelioma, hepatobiliary (hepatic and biliary duct), hepatocellular carcinoma, a primary or secondary CNS tumor, a primary or secondary brain tumor, lung cancer (NSCLC and SCLC), bone cancer, pancreatic cancer, skin cancer, cancer of the head or neck, melanoma, ovarian cancer, colon cancer, rectal cancer, cancer of the anal region, stomach cancer, gastrointestinal (such as gastric, colorectal, and duodenal cancers), breast cancer (such as triple-negative breast cancer (TNBC), progesterone-receptor positive breast cancer (PR+), estrogen-receptor positive breast cancer (ER+) and double positive breast cancer), uterine cancer, carcinoma of the fallopian tubes, carcinoma of the endometrium, carcinoma of the cervix, carcinoma of the vagina, carcinoma of the vulva, Hodgkin's Disease, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, leukemias (such as acute myeloid leukemia (AML) and acute lymphoblastic leukemia (ALL), chronic myeloid leukemia), lymphocytic lymphomas, cancer of the bladder, cancer of the kidney or ureter, renal cell carcinoma, carcinoma of the renal pelvis, neoplasms of the central nervous system (CNS), primary CNS lymphoma, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, and all cancers represented by the PTK7-expressing cell types shown in Tables 8 and 9 or a combination of one or more of the cancers disclosed herein.

The phrase "effective amount", "effective dosage" or as used herein refers to an amount of a drug, compound or pharmaceutical composition necessary to achieve any one or more beneficial or desired therapeutic results. For prophylactic use, beneficial or desired results include eliminating or reducing the risk, lessening the severity, or delaying the outset of the disorder, including biochemical, histological and/or behavioral symptoms of the disorder, its complications and intermediate pathological phenotypes presenting during development of the disorder. For therapeutic use, beneficial or desired results include clinical results such as reducing incidence or amelioration of one or more symptoms of various PTK7 associated disorders decreasing the dose of other medications required to treat the disorder, enhancing the effect of another medication, and/or delaying the progression of the PTK7 associated disorder of patients.

In one aspect, the invention provides a method for treating a disorder associated with PTK7 expression in a subject. The invention also provides an antibody-drug conjugate, or a pharmaceutical composition, as described herein, for use in a method for treating a disorder associated with PTK7 expression in a subject. The invention further provides the use of an antibody-drug conjugate, or a pharmaceutical composition, as described herein, in the manufacture of a medicament for treating a disorder associated with PTK7 expression in a subject.

In some aspects of the invention, the method of treating a disorder associated with PTK7 expression in a subject includes administering to the subject in need thereof an effective amount of a composition (e.g., pharmaceutical composition) having the PTK7 antibody-drug conjugates as described herein. The disorders associated with PTK7 expression include, but are not limited to, abnormal PTK7 expression, altered or aberrant PTK7 expression, PTK7 overexpression, and a proliferative disorder (e.g., cancer).

In one aspect of the invention, the disorder is cancer, including, but not limited to, mesothelioma, hepatobiliary (hepatic and biliary duct), hepatocellular carcinoma, a primary or secondary CNS tumor, a primary or secondary brain tumor, lung cancer (NSCLC and SCLC), bone cancer, pancreatic cancer, skin cancer, cancer of the head or neck, melanoma, ovarian cancer, colon cancer, rectal cancer, cancer of the anal region, stomach cancer, gastrointestinal (such as gastric, colorectal, and duodenal cancers), breast cancer (such as triple-negative breast cancer (TNBC), progesterone-receptor positive breast cancer (PR+), estrogen-receptor positive breast cancer (ER+) and double positive breast cancer), uterine cancer, carcinoma of the fallopian tubes, carcinoma of the endometrium, carcinoma of the cervix, carcinoma of the vagina, carcinoma of the vulva, Hodgkin's Disease, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, leukemias (such as acute myeloid leukemia (AML) and acute lymphoblastic leukemia (ALL), chronic myeloid leukemia), lymphocytic lymphomas, cancer of the bladder, cancer of the kidney or ureter, renal cell carcinoma, carcinoma of the renal pelvis, neoplasms of the central nervous system (CNS), primary CNS lymphoma, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, and all cancers represented by the PTK7-expressing cell types shown in Tables 8 and 9 or a combination of one or more of the cancers disclosed herein.

In another embodiment, cancers suitable for targeting using the anti-PTK7 antibody-drug conjugate include PTK7-expressing primary and metastatic cancers, such as breast cancer (such as triple-negative breast cancer (TNBC), progesterone-receptor positive breast cancer (PR+), estrogen-receptor positive breast cancer (ER+) and double positive breast cancer); ovarian cancer; colorectal cancer; esophageal cancer; gastric cancer; melanoma; sarcoma; kidney cancer; pancreatic cancer; prostate cancer; liver cancer, such as hepatocellular carcinoma (HCC); and lung cancer, such as non-small cell lung cancer (NSCLC) and small cell lung cancer (SCLC).

In a more specific embodiment, cancers suitable for targeting using anti-PTK7 antibody-drug conjugates include PTK7-expressing primary and metastatic cancers, such as breast cancer (such as triple-negative breast cancer (TNBC), progesterone-receptor positive breast cancer (PR+), estrogen-receptor positive breast cancer (ER+) and double positive breast cancer) NSCLC, prostate cancer and esophageal cancer. In a more specific embodiment, cancers suitable for targeting using anti-PTK7 antibody-drug conjugates include PTK7-expressing primary and metastatic cancers, such as breast cancer (such as triple-negative breast cancer (TNBC)) and NSCLC.

In some aspects of the invention, provided is a method of inhibiting tumor growth or progression in a subject who has a PTK7 expressing tumor, including administering to the subject in need thereof an effective amount of a composition having the PTK7 antibody-drug conjugates as described herein. In other aspects of the invention, provided is a method of inhibiting metastasis of PTK7 expressing cancer cells in a subject, including administering to the subject in need thereof an effective amount of a composition having the PTK7 antibody-drug conjugates as described herein. In other aspects of the invention, provided is a method of inducing regression of a PTK7 expressing tumor regression in a subject, including administering to the subject in need thereof an effective amount of a composition having the PTK7 antibody-drug conjugates as described herein. In other aspects, the invention provides an antibody-drug conjugate, or a pharmaceutical composition, as described herein, for use in a method as described above. In other aspects the invention provides the use of an antibody-drug conjugate, or a pharmaceutical composition, as described herein, in the manufacture of a medicament for use in the methods described above.

Thus, patients to be treated with PTK7 antibody-drug conjugates of the invention may be selected based on biomarker expression, including but not limited to mRNA (qPCR) of bulk tumor samples and elevated expression of PTK7 antigen which results in a patient population selected for enriched target expression rather than tumor origin or histology. Target expression can be measured as a function of the number of cells staining combined with the intensity of the cells staining. For example, classification of high expression of PTK7 includes those patients with greater than 30% (i.e., 40%, 50% or 60%) of the cells tested by immunohistochemical staining positive for PTK7 at a level of 3+ (on a scale of 1 to 4), while moderate expression of the PTK7 can include those patients with greater than 20% of the cell cells staining at 1+ to 2+. Target expression can also be measured by detecting PTK7 expression on tumor initiating cells (TIC) as described herein.

Biomarkers other than expression of PTK7 can be also used for patient selection, including characterization of the tumor based on multi-drug resistance (MDR), for example. Nearly 50% of human cancers are either completely resistant to chemotherapy or respond only transiently, after which they are no longer affected by commonly used anticancer drugs. This phenomenon is referred to as MDR and is inherently expressed by some tumor types, while others acquire MDR after exposure to chemotherapy treatment. The drug efflux pump P-glycoprotein mediates a majority of the MDR associated with cytotoxic chemotherapeutics. Phenotypic and functional analysis of MDR mechanisms present in cancer patient tumor specimens can be conducted in order to relate specific MDR mechanism(s) with resistance to chemotherapy in specific tumor types.

Cancer growth or abnormal proliferation refers to any one of a number of indices that suggest change within cells to a more developed cancer form or disease state. Inhibition of growth of cancer cells or cells of a non-neoplastic proliferative disorder may be assayed by methods known in the art, such as delayed tumor growth and inhibition of metastasis. Other indices for measuring inhibition of cancer growth include a decrease in cancer cell survival, a decrease in tumor volume or morphology (for example, as determined using computed tomographic (CT), sonography, or other imaging method), destruction of tumor vasculature, improved performance in delayed hypersensitivity skin test, an increase in the activity of cytolytic T-lymphocytes, and a decrease in levels of tumor-specific antigens.

Desired outcomes of the disclosed therapeutic methods are generally quantifiable measures as compared to a control or baseline measurement. As used herein, relative terms such as "improve," "increase," or "reduce" indicate values relative to a control, such as a measurement in the same individual prior to initiation of treatment described herein, or a measurement in a control individual (or multiple control individuals) in the absence of the treatment described herein. A representative control individual is an individual afflicted with the same form of hyperproliferative disorder as the individual being treated, who is about the same age as the individual being treated (to ensure that the stages of the disorder in the treated individual and the control individual are comparable.

Changes or improvements in response to therapy are generally statistically significant. As used herein, the term "significance" or "significant" relates to a statistical analysis of the probability that there is a non-random association between two or more entities. To determine whether or not a relationship is "significant" or has "significance," statistical manipulations of the data can be "p-value." Those p-values that fall below a user-defined cut-off point are regarded as significant. A p-value less than or equal to 0.1, less than 0.05, less than 0.01, less than 0.005, or less than 0.001 may be regarded as significant.

As described herein above under the heading "III. Functional Assays for Characterization of PTK7 Antibody-Drug Conjugates," the present invention also provides methods for targeting tumor initiating cells. More particularly, PTK7 antibody-drug conjugates of the invention may deplete, silence, neutralize, eliminate or inhibit growth, propagation or survival of tumor cells, including tumor initiating cells.

Thus, PTK7 antibody-drug conjugates disclosed herein are also useful for reducing the frequency of tumor initiating cells in a tumor sample. For example, the method can include the steps contacting a tumor cell population, wherein the population comprises tumor initiating cells and tumor cells other than tumor initiating cells, with a PTK7 antibody-drug conjugate; whereby the percentage of tumor initiating cells in the cell population is reduced. As used herein, the term "tumor initiating cell" also refers to cancer stem cells of various hematologic malignancies, which are not characterized by a tumor per se. The contacting step may be performed in vitro, wherein the tumor cell population is contained in a biological sample, as described herein above. Alternatively, the contacting step may be performed in vivo as occurs following administration of a PTK7 antibody-drug conjugate to a subject.

IV.C. In Vivo Detection and Diagnosis

In another aspect, provided is a method of detecting, diagnosing, and/or monitoring a disorder associated with PTK7 expression. For example, the PTK7 antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

Following administration of a PTK7 antibody-drug conjugate to a subject, wherein the drug is a detectable label, and after a time sufficient for binding, the biodistribution of PTK7-expressing cells bound by the antibody may be visualized. The disclosed diagnostic methods may be used in combination with treatment methods. In addition, PTK7 antibody-drug conjugates of the invention may be administered for the dual purpose of detection and therapy.

Representative non-invasive detection methods include scintigraphy (e.g., SPECT (Single Photon Emission Computed Tomography), PET (Positron Emission Tomography), gamma camera imaging, and rectilinear scanning), magnetic resonance imaging (e.g., convention magnetic resonance imaging, magnetization transfer imaging (MTI), proton magnetic resonance spectroscopy (MRS), diffusion-weighted imaging (DWI) and functional MR imaging (fMRI)), and ultrasound.

IV.D. Formulation

The present invention further provides pharmaceutical compositions including any of the PTK7 antibody-drug conjugates disclosed herein and a pharmaceutically acceptable carrier. Further, the compositions can include more than one PTK7 antibody or PTK7 antibody-drug conjugate (e.g., a mixture of PTK7 antibodies that recognize different epitopes of PTK7). Other exemplary compositions include more than one PTK7 antibody or PTK7 antibody-drug conjugate that recognize the same epitope(s), or different species of PTK7 antibodies or PTK7 antibody-drug conjugate that bind to different epitopes of PTK7 (e.g., human PTK7).

The composition used in the present invention can further include pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). "Pharmaceutically acceptable salt" as used herein refers to pharmaceutically acceptable organic or inorganic salts of a molecule or macromolecule. Pharmaceutically acceptable excipients are further described herein.

Various formulations of the PTK7 antibody or the PTK7 antibody-drug conjugate may be used for administration. In some aspects of the invention, the PTK7 antibody or the PTK7 antibody-drug conjugate may be administered neat. The PTK7 antibody or the PTK7 antibody-drug conjugate and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some aspects of the invention, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Therapeutic formulations of the PTK7 antibody or the PTK7 antibody-drug conjugate used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the PTK7 antibody or the PTK7 antibody-drug conjugate are prepared by methods known in the art, such as described in Eppstein, et al., Proc. Natl. Acad. Sci. USA 82:3688-3692 (1985); Hwang, et al., Proc. Natl Acad. Sci. USA 77:4030-4034 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition including phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic PTK7 antibody or PTK7 antibody-drug conjugate compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can include an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. TWEEN™ 20, 40, 60, 80 or 85) and other sorbitans (e.g. Span™ 20, 40, 60, 80 or 85). Compositions with a surface-active agent will conveniently include between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPO-SYN™, INFONUTROL™, LIPOFUNDIN™ and LIPIPH-YSAN™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can include fat droplets between 0.1 and 1.0 µm, particularly 0.1 and 0.5 µm, and have a pH in the range of 5.5 to 8.0.

The emulsion compositions can be those prepared by mixing a PTK7 antibody or a PTK7 antibody-drug conjugate with INTRALIPID™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some aspects of the invention, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The invention also provides kits for use in the instant methods. Kits of the invention include one or more containers including the PTK7 antibody or the PTK7 antibody-drug conjugate as described herein and instructions for use in accordance with any of the methods of the invention described herein. Generally, these instructions include a description of administration of the PTK7 antibody or the PTK7 antibody-drug conjugate for the above described therapeutic treatments.

The instructions relating to the use of the PTK7 antibodies or the PTK7 antibody conjugates as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a PTK7 antibody or PTK7 antibody-drug conjugate. The container may further include a second pharmaceutically active agent.

Kits may optionally provide additional components such as buffers and interpretive information. Normally, the kit includes a container and a label or package insert(s) on or associated with the container.

IV.E. Dose and Administration

For in vitro and in vivo applications, PTK7 antibody-drug conjugates are provided or administered in an effective dosage. In a clinical context, an effective dosage of drug, compound, or pharmaceutical composition is an amount sufficient to accomplish prophylactic or therapeutic treatment either directly or indirectly. An effective dosage can be administered in one or more administrations. An effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. For detection of PTK7-positive cells using the disclosed PTK7 antibody-drug conjugates, a detectable amount of a composition of the invention is administered to a subject, i.e., a dose of the conjugate such that the presence of the conjugate may be determined in vitro or in vivo.

For example, when administered to a cancer-bearing subject, an effective amount includes an amount sufficient to elicit anti-cancer activity, including cancer cell cytolysis, inhibition of cancer cell proliferation, induction of cancer cell apoptosis, reduction of cancer cell antigens, delayed tumor growth, and/or inhibition of metastasis. Tumor shrinkage is well accepted as a clinical surrogate marker for efficacy. Another well accepted marker for efficacy is progression-free survival.

The PTK7 antibody or the PTK7 antibody-drug conjugates can be administered to an individual via any suitable route. It should be understood by persons skilled in the art that the examples described herein are not intended to be limiting but to be illustrative of the techniques available. Accordingly, in some aspects of the invention, the PTK7 antibody or the PTK7 antibody conjugate is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the PTK7 antibody or the PTK7 antibody-drug conjugate can be aerosolized using a fluorocarbon formulation and a metered dose inhaler, or inhaled as a lyophilized and milled powder.

In some aspects of the invention, the PTK7 antibody or the PTK7 antibody-drug conjugate is administered via site-specific or targeted local delivery techniques. Examples of site-specific or targeted local delivery techniques include various implantable depot sources of the PTK7 antibody or the PTK7 antibody-drug conjugate or local delivery catheters, such as infusion catheters, indwelling catheters, or needle catheters, synthetic grafts, adventitial wraps, shunts and stents or other implantable devices, site specific carriers, direct injection, or direct application. See, e.g. PCT International Publication No. WO 2000/53211 and U.S. Pat. No. 5,981,568.

PTK7 antibodies or the PTK7 antibody-drug conjugates as described herein can be administered using any suitable method, including by injection (e.g., intraperitoneally, intravenously, subcutaneously, intramuscularly, etc.). The PTK7 antibody or the PTK7 antibody-drug conjugate can also be administered via inhalation, as described herein. Generally, for administration of a PTK7 antibody and a PTK7 antibody-drug conjugate, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the disorder, the treatment is sustained until a desired suppression of symptoms occurs or until sufficient therapeutic levels are achieved, for example, to inhibit or delay tumor growth/progression or metastases of cancer cells. An exemplary dosing regimen includes administering an initial dose of about 2 mg/kg, followed by a weekly maintenance dose of about 1 mg/kg of the PTK7 antibody or PTK7 antibody-drug conjugate, or followed by a maintenance dose of about 1 mg/kg every other week. Other exemplary dosing regimens include administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some aspects of the invention, dosing from one to four times a week is contemplated. In other aspects, dosing once a month or once every other month or every three months is contemplated, as well as weekly, bi-weekly and every three weeks. The progress of this therapy may be easily monitored by conventional techniques and assays. The dosing regimen (including the PTK7 antibody or the PTK7 antibody-drug conjugate used) can vary over time.

For the purpose of the present invention, the appropriate dosage of a PTK7 antibody or a PTK7 antibody-drug conjugate will depend on the PTK7 antibody or the PTK7 antibody-drug conjugate (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. The clinician may administer a PTK7 antibody or a PTK7 antibody-drug conjugate until a dosage is reached that achieves the desired result and beyond. Dose and/or frequency can vary over course of treatment, but may stay constant as well. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of PTK7 antibodies or PTK7 antibody-drug conjugates may be appropriate. Various formulations and devices for achieving sustained release are known in the art.

In some aspects of the invention, dosages for a PTK7 antibody or a PTK7 antibody-drug conjugate may be determined empirically in individuals who have been given one or more administration(s) of the PTK7 antibody or the PTK7 antibody-drug conjugate. Individuals are given incremental dosages of a PTK7 antibody or a PTK7 antibody-drug conjugate. To assess efficacy, an indicator of the disorder can be followed.

Administration of a PTK7 antibody or a PTK7 antibody-drug conjugate in accordance with the method in the present invention can be continuous or intermittent, depending, for example, upon the recipient's physiological disorder, whether the purpose of the administration is therapeutic or prophylactic, and other factors known to skilled practitioners. The administration of a PTK7 antibody or a PTK7 antibody-drug conjugate may be essentially continuous over a preselected period of time or may be in a series of spaced doses.

IV.F. Combination Therapies

In some aspects of the invention, the methods described herein further include a step of treating a subject with an additional form of therapy. In some aspects, the additional form of therapy is an additional anti-cancer therapy including, but not limited to, chemotherapy, radiation, surgery, hormone therapy, and/or additional immunotherapy.

The disclosed PTK7 antibody-drug conjugates may be administered as an initial treatment, or for treatment of disorders that are unresponsive to conventional therapies. In addition, the PTK7 antibody-drug conjugates may be used in combination with other therapies (e.g., surgical excision, radiation, additional anti-cancer drugs etc.) to thereby elicit additive or potentiated therapeutic effects and/or reduce hepatocytotoxicity of some anti-cancer agents. PTK7 antibody-drug conjugates of the invention may be co-administered or co-formulated with additional agents, or formulated for consecutive administration with additional agents in any order.

Representative agents useful for combination therapy include any of the drugs described herein above as useful for preparation of PTK7 antibody-drug conjugates under the subheading "Drugs." PTK7 antibody-drug conjugates of the invention may also be used in combination with other therapeutic antibodies and antibody-drug conjugates, including anti-PTK7 antibodies other than the disclosed anti-PTK7 antibodies, as well as antibodies and conjugates targeting a different antigen. Representative antibodies, which may be used alone or as an antibody-drug conjugate, include anti-5T4 antibodies (e.g., A1, A2, and A3), anti-CD19 antibodies, anti-CD20 antibodies (e.g., RITUXAN®, ZEVALIN®, BEXXAR®), anti-CD22 antibodies, anti-CD33 antibodies (e.g., MYLOTARG®), anti-CD33 antibody-drug conjugates, anti-Lewis Y antibodies (e.g., Hu3S193, Mthu3S193, AGmthu3S193), anti-HER-2 antibodies (e.g., HERCEPTIN® (trastuzumab), MDX-210, OMNITARG® (pertuzumab, rhuMAb 2C4)), anti-CD52 antibodies (e.g., CAMPATH®), anti-EGFR antibodies (e.g., ERBITUX® (cetuximab), ABX-EGF (panitumumab)), anti-VEGF antibodies (e.g., AVASTIN® (bevacizumab)), anti-DNA/histone complex antibodies (e.g., ch-TNT-1/b), anti-CEA antibodies (e.g., CEA-Cide, YMB-1003) hLM609, anti-CD47 antibodies (e.g., 6H9), anti-VEGFR2 (or kinase insert domain-containing receptor, KDR) antibodies (e.g., IMC-1C11), anti-Ep-CAM antibodies (e.g., ING-1), anti-FAP antibodies (e.g., sibrotuzumab), anti-DR4 antibodies (e.g., TRAIL-R), anti-progesterone receptor antibodies (e.g., 2C5), anti-CA19.9 antibodies (e.g., GIVAREX®) and anti-fibrin antibodies (e.g., MH-1).

The disclosed PTK7 antibody-drug conjugates may also be administered together with one or more combinations of cytotoxic agents as part of a treatment regimen. Useful cytotoxic preparations for this purpose include CHOPP (cyclophosphamide, doxorubicin, vincristine, prednisone and procarbazine); CHOP (cyclophosphamide, doxorubicin, vincristine, and prednisone); COP (cyclophosphamide, vincristine, prednisone); CAP-BOP (cyclophosphamide, doxorubicin, procarbazine, bleomycin, vincristine and prednisone); m-BACOD (methotrexate, bleomycin, doxorubicin, cyclophosphamide, vincristine, dexamethasone, and leucovorin; ProMACE-MOPP (prednisone, methotrexate, doxorubicin, cyclophosphamide, etoposide, leukovorin, mechloethamine, vincristine, prednisone and procarbazine); ProMACE-CytaBOM (prednisone, methotrexate, doxorubicin, cyclophosphamide, etoposide, leukovorin, cytarabine, bleomycin and vincristine); MACOP-B (methotrexate, doxorubicin, cyclophosphamide, vincristine, prednisone, bleomycin and leukovorin); MOPP (mechloethamine, vincristine, prednisone and procarbazine); ABVD (adriamycin/doxorubicin, bleomycin, vinblastine and dacarbazine); MOPP (mechloethamine, vincristine, prednisone and procarbazine) alternating with ABV (adriamycin/doxorubicin, bleomycin, vinblastine); MOPP (mechloethamine, vincristine, prednisone and procarbazin) alternating with ABVD (adriamycin/doxorubicin, bleomycin, vinblastine and dacarbazine); ChlVPP (chlorambucil, vinblastine, procarbazine, prednisone); IMVP-16 (ifosfamide, methotrexate, etoposide); MIME (methyl-gag, ifosfamide, methotrexate, etoposide); DHAP (dexamethasone, high-dose cytaribine and cisplatin); ESHAP (etoposide, methylpredisolone, HD cytarabine, and cisplatin); CEPP(B) (cyclophosphamide, etoposide, procarbazine, prednisone and bleomycin); CAMP (lomustine, mitoxantrone, cytarabine and prednisone); and CVP-1 (cyclophosphamide, vincristine and prednisone); DHAP (cisplatin, high-dose cytarabine and dexamethasone); CAP (cyclophosphamide, doxorubicin, cisplatin); PV (cisplatin, vinblastine or vindesine); CE (carboplatin, etoposide); EP (etoposide, cisplatin); MVP (mitomycin, vinblastine or vindesine, cisplatin); PFL (cisplatin, 5-fluorouracil, leucovorin); IM (ifosfamide, mitomycin); IE (ifosfamide, etoposide); IP (ifosfamide, cisplatin); MIP (mitomycin, ifosfamide, cisplatin); ICE (ifosfamide, carboplatin, etoposide); PIE (cisplatin, ifosfamide, etoposide); Viorelbine and cisplatin; Carboplatin and paclitaxel; CAV (cyclophosphamide, doxorubicin, vincristine); CAE (cyclophosphamide, doxorubicin, etoposide); CAVE (cyclophosphamide, doxorubicin, vincristine, etoposide); EP (etoposide, cisplatin); and CMCcV (cyclophosphamide, methotrexate, lomustine, vincristine).

PTK7 antibody-drug conjugates may be used in combination with systemic anti-cancer drugs, such as epithilones (BMS-247550, Epo-906), reformulations of taxanes (Abraxane, Xyotax), microtubulin inhibitors (MST-997, TTI-237), or with targeted cytotoxins such as CMD-193 and SGN-15. Additional useful anti-cancer agents include TAXOTERE®, TARCEVA®, GEMZAR® (gemcitabine), 5-FU, AVASTIN® ERBITUX®, TROVAX®, anatumomab mafenatox, letrazole, docetaxel, and anthracyclines.

For combination therapies, a PTK7 antibody-drug conjugate and/or one or more additional therapeutic or diagnostic agents are administered within any time frame suitable for performance of the intended therapy or diagnosis. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s). The administration of a PTK7 antibody-drug conjugate in combination with a second therapeutic agent preferably elicits a greater effect than administration of either alone.

In some aspects of the invention, the additional form of therapy includes administering one or more therapeutic agent in addition to the PTK7 antibodies or the PTK7 antibody-drug conjugates as described herein. The therapeutic agents include, but are not limited to, a second antibody (e.g., an anti-VEGF antibody, an anti-HER2 antibody, anti-CD25 antibody, and/or an anti-CD20 antibody), an angiogenesis inhibitor, a cytotoxic agent, an anti-inflammatory agent (e.g., paclitaxel, docetaxel, cisplatin, doxorubicin, prednisone, mitomycin, progesterone, tamoxifen, or fluorouracil).

In some aspects of the invention, more than one PTK7 antibody or PTK7 antibody-drug conjugate may be present. At least one, at least two, at least three, at least four, at least five different or more PTK7 antibody or PTK7 antibody-drug conjugate can be present. Generally, those PTK7 antibodies or PTK7 antibody-drug conjugates may have complementary activities that do not adversely affect each other. For example, one or more of the following PTK7 antibody may be used: a first PTK7 antibody directed to one epitope on PTK7 and a second PTK7 antibody directed to a different epitope on PTK7.

The disclosed combination therapies may elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

As used throughout the detailed description, the term "about" means a value+/−1% of the value following the term "about," unless otherwise indicated.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

Generation and Humanization of Anti-PTK7 Antibodies

PTK-7 antibodies in the form of murine antibodies were produced in accordance with procedures known in the art and as described in PCT International Publication No. WO 2012/112943. Murine antibodies generated were humanized using complementarity determining region (CDR) grafting. Human frameworks for heavy and light chains were selected based on sequence and structure similarity with respect to functional human germline genes. Structural similarity was evaluated by comparing the mouse canonical CDR structure to human candidates with the same canonical structures as described in Chothia et al. (supra).

More particularly, murine antibodies designated herein mu23, mu24, and mu58 described in PCT International Publication No. WO 2012/112943 were humanized using a computer aided CDR-grafting method (Abysis Database, UCL Business Plc.) and standard molecular engineering techniques to provide humanized mu23, mu24, and mu58, hereinafter hu23, hu24, and hu58, respectively. The human framework regions of the variable regions were selected based on their highest sequence homology to the mouse framework sequence and its canonical structure. For the purposes of the analysis, the assignment of amino acids to each of the CDR domains was in accordance with the Kabat et al. numbering. Several humanized antibody variants were made in order to generate the optimal humanized antibody with the humanized antibodies generally retaining the antigen-binding complementarity determining regions (CDRs) from the mouse hybridoma in association with human framework regions. Hu23, hu24, and hu58 mAbs bound to the human PTK7 antigen with similar affinity to their murine counterparts as measured using the BIACORE® system.

Molecular engineering procedures were conducted using art recognized techniques. Total mRNA was extracted from the hybridomas according to the manufacturer's protocol (TRIZOL® Plus RNA Purification System, Life Technologies). A sequence specific 5' leader sequence primer, designed to amplify each hybridoma, was used in combination with 3' human Cγ1 primer to amplify and clone the variable regions of each humanized antibody. Similarly a 5'Vk leader sequence designed specifically to amplify each of the Vk regions combined with a single reverse primer specific to the human kappa constant region were used to amplify and clone the kappa light chain. The amplified fragments were cloned as chimeric human gamma1/kappa chains and served as a bench mark for each humanized mAb.

From the nucleotide sequence information, data regarding V, D and J gene segments of the heavy and light chains of murine antibodies mu23, mu24, and mu58 were obtained. Based on the sequence data, new primer sets specific to the leader sequence of the Ig VH and Vk chain of the antibodies were designed for cloning of the recombinant monoclonal antibody. Subsequently the V-(D)-J sequences were aligned with mouse Ig germ line sequences.

Heavy chain genes of mu23 were identified as VH3609 (V), DSP2.3 (D) and JH3. The heavy chain genes of mu24 were identified as VHJ558 (V), DSP2.7 (D) and JH4. The heavy chain genes of mu58 were identified as IGHV 4-1 (V), DFL 16.1 (D) and JH4. All three light chains were K class. Light chain genes were identified as IGKVI4-111 and JK5 for the mu23, IGKV3-5 and JK1 for the mu24, and IGKV17-121 and JK4 germ line sequences for mu58. These results are summarized in the Table 2 below.

TABLE 2

| Clone | VH | DH | JH | VL | JL |
|---|---|---|---|---|---|
| mu23 | VH3609 | DSP2.3 | JH3 | IGKVI4-111 | JK5 |
| mu24 | VHJ558 | DSP2.7 | JH4 | IGKV3-5 | JKI |
| mu58 | IGHV4-1 | DFL16.1 | JH4 | IGKV17-121 | JK4 |

The obtained heavy and light chain sequences from all three clones were aligned to the functional human variable region sequences and reviewed for homology and canonical structure. The results of the humanized heavy and light chain analysis are shown below in Tables 3 and 4 respectively, for the humanized anti-PTK7 antibodies hu23, hu24, and hu58.

TABLE 3

| Hu-manized mAb | human VH | human DH | human JH | % homology to human germ line sequence | % homology to mouse germ line sequence |
|---|---|---|---|---|---|
| hu23 | VH2-5 | IGHD5-5 | JH4 | 91 | 81 |
| hu24 | VH1-3 | IGHD4-23 | JH6 | 82 | 82 |
| hu58 | VH3-7 | IGHD2-8 | JH6 | 86 | 88 |

TABLE 4

| Hu-manized mAb | human VK | human JK | % homology to human germ line sequence | % homology to mouse sequence |
|---|---|---|---|---|
| hu23 | O8 | JK5 | 91 | 81 |
| hu24 | L6 | JK1 | 82 | 82 |
| hu58 | B2 | JK4 | 86 | 88 |

The amino acid sequences and associated nucleic acid sequence of hu23, hu24 and hu58 are shown above in Table 1 above. The amino acid sequences of the VH region for hu23, hu24, and hu58 are shown in SEQ ID NO: 1, SEQ ID NO: 25, and SEQ ID NO: 49 respectively, with the corresponding nucleic acid sequences set forth in SEQ ID NO: 2, SEQ ID NO: 26, and SEQ ID NO: 50 respectively. The amino acid sequence of the kappa VL region of hu23, hu24, and hu58 are shown in SEQ ID NO: 15, SEQ ID NO: 39, and SEQ ID NO: 63 respectively, with the corresponding nucleic acid sequences set forth in SEQ ID NO: 16, SEQ ID NO: 40, and SEQ ID NO: 64 respectively.

As demonstrated in the Examples below each of the aforementioned humanized antibodies functions as an effective anti-PTK7 antibody-drug conjugate in accordance with the teachings herein.

Example 2

Expression of Humanized Antibodies

The anti-PTK7 antibodies hu23, hu24, and hu58 were expressed and isolated using art recognized techniques and as described in PCT International Publication No. WO 2012/112943. Synthetic humanized variable DNA fragments (Integrated DNA Technologies) of the heavy chains were cloned into human IgG 1 expression vectors. The variable light chain fragments were cloned into human C-kappa expression vectors. Each antibody was expressed by co-transfection of the corresponding heavy and the light chain into CHO cells.

More particularly, for antibody production, directional cloning of the humanized variable gene PCR products into human immunoglobulin expression vectors was undertaken. All primers used in Ig gene-specific PCRs included restriction sites, AgeI and XhoI for IgH, XmaI and DraIII for Igk, which allowed direct cloning into expression vectors containing the human IgG 1, and Igk constant regions, respectively. In brief, PCR products were purified with Qiaquick PCR purification kit (Qiagen, Inc.) followed by digestion with AgeI and XhoI (IgH), XmaI and DraIII (Igk), respectively. Digested PCR products were purified prior to ligation into expression vectors. Ligation reactions were performed in a total volume of 10 μL with 200U T4-DNA Ligase (New England Biolabs), 7.5 μL of digested and purified gene-specific PCR product and 25 ng linearized vector DNA. Competent *E. coli* DH10B bacteria (Life Technologies) were transformed via heat shock at 42° C. with 3 μL ligation product and plated onto ampicillin plates (100 μg/mL). The AgeI-EcoRI fragment of the VH region was than inserted into the same sites of pEE6.4HuIgG1 (Lonza AG) expression vector while the synthetic XmaI-DraIII VK insert was cloned into the XmaI-DraIII sites of the respective pEE12.4Hu-Kappa expression vector.

Cells producing humanized antibodies were generated by transfection of HEK 293 cells with the appropriate plasmids using 293fectin. Plasmid DNA was purified with QIAprep Spin columns (Qiagen). Human embryonic kidney (HEK) 293T (ATCC No CRL-11268) cells were cultured in 150 mm plates (Falcon, Becton Dickinson) under standard conditions in Dulbecco's Modified Eagle's Medium (DMEM) supplemented with 10% heat inactivated FCS, 100 μg|mL streptomycin, 100 U/mL penicillin G (all from Life Technologies).

For transient transfections cells were grown to 80% confluency. Equal amounts of IgH and corresponding IgL chain vector DNA (12.5 μg of each vector DNA) was added to 1.5 mL OptiMEM mixed with 50 μL HEK 293 transfection reagent in 1.5 mL opti-MEM. The mix was incubated for 30 minutes at room temperature and distributed evenly to the culture plate. Supernatants were harvested three days after transfection, replaced by 20 mL of fresh DMEM supplemented with 10% FBS and harvested again at day 6 after transfection. Culture supernatants were cleared from cell debris by centrifugation at 800×g for 10 minutes and stored at 4° C. Recombinant chimeric and humanized antibodies were purified with Protein G beads (GE Healthcare). Further purification of hu23 and hu24 by ion exchange chromatography was required in order to achieve consistent, reproducible bioconjugation to vc0101 and mc8261. Without the additional purification step, the efficiency of thiol reduction and thus the resulting ADC drug-to-antibody ratio (DAR), described in Example 10, fluctuated dramatically and unpredictably. The requirement for the additional purification was not anticipated but was determined empirically.

Example 3

Characterization of hu24 Binding

A comparison of the chimeric and humanized clone 24 mAbs was determined by SPR using a Biacore™ 2000 (GE Healthcare). An antihuman antibody capture kit was used to immobilize capture mAbs on a CM5 biosensor chip. Prior to each antigen injection cycle, humanized mAb at a concentration of 2 μg/mL was captured on the surface with a contact time of 2 minutes and a flow rate of 5 μL/minute. The captured mAb loading from baseline was constant at 80-120 response units. Following test article capture and 1 minute baseline, monomeric human PTK7 protein was flowed over the surface at concentrations of 50, 25, and 12.5 nM for a 2-minute association phase followed by a 2-minute dissociation phase at a flow rate of 5 μL/minute. Following each cycle, the anti-human capture surface was regenerated with 30 seconds contact time of 3M $MgCl_2$ at 10 μL/minute.

Biacore™ data was processed by initially subtracting a control IgG surface from the specific mAb binding surface. The response data was then truncated to the association and dissociation phase. The resulting response curves with three different antigen concentrations were used to fit a 1:1 Langmuir binding model and to generate an apparent affinity by the calculated $K_{on}$ and $K_{off}$ kinetics constants, with equilibrium dissociation constant defined as $Kd=K_{off}/K_{on}$. All data analysis steps were completed in BiaEvaluation Software 3.1 (GE Healthcare).

The calculated affinity and kinetic constants were determined to be within 2-fold between the chimeric and humanized mAbs (Table 5).

TABLE 5

Affinity Constants of Chimeric and Humanized clone 24 mAbs to Human PTK7

| Test mAb | $K_{on}$ ($M^{-1}s^{-1}$) | $K_{off}$ ($s^{-1}$) | Kd (nM) |
|---|---|---|---|
| Chimeric clone 24 | 3.9E+05 | 2.3E−04 | 0.6 |
| Humanized clone 24 (hu24) | 2.7E+05 | 3.1E−04 | 1.2 |

$K_{on}$ = Association rate constant; $K_{off}$ = Dissociation rate constant; Kd = Equilibrium dissociation constant; M = Molar; mAb = Monoclonal antibody; s = Seconds; nM = Nanomolar; Recombinant human PTK7 ectodomain was used.

In order to determine the epitope recognized by hu24 mAb, its binding to several variants of the PTK7 ectodomain was evaluated. The PTK7 ectodomain is comprised of 7 Ig domains, and the variants were designed to include two or more contiguous Ig domains. Variants were expressed as Fc fusion proteins, and hu24 binding was determined by ELISA.

Constructs were designed with primers that amplified various contiguous PTK7 Ig domains as predicted by structural homology. The resulting sequences were fused in-frame with and upstream of the human immunoglobulin G2 (IgG2) Fc domain using standard molecular biology techniques. The Fc fusion proteins were transfected into mammalian cells and supernatants were harvested 72 hours later. Anti-PTK7 mAb hu24 was tested by ELISA for its ability to bind to the PTK7 protein variants with defined Ig domains.

The results show that Ig domains 1-4 are required for hu24 binding to PTK7 (Table 6) and imply that the mAb recognizes tertiary structural characteristics of PTK7.

TABLE 6

Binding of hu24 mAb to PTK7 Domains

| | PTK7 ECD Ig Domains in Construct | | | | | |
|---|---|---|---|---|---|---|
| | 1-2 | 2-3 | 1-4 | 1-5 | 3-7 | 6-7 | 1-7 |
| hu24 mAb binding | − | − | + | + | − | − | + |

ECD = Extracellular Domains.
Ig = Immunoglobulin.
Domains 1-2 = Residue 31-236;
Domains 2-3 = Residues 110-321;
Domains 1-4 = Residues 31-409;
Domains 1-5 = Residues 31-510;
Domains 3-7 = Residues 230-703;
Domains 6-7 = Residues 503-703;
Domains 1-7 = Full length ECD, Residues 31-703.

Experiments were performed to characterize the cell binding properties of anti-PTK7 mAb hu24. To confirm antigen specificity, binding was evaluated in cell lines with either substantial or negligible PTK7 expression as determined by immunoblotting.

Whole cell extracts were resolved by gel electrophoresis and transferred to nitrocellulose membrane. The membrane was incubated with hu6M024 in Tris-buffered saline with 0.1% Tween-20 (TBST)) with 5% weight/volume non-fat milk, then washed with TBST, incubated with horseradish peroxidase-conjugated goat anti-human antibody (Santa Cruz Biotechnology No sc-2453) and washed extensively before exposure to a chemiluminscent substrate.

Figure 2B:
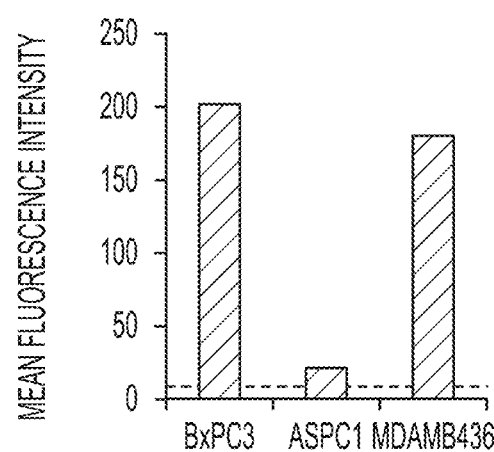

Immunoblotting indicated substantial expression of PTK7 in cell lines BxPC3 and MDAMB436 and negligible expression of PTK7 in cell line ASPC1 (FIG. 2A). The flow cytometry based cell binding results with hu24 were fully consistent with the immunoblotting data (FIG. 2B) which demonstrated the antigen specificity of hu24.

Additional flow cytometry experiments were conducted to evaluate binding of hu24 mAb to cancer cell lines with endogenous expression of PTK7. Briefly, adherent cells were dissociated with TrypLE™ Express (Gibco® No 12604-021) which was then neutralized with culture media. Suspension cells were harvested by centrifugation. Cells were resuspended in staining buffer (PBS with 3% BSA) with the stated concentration of mAb and incubated on ice for 30 minutes. Cells were washed in staining buffer, resuspended in staining buffer with phycoerythrin (PE)-labeled anti-human antibody (Jackson ImmunoResearch No 109-115-098) and incubated on ice for 30 minutes. Cells were washed, resuspended in staining buffer with 7-AAD viability stain (BD Biosciences, Pharmingen No 51-68981E) and analyzed by flow cytometry with a BD FACSCalibur™. The mean fluorescence intensity (MFI) in the PE channel of the viable cell population was determined for each sample.

Hu24 mAb exhibited binding to various cancer cell lines at the lowest concentration tested (0.1 µg/ml). In contrast, the control antibody did not show appreciable binding at the highest concentration tested (10 µg/ml) (Table 7).

TABLE 7

Binding Properties of hu24 mAb to Cancer Cell Lines

| Cancer Cell Line (tumor type) | MFI, Control mAb | MFI, hu6M024 mAb | | |
|---|---|---|---|---|
| | 10 µg/mL | 0.1 µg/mL | 1 µg/mL | 10 µg/mL |
| H661 (lung cancer) | 4.2 | 60 | 243 | 309 |
| H446 (lung cancer) | 11 | 95 | 342 | 411 |
| U2OS (osteosarcoma) | 5.3 | 122 | 385 | 431 | mAb = monoclonal antibody; MFI = mean fluorescence intensity; µg/mL = micrograms per milliliter.

Example 4

Expression of PTK7 in Various Cancer Cell Lines

Anti-PTK7 antibodies hu23 and hu24 exhibited specific binding to cultured cancer cell lines that were established from a broad range of tumor types, including solid and hematological indications, see Table 8 below. Adherent cells were dissociated using TrypLE Express (GIBCO), neutralized with cell culture media and counted. Cells were plated into a U-bottom 96-well plate with $5 \times 10^5$ cells/100 µL media/well. The plate was centrifuged at 300×g, for 5 minutes at 4° C. to pellet cells and the supernatant was discarded. Each pellet was resuspended in 10 µg/mL hu23, hu24 or non-binding control antibody in 3% BSA in PBS, and the plate was incubated on ice for 30 minutes. The plate was centrifuged and the cell pellets were washed in 200 µL ice-cold 3% BSA in PBS. Each cell pellet was resuspended in 100 µL of R-phycoerythrin (PE)-conjugated goat anti-human IgG Fc fragment that had been diluted 1:50 in 3% BSA in PBS, and the plate was incubated on ice for 30 minutes. The plate was centrifuged and the cell pellets were washed in 200 µL of 3% BSA in PBS at 4° C. Each pellet was resuspended in 100 µL 3% BSA in PBS and transferred to a 5 mL polycarbonate tube containing 250 µL 3% BSA in PBS. The samples were analyzed by flow cytometry using 5 µL 7-Amino-Actinomycin D (7-AAD) staining solution per sample as a viability stain. Non-viable cells were excluded from the analysis.

The data in Table 8 shows mean fluorescent intensities (MFI) of antibody binding to cancer cell lines by flow cytometry. Cell binding with humanized antibodies hu23 and hu24 indicates PTK7 expression in numerous cell lines. PTK7 expression is prominent in various non-small cell lung cancer (NSCLC), small cell lung cancer (SCLC), colon, breast, pancreatic, and erythroleukemic cancer cell lines. A negative control antibody that does not bind to PTK7 was used for comparison.

TABLE 8

| Cell Line | Tumor type of origin | Mean Fluorescent Intensity (10 µg/ml Ab) | | |
|---|---|---|---|---|
| | | hu24 | hu23 | Negative Control Ab |
| H520 | Lung (NSCLC) | 1384 | 1212 | 4.8 |
| H446 | Lung (SCLC) | 937 | 915 | 7.1 |
| H1048 | Lung (SCLC) | 955 | 900 | 4.4 |
| DMS114 | Lung (SCLC) | 793 | 568 | 9.9 |
| HCT116 | Colon | 629 | 436 | 17.8 |
| H69 | Lung (SCLC) | 404 | 391 | 11.2 |
| MDAMB468 | Breast (BR) | 364 | 302 | 12 |
| MDAMB361-DYT2 | Breast (BR) | 295 | 227 | 8.7 |
| BxPC3 | Pancreatic | 207 | 192 | 4.6 |
| MDAMB436 | Breast (BR) | 189 | 171 | 3.5 |
| H1299 | Lung (NSCLC) | 70.9 | 59.2 | 3 |
| SKBR3 | Breast (BR) | 39.7 | 31.2 | 14.9 |
| DU4475 | Breast (BR) | 697 | ND | 3.8 |
| DMS79 | Lung (SCLC) | 682 | ND | 8.5 |
| H522 | Lung (NSCLC) | 672 | ND | 3.8 |
| MiaPaca | Pancreatic | 611 | ND | 3.5 |
| H358 | Lung (NSCLC) | 474 | ND | 4.5 |
| HCC70 | Breast (BR) | 474 | ND | 9.4 |
| H1975 | Lung (NSCLC) | 444 | ND | 4.8 |
| H526 | Lung (NSCLC) | 438 | ND | 12.2 |
| H661 | Lung (NSCLC) | 376 | ND | 3.8 |
| HCC1937 | Breast (BR) | 370 | ND | 7.8 |
| H596 | Lung (NSCLC) | 355 | ND | 21.4 |
| HCC827 | Lung (NSCLC) | 251 | ND | 5.8 |
| Hs700T | Pancreatic | 241 | ND | 4.9 |
| HCC38 | Breast (BR) | 227 | ND | 7.2 |
| TF1a | Erythroleukemia (AML) | 208 | ND | 6.2 |
| H2110 | Lung (NSCLC) | 171 | ND | 4.9 |
| KG1 | Erythroleukemia (AML) | 159 | ND | 5.2 |
| TF1 | Erythroleukemia (AML) | 135 | ND | 5.9 |
| Hs578T | Breast (BR) | 124 | ND | 2.7 |
| BT-549 | Breast (BR) | 114 | ND | 3.6 |
| HCC1806 | Breast (BR) | 77.5 | ND | 4.6 |
| Kasumi-1 | Erythroleukemia (AML) | 68.2 | ND | 5.3 |
| K562 | Chronic Myelogenous leukemia (CML) | 56.1 | ND | 54.7 |
| HEL | Erythroleukemia (AML) | 46 | ND | 15.7 |
| RL | Non-Hodgkin's lymphoma (NHL) | 44.2 | ND | 29.8 |
| Raji | Non-Hodgkin's lymphoma (NHL) | 36.3 | ND | 20.3 |
| HL60 MX2 | Promyelocytic leukemia (AML) | 25.7 | ND | 25.2 |
| HEL92.1 | Erythroleukemia (AML) | 23 | ND | 7.7 |
| NB4 | Promyelocytic leukemia (AML) | 19.5 | ND | 6.8 |
| RPMI8226 | Multiple myeloma | 17.8 | ND | 8.3 |
| HL60 | Promyelocytic leukemia (AML) | 12.7 | ND | 10.9 |
| MV411 | Monocytic leukemia | 10.1 | ND | 7.7 |
| U937 | Monocytic leukemia | 5.8 | ND | 5.0 |
| ASPC1 | Pancreatic | 4.5 | ND | 2.6 |
| THP-1 | Monocytic leukemia | 4.0 | ND | 4.0 |
| EKVX | Lung (NSCLC) | 3.8 | ND | 3.1 |

ND = no data.

Microarray data shown in Table 9 for 29 PDX tumor lines was generated using Agilent SurePrint GE 8×60 v2 arrays using total RNA isolated from PDX tumor cells. Processing of the raw microarray data collected with a single color included background subtraction and quantile normalization. Normalized data was log base 2 transformed, generating gene expression values for use in downstream analyses. This data reflects the relative amount of PTK7 expression associated with the indicated PDX cell line. BR=Breast, LU=Lung, OV=Ovarian, SK=Melanoma, CR=Colorectal, LIV=Liver.

TABLE 9

| PDX Cell Line | Relative mRNA level |
|---|---|
| BR13 | 484.4 |
| BR22 | 714.1 |
| BR31 | 210.8 |
| BR56 | 393.4 |
| BR64 | 237.2 |
| BR120 | 319.6 |
| BR36 | 324.0 |
| BR133 | 639.1 |
| LU176 | 643.6 |
| LU135 | 576.0 |
| LU58 | 113.8 |
| OV39 | 238.9 |
| OV45 | 410.1 |
| OV55 | 364.6 |
| SK23 | 464.7 |
| SK25 | 171.3 |
| SK19 | 484.4 |
| LU86 | 288.0 |
| LU95 | 377.4 |
| LU64 | 247.3 |
| LU49 | 56.5 |
| LU70 | 221.3 |

TABLE 9-continued

| PDX Cell Line | Relative mRNA level |
|---|---|
| LU50 | 195.4 |
| CR2 | 286.0 |
| CR14 | 187.4 |
| CR42 | 471.1 |
| CR88 | 143.0 |
| LIV13 | 75.6 |
| LIV40 | 254.2 |

PTK7 expression was also evaluated by immunohistochemistry in seven PDX models in immune compromised mice: four triple-negative breast cancer PDXs (BR13, BR22, BR31 and BR5); one progesterone receptor positive (PR+) breast cancer PDX (BR36); and two NSCLC PDXs (NSCLC135 and NSCLC176).

Briefly, a tissue fragment from each xenograft was formalin-fixed, processed and paraffin embedded (FFPE) using standard histological procedures. Five-micron sections were cut onto charged slides, dried, deparaffinized in xylene and rehydrated with graded alcohols to distilled water. Heat-induced epitope retrieval was performed in Borg Decloaker (Biocare Medical) using a Retriever 2100 pressure cooker (Electron Microscopy Sciences) and cooled to room temperature (RT) for 20 minutes (min). Endogenous peroxidase was quenched with Peroxidazed 1 (Biocare Medical) for 10 min at RT. Non-specific protein interactions were blocked with Background Punisher (Biocare Medical) for 10 min at RT. Tissue sections were incubated with primary antibody at 0.5 µg/mL for 1 hour at RT. Primary antibodies were either rabbit anti-PTK7 clone (Stem CentRx™ Inc) or rabbit isotype control (DA1E) mAb immunoglobulin G (IgG) XP® (Cell Signaling Technologies no. 3900). Binding of primary antibody was detected with SignalStain® Boost IHC Detection Reagent (Cell Signaling Technologies no. 8114) for 30 min at RT. Staining was developed with DAB+ (3',3'-Diaminobenzidine; DAKO) for 5 min at RT. Slides were briefly counterstained in CAT hematoxylin (Biocare Medical), washed in water, dehydrated in graded alcohols, cleared in xylene, and coverslipped with Permount™ Mounting Medium (Fisher Chemicals).

PTK7 was observed on the plasma membrane in all of the PDX models (FIG. 3).

Example 5

Expression of PTK7 in Various Tumor Tissues

PTK7 mRNA expression was determined in primary human tumors. Briefly, frozen tumor and normal tissues were fragmented, and mRNA was isolated with Qiagen RN easy Mini kit (Qiagen, cat#74106). RNA quantitation and quality assessment was performed using the HT RNA microfluidic LabChip assay and LabChip GX microfluidic capillary electrophoresis instrument (Perkin Elmer). RNA for each of the samples was diluted so that the quantity fell within the linear range of the instrument (25-250 ng/µL). Isolated RNA samples were reverse transcribed to cDNA using the Life Technologies, High Capacity RNA-to-cDNA Kit (cat #4387406) following a protocol outlined in the manufacturer's directions. The qRT-PCR reaction was performed using the TaqMan Probe-Based Gene Expression Analysis and ABI ViiA7 Real-Time PCR Systems (Life Technologies). Target gene and endogenous controls were run in quadruplicate for each probe set on pre-fabricated TaqMan low density array cards. ExpressionSuite Software v1.0.3 (Life Technologies) was used to generate automated threshold values for signal amplification for a majority of samples. Rarely were automated thresholds adjusted manually. Amplification plots resulting in Ct values >35 were discarded, as were those plots that generated a Ct value but did not display a trend of logarithmic amplification. All Ct values were exported from the ExpressionSuite software and relative quantification calculations were performed in Microsoft Excel 2010 (Microsoft Corporation, Inc).

Figure 4A:
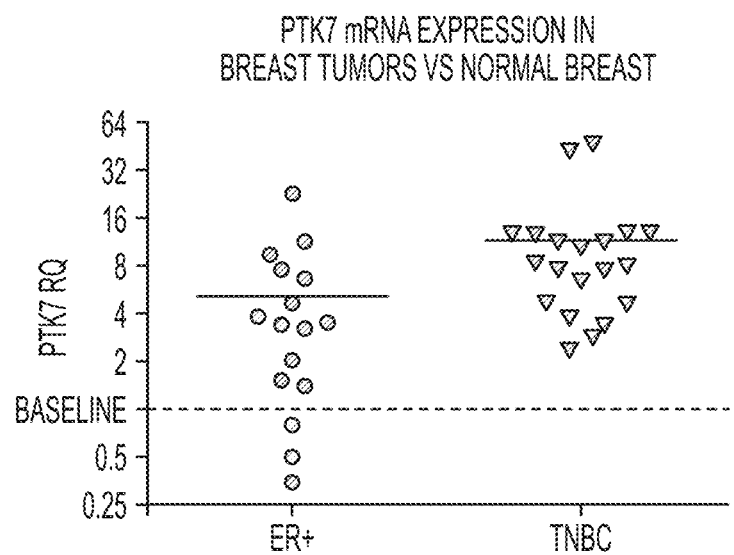
FIGS. 4A-C are graphs showing PTK7 mRNA expression in primary tumors. (A) breast cancers; (B) NSCLC cancers and (C) ovarian cancer are shown.
Figure 4B:
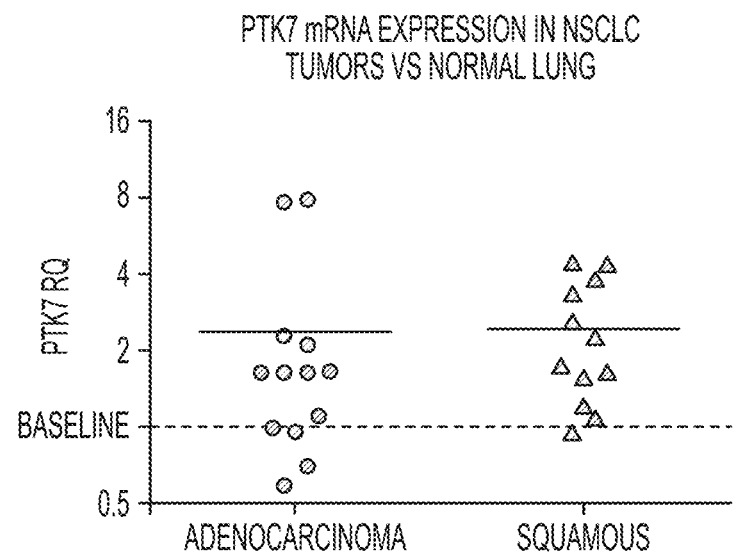
Figure 4C:
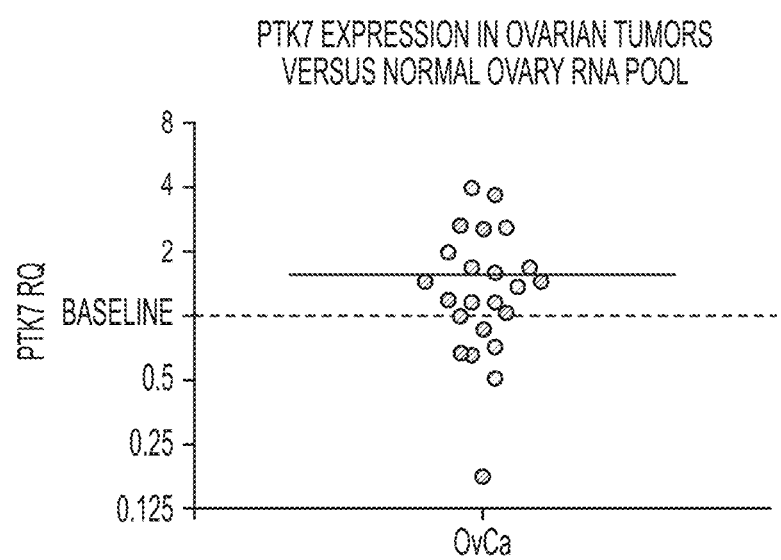

FIGS. 4A-C show the levels of PTK7 mRNA in (A) breast, (B) NSLC and (C) ovarian cancers. Quantitation of PTK7 expression was assessed using the relative fold difference (RQ) or comparative Ct method, $(2^{-\Delta\Delta Ct})$ method using the equation $RQ=2^{-\Delta\Delta Ct}$. The RQ data represents fold difference PTK7 expression relative to control RNA samples. For breast carcinoma samples a normal breast RNA sample purchased from BioChain (Newark, Calif., cat# R1234086-50, lot# B610189, 75 year old female) was used to generate RQ data. For lung cancer the RQ data reported represents fold differences in PTK7 expression relative to normal lung RNA purchased from Life Technologies (cat #AM7968, lot #1308017, 80 year old female). For ovarian carcinoma samples the RQ data reported represents fold differences in PTK7 expression relative to RNA isolated from normal ovary tissue (tissue ID #0204C011C) provided by the Cleveland Clinic (Cleveland, Ohio). RQ values for all tumors was also calculated relative to a RNA pool from normal human tissues (BioChain, cat#R4234565, lot #B611043), as well as to a Universal Human Reference RNA pool (Agilent, cat #740000), which is comprised of equal parts RNA from 10 unique cancer cell lines.

Breast, NSCLC and ovarian tumors showed increased PTK7 mRNA expression as compared to the corresponding normal tissue (FIGS. 4A-C. The overexpression in the TNBC was most notable, while overexpression in ovarian tumors was modest.

Figure 5:
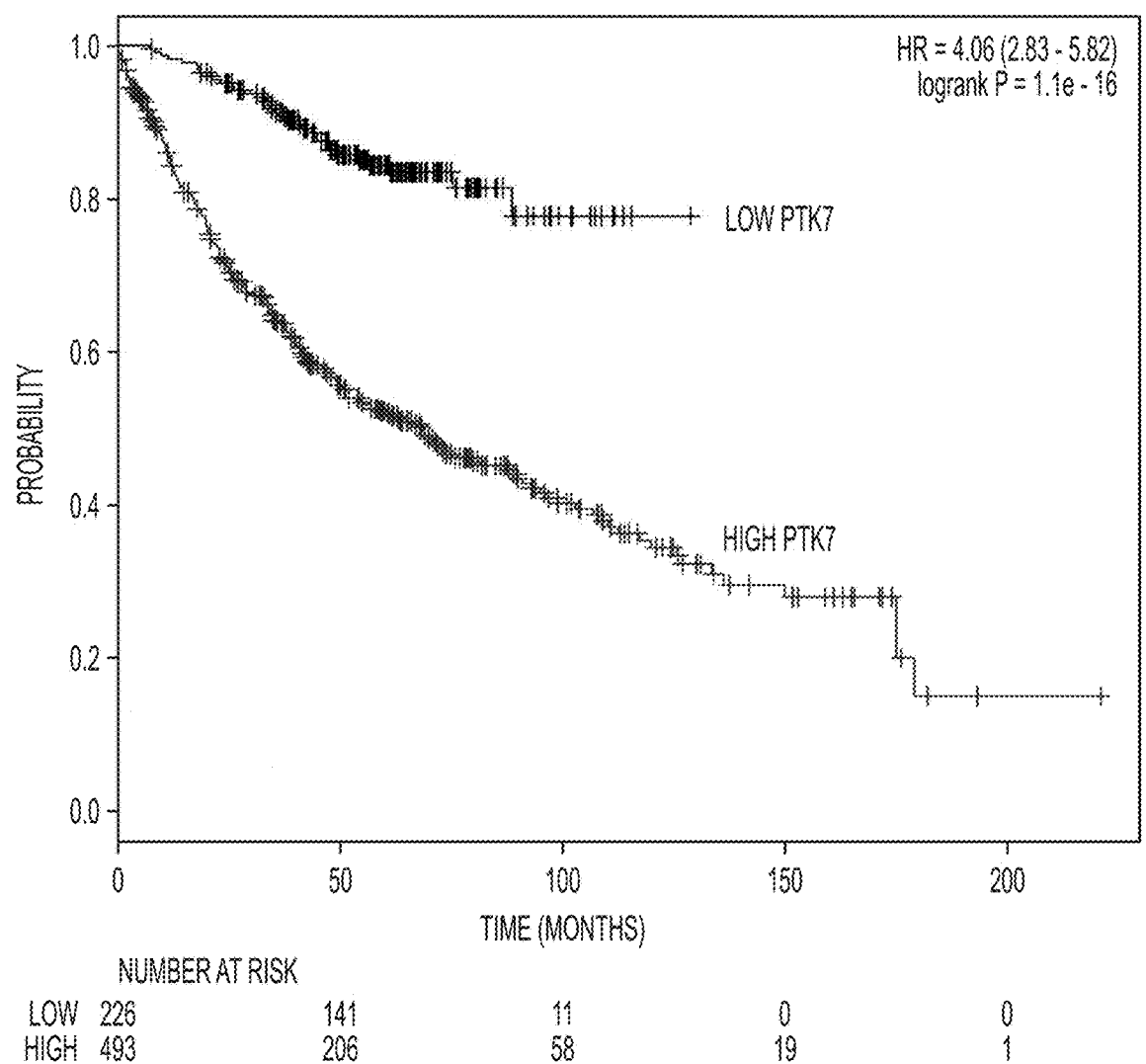
FIG. 5 is a graph showing a correlation between higher PTK7 mRNA expression and worse overall survival rates in NSCLC patients.

FIG. 5 shows a correlation between higher PTK7 mRNA expression and worse overall survival in NSCLC patients. To determine whether PTK7 expression is associated with survival endpoint in lung cancer, Kaplan-Meier analysis was applied to bioinformatics dataset with freeware http://kmplot.com/analysis (Gyorffy et al., 2013, PloS One. 18; 8(12): e82241). PTK7 mRNA levels and patient survival data were plotted for 719 NSCLC-adenocarcinoma patients using the tool's auto-select best cutoff. High PTK7 expression was associated with shorter survival (hazard ratio HR=4.06, logrank P=1.1E-16).

PTK7 protein expression was seen in esophageal cancer. A tissue microarray (ES1502 from US Biomax) was used for immunohistochemistry. Briefly, sections from formalin-fixed paraffin-embedded tumor blocks were cut at 5 microns and baked onto glass slides. The slides were cleared in Xylene and rehydrated in graded alcohol washes ending in de-ionized water. The slides were retrieved in pH6 Citrate HIER buffer in the Retriever 2100 (Electron Microscopy). Peroxidazed, a hydrogen peroxide block solution (Biocare Medical), was applied to the slides for 10 min. The slides were washed with TBST 2×, followed by Background Punisher, a protein block, (Biocare Medical) for 10 min. The primary antibody, H.235 (Lot #: 110325MM, Stock concentration: 12.7 mg/mL) was applied for 60 min at a concentration of 2 ug/mL. After washing with TBST (2×), the secondary antibody, DAKO anti-mouse Envision+, was applied for 30 min. After washing again with TBST (2×), the slides were developed with Betazoid DAB+ (Biocare Medical) for 5 min. The slides were then counterstained in CAT Hematoxylin (Biocare Medical) for 30 seconds and coverslipped.

Forty out of 70 tumor samples scored positive for PTK7 expression on the cell membrane. Of the 40 samples that were PTK7 positive, 1 exhibited high expression, 11 exhibited moderate expression and 28 exhibited low expression.

PTK7 protein expression was seen in prostate cancer. A tissue microarray (BC19013 from Biomax) was used for immunohistochemistry as described above for esophageal cancer. Eleven out of 26 tumor samples scored positive for PTK7 expression. Of the 11 samples that were PTK7 positive, 2 exhibited moderate expression and 9 exhibited low expression.

Example 6

Measurement of PTK7 Protein in Serum

Reports in the literature have characterized cleavage of PTK7 at the plasma membrane which results in the shedding of part of the extracellular domain (Golubkov et al., 2010, J Biol Chem 285(46):35740-9; Golubkov et al., 2012, J Biol Chem 287(50):42009-18; Na et al., 2012, J Biol Chem 287(30):25001-9). Circulating antigen could impact the pharmacokinetics of therapeutic compounds such as a PTK7 ADC. Circulating levels of shed PTK7 were evaluated from various serum sources. PTK7 protein levels were measured with a quantitative assay using the Meso Scale Discovery (MSD®) platform.

Serum samples from healthy humans were purchased from the Stanford University Blood Bank. Serum samples from cancer patients were purchased from Asterand Inc and Bioreclamation Inc. Cynomolgus monkey serum samples were purchased from Bioreclamation Inc.

Mouse serum samples were obtained from immune-compromised mice that harbored human tumor xenografts. Female non-obese diabetic-severe combined immunodeficiency (NOD-scid) mice were purchased from Harlan Laboratories® and housed in accordance with Institutional Animal Care and Use Committee (IACUC) guidelines. Patient-derived xenografts (PDX) were established by direct implantation of freshly resected human tumor samples and propagated by passaging xenografts into naïve animals. The xenografts were derived from primary tumor resection samples that were procured from clinical sites following Institutional Review Board for the Protection of Human Subjects approval and in accordance with Health Insurance Portability and Accountability Act (HIPAA) regulations.

The assay to measure levels of PTK7 protein utilized two specific anti-PTK7 monoclonal antibodies (mAbs) that had been generated by hybridoma technology. The mAbs bind human and cynomolgus monkey PTK7 but not murine PTK7. The assay was developed on the MSD® platform and was optimized for a linear response. A MSD® high bind plate was coated with PTK7-specific mAb H2.35 at 1 µg/ml in phosphate-buffered saline (PBS). The plate was incubated at 4° C. overnight. The next day the plate was washed and the second mAb was added. For human and monkey samples, 25 µl of sulfo-tagged PTK7-specific mAb 6M38 was added at 0.5 µg/ml in MSD® diluent2 (MSD #R51BB-4), and for tumor-bearing mouse samples, biotinylated 6M38 was added at 0.5 µg/ml in MSD® Diluent 2 (MSD #R51BB-4) followed by horseradish peroxidase-conjugated streptavidin. The plate was incubated with shaking for 30 minutes. After the incubation, without washing, serum samples or varying amounts of recombinant PTK7 protein were added to the wells and incubated for 2 hours on a plate shaker. The serum samples were diluted 4× to 25% final in MSD® Diluent 2. The plates were washed 3 times with phosphate-buffered saline with 0.2% Tween-20. MSD® 1× Read buffer (MSD #R92TC-3) was added to the plates (150 µl per well), and the plates were read on the MSD® Sector Imager. Values for serum samples were interpolated from the standard curve based on recombinant protein.

Figure 6:
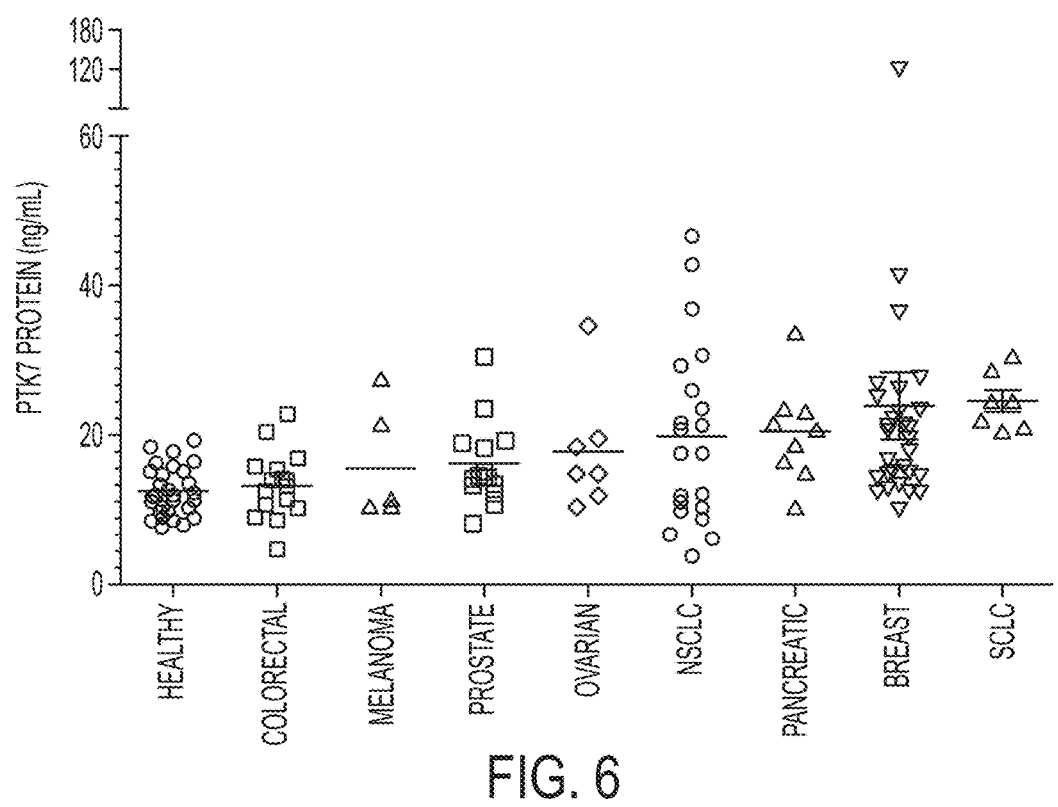
FIG. 6 is a graph showing PTK7 protein levels in serum from healthy humans and cancer patients representing 8 different tumor types. The horizontal lines indicate the mean value for each group.

The levels of PTK7 protein in human serum were measured in samples from healthy humans and cancer patients that represented 8 tumor types. The results are summarized in Table 10. The reported value in each category indicates the mean of all individual samples. The mean value of PTK7 in serum from healthy humans was 12.4±3.3 ng/mL. In general, the mean values for cancer patients were slightly higher, ranging up to 24.6±3.8 ng/mL and with a broader distribution of individual values (FIG. 6).

TABLE 10

PTK7 Protein Levels in Human Serum

| Sample Type | Number of Samples | PTK7 Protein Level (ng/mL) |
| --- | --- | --- |
| Healthy human | 30 | 12.4 ± 3.3 |
| Breast cancer patients | 29 | 24.0 ± 24.1 |
| Colorectal cancer patients | 17 | 13.3 ± 4.3 |
| Melanoma patients | 6 | 15.4 ± 7.4 |
| Non-small cell lung cancer patients | 21 | 19.8 ± 12.1 |
| Ovarian cancer patients | 7 | 17.9 ± 8.1 |
| Pancreatic cancer patients | 9 | 20.4 ± 6.5 |
| Prostate cancer patients | 14 | 16.2 ± 5.7 |
| Small cell lung cancer patients | 7 | 24.6 ± 3.8 | ng/mL = nanograms per milliliter.
Measurements are provided as Mean ± Standard Deviation of the Mean for the independent biological samples.

The levels of PTK7 protein in naïve cynomolgus monkey serum were measured in samples from 29 animals. The mean value was 35.8±13.4 ng/mL (Table 11) which is higher than the corresponding values for healthy humans and cancer patients.

TABLE 11

PTK7 Protein Levels in Cynomolgus Monkey Serum

| Sample Type | Number of samples | PTK7 Protein Level (ng/mL) |
| --- | --- | --- |
| Healthy cynomolgus monkey | 29 | 35.8 ± 13.4 | ng/mL = nanograms per milliliter.
Measurement is provided as Mean ± Standard Deviation of the Mean for the independent biological samples.

Mouse serum samples were obtained from immune-compromised mice that harbored human tumor xenografts. Specifically, the xenografts were PDXs which typically preserve the architecture and genotype of the human tumors from which they are derived (DeRose et al, 2011, Nat Med 17(11):1514-20). The mean values of PTK7 protein in serum for all 11 tumor types were <1 ng/mL for all tumor types (Table 12) and, thus, significantly lower than the values obtained for human and monkey. Since the mAbs used in the assay do not cross-react with murine PTK7, the values are interpreted as human PTK7 protein that was shed from the tumor xenografts and not normal murine tissues.

TABLE 12

PTK7 Protein Levels in Tumor-Bearing Mouse Serum

| Tumor Xenograft | Number of Tumor Models | PTK7 Protein Level (ng/mL) |
|---|---|---|
| Naïve (no xenograft) | Not applicable | 0 ± 0 |
| Breast cancer | 11 | 0.454 ± 0.872 |
| Colorectal cancer | 29 | 0.023 ± 0.083 |
| Head and neck cancer | 2 | 0.355 ± 0.501 |
| Kidney cancer | 7 | 0.004 ± 0.009 |
| Liver cancer | 7 | 0.008 ± 0.021 |
| Non-small cell lung cancer | 20 | 0.065 ± 0.104 |
| Ovarian cancer | 9 | 0.053 ± 0.086 |
| Pancreatic cancer | 9 | 0.018 ± 0.055 |
| Prostate cancer | 2 | 0 ± 0 |
| Skin cancer | 9 | 0.208 ± 0.307 |
| Small cell lung cancer | 10 | 0.004 ± 0.011 | ng/mL = nanograms per milliliter.
Measurements are provided as Mean ± Standard Deviation of the Mean for the tumor models. Values for individual models were the median of measurements from 1 to 12 tumor-bearing animals.

Example 7

Internalization

Antibody internalization is a critical characteristic for delivering ADCs for cytotoxicity in PTK7 expressing cells. Anti-PTK7 antibody hu24 was observed to internalize into cancer cells, which suggests that the antibody is a suitable vehicle for delivering a toxin into the cells. Adherent cells were dissociated using TrypLE Express (Gibco), neutralized with cell culture media and then counted. Cells were aliquoted into a U-bottom 96 well plate with $5 \times 10^5$ cells/100 µL media per well. The plate was centrifuged at 300×g, for 5 minutes at 4° C. to pellet the cells and the supernatants were aspirated. All reagents were kept on ice for the following steps.

Each cell pellet was resuspended in 3 µg/ml hu24 or non-binding antibody (Human IgG, Thermo Scientific) in 100 µL 3% BSA in PBS. The plate was incubated on ice for 30 minutes and then centrifuged, and the cell pellets were washed in 200 µL 3% BSA in PBS. The cell pellets were resuspended in 100 µL 37° C. pre-warmed cell culture media and placed in a 37° C. incubator for 1 or 4 hours. The cell pellets to be incubated at 4° C. were similarly resuspended and then placed on ice. After the incubations, samples were centrifuged, supernatants aspirated and washed with 200 µL/well ice cold 3% BSA in PBS and resuspended in 100 µL/well ice-cold 3% BSA in PBS and placed on ice. All samples are then centrifuged, supernatants were aspirated, each cell pellet was resuspended in 100 µL of Allophycocyanin (APC)-conjugated anti-Human IgG Fc fragment that had been diluted 1:50 in ice-cold 3% BSA in PBS. The plate was incubated on ice for 30 minutes and then centrifuged, and the cell pellets were washed in 200 µL 3% BSA in PBS, resuspended in 100 µL 3% BSA in PBS, and transferred to a 5 mL polycarbonate tube containing 250 µL 3% BSA in PBS. The samples were analyzed by flow cytometry using 5 µL 7-AAD per sample as a viability stain. The mean fluorescent intensity (MFI) was measured for each sample with non-viable cells excluded from the analysis. The value for "% internalized" was calculated as (100%−[MFI after incubation/MFI before incubation]). The results in Table 13 indicate that the hu24 antibody was internalized into all the cell lines tested, and that the internalization was temperature-dependent, thus reflecting active (not passive) internalization by the cell.

TABLE 13

| Cell line | % internalization (relative to start of experiment) | | | | Number of experiments |
|---|---|---|---|---|---|
| | 1 hr at 37° C. | 4 hrs at 37° C. | 1 hr at 4° C. | 4 hrs at 4° C. | |
| BT549 | 14.3 ± 9.8 | 42.5 ± 9.1 | 4.3 ± 8.1 | 8.5 ± 7.7 | 6 |
| H661 | 21.2 ± 12.7 | 36 ± 17.4 | 2.2 ± 11.5 | 2 ± 5.6 | 5 |
| MDAMB468 | 21.7 ± 5.7 | 34.3 ± 9.0 | 7.0 ± 0.8 | 9.3 ± 2.5 | 3 |

Example 8

Cytotoxicity Mediated by Saporin-Conjugated Anti-Human Fab Fragment

An in vitro cytotoxicity assay was performed to determine whether hu23 or hu24 antibody can mediate the delivery of a cytotoxic agent to cell lines. In this respect, anti-human IgG Fab fragment covalently linked to the saporin toxin (Advanced Targeting Systems) was combined with unlabeled hu23, hu24 or 8.84 Ab (non-binding, negative control antibody) and then incubated with cells for 4 days (PTK7 expressing cells H446 and DMS114) or 7 days (OE19 non-PTK7 expressing cells; OE21 PTK7 expressing cells) after which cell viability was measured.

In one experiment, H446 or DMS114 cancer cell lines were plated into a clear flat-bottom tissue culture plate at 9600 cells per well (H446) or 6400 cells per well (DMS114) in 100 µl of cell culture media. The cells were incubated overnight at 37° C. in a 5% $CO_2$ incubator. On the following day, 50 µl of hu23, hu24 or 8.84 Ab pre-mixed with saporin-conjugated anti-human IgG Fab (Fab-ZAP; Advanced Targeting Systems) at 1:2 molar ratio was added to the cells on a 10-point concentration curve with triplicate samples starting with 1 µg/ml with 1:3 dilutions in cell culture media. The plate was incubated in a 37° C., 5% $CO_2$ incubator for 4 days. To measure cell viability, the MTS assay (Promega Cell Titer 96 Aqueous Non-Radioactive Cell Proliferation Assay) was used according to the supplier's instructions. 30 µL of the combined MTS reagent was added to each well. The plate was incubated in a 37° C., 5% $CO_2$ incubator for 2 hours. The Optical Density (OD) was determined at 490 nm with a 96-well plate reader. The average reading from wells with media alone was subtracted from the readings of wells with cells to control for background OD. The data was subjected to logistic non-linear regression analysis (GraphPad Prism Software) in order to determine the concentration of primary antibody at which cell viability was inhibited by 50% (IC50).

The data in Table 14 indicates that both anti-PTK7 antibodies hu23 and hu24 conferred saporin-mediated cytotoxicity to the H446 and DMS114 cells, while the 8.84 negative control antibody did not. The results demonstrate that the activity of hu23 and hu24 was specific for PTK7 expressing cells.

TABLE 14

| Cell Line | IC50 Values (ng/mL) | | |
|---|---|---|---|
| | hu23 + Fab-ZAP | hu24 + Fab-ZAP | 8.84 + Fab-ZAP |
| H446 | 44.7 | 60.3 | >1000 |
| DMS114 | 10.3 | 12.0 | >1000 |

In another experiment, the saporin assay was performed on two cell lines derived from esophageal cancers, OE19 and OE21 (Sigma Aldrich). To determine PTK7 expression on the cell lines, the cells were cultured and single cell suspensions were isolated using Versene (Invitrogen). Cells were washed in PBS/2% FCS and incubated with hu24 antibody or HuIgG1 (isotype control) at a concentration of 5 µg/mL for 30 minutes. Cells were washed again in PBS/2% FCS, then incubated at 1:200 with anti-human Alexa Fluor647 (Jackson Immunoresearch) for 20 minutes. Cells were washed again, resuspended in DAPI, and then analyzed on a BD FACSCanto to determine the change in mean fluorescence intensity (ΔMFI). OE19 cells did not exhibit staining fluorescence above the isotype control (ΔMFI=0) whereas the OE21 cells exhibited almost a two-log increase in fluorescence intensity (ΔMFI=5976), which indicated the expression of PTK7 on the surface of OE21, an esophageal squamous cell carcinoma.

To determine whether hu24 can mediate the delivery of cytotoxic agents, 2500 cells/well of a dissociated single cell suspension from either OE21 or OE19 were plated on BD Tissue Culture plates (BD Biosciences) in culture medium. One day after plating, various concentrations of purified hu24 and a fixed concentration of 4 nM anti-HuIgG Fab fragment covalently linked to saporin (Advanced Targeting Systems) were added to the cultures. After a 7-day incubation, viable cell numbers were enumerated using CELL TITER GLO® (Promega) as per manufacturer's instructions. Raw luminescence counts using cultures containing cells with the saporin Fab fragment were set as 100% reference values and all other counts calculated accordingly (referred to as "Normalized RLU"). Using this assay it was demonstrated that hu24 mediated cytotoxicity against OE21 cells, but not OE19 cells, and the isotype control did not affect cell counts, as shown in Table 15. These results indicate that cell binding of the antibody hu24 is required to elicit the saporin-mediated cytotoxicity to PTK7 expressing cell but has no effect on a non-PTK7 expressing cell.

TABLE 15

| Cell Line | IC50 Values (µg/ml) | |
|---|---|---|
| | hu24 + Fab-ZAP | HuIgG1 control + Fab-ZAP |
| OE21 | 0.5 | >100 |
| OE19 | >100 | >100 |

Example 9

Synthesis of vc0101 and mc8261

The synthesis of vc0101 (vc is the linker and 0101 is the drug) and mc8261 (mc is the linker and 8261 is the drug) was prepared according to the methods described in International Publication No. WO/2013/072813, which is herein incorporated by reference in its entirety.

A. Experimental Method for the Synthesis of vc0101

Preparation of N-[6-(2,5-dioxo-2,5-dihydro-1H-pyrrol-1-yl)hexanoyl]-L-valyl-N-{4-[(21S,24S,25R)-24-[(2S)-butan-2-yl]-25-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-18,18,23-trimethyl-3,16,19,22-tetraoxo-21-(propan-2-yl)-2,7,10,13,26-pentaoxa-4,17,20,23-tetraazaheptacos-1-yl]phenyl}-N~5~-carbamoyl-L-ornithinamide (vc0101).

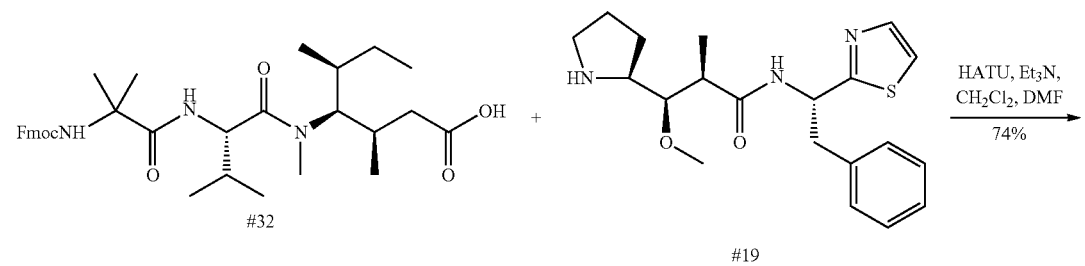

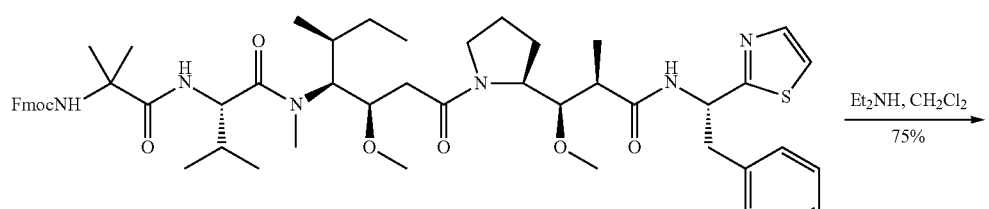

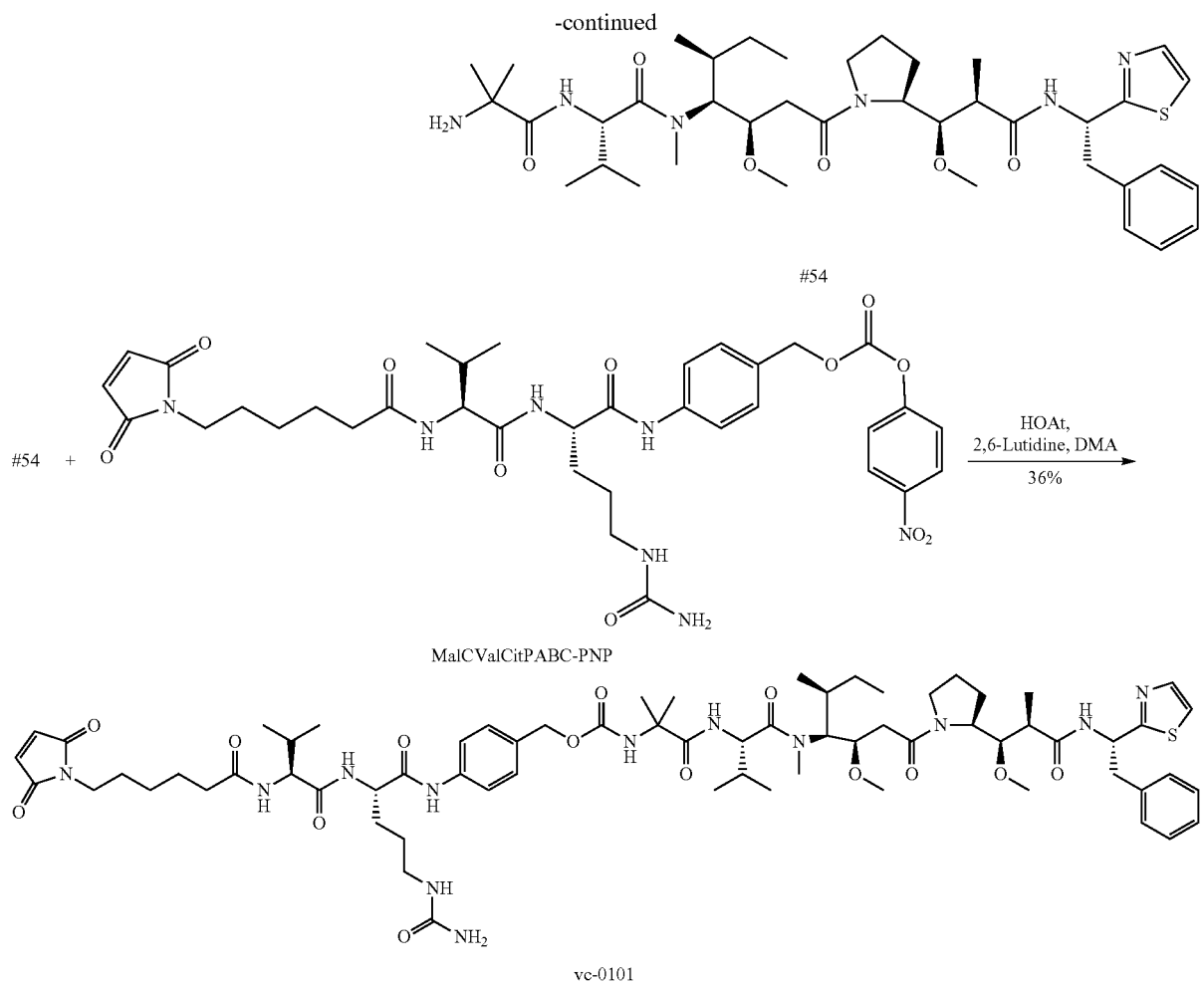

54

MalCValCitPABC-PNP vc-0101

Step 1.

Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#53). To a solution of compound #32 (2.05 g, 2.83 mmol, 1 eq.) in dichloromethane (20 mL, 0.1 M) and N,N-dimethylformamide (3 mL) was added the amine #19 (2.5 g, 3.4 mmol, 1.2 eq.), HATU (1.29 g, 3.38 mmol, 1.2 eq.) and triethylamine (1.57 mL, 11.3 mmol, 4 eq.). The mixture was stirred at room temperature while reaction progress was monitored by LC-MS and TLC. Once complete, the reaction was concentrated in vacuo, the residue was azeotroped three times with heptanes, and the resulting crude product was purified by silica gel chromatography (Gradient: 0% to 55% acetone in heptane), producing compound #53 (2.42 g, 74%) as a solid. LC-MS: m/z 965.7 [M+H+], 987.6 [M+Na+], retention time=1.04 minutes (Protocol H-below); HPLC (Protocol A-below): m/z 965.4 [M+H+], retention time=11.344 minutes (purity >97%); $^1$H NMR (400 MHz, DMSO-d$_6$), presumed to be a mixture of rotamers, characteristic signals: δ 7.86-7.91 (m, 2H), [7.77 (d, J=3.3 Hz) and 7.79 (d, J=3.2 Hz), total 1H], 7.67-7.74 (m, 2H), [7.63 (d, J=3.2 Hz) and 7.65 (d, J=3.2 Hz), total 1H], 7.38-7.44 (m, 2H), 7.30-7.36 (m, 2H), 7.11-7.30 (m, 5H), [5.39 (ddd, J=11.4, 8.4, 4.1 Hz) and 5.52 (ddd, J=11.7, 8.8, 4.2 Hz), total 1H], [4.49 (dd, J=8.6, 7.6 Hz) and 4.59 (dd, J=8.6, 6.8 Hz), total 1H], 3.13, 3.17, 3.18 and 3.24 (4 s, total 6H), 2.90 and 3.00 (2 br s, total 3H), 1.31 and 1.36 (2 br s, total 6H), [1.05 (d, J=6.7 Hz) and 1.09 (d, J=6.7 Hz), total 3H].

Step 2.

Synthesis of 0101: 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (#54).

To a solution of compound #53 (701 mg, 0.726 mmol) in dichloromethane (10 mL, 0.07 M) was added diethylamine (10 mL), and the reaction mixture was stirred at room temperature while reaction progress was monitored by LC-MS and TLC. Once complete, the reaction was concentrated in vacuo, the residue was azeotroped three times with heptanes, and the resulting crude product was purified by silica gel chromatography (Gradient: 0% to 10% methanol in dichloromethane). The residue was diluted with diethyl ether and heptane and was concentrated in vacuo to afford #54 (406 mg, 75%) as a white solid. LC-MS: m/z 743.6 [M+H+], retention time=0.70 minutes (Protocol F-below); HPLC (Protocol A-below): m/z 743.4 [M+H+], retention time=6.903 minutes, (purity >97%); $^1$H NMR (400 MHz, DMSO-d$_6$), presumed to be a mixture of rotamers, characteristic signals: δ [8.64 (br d, J=8.5 Hz) and 8.86 (br d, J=8.7 Hz), total 1H], [8.04 (br d, J=9.3 Hz) and 8.08 (br d, J=9.3

Hz), total 1H], [7.77 (d, J=3.3 Hz) and 7.80 (d, J=3.2 Hz), total 1H], [7.63 (d, J=3.3 Hz) and 7.66 (d, J=3.2 Hz), total 1H], 7.13-7.31 (m, 5H), [5.39 (ddd, J=11, 8.5, 4 Hz) and 5.53 (ddd, J=12, 9, 4 Hz), total 1H], [4.49 (dd, J=9, 8 Hz) and 4.60 (dd, J=9, 7 Hz), total 1H], 3.16, 3.20, 3.21 and 3.25 (4 s, total 6H), 2.93 and 3.02 (2 br s, total 3H), 1.21 (s, 3H), 1.13 and 1.13 (2 s, total 3H), [1.05 (d, J=6.7 Hz) and 1.10 (d, J=6.7 Hz), total 3H], 0.73-0.80 (m, 3H).

Step 3.

Synthesis of vc0101: N-[6-(2,5-dioxo-2,5-dihydro-1H-pyrrol-1-yl)hexanoyl]-L-valyl-N-{4-[(21S,24S,25R)-24-[(2S)-butan-2-yl]-25-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-18,18,23-trimethyl-3,16,19,22-tetraoxo-21-(propan-2-yl)-2,7,10,13,26-pentaoxa-4,17,20,23-tetraazaheptacos-1-yl]phenyl}-N-5~-carbamoyl-L-ornithinamide.

The coupling of compound 0101 (#54) to linker vc (N-[6-(2,5-dioxo-2,5-dihydro-1H-pyrrol-1-yl)hexanoyl]-L-valyl-N⁵-carbamoyl-N-[4-({[(4-nitrophenoxy)carbonyl]oxy}methyl)phenyl]-L-ornithinamide) (MalcValCitPABC-PNP) was accomplished according to General Procedure E (below) using appropriate quantities of DMA as the solvent, and HOAT and 2,6-Lutidine as additives, and the resulting crude desired material was purified according the Method D (below) to give 33 mg (36%) of the desired product. Under conditions specified in Protocol A (below) with the column maintained at 45° C., this material gave an HPLC retention time of 9.114 minutes (Protocol A-below); LC-MS: m/z 1342.6 [M+H⁺], retention time 3.48 minutes (Protocol H-below).

B. Experimental Method for the Synthesis of mc8261

Preparation of N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (mc8261).

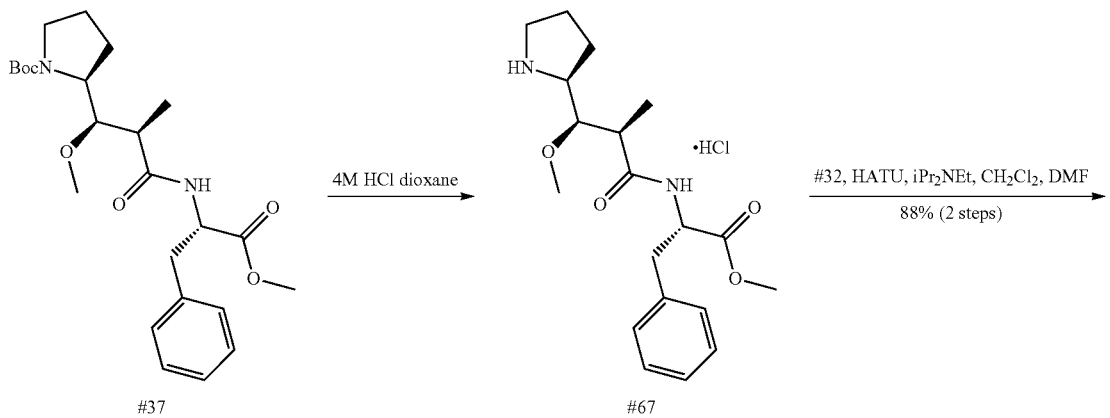

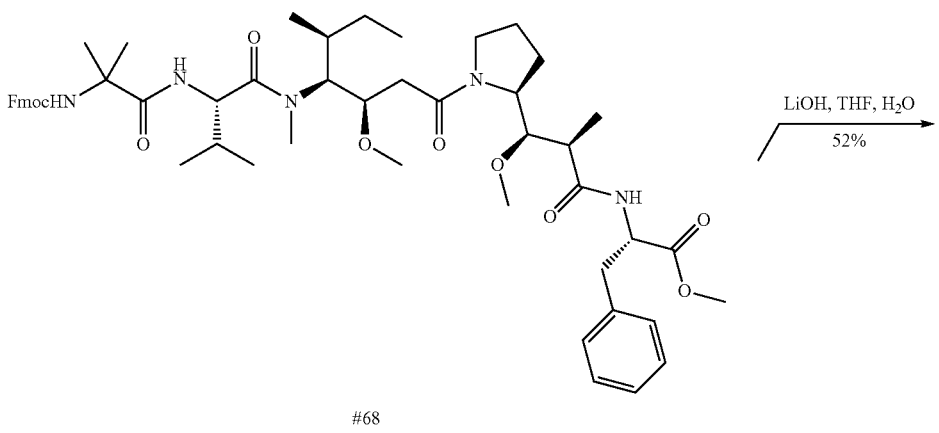

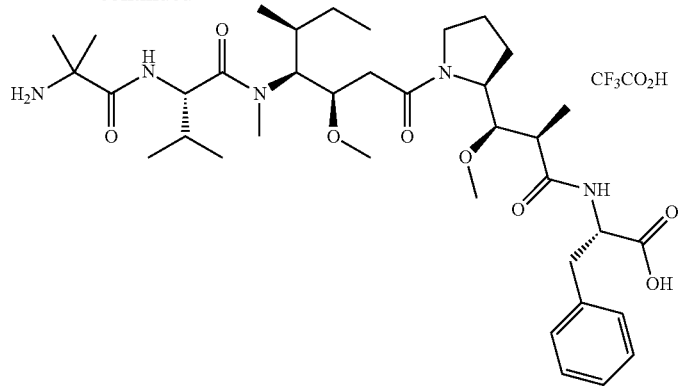

69

Step 1.

Synthesis of methyl N-{(2R,3R)-3-methoxy-2-methyl-3-[(2S)-pyrrolidin-2-yl]propanoyl}-L-phenylalaninate, hydrochloride salt (#67). According to General Procedure C (below), from #37 (2.39 g, 5.33 mmol, 1 eq.), dioxane (10 mL, 0.53 M) and a 4 M hydrochloric acid solution in dioxane (10 mL, 40 mmol, 7.5 eq.) was synthesized #67 (2.21 g) as a white solid, which was used in the next step without further purification. LC-MS: m/z 349.2 [M+H$^+$], retention time=0.53 minutes; $^1$H NMR (400 MHz, DMSO-d$_6$) δ 9.45-9.58 (br m, 1H), 8.63 (d, J=8.1 Hz, 1H), 8.51-8.62 (br m, 1H), 7.25-7.33 (m, 4H), 7.18-7.25 (m, 1H), 4.50 (ddd, J=10.8, 8.1, 4.5 Hz, 1H), 3.65 (s, 3H), 3.54 (dd, J=6.8, 4.5 Hz, 1H), 3.20 (s, 3H), 3.11 (dd, J=13.8, 4.5 Hz, 1H), 2.99-3.14 (br m, 3H), 2.89 (dd, J=13.8, 10.9 Hz, 1H), 2.44-2.50 (m, 1H, assumed; partially obscured by solvent peak), 1.77-1.89 (m, 1H), 1.60-1.73 (m, 2H), 1.46-1.57 (m, 1H), 1.05 (d, J=6.8 Hz, 3H).

Step 2.

Synthesis of N-[(9H-fluoren-9-ylmethoxy)carbonyl]-2-methylalanyl-N-[(3R,4S,5S)-3-methoxy-1-{(2S)-2-[(1R,2R)-1-methoxy-3-{[(2S)-1-methoxy-1-oxo-3-phenylpropan-2-yl]amino}-2-methyl-3-oxopropyl]pyrrolidin-1-yl}-5-methyl-1-oxoheptan-4-yl]-N-methyl-L-valinamide (#68). According to General Procedure D (below), from #32 (353 mg, 0.488 mmol, 1 eq.),

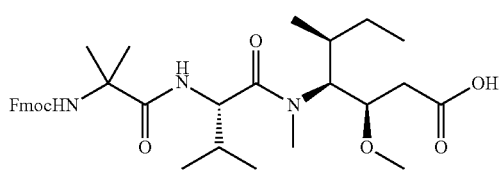

32 in dichloromethane (10 mL, 0.04 M), amine #67 (271 mg, ≤0.588 mmol, 1.3 eq.), HATU (223 mg, 0.586 mmol, 1.2 eq.) and diisopropylethylamine (238 μL, 1.71 mmol, 3.5 eq.) was synthesized the crude desired material, which was purified by silica gel chromatography (Gradient: 0% to 40% acetone in heptane), affording #68 (404 mg, 88% over two steps) as a solid. LC-MS: m/z 940.7 [M+H$^+$], 962.7 [M+Na$^+$], retention time=1.04 minutes; HPLC (Protocol C-below): retention time=9.022 minutes; $^1$H NMR (400 MHz, DMSO-d$_6$), presumed to be a mixture of rotamers, characteristic signals: δ [8.25 (br d, J=8 Hz) and 8.48 (br d, J=8 Hz), total 1H], 7.89 (d, J=7.4 Hz, 2H), 7.67-7.75 (m, 2H), 7.38-7.44 (m, 2H), 7.31-7.36 (m, 2H), 7.14-7.24 (m, 5H), 4.43-4.69 (m, 3H), 4.17-4.26 (m, 3H), 3.91-3.99 (br m, 1H), 3.63 and 3.65 (2 s, total 3H), 3.19 and 3.24 (2 s, total 3H), 3.14 and 3.15 (2 s, total 3H), 2.90 and 2.99 (2 br s, total 3H), 1.36 and 1.37 (2 br s, total 3H), 1.30 and 1.32 (2 s, total 3H), [1.02 (d, J=6.8 Hz) and 1.06 (d, J=6.6 Hz), total 3H].

Step 3A.

Synthesis of 8261: 2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, trifluoroacetic acid salt (#69).

To a solution of #68 (143 mg, 0.152 mmol, 1 eq.) in tetrahydrofuran (5 mL, 0.02 M) was added a solution of lithium hydroxide (9.10 mg, 0.378 mmol, 2.5 eq.) in water (3 mL). After 5 hours, the reaction was concentrated in vacuo, azeotroped three times with heptane, dissolved in dimethyl sulfoxide (2.2 mL) and purified by reverse phase chromatography (Method C-below) to give #69 (56 mg, 52%). HPLC (Protocol A-below at 45° C.): 704.4 [M+H$^+$], retention time=6.623 minutes; $^1$H NMR (400 MHz, DMSO-d$_6$), presumed to be a mixture of rotamers, characteristic signals: δ 8.08-8.22 and 8.37-8.49 (2 m, total 5H), 7.12-7.28 (m, 5H), 3.18, 3.20 and 3.24 (3 s, total 6H), 2.95 and 3.04 (2 br s, total 3H), 1.52 and 1.53 (2 s, total 3H), 1.39 and 1.41 (2 s, total 3H), [1.02 (d, J=6.8 Hz) and 1.05 (d, J=6.6 Hz), total 3H], 0.74-0.81 (m, 3H).

Step 4:

Synthesis of mc8261: N-[6-(2,5-dioxo-2,5-dihydro-1H-pyrrol-1-yl)hexanoyl]-2-methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide.

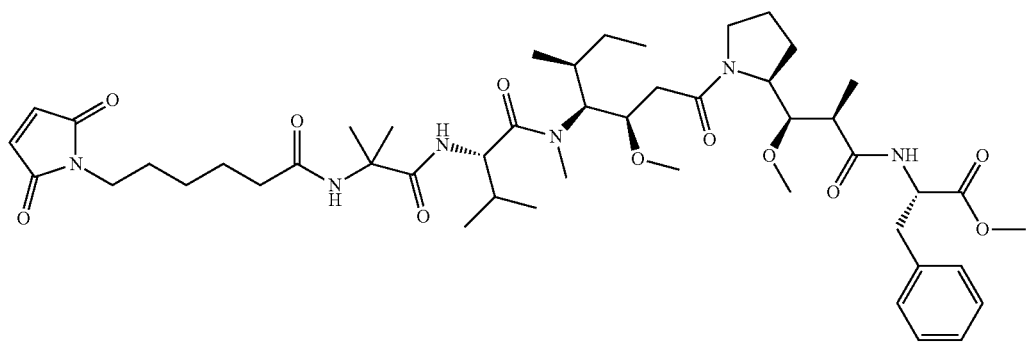

mc-8261

The coupling of compound 8261 (#69) to linker maleimidocaproyl (mc):

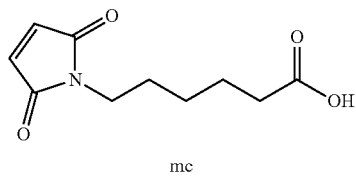 [SMILES: O=C(O)CCCCCN1C(=O)C=CC1=O]

mc was accomplished according to General Procedure D (below) and the resulting crude desired material was purified according the Method C (below) to give 30.2 mg (24%) of the desired product. Under conditions specified in Protocol A (below) with the column maintained at 45° C., this material gave an HPLC retention time of 9.058 minutes (Protocol A-below); LC-MS: m/z 897.7 [M+H$^+$], retention time 0.81 minutes (Protocol H-below).

C. General Procedures, Methods and Protocols

General Procedure C:

Boc removal or tert-butyl ester (also refers to t-Bu ester) cleavage using hydrochloric acid in dioxane. To either a solution of Boc-containing compound or tert-butyl ester-containing compound in dioxane (or in some cases no solution, or other relevant solvent) was added a 4 M solution of hydrochloric acid in dioxane. Reaction progress was monitored by LC-MS (or HPLC or TLC). The reaction was concentrated in vacuo and in some cases azeotroped one to four times with heptanes.

General Procedure D:

coupling with O-(7-azabenzotriazol-1-yl)-N,N,N',N'-tetramethyluronium hexafluorophosphate (HATU). To a stirring solution of the amine (1.0 eq.) and acid (1.0-2.0 eq.) in dichloromethane, N,N-dimethylformamide (also referred to as DMF), or a mixture of both, HATU (1.0-2.0 eq.) was added followed by triethylamine (2.0-4.0 eq.) or diisopropylethylamine (2.0-4.0 eq., also referred to as Hunig's base). Reaction progress was monitored by LC-MS (or HPLC or TLC); the reaction was usually completed within three hours. Solvents were removed in vacuo. The residue was purified by silica gel or reverse phase chromatography or in some cases azeotroped three times with heptanes, diluted with a small amount of ethyl acetate before being reduced down onto silica or C18 bonded silica and purified by silica gel or reverse phase chromatography.

General Procedure E:

coupling with N-[6-(2,5-dioxo-2,5-dihydro-1H-pyrrol-1-yl)hexanoyl]-L-valyl-N$^5$-carbamoyl-N-[4-({[(4-nitrophenoxy)carbonyl]oxy}methyl)phenyl]-L-ornithinamide (MalcValCitPABC-PNP). To a mixture of the payload amine (1 eq.) and N-[6-(2,5-dioxo-2,5-dihydro-1H-pyrrol-1-yl)hexanoyl]-L-valyl-N$^5$-carbamoyl-N-[4-({[(4-nitrophenoxy)carbonyl]oxy}methyl)phenyl]-L-ornithinamide (MalcValCitPABC-PNP, Eur. Pat. Appl. (1994), EP624377, 1.0-2.0 eq.) in N,N-dimethylformamide or dimethylacetamide (also referred to as DMA), pyridine (0.0-4.0 eq.), diisopropylethylamine (0.0-4.0 eq.), 2,6-dimethylpyridine (0.0-4.0 eq., also referred to as 2,6-Luditine) and 1-hydroxybenzotriazole hydrate (0.01-1.1 eq. also referred to as HOBT) or 3H-[1,2,3]triazolo[4,5-b]pyridin-3-ol (0.01-1.1 eq., also referred to as HOAT) was added. After stirring at 40° C.-50° C. for 1-48 hours, the reaction mixture was concentrated in vacuo and azeotroped three times with heptane. The crude material was purified by reverse phase chromatography according to the specified method to afford the desired material.

Method C:

Column: Phenomenex Luna C18, 100×30 mm, 10 µm; Mobile phase A: 0.02% trifluoroacetic acid in water (v/v); Mobile phase B: 0.02% trifluoroacetic acid in methanol (v/v); Gradient: 10% to 90% B over 20 minutes; Flow rate: 20 mL/minute. Temperature: not controlled; Detection: DAD 210 nm, 254 nm; Injection Volume: variable; Instrument: Gilson.

Method D:

Column: Phenomenex Synergi Max-RP, 150×21.2 mm, 4 µm; Mobile phase A: 0.1% formic acid in water; Mobile phase B: 0.1% formic acid in acetonitrile; Gradient: 30% B for 1.5 minutes, 30% to 60% B over 8.5 minutes, 60 to 100% B over 0.5 minutes then 100% B over 2 minutes; Flow rate: 27 mL/minute; Detection: DAD 210-360 nm; MS (+) range 150-20005 daltons; Instrument: Waters FractionLynx.

Protocol A:

Column: Phenomenex Luna C18 (2), 150×3.0 mm, 5 µm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B for 1 minute; Flow rate: 0.75 mL/minute. Temperature: 25° C.; Detection: DAD 215 nm; MS (+) range 150-2000 daltons; Injection volume: 10 µL Instrument: Agilent 1200 LCMS.

Protocol C:

Column: Phenomenex Luna C18 (2), 150×3.0 mm, 5 µm; Mobile phase A: 0.02% trifluoroacetic acid in water (v/v); Mobile phase B: 0.02% trifluoroacetic acid in methanol (v/v); Gradient: 50% to 100% B over 10 minutes; Flow rate:

0.75 mL/minute. Temperature: not controlled; Detection: DAD 215 nm, 254 nm; Injection volume: 10 µL; Instrument: Agilent 1100 HPLC.

Protocol F:

Column: Waters Acquity UPLC BEH, C18, 2.1×50 mm, 1.7 µm; Mobile phase A: 0.1% formic acid in water (v/v); Mobile phase B: 0.1% formic acid in acetonitrile (v/v); Gradient: 5% B over 0.1 minute, 5% to 95% B over 0.7 minute, 95% B over 0.1 minute; Flow rate: 1.25 mL/minute. Temperature: 60° C.; Detection: 200-450 nm; MS (+) range 100-1200 daltons; Injection volume: 5 µL; Instrument: Waters Acquity.

Protocol H:

Column: Phenomenex Gemini-NX, C18, 4.6×50 mm, 3 µm, 110 Å; Mobile phase A: 0.1% formic acid in water (v/v); Mobile phase B: 0.1% formic acid in acetonitrile (v/v); Gradient: 0% to 100% B over 4.10 minutes, linear then 100% B over 0.4 minute; Flow rate: 1.5 mL/minute. Temperature: 60° C.; Detection: DAD 200-450 nm; MS (+) range 100-2000 daltons; Injection volume: 5 µL; Instrument: Agilent.

Example 10

Bioconjugation of the Anti-PTK7 Antibodies

A. Anti-PTK7-vc0101 Antibody-Drug Conjugates

In the present invention, anti-PTK7 antibodies hu23, hu24 and hu58 were conjugated to vc0101 to generate hu23-vc0101 ADC, hu24-vc0101 ADC and hu58-vc0101 ADC, or conjugated to mc8261 to generate hu23-mc8261 ADC, hu24-mc8261 ADC and hu58-mc8261 ADC. The conjugation of hu23, hu24, and hu58 to vc0101 mc8261 was achieved by derivatizations of the side chains of cysteine residues. These cysteines are normally paired as inter-chain cysteine disulfide bridges, of which there are 4 conserved pairs (involving 8 cysteine residues) on an IgG1 antibody. Partial reduction of these disulfide linkages provides a distribution of free thiols that can be functionalized with the maleimide handle on the vc linker. Specifically, an anti-PTK7 antibodies of the present invention were partially reduced via addition of 2.4 molar excess of tris(2-carboxyethyl)phosphine (TCEP) in 100 mM HEPES (4-(2-hydroxyethyl)-1-piperazineethanesulfonic acid buffer), pH 7.0 and 1 mM diethylenetriaminepentaacetic acid (DTPA) for 2 hours at 37° C. The vc0101 or mc8261 linker-payload was then added to the reaction mixture at a linker-payload/antibody molar ratio of 7 and reacted for an additional 1 hour at 25° C. in the presence of 15% v/v of dimethylacetamide (DMA). After the 1 hour incubation period, 3-fold excess of N-ethylmaleimide was added to cap the unreacted thiols and was allowed to react for 15 minutes, followed by addition of 6-fold excess L-Cys to quench any unreacted linker-payload.

The reaction mixture was dialyzed overnight at 4° C. in phosphate buffered saline (PBS), pH 7.4, and purified via size exclusion chromatography (SEC; AKTA explorer, Superdex 200). The final ADC drug substance was formulated in 20 mM Histidine, 85 mg/mL Sucrose, pH 5.8 buffer.

The anti-PTK antibody-drug conjugates were further characterized via SEC for purity and hydrophobic interaction chromatography (HIC), and liquid chromatography electrospray ionization mass spectrometry (LC-ESI MS) which was used to calculate drug-antibody ratio (drug loading). The protein concentration was determined via ultraviolet (UV) spectrophotometry. This method provides an antibody-drug conjugate as a heterogeneous mixture of functionalized antibodies that contain an average drug-to-antibody ratio (DAR) of approximately 4 mol/mol.

Figure 7:
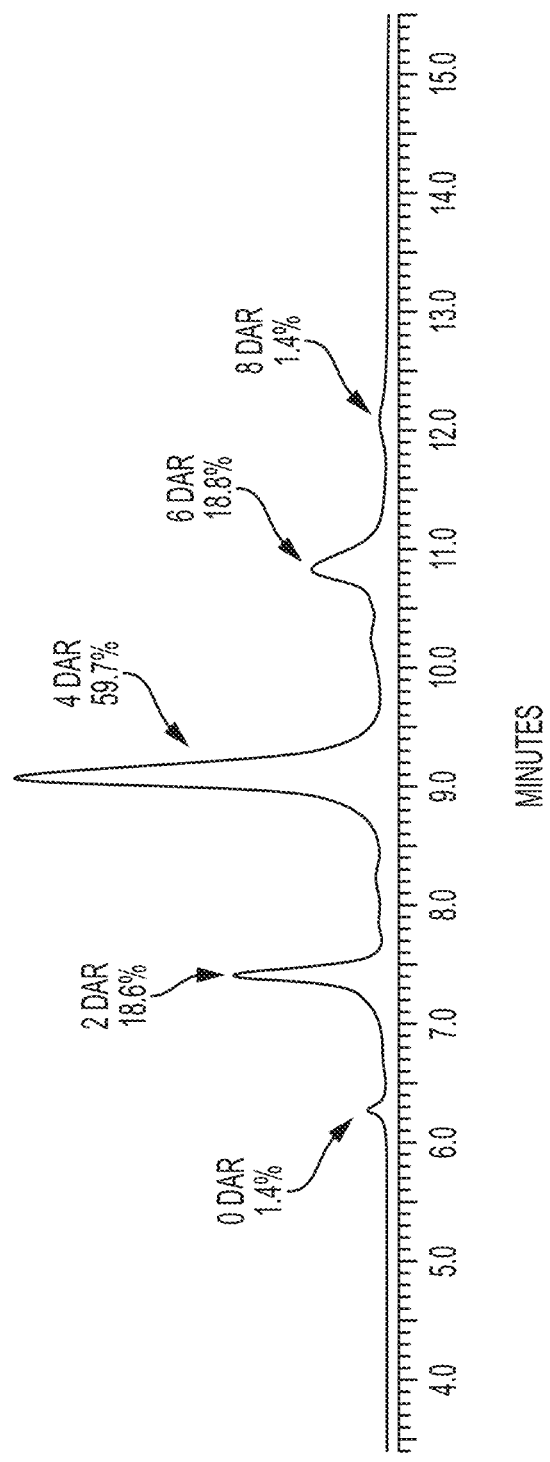
FIG. 7 provides the hydrophobic interaction chromatography (HIC) analysis of hu24-vc0101.

The drug distribution profile was assessed via HIC for hu24-vc0101 and presented in the chromatogram in FIG. 7. Briefly, analytical HIC was performed on TSK gel butyl-NPR column. The ADC was bound to the column in 1.5 M ammonium sulfate, 50 mM potassium phosphate dibasic, pH 7 and eluted with 50 mM potassium phosphate dibasic and 20% isopropanol (IPA), pH 7.

B. Anti-PTK7-AcBut CM Antibody-Drug Conjugates

In the present invention, anti-PTK7 antibodies hu23, hu24 and hu58 were conjugated to AcBut-N-acetyl-γ-calicheamicin dimethyl hydrazide (AcButCM) OSu ester to generate hu23-AcButCM ADC, hu24-AcButCM ADC and hu58-AcButCM ADC as shown below, wherein X can be any antibody, such as hu23, hu24 and hu58.

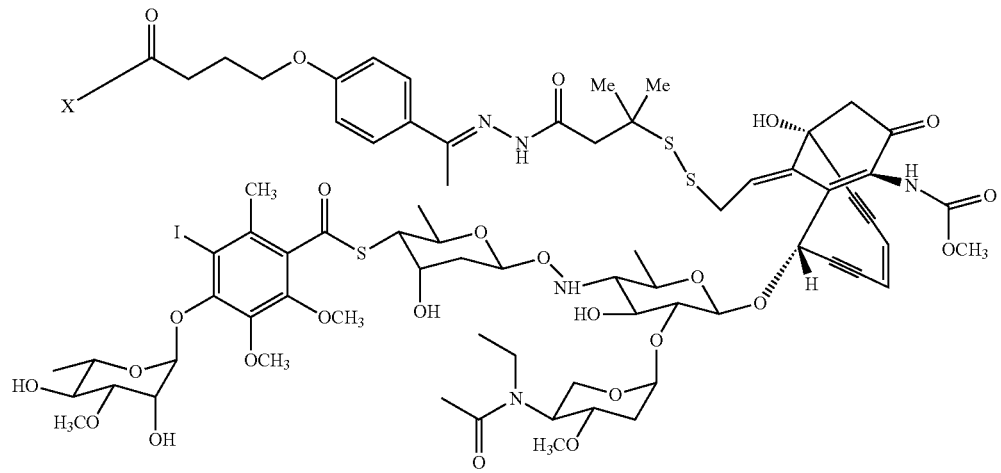

The reaction mixture included 10 mg/ml or less anti-PTK7 antibody and AcButCM OSu ester at a molar ratio of 4-4.5 to 1. High agitation was conducted during the addition of AcButCM to a mixing vortex. The reaction pH was 8.3 and the concentrations of other reaction components were as follows: 180 mM HEPES buffer, 41 mM sodium decanoate, and 8% (v/v) ethanol. The reaction was conducted at 33° C. for 5 minutes. After the conjugation reaction was completed, the reaction mixture was diluted slowly with 1.3 volumes of 1M $K_2HPO_4$ adjusted to pH 8.5 with mixing.

To purify, the diluted above reaction mixture was loaded in two batches on a Butyl Sepharose-4 Fast Flow HIC column (GE Healthcare) that was previously equilibrated in five column volumes (cv) of 0.52M potassium phosphate buffer, pH 8.5. The protein loaded on the column was 3.5 mg/ml of bed volume. The flow rate was 15 ml/minute through the sample loading and 22 ml/minute throughout the wash and elution phase of the chromatography. This improved gradient removes higher DAR ADCs that were bound to the column.

The unbound fraction during the loading was predominantly reaction reagents and most of the unconjugated antibody, which was discarded. The column was then washed with 0.3 cv of 0.52M potassium phosphate buffer, pH 8.5, to remove any remaining reagents. A step gradient with 1 cv from 0.52M to 0.4M potassium phosphate buffer, pH 8.5 was then used to elute any loosely bound unconjugated antibody along with low loaded anti-PTK7-AcButCM, if present. The main fraction was then eluted using a step gradient of 1 cv from 0.4M to 5 mM potassium phosphate buffer, pH 8.5, to provide anti-PTK7-AcButCM having a DAR in the range of 3 to 5, toward the end of the gradient. If anti-PTK7-AcButCM conjugates with a higher DAR were present, the fraction was eluted using a gradient of 2 cv of 5 mM potassium phosphate buffer, pH 8.5, and then an elution of pure deionized water. Any anti-PTK7-AcButCM conjugates with a higher DAR that remained bound after the deionized water elution were eluted using 2 cv of 10 mM sodium hydroxide containing 20% ethanol. The purified batches contained anti-PTK7-AcButCM conjugates with a DAR of 3 to 5.

This improved conjugation and purification processes generated ADCs having a DAR that was less than 6, and in some aspects in the range of 3 to 5. Further, the processes generated a narrower distribution of loading, for example, less heterogeneity within the product. Improvements to the conjugation and purification processes further included: 1) decreasing the AcButCM to anti-PTK7 antibody ratio to 4-4.5 to 1 to generate an ADC having a lower DAR, 2) conducting high agitation during addition of AcButCM to anti-PTK7 antibody to generate ADCs with low amounts of unconjugated antibody (free antibody), 3) reducing incubation time to 5 minutes, compared to 60-90 minutes, to provide low aggregates and 4) a reduction in ethanol amount to 6-8% to provide low aggregates. The purified pooled peaks from both batches were dialyzed twice against a formulated buffer to facilitate storage in a frozen state. The formulated buffer composition was 20 mM Tris, 7.5% sucrose, 0.01% polysorbate 80, 10 mM NaCl, pH 8.0.

Example 11

Binding Characteristics of hu24 mAb and hu24 ADC

To determine whether hu24 mAb and hu24-vc0101 ADC bind to the cynomolgus monkey ortholog of PTK7, the cynomologus monkey PTK7 protein was cloned and expressed. Sequence analysis revealed that the protein is 97.9% identical to the human PTK7 protein.

Surface plasmon resonance (SPR) analysis was conducted to characterize the binding characteristics of the mAb and ADC to human and cynomolgus monkey PTK7 protein ectodomains. Binding was determined to be comparable by SPR analysis. There was no significant difference in affinities between mAb and ADC for human or cynomolgus monkey PTK7 protein (Table 16). All $K_{on}$ measurements are within 3-fold and all $K_{off}$ measurements are within 2-fold, ranges considered in the field to be within typical systematic error and therefore not likely to be physiologically significant.

TABLE 16

Affinity Constants of hu24 and hu24-vc0101 for Human PTK7 and Cynomolgus Monkey PTK7

| Test Article | Antigen Species | $K_{on}$ ($M^{-1}s^{-1}$) | $K_{off}$ ($s^{-1}$) | Kd (nM) |
|---|---|---|---|---|
| hu24 mAb | Human | 7.9E+05 | 5.4E−04 | 0.7 |
| | Cynomolgus | 4.3E+05 | 5.2E−04 | 1.2 |
| hu24-vc0101 | Human | 5.1E+05 | 5.3E−04 | 1.4 |
| | Cynomolgus | 2.8E+05 | 1.0E−03 | 3.6 |

$K_{on}$ = Association rate constant;
$K_{off}$ = Dissociation rate constant;
Kd = Equilibrium dissociation constant;
M = Molar;
mAb = Monoclonal antibody;
nM = Nanomolar;
s = Seconds The ability of anti-PTK7 mAbs to bind to PTK7 orthologs was also evaluated by sandwich ELISA. Briefly, human, cynomolgus monkey, rat or mouse PTK7-His tagged protein was captured on an ELISA plate by direct coating. All antigens were captured at 1 µg/ml, 100 µl/well. Hu24 mAb and hu24-vc0101 ADC were serially diluted starting with 810 ng/ml and added to the washed and blocked wells to test for binding to the antigen. mAb and ADC binding was detected by polyclonal anti-human IgG horseradish peroxidase conjugate and read out with TMB substrate.

Both mAb and ADC bound comparably to human and cynomolgus monkey PTK7 proteins by ELISA (Table 17). Together with the SPR results, these results confirmed cross-reactivity to cynomolgus monkey PTK7 and demonstrated that the bioconjugation process did not change of the observed binding characteristics of the mAb. However, neither mAb nor ADC exhibited detectable binding to rat or mouse PTK7 protein at 100-fold higher antigen concentration than needed to observe binding to human PTK7 (Table 17). Rat and mouse antigens were confirmed to be correctly folded by binding to known cross reactive antibodies (data not shown).

TABLE 17

Binding of hu24 and hu24-vc0101 to PTK7 proteins by ELISA

| | ED50 values (ng/mL) | | | |
|---|---|---|---|---|
| | Human PTK7 | Cynomolgus PTK7 | Rat PTK7 | Mouse PTK7 |
| hu24 mAb | 4.7 | 5.0 | No binding | No binding |
| hu24-vc0101 | 6.6 | 7.4 | No binding | No binding |

ADC = Antibody-drug conjugate;
ED50 = Effective dose that gives 50% maximum signal;
mAb = Monoclonal antibody;
ng/mL = Nanograms per milliliter Unconjugated hu24 and hu24 conjugated to vc0101 were compared for their ability to bind to PTK7 expressing cells by flow cytometry using the methods described in Example 3. Briefly, cultured H1975 or EKVX cells were harvested and incubated at 4° C. with hu24-vc0101 ADC or unconjugated hu24 mAb followed by fluorophore-conjugated secondary mAb and a viability stain and then analyzed by flow cytometry.

Table 18 provides the mean channel fluorescence of the viable cell population. Comparable data was obtained in an independent replicate experiment thus conjugation of hu24 to the linker payload does not alter its binding to PTK7 expressing cells.

TABLE 18

Comparable Cell Binding of Conjugated and Unconjugated hu24

| Cell Line | Test Article | Concentration of hu24-vc0101 ADC or hu24 mAb | | | |
|---|---|---|---|---|---|
| | | 0.1 μg/mL | 0.3 μg/mL | 1 μg/mL | 3 μg/mL |
| H1975 | hu24-vc0101 ADC | 94 | 196 | 302 | 341 |
| | hu24 mAb | 91 | 183 | 310 | 348 |
| EKVX | hu24-vc0101 ADC | 4 | 4 | 4 | 5 |
| | hu24 mAb | 4 | 4 | 4 | 5 |

Example 12

In Vitro Cytotoxicity Assays

The cytotoxicity of the antibody-drug conjugate hu24-vc0101 was evaluated on cell lines that express the target PTK7. The engineered HEK293T-PTK7 over-expressing cell line was plated into a clear flat-bottom tissue culture plate (BD Falcon) at 500 cells per 180 μL of cell culture media per well. Human cancer cell lines were also tested in this assay and plated at a density that was previously determined to be optimal for each cell line according to their rate of growth (H661 1500 cells/well and H446 9600 cells/well in 150 μl). The cells were incubated overnight at 37° C. in a 5% $CO_2$ incubator. On the following day, the hu24-vc0101 ADC and the 8.84 Ab-vc0101 ADC (negative control) were added to the cells on a 10 point concentration curve in triplicate samples starting with 3 or 10 μg/mL with 1:3 dilutions in cell culture media. The plate was incubated in a 37° C., 5% $CO_2$ incubator for 4 days. The MTS assay (Promega CellTiter 96 Aqueous Non-Radioactive Cell Proliferation Assay) was used according to the supplier's instructions. 30 μL (H446, H661) or 40 μL (HEK293T-PTK7) of the combined MTS reagent was added to each well, and the plate was incubated in a 37° C., 5% $CO_2$ incubator for 2 hours. The OD was determined at 490 nm with a 96-well plate reader. The average reading from wells with media alone was subtracted from the readings of wells with cells to control for background OD. The data was subjected to logistic non-linear regression analysis (GraphPad Prism Software) in order to determine the concentration of antibody-drug conjugate at which cell viability was inhibited by 50% (IC50).

Table 19 provides IC50 values for the hu24-vc0101 ADC in the cytotoxicity assay. In all three cell lines, hu24-vc0101 elicited potent cytotoxicity whereas the non-binding 8.84 Ab-vc0101 did not; these data demonstrate that the potent cytotoxicity of hu24-vc0101 was dependent on anti-PTK7 antibody.

TABLE 19

| | IC50 Values (ng/mL) | | |
|---|---|---|---|
| Cell Line | hu24-vc0101 ADC | 8.84 Ab-vc0101 ADC | Free 0101 |
| HEK293-PTK7 | 1.7 | >3000 | ND |
| H661 | 27.5 ± 20.5 | >10000 | 0.33 |
| H446 | 7.6 ± 5.0 | >10000 | 0.59 |

ND = not determined

Example 13

In Vivo Efficacy of Anti-PTK7 Antibody-Drug Conjugates

The effects of anti-PTK7 antibody-drug conjugates were further evaluated on the in vivo growth of human tumor patient-derived xenografts (PDX). Primary tumor resection samples were procured from clinical sites following Institutional Review Board for the Protection of Human Subjects approval and in accordance with HIPAA regulations. Tumor fragments were stored and shipped in Hypothermasol (Biolife Solutions) on ice and were embedded in Matrigel (BD) containing a proprietary mix of growth factors and implanted subcutaneously into the mammary fatpad of female NOD/SCID mice within 24 hours of resection. Mice were monitored for health status daily and for tumor growth initially by visual inspection twice per week. Once the tumors were palpable, measurements of tumor volume began to track tumor growth and estimate cell doubling time. Tumor volume was estimated using the equation $V=(A*B^2)/2$ where A is the long axis and B is the short axis. When tumors reached a volume of 500 mm³ to 1,500 mm³, they were harvested for study and for re-transplant as a patient-derived xenograft (PDX). Depending on the line, mechanical and/or chemical dissociation can be used to separate the individual cells for passage. Live cells were inoculated into naïve animals with 10,000 to 50,000 cells per animals For efficacy studies, tumors were harvested from passaging studies and cells were dissociated into single cell suspension. Preparations were counted for live cells using Trypan blue exclusion and 10,000 to 50,000 cells were inoculated per mouse in Matrigel. To account for differential growth rates of PDX, at least 25% more animals were started to allow for minimal tumor volume variance at randomization. Tumor growth was initially followed by palpability with measurements beginning once tumor volumes reached about 30 mm³. Studies were randomized based on tumor size once a cohort of tumor-bearing mice reached 140 mm³ to 180 mm³. Animals were dosed by intraperitoneal injection twice a week for two weeks (q4dx4). Study groups were followed until individual mice or entire group tumor measurements reached 1200 mm³ when sacrifice was indicated in accordance with IACUC protocol. For selected dosing studies, pharmacokinetic submandibular bleeds were performed at 2 hours, 36 hours and 72 hours. A volume of 10 μL of blood was immediately pipetted into 90 μL of HBS-P (GE Healthcare). Samples were stored at −80° C. prior to analysis. For each tumor measurement the tumor volume±standard error of the mean (SEM) is provided. GT=Group Terminated due to large tumor size. All studies included a control antibody drug conjugate comprised of a non-binding hIgG1 antibody conjugated to the same linker-payload being analyzed and with comparable drug-to-antibody ratio (DAR) and loading distribution.

Tables 20-37 demonstrate the effectiveness of the antibody-drug conjugates hu23-vc0101, hu24-vc0101, hu58-vc0101, hu23-AcButCM, hu24-AcButCM and hu58-AcButCM in PDX models established using various human tumor cells that have a relative PTK7 expression determined to be low, medium, or high.

A. Breast Cancer (BR)

Figure 8:
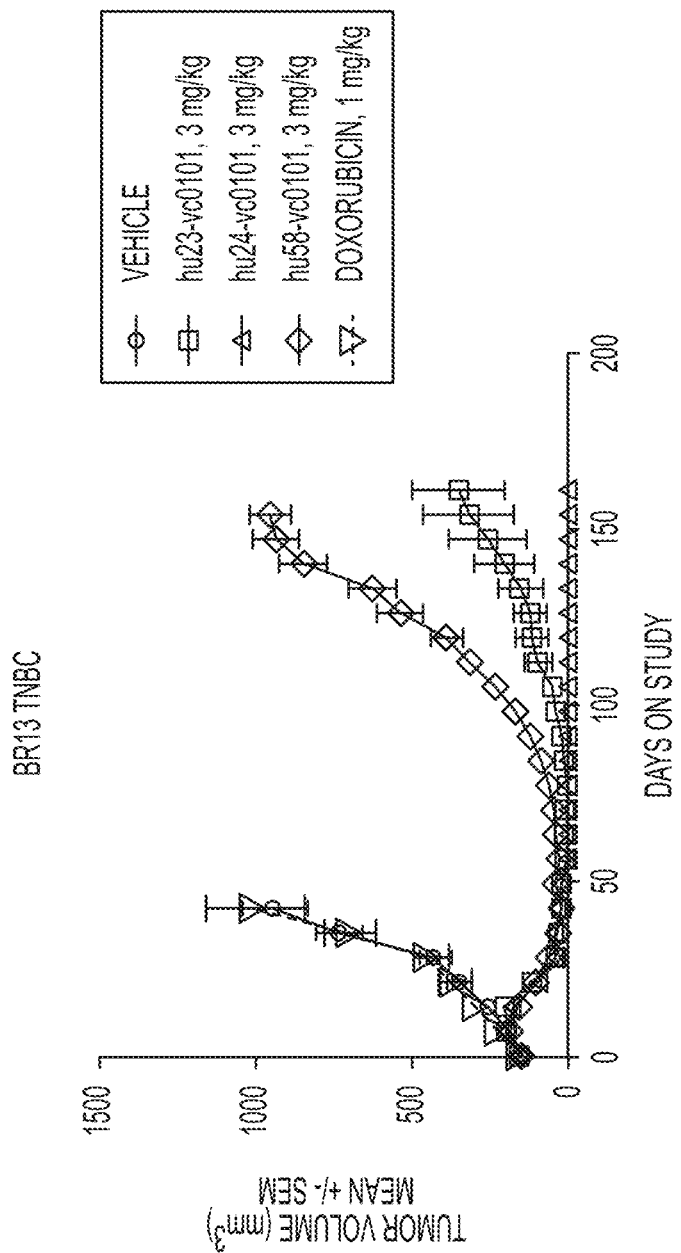
FIG. 8 is a graph showing the efficacy of anti-PTK7-vc0101 ADCs in the Breast-13 (BR13) triple-negative breast cancer (TNBC) PDX.

Table 20 and FIG. 8 show that the hu23-vc0101, hu24-vc0101, and hu58-vc0101 ADCs are all effective in a PDX model using the human Breast-13 (BR13) triple-negative breast cancer (TNBC) PDX model (high PTK7 expression) compared to vehicle and drug controls. The hu24-vc0101 ADC was more effective than both hu23-vc0101 and hu58-vc0101 in the BR13 PDX model. All of the PTK7 ADCs tested were more effective than doxorubicin, which is a standard of care treatment for TNBC.

hu24-vc0101. Treatment with hu24-vc0101 yielded sustained tumor regression for over 200 days and demonstrated greater inhibition of tumor growth compared to anti-PTK7-mc8261 ADCs.

Figure 11:
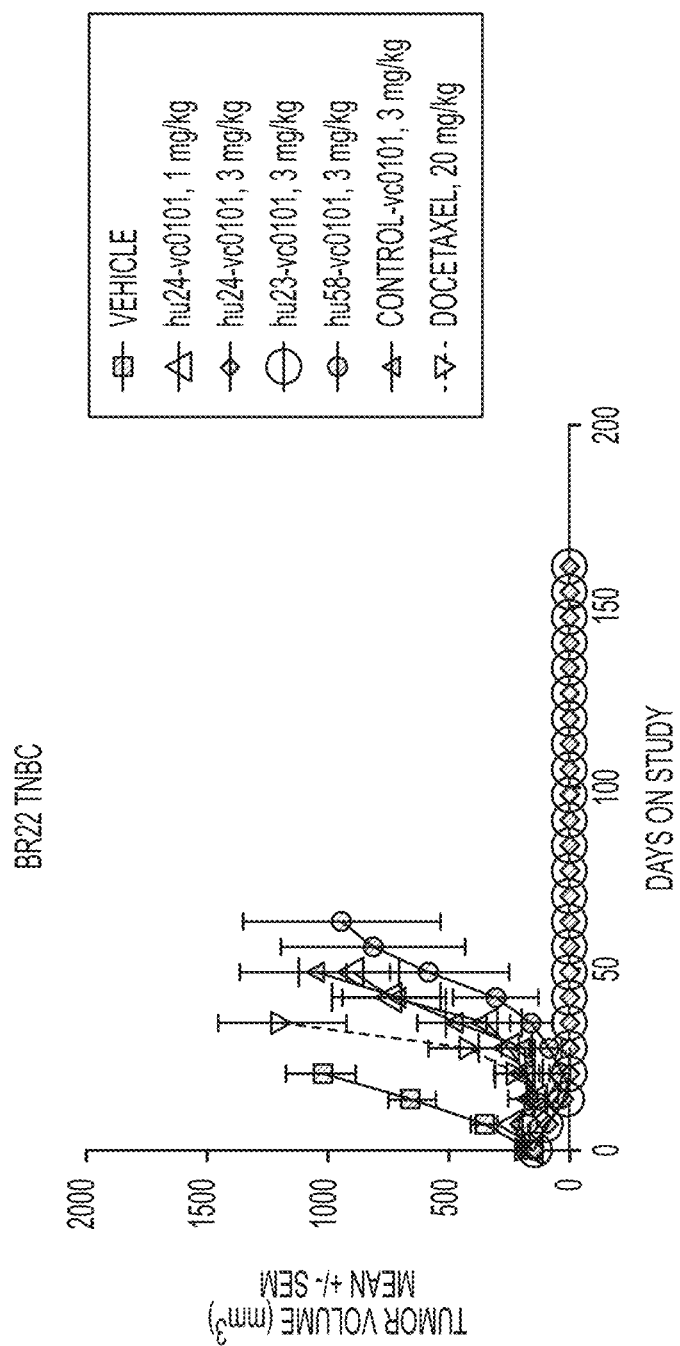
FIG. 11 is a graph showing the efficacy of anti-PTK7-vc0101 ADCs in the Breast-22 (BR22) TNBC PDX.

Table 21 and FIG. 11 show that the hu23-vc0101, hu24-vc0101, and hu58-vc0101 ADCs are all effective in a PDX model using the human Breast-22 (BR22) TNBC PDX model (high PTK7 expression) compared to vehicle and drug controls. In this model the hu23-vc0101 and hu24-vc0101 ADCs were more effective than hu58-vc0101, demonstrating similar antibodies to the same target (PTK7) have varying degrees of efficacy. All of the PTK7 ADCs tested were more effective than docetaxel, which is a standard of care treatment for TNBC. Notably, docetaxel and the drug

TABLE 20

Efficacy of anti-PTK7-vc0101 ADCs in BR13 TNBC PDX.

| Day | Vehicle | 1 mg/kg Doxorubicin | 3 mg/kg Control-vc0101 | 3 mg/kg hu23-vc0101 | 3 mg/kg hu24-vc0101 | 3 mg/kg hu58-vc0101 |
|---|---|---|---|---|---|---|
| 0 | 144 ± 13 | 156 ± 13 | 153 ± 9 | 154 ± 9 | 153 ± 10 | 151 ± 10 |
| 7 | 174 ± 13 | 219 ± 29 | 211 ± 17 | 199 ± 12 | 194 ± 12 | 183 ± 14 |
| 14 | 255 ± 22 | 295 ± 39 | 277 ± 28 | 206 ± 16 | 175 ± 17 | 159 ± 15 |
| 21 | 349 ± 40 | 353 ± 45 | 323 ± 44 | 116 ± 16 | 97 ± 11 | 110 ± 12 |
| 28 | 428 ± 48 | 432 ± 50 | 413 ± 48 | 48 ± 7 | 41 ± 4 | 61 ± 13 |
| 35 | 734 ± 74 | 696 ± 84 | 537 ± 66 | 39 ± 6 | 37 ± 5 | 37 ± 3 |
| 42 | 940 ± 105 | 1001 ± 159 | 591 ± 74 | 23 ± 7 | 20 ± 5 | 27 ± 3 |
| 49 | GT | GT | 775 ± 87 | 23 ± 7 | 19 ± 7 | 40 ± 5 |
| 56 | GT | GT | 952 ± 89 | 15 ± 6 | 4 ± 4 | 32 ± 3 |
| 63 | GT | GT | 1181 ± 119 | 6 ± 4 | 0 ± 0 | 40 ± 6 |
| 70 | GT | GT | 1287 ± 98 | 7 ± 5 | 0 ± 0 | 48 ± 7 |
| 77 | GT | GT | 1449 ± 125 | 8 ± 5 | 0 ± 0 | 64 ± 10 |
| 84 | GT | GT | GT | 14 ± 10 | 0 ± 0 | 85 ± 15 |
| 91 | GT | GT | GT | 20 ± 11 | 0 ± 0 | 119 ± 28 |
| 98 | GT | GT | GT | 39 ± 18 | 0 ± 0 | 165 ± 26 |
| 105 | GT | GT | GT | 52 ± 22 | 0 ± 0 | 236 ± 29 |
| 112 | GT | GT | GT | 94 ± 41 | 0 ± 0 | 314 ± 37 |
| 119 | GT | GT | GT | 116 ± 50 | 0 ± 0 | 389 ± 51 |
| 126 | GT | GT | GT | 123 ± 52 | 0 ± 0 | 538 ± 73 |
| 133 | GT | GT | GT | 152 ± 71 | 0 ± 0 | 624 ± 76 |
| 140 | GT | GT | GT | 204 ± 97 | 0 ± 0 | 849 ± 78 |
| 147 | GT | GT | GT | 257 ± 125 | 0 ± 0 | 935 ± 74 |
| 154 | GT | GT | GT | 318 ± 141 | 0 ± 0 | 954 ± 65 |
| 161 | GT | GT | GT | 352 ± 148 | 0 ± 0 | GT |

Figure 10:
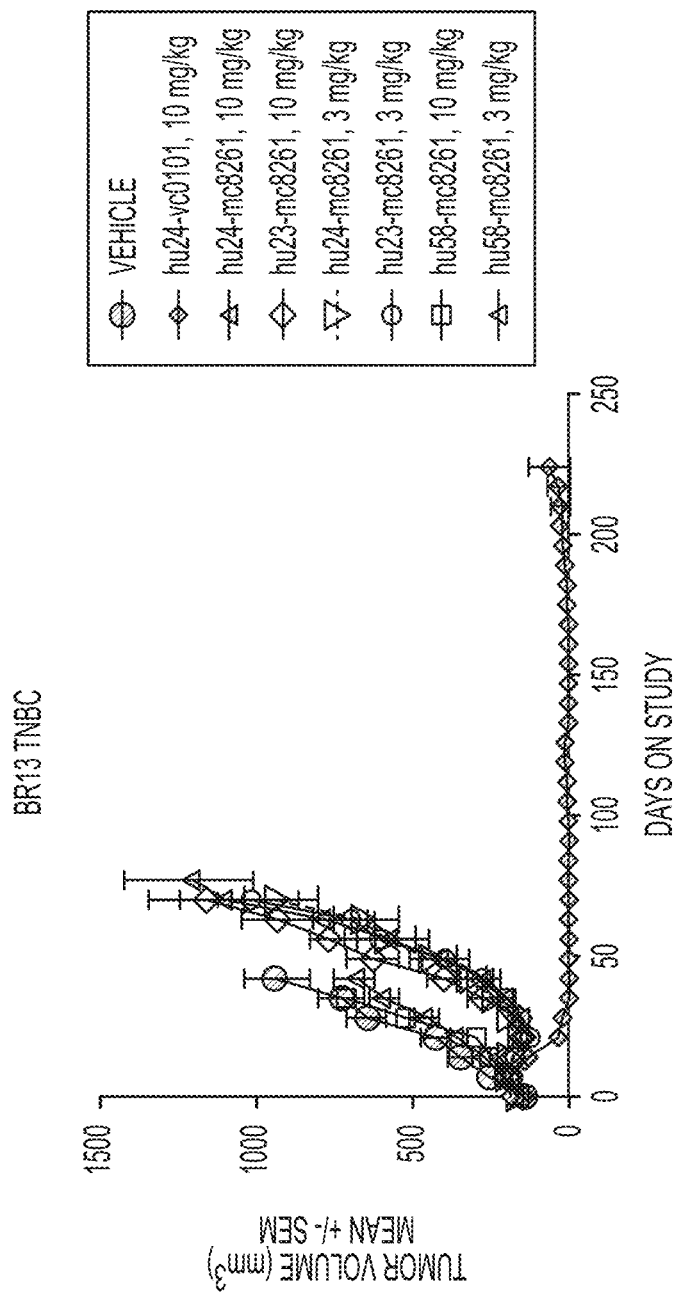
FIG. 10 is a graph of the data of FIG. 9 showing the efficacy of hu24-vc0101 and anti-PTK7-mc8261 ADCs in the BR13 TNBC PDX.

FIGS. 9 and 10 show the efficacy of the hu23-mc8261, hu24-mc8261, and hu58-mc8261 ADCs in the BR13 TNBC PDX model (high PTK7 expression) in comparison to component of the ADCs, auristatin 0101, have similar mechanisms of action in that they inhibit tubulin polymerization.

TABLE 21

Efficacy of anti-PTK7-vc0101 ADCs in BR22 TNBC PDX.

| Day | Vehicle | 20 mg/kg Docetaxel | 3 mg/kg Control-vc0101 | 1 mg/kg hu24-vc0101 | 3 mg/kg hu24-vc0101 | 3 mg/kg hu58-vc0101 | 3 mg/kg hu23-vc0101 |
|---|---|---|---|---|---|---|---|
| 0 | 171 ± 19 | 182 ± 21 | 164 ± 14 | 172 ± 22 | 170 ± 19 | 143 ± 7 | 150 ± 9 |
| 7 | 354 ± 52 | 154 ± 23 | 221 ± 34 | 245 ± 28 | 89 ± 22 | 169 ± 13 | 100 ± 11 |
| 14 | 655 ± 99 | 107 ± 51 | 207 ± 49 | 157 ± 48 | 21 ± 5 | 49 ± 12 | 10 ± 6 |
| 21 | 1028 ± 142 | 218 ± 98 | 129 ± 40 | 213 ± 97 | 0 ± 0 | 38 ± 24 | 1 ± 1 |
| 28 | GT | 418 ± 165 | 209 ± 71 | 266 ± 114 | 0 ± 0 | 84 ± 55 | 0 ± 0 |
| 35 | GT | 1191 ± 264 | 482 ± 142 | 357 ± 156 | 0 ± 0 | 157 ± 91 | 0 ± 0 |
| 42 | GT | GT | 724 ± 212 | 758 ± 225 | 0 ± 0 | 301 ± 178 | 0 ± 0 |
| 49 | GT | GT | 1054 ± 308 | 912 ± 203 | 0 ± 0 | 584 ± 339 | 0 ± 0 |
| 56 | GT | GT | GT | GT | 0 ± 0 | 813 ± 381 | 0 ± 0 |
| 63 | GT | GT | GT | GT | 0 ± 0 | 943 ± 409 | 0 ± 0 |
| 70 | GT | GT | GT | GT | 0 ± 0 | GT | 0 ± 0 |
| 77 | GT | GT | GT | GT | 0 ± 0 | GT | 0 ± 0 |
| 84 | GT | GT | GT | GT | 0 ± 0 | GT | 0 ± 0 |

TABLE 21-continued

Efficacy of anti-PTK7-vc0101 ADCs in BR22 TNBC PDX.

| Day | Vehicle | 20 mg/kg Docetaxel | 3 mg/kg Control-vc0101 | 1 mg/kg hu24-vc0101 | 3 mg/kg hu24-vc0101 | 3 mg/kg hu58-vc0101 | 3 mg/kg hu23-vc0101 |
|---|---|---|---|---|---|---|---|
| 91  | GT | GT | GT | GT | 0 ± 0 | GT | 0 ± 0 |
| 98  | GT | GT | GT | GT | 0 ± 0 | GT | 0 ± 0 |
| 105 | GT | GT | GT | GT | 0 ± 0 | GT | 0 ± 0 |
| 112 | GT | GT | GT | GT | 0 ± 0 | GT | 0 ± 0 |
| 119 | GT | GT | GT | GT | 0 ± 0 | GT | 0 ± 0 |
| 126 | GT | GT | GT | GT | 0 ± 0 | GT | 0 ± 0 |
| 133 | GT | GT | GT | GT | 0 ± 0 | GT | 0 ± 0 |
| 140 | GT | GT | GT | GT | 0 ± 0 | GT | 0 ± 0 |
| 147 | GT | GT | GT | GT | 0 ± 0 | GT | 0 ± 0 |
| 154 | GT | GT | GT | GT | 0 ± 0 | GT | 0 ± 0 |
| 161 | GT | GT | GT | GT | 0 ± 0 | GT | 0 ± 0 |

Table 22 shows the hu23-AcButCM, hu24-AcButCM, and hu58-AcButCM ADCs were all effective in the BR22 TNBC PDX model (high PTK7 expression) compared to vehicle and drug controls. However, hu58-AcButCM was more effective than both hu23-AcButCM and hu24-AcButCM, illustrating the unpredictable nature of the use of various payloads with similar antibodies to the same target. The hu23-vc0101 and hu24-vc0101 ADCs were more effective than hu58-vc0101, whereas the hu58-AcButCM was more effective than both hu23-AcButCM and hu24-AcButCM ADCs. All of the PTK7 ADCs tested were more effective than doxorubicin, which is a standard of care treatment for TNBC.

TABLE 22

Efficacy of ADCs in BR22 TNBC PDX.

| Day | Vehicle | 1.5 mg/kg Doxorubicin | 0.3 mg/kg Control-AcButCM | 0.3 mg/kg hu23-AcButCM | 0.3 mg/kg hu58-AcButCM | 0.3 mg/kg hu24-AcButCM |
|---|---|---|---|---|---|---|
| 0   | 303 ± 16 | 297 ± 17 | 186 ± 16   | 186 ± 15  | 157 ± 13  | 193 ± 16 |
| 14  | 797 ± 71 | 641 ± 39 | 456 ± 55   | 140 ± 15  | 30 ± 5    | 185 ± 71 |
| 28  | GT | GT | 1019 ± 148 | 11 ± 2    | 0 ± 0     | 32 ± 28 |
| 63  | GT | GT | GT         | 100 ± 83  | 10 ± 10   | 118 ± 117 |
| 91  | GT | GT | GT         | 652 ± 479 | 67 ± 67   | 723 ± 695 |
| 119 | GT | GT | GT         | 999 ± 527 | 125 ± 125 | 862 ± 797 |
| 133 | GT | GT | GT         | GT        | 125 ± 125 | 968 ± 794 |
| 161 | GT | GT | GT         | GT        | 125 ± 125 | 1538 ± 1098 |
| 175 | GT | GT | GT         | GT        | 150 ± 150 | GT |

Figure 13:
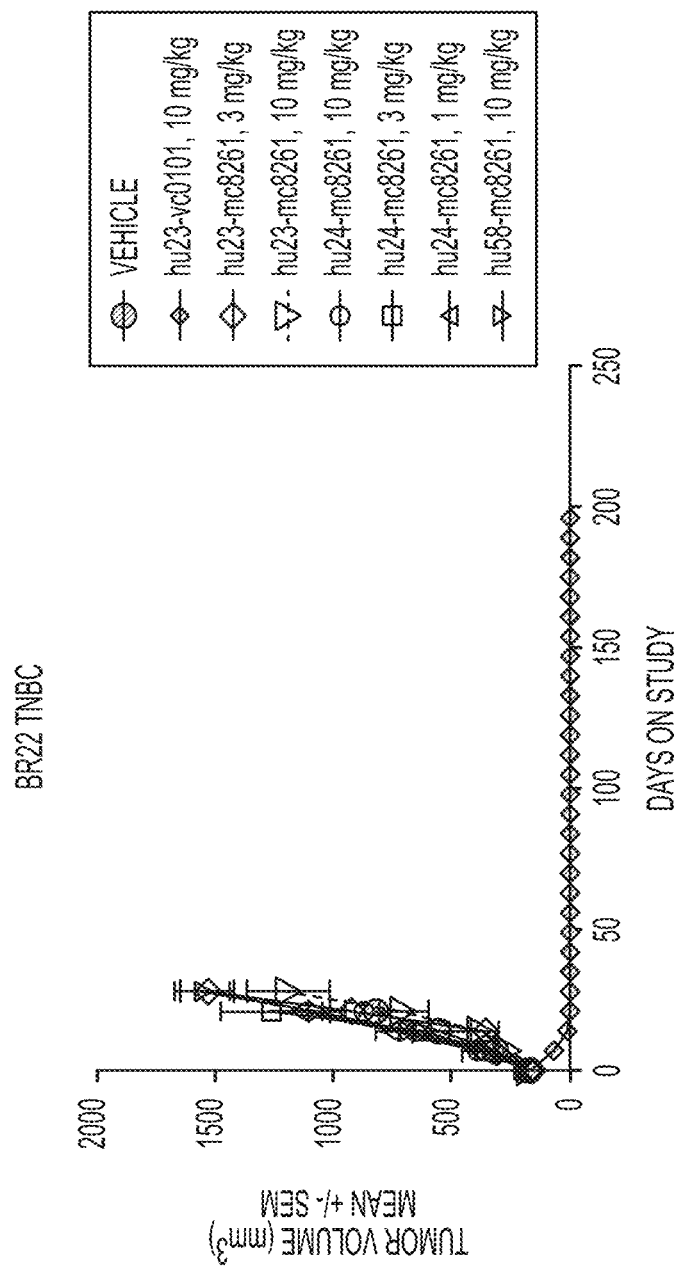
FIG. 13 is a graph of the data of FIG. 12 showing the efficacy of hu23-vc0101 and anti-PTK7-mc8261 ADCs in the BR22 TNBC PDX.

FIGS. 12 and 13 show the efficacy of the hu23-mc8261, hu24-mc8261, and hu58-mc8261 ADCs in the BR22 TNBC PDX model (high PTK7 expression) in comparison to hu23-vc0101. Treatment with hu23-vc0101 yielded sustained tumor regressions for over 200 days and demonstrated greater inhibition of tumor growth as compared to anti-PTK7-mc8261 ADCs.

Figure 14:
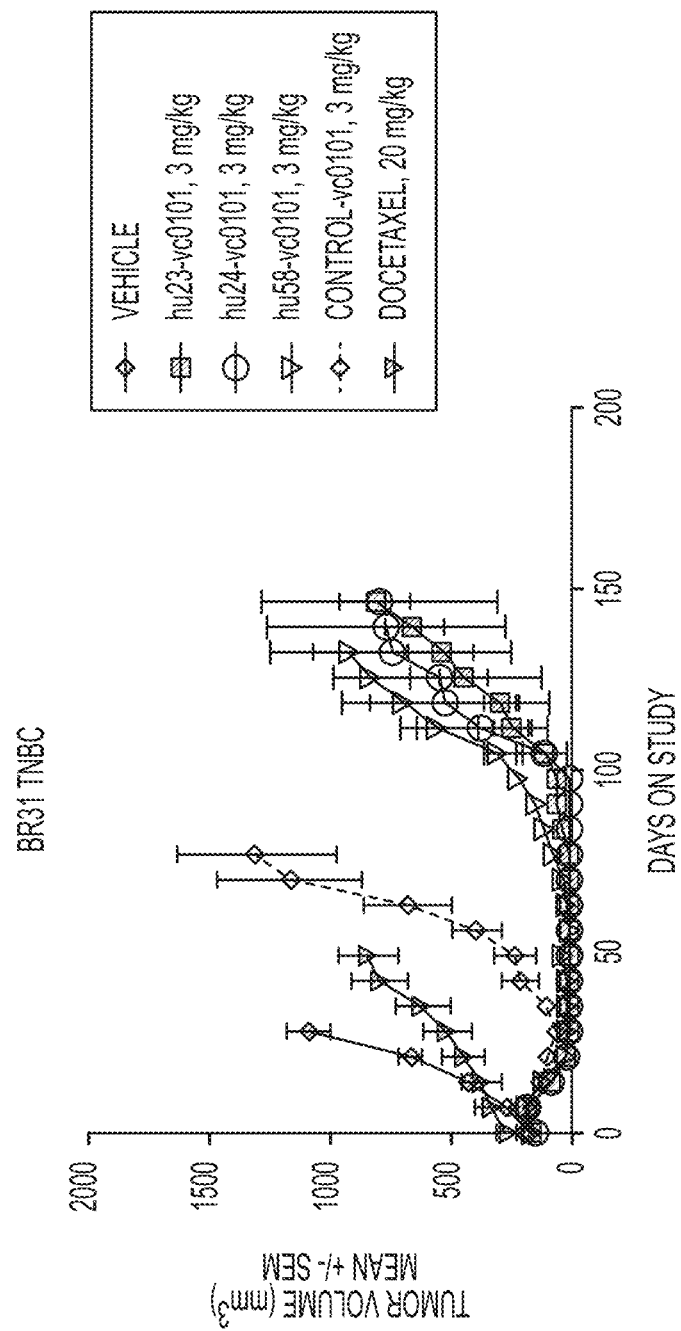
FIG. 14 is graph showing the efficacy of anti-PTK7-vc0101 ADCs in the Breast-31 (BR31) TNBC PDX.

Tables 23-25 and FIG. 14 show the efficacy of the hu23-vc0101, hu24-vc0101, hu58-vc0101, hu23-mc8261 and hu24-mc8261, hu58-mc8261 and hu23-AcButCM, hu24-AcButCM, hu58-AcButCM ADCs in the Breast-31 (BR31) TNBC PDX model (high PTK7 expression). In this model, all three ADCS having vc0101 linker-payload were more effective than the ADCs having AcButCM or mc8261. This result was unexpected since the AcButCM linker payload was generally more potent than the vc0101 linker payload in the in vivo PDX models tested. In addition, the PTK7-vc0101 ADCs were more effective than docetaxel and the PTK7-AcButCM ADCs were more effective than doxorubicin. Both docetaxel and doxorubicin are standards of care for TNBC.

TABLE 23

Efficacy of anti-PTK7-vc0101 ADCs in BR31 TNBC PDX.

| Day | Vehicle | 20 mg/kg Docetaxel | 3 mg/kg Control-vc0101 | 3 mg/kg hu23-vc0101 | 3 mg/kg hu24-vc0101 | 3 mg/kg hu58-vc0101 |
|---|---|---|---|---|---|---|
| 0  | 159 ± 10  | 259 ± 47  | 148 ± 12 | 164 ± 14 | 159 ± 15 | 158 ± 12 |
| 7  | 269 ± 17  | 331 ± 70  | 227 ± 23 | 178 ± 23 | 188 ± 12 | 170 ± 25 |
| 14 | 425 ± 32  | 371 ± 82  | 133 ± 10 | 79 ± 8   | 82 ± 7   | 100 ± 11 |
| 21 | 668 ± 50  | 451 ± 91  | 101 ± 21 | 28 ± 7   | 21 ± 3   | 38 ± 3 |
| 28 | 1088 ± 93 | 510 ± 103 | 70 ± 17  | 8 ± 3    | 0 ± 0    | 21 ± 7 |
| 35 | GT        | 614 ± 117 | 105 ± 28 | 0 ± 0    | 0 ± 0    | 8 ± 5 |
| 42 | GT        | 790 ± 117 | 21 ± 76  | 0 ± 0    | 0 ± 0    | 0 ± 0 |

TABLE 23-continued

Efficacy of anti-PTK7-vc0101 ADCs in BR31 TNBC PDX.

| Day | Vehicle | 20 mg/kg Docetaxel | 3 mg/kg Control-vc0101 | 3 mg/kg hu23-vc0101 | 3 mg/kg hu24-vc0101 | 3 mg/kg hu58-vc0101 |
|---|---|---|---|---|---|---|
| 49 | GT | 837 ± 126 | 234 ± 83 | 2 ± 0 | 0 ± 0 | 30 ± 18 |
| 56 | GT | ND | 393 ± 103 | 2 ± 1 | 0 ± 0 | 3 ± 1 |
| 63 | GT | 1131 ± 148 | 680 ± 181 | 2 ± 1 | 0 ± 0 | 17 ± 9 |
| 70 | GT | 1317 ± 182 | 1169 ± 300 | 8 ± 3 | 0 ± 0 | 35 ± 18 |
| 77 | GT | GT | 1300 ± 331 | 13 ± 4 | 1 ± 1 | 70 ± 24 |
| 84 | GT | GT | GT | 32 ± 10 | 2 ± 2 | 108 ± 32 |
| 91 | GT | GT | GT | 59 ± 24 | 10 ± 10 | 143 ± 36 |
| 98 | GT | GT | GT | 59 ± 15 | 13 ± 13 | 213 ± 46 |
| 105 | GT | GT | GT | 115 ± 35 | 111 ± 92 | 295 ± 68 |
| 112 | GT | GT | GT | 249 ± 75 | 370 ± 269 | 551 ± 155 |
| 119 | GT | GT | GT | 293 ± 72 | 521 ± 429 | 691 ± 143 |
| 126 | GT | GT | GT | 449 ± 100 | 551 ± 428 | 826 ± 155 |
| 133 | GT | GT | GT | 541 ± 135 | 745 ± 499 | 914 ± 155 |
| 140 | GT | GT | GT | 658 ± 130 | 765 ± 494 | GT |
| 147 | GT | GT | GT | 810 ± 145 | 794 ± 488 | GT |

TABLE 24

Efficacy of anti-PTK7-mc8261 ADCs in BR31 TNBC PDX.

| Day | Vehicle | 10 mg/kg hu23-mc8261 | 10 mg/kg hu24-mc8261 | 10 mg/kg hu58-mc8261 |
|---|---|---|---|---|
| 0 | 159 ± 10 | 154 ± 8 | 154 ± 9 | 161 ± 13 |
| 7 | 269 ± 17 | 238 ± 21 | 202 ± 20 | 225 ± 21 |
| 14 | 425 ± 32 | 304 ± 12 | 275 ± 35 | 280 ± 29 |
| 21 | 668 ± 50 | 383 ± 32 | 370 ± 53 | 390 ± 39 |
| 28 | 1088 ± 93 | 601 ± 70 | 609 ± 81 | 635 ± 55 |
| 35 | GT | 857 ± 88 | 862 ± 139 | 889 ± 118 |

TABLE 25

Efficacy of anti-PTK7-AcButCM ADCs in BR31 TNBC PDX.

| Day | Vehicle | 1.5 mg/kg Doxorubicin | 0.3 mg/kg Control-AcButCM | 0.3 mg/kg hu58-AcButCM | 0.3 mg/kg hu23-AcButCM | 0.3 mg/kg hu24-AcButCM |
|---|---|---|---|---|---|---|
| 0 | 159 ± 10 | 160 ± 11 | 145 ± 11 | 145 ± 12 | 144 ± 9 | 149 ± 11 |
| 7 | 269 ± 17 | 304 ± 20 | 223 ± 25 | 199 ± 21 | 236 ± 20 | 188 ± 14 |
| 28 | 1088 ± 93 | 759 ± 111 | 675 ± 158 | 270 ± 42 | 236 ± 36 | 106 ± 7 |
| 35 | GT | GT | 869 ± 204 | 381 ± 46 | 339 ± 69 | 139 ± 15 |
| 63 | GT | GT | GT | 885 ± 150 | 920 ± 208 | 299 ± 41 |
| 77 | GT | GT | GT | GT | GT | 590 ± 104 |
| 84 | GT | GT | GT | GT | GT | 882 ± 183 |

Figure 15:
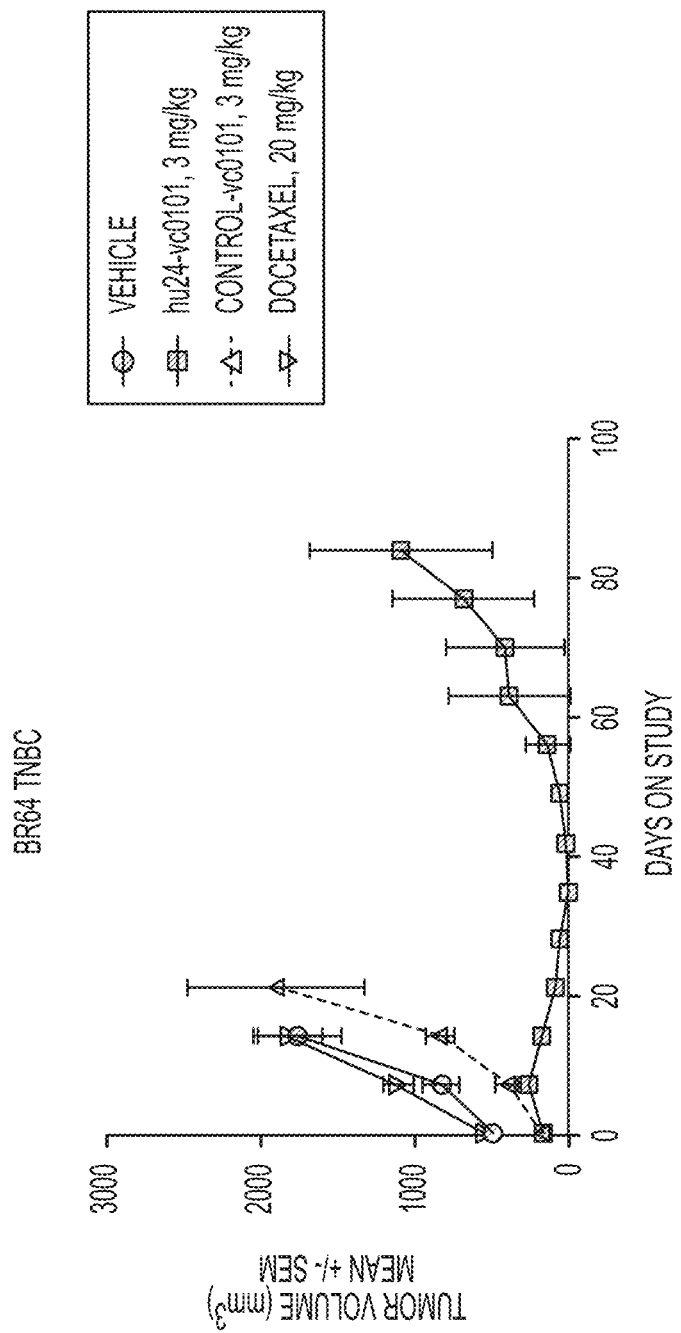
FIG. 15 is a graph showing the efficacy of hu24-vc0101 ADC in the Breast-64 (BR64) TNBC PDX.

Table 26 and FIG. 15 show the hu24-vc0101 ADC was effective in the human Breast-64 (BR64) TNBC PDX model (medium PTK7 expression) compared to vehicle and drug controls. The data demonstrates that a PDX model having a moderate expression of the PTK7 target was targeted effectively with hu24-vc0101. Hu24-vc0101 was more effective than docetaxel, a standard of care for TNBC.

TABLE 26

Efficacy of hu24-vc0101 in BR64 TNBC PDX.

| Day | Vehicle | 20 mg/kg Docetaxel | 3 mg/kg Control-vc0101 | 3 mg/kg hu24-vc0101 |
|---|---|---|---|---|
| 0 | 499 ± 36 | 543 ± 46 | 190 ± 30 | 173 ± 24 |
| 7 | 832 ± 119 | 1112 ± 97 | 418 ± 62 | 271 ± 30 |
| 14 | 1768 ± 284 | 1805 ± 206 | 839 ± 91 | 180 ± 55 |
| 21 | GT | GT | 1907 ± 576 | 96 ± 30 |
| 28 | GT | GT | GT | 53 ± 21 |
| 35 | GT | GT | GT | 15 ± 6 |
| 42 | GT | GT | GT | 27 ± 22 |
| 49 | GT | GT | GT | 65 ± 58 |
| 56 | GT | GT | GT | 144 ± 141 |
| 63 | GT | GT | GT | 394 ± 392 |
| 70 | GT | GT | GT | 422 ± 385 |
| 77 | GT | GT | GT | 690 ± 460 |
| 84 | GT | GT | GT | 1094 ± 594 |

Figure 16:
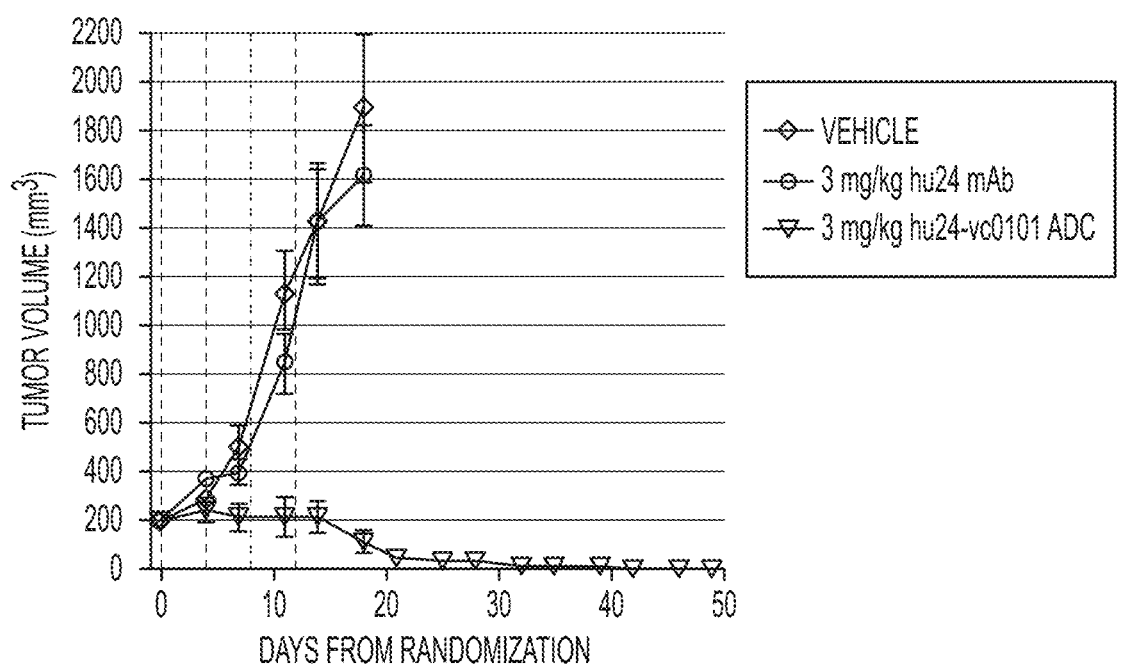
FIG. 16 is a graph showing the efficacy of hu24-vc0101 ADC in the BR5 TNBC PDX.

FIG. 16 shows the efficacy of the hu24-vc0101, and the lack of efficacy of the unconjugated hu24, in the BR5 TNBC PDX model. Mice harboring Br5 human breast cancer xenografts were dosed every four days for four cycles (Q4Dx4) with hu24-vc0101 ADC, unconjugated hu24 mAb or vehicle. Tumor measurements were recorded twice a week using digital calipers and are shown as Mean±SEM. The 3 mg/kg dose of hu24-vc0101 ADC caused tumor regression without tumor growth through day 49. In contrast, the unconjugated hu24 mAb did not inhibit tumor growth (FIG. 16). Thus the observed efficacy is dependent on delivery of the linker-payload.

Figure 17:
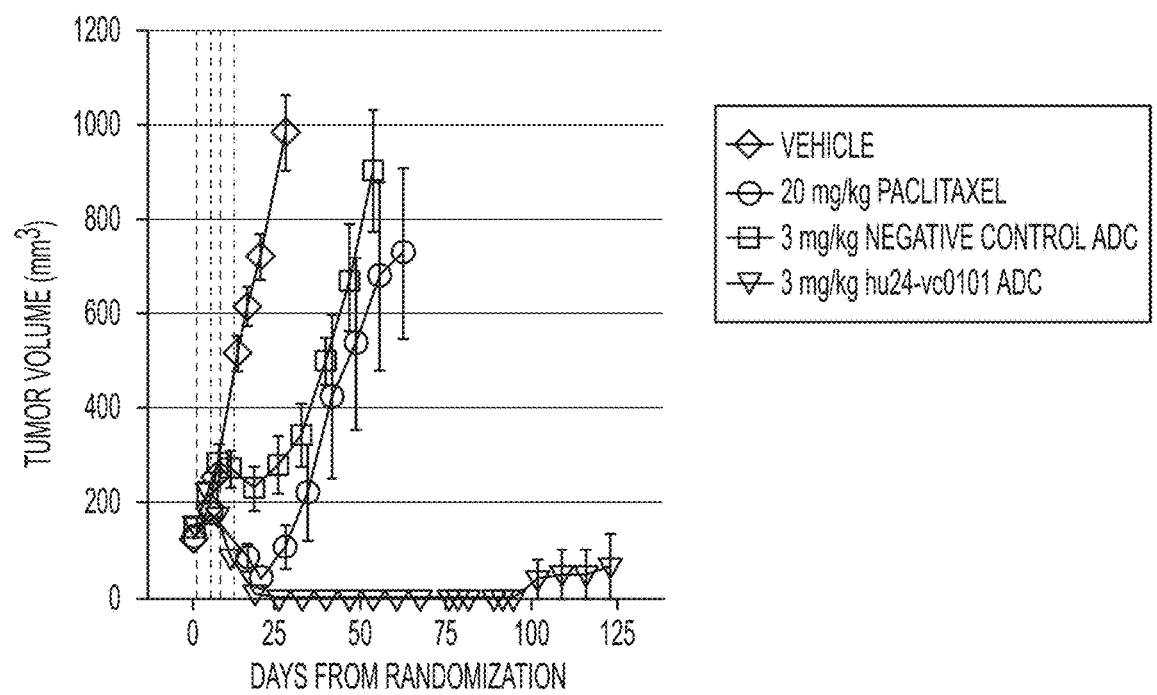
FIG. 17 is a graph showing the efficacy of hu24-vc0101 ADC in the BR36 PR+ TNBC PDX.

FIG. 17 shows the efficacy of the hu24-vc0101 in comparison to paclitaxel in the BR36 PR+ TNBC PDX model. Mice harboring BR36 human breast cancer xenografts were dosed Q4Dx4 with hu24-vc0101 ADC, paclitaxel, negative control ADC or vehicle. Tumor measurements were recorded twice a week using digital calipers and are shown as Mean±SEM. The 3 mg/kg dose of hu24-vc0101 ADC caused tumor regression without tumor growth through day 103. Hu24-vc0101 out preformed paclitaxel administered at the MTD. The negative control ADC exhibited only modest activity (FIG. 17).

B. Small Cell Lung Cancer (SCLC)

The data in Tables 27-28 illustrate the effectiveness of the hu24-vc0101 and hu24-AcButCM ADCs in the small cell lung cancer-64 (LU64) PDX model (low PTK7 expression). In this model, both ADCs were shown to be effective in this PDX of low PTK7 expression although the ADCs having an AcButCM linker payload were more effective than ADCs having a vc0101 linker payload. Both hu24-vc0101 and hu24-AcButCM were more effective than the standard of care for SCLC (which is cisplatin plus etoposide).

Table 29 shows the efficacy of the hu23-mc8261, hu24-mc8261, and hu58-mc8261 ADCs in the LU64 PDX model (low PTK7 expression). Treatment with hu24-vc0101 demonstrated greater inhibition of tumor growth than the anti-mc8261 ADCs in this model.

TABLE 29

Efficacy of anti-PTK7-mc8261 ADCs in LU64 PDX.

| Day | Vehicle | 10 mg/kg hu23-mc8261 | 10 mg/kg hu24-mc8261 | 10 mg/kg hu58-mc8261 |
|---|---|---|---|---|
| 0 | 184 ± 24 | 171 ± 11 | 170 ± 12 | 177 ± 15 |
| 7 | 269 ± 26 | 239 ± 14 | 257 ± 29 | 279 ± 32 |
| 14 | 417 ± 16 | 311 ± 19 | 330 ± 45 | 364 ± 31 |
| 21 | 591 ± 37 | 455 ± 38 | 435 ± 76 | 517 ± 47 |
| 28 | 738 ± 103 | 572 ± 51 | 622 ± 119 | 760 ± 74 |
| 35 | 771 ± 92 | 770 ± 92 | 903 ± 197 | 1029 ± 95 |
| 42 | 970 ± 64 | 1088 ± 116 | GT | GT |

Tables 30-31 show the efficacy of the hu24-vc0101, hu23-vc0101 and hu24-AcButCM ADCs in the small cell lung cancer-86 (LU86) PDX model (high PTK7 expression). In this model, both hu24-vc0101 and hu23-vc0101 were effective in suppressing tumor growth. Hu24-vc0101 was more effective than the control-vc0101 ADC. However, the hu24-AcButCM ADC was more potent than both of the ADCs having a vc0101 linker payload (Table 22) providing further example of the general greater potency of AcButCM compared to vc0101 in SCLC models. Hu24-AcButCM was more effective than cisplatin plus etoposide, which is a standard of care for SCLC.

TABLE 27

Efficacy of hu24-vc0101 ADCs in LU64 PDX.

| Day | Vehicle | 5 mg/kg Cisplatin + 24 mg/kg Etoposide | 3 mg/kg Control-vc0101 | 10 mg/kg Control-vc0101 | 3 mg/kg hu24-vc0101 | 10 mg/kg hu24-vc0101 |
|---|---|---|---|---|---|---|
| 0 | 139 ± 12 | 139 ± 10 | 156 ± 11 | 168 ± 14 | 166 ± 15 | 178 ± 19 |
| 7 | 241 ± 25 | 25 ± 5 | 255 ± 26 | 312 ± 38 | 252 ± 11 | 348 ± 32 |
| 14 | 376 ± 33 | 31 ± 5 | 379 ± 26 | 433 ± 49 | 310 ± 38 | 391 ± 42 |
| 21 | 613 ± 39 | 77 ± 22 | 493 ± 38 | 619 ± 72 | 389 ± 35 | 377 ± 66 |
| 28 | 1087 ± 86 | 151 ± 38 | 718 ± 92 | 824 ± 85 | 537 ± 67 | 500 ± 76 |
| 35 | GT | 214 ± 54 | 912 ± 158 | GT | 651 ± 70 | 618 ± 113 |
| 42 | GT | 285 ± 72 | GT | GT | 932 ± 128 | 773 ± 141 |
| 49 | GT | 738 ± 127 | GT | GT | GT | 838 ± 171 |
| 56 | GT | 1011 ± 172 | GT | GT | GT | 1054 ± 185 |
| 63 | GT | GT | GT | GT | GT | 1367 ± 290 |

TABLE 28

Efficacy of hu24-AcButCM ADCs in LU64 PDX.

| Day | Vehicle | 5 mg/kg Cisplatin + 24 mg/kg Etoposide | 0.1 mg/kg Control-AcButCM | 0.02 mg/kg hu24-AcButCM | 0.05 mg/kg hu24-AcButCM | 0.1 mg/kg hu24-AcButCM |
|---|---|---|---|---|---|---|
| 0 | 139 ± 12 | 139 ± 10 | 171 ± 11 | 137 ± 10 | 137 ± 10 | 136 ± 9 |
| 21 | 613 ± 39 | 77 ± 22 | 575 ± 45 | 13 ± 4 | 1 ± 1 | 0 ± 0 |
| 28 | 1087 ± 86 | 151 ± 38 | 723 ± 77 | 12 ± 4 | 0 ± 0 | 0 ± 0 |
| 35 | GT | 214 ± 54 | 998 ± 107 | 24 ± 10 | 0 ± 0 | 0 ± 0 |
| 42 | GT | 285 ± 72 | GT | 36 ± 17 | 0 ± 0 | 0 ± 0 |
| 56 | GT | 1011 ± 172 | GT | 168 ± 55 | 0 ± 0 | 0 ± 0 |
| 63 | GT | GT | GT | 274 ± 89 | 0 ± 0 | 0 ± 0 |
| 105 | GT | GT | GT | 760 ± 206 | 0 ± 0 | 0 ± 0 |
| 112 | GT | GT | GT | GT | 0 ± 0 | 0 ± 0 |
| 168 | GT | GT | GT | GT | 0 ± 0 | 0 ± 0 |

TABLE 30

Efficacy of anti-PTK7-vc0101 ADCs in LU86 PDX.

| Day | Vehicle | 3 mg/kg Control-vc0101 | 0.3 mg/kg hu24-vc0101 | 1 mg/kg hu24-vc0101 | 3 mg/kg hu24-vc0101 | 3 mg/kg hu23-vc0101 |
|---|---|---|---|---|---|---|
| 0 | 139 ± 11 | 164 ± 19 | 145 ± 11 | 143 ± 12 | 141 ± 11 | 200 ± 23 |
| 7 | 334 ± 44 | 228 ± 45 | 362 ± 39 | 282 ± 46 | 194 ± 24 | 42 ± 11 |
| 14 | 758 ± 100 | 310 ± 39 | 758 ± 62 | 363 ± 77 | 56 ± 11 | 0 ± 0 |
| 21 | 1213 ± 140 | 394 ± 57 | 1441 ± 97 | 420 ± 115 | 5 ± 4 | 0 ± 0 |
| 28 | GT | 748 ± 102 | GT | 621 ± 159 | 0 ± 0 | 0 ± 0 |
| 35 | GT | 1279 ± 198 | GT | 784 ± 141 | 0 ± 0 | 0 ± 0 |
| 42 | GT | GT | GT | 915 ± 105 | 0 ± 0 | 0 ± 0 |
| 49 | GT | GT | GT | GT | 0 ± 0 | 0 ± 0 |
| 56 | GT | GT | GT | GT | 0 ± 0 | 0 ± 0 |
| 63 | GT | GT | GT | GT | 17 ± 17 | 0 ± 0 |
| 70 | GT | GT | GT | GT | 73 ± 45 | 0 ± 0 |
| 77 | GT | GT | GT | GT | 121 ± 67 | 0 ± 0 |
| 84 | GT | GT | GT | GT | 204 ± 90 | 0 ± 0 |
| 91 | GT | GT | GT | GT | 477 ± 272 | 0 ± 0 |
| 98 | GT | GT | GT | GT | 570 ± 270 | 0 ± 0 |
| 105 | GT | GT | GT | GT | 689 ± 281 | 19 ± 19 |
| 112 | GT | GT | GT | GT | GT | 72 ± 72 |
| 119 | GT | GT | GT | GT | GT | 154 ± 154 |
| 203 | GT | GT | GT | GT | GT | 154 ± 154 |

TABLE 31

Efficacy of hu24-AcButCM ADCs in LU86 PDX.

| Day | Vehicle | 5 mg/kg Cisplatin + 24 mg/kg Etoposide | 0.3 mg/kg Control-AcButCM | 0.03 mg/kg hu24-AcButCM | 0.1 mg/kg hu24-AcButCM | 0.3 mg/kg hu24-AcButCM |
|---|---|---|---|---|---|---|
| 0 | 206 ± 25 | 149 ± 13 | 158 ± 20 | 147 ± 13 | 143 ± 12 | 150 ± 13 |
| 14 | 1019 ± 6 | 468 ± 47 | 393 ± 115 | 756 ± 79 | 443 ± 90 | 73 ± 25 |
| 21 | GT | 946 ± 77 | 571 ± 173 | 1245 ± 138 | 548 ± 120 | 18 ± 5 |
| 28 | GT | GT | 788 ± 166 | GT | 761 ± 154 | 3 ± 2 |
| 35 | GT | GT | 962 ± 176 | GT | 908 ± 155 | 0 ± 0 |
| 42 | GT | GT | GT | GT | GT | 0 ± 0 |
| 112 | GT | GT | GT | GT | GT | 0 ± 0 |
| 140 | GT | GT | GT | GT | GT | 0 ± 0 |
| 154 | GT | GT | GT | GT | GT | 0 ± 0 |
| 203 | GT | GT | GT | GT | GT | 0 ± 0 |

Table 32 shows the efficacy of the hu23-mc8261, hu24-mc8261, and hu58-mc8261 ADCs in the LU86 PDX model (high PTK7 expression). Treatment with hu23-vc0101 yielded sustained tumor regression in the LU86 PDX model and demonstrated greater inhibition of tumor growth as compared to anti-PTK7-mc8261 ADCs

TABLE 32

Efficacy of anti-PTK7-mc8261 ADCs in LU86 PDX.

| Day | Vehicle | 10 mg/kg hu23-mc8261 | 10 mg/kg hu24-mc8261 | 10 mg/kg hu58-mc8261 |
|---|---|---|---|---|
| 0 | 147 ± 11 | 159 ± 13 | 159 ± 14 | 158 ± 15 |
| 7 | 317 ± 33 | 228 ± 29 | 257 ± 27 | 225 ± 20 |
| 14 | 672 ± 62 | 256 ± 30 | 300 ± 37 | 321 ± 34 |
| 21 | 1233 ± 83 | 340 ± 48 | 383 ± 65 | 425 ± 42 |
| 28 | GT | 455 ± 68 | 544 ± 90 | 574 ± 57 |
| 35 | GT | 740 ± 78 | 815 ± 117 | 736 ± 76 |
| 42 | GT | 870 ± 99 | 903 ± 157 | 887 ± 106 |
| 49 | GT | 1165 ± 137 | 1333 ± 173 | 1265 ± 206 |

Figure 18A:
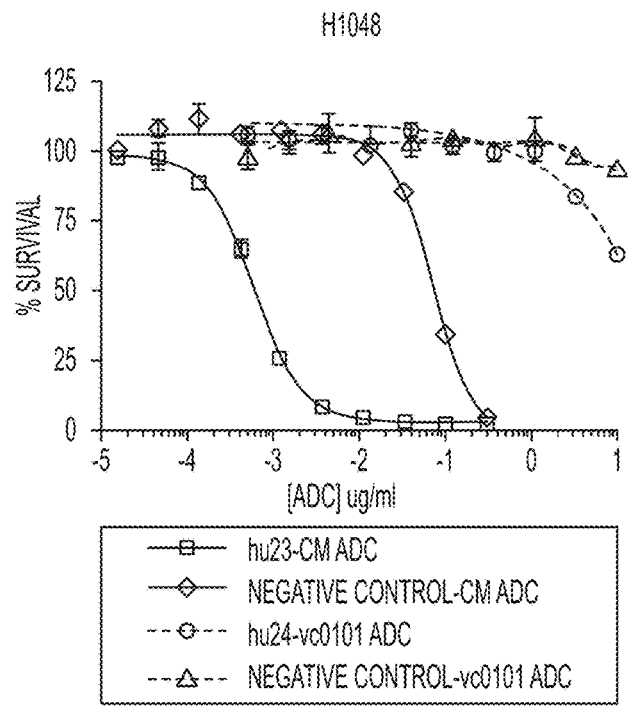
FIGS. 18A-B is a graph showing the efficacy of hu24-vc0101 and hu23-AcBut CM in two different SCLC PDX models (A) H1048 PDX model and (B) SCLC 95 PDX model.
Figure 18B:
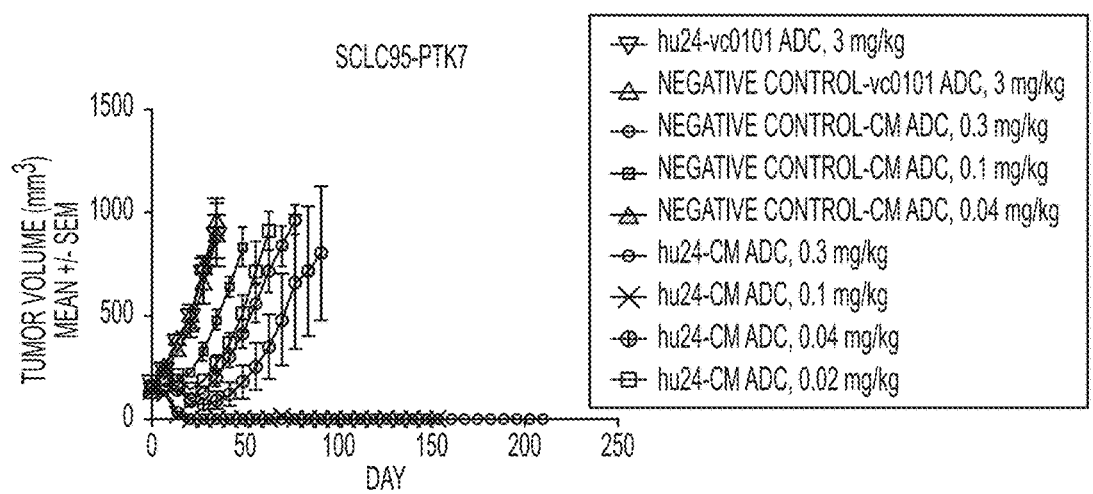
Figure 19A:
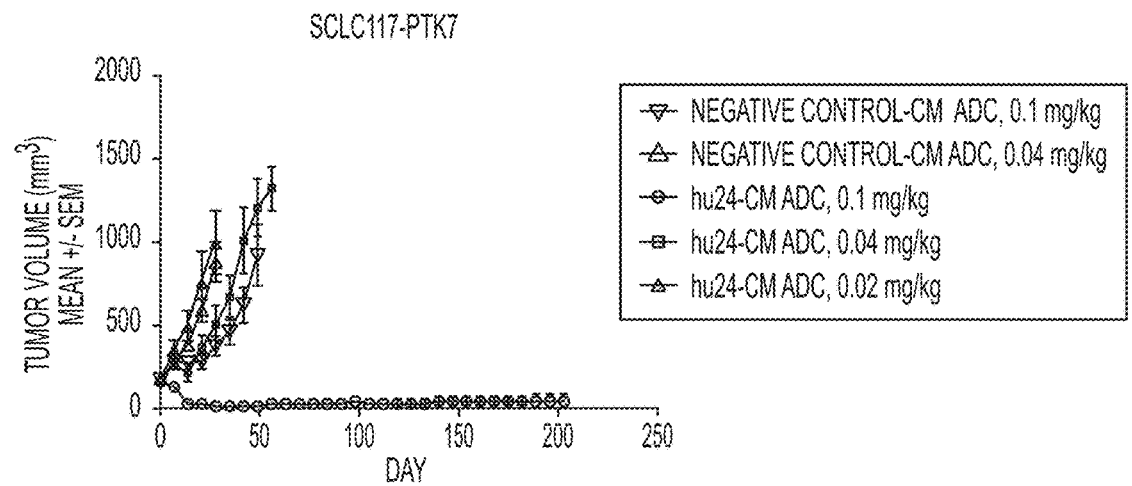
FIGS. 19A-B is a graph showing the efficacy of hu24-AcButCM in two different SCLC PDX models (A) a SCLC 117 PDX model and (B) a SCLC 102 PDX model.
Figure 19B:
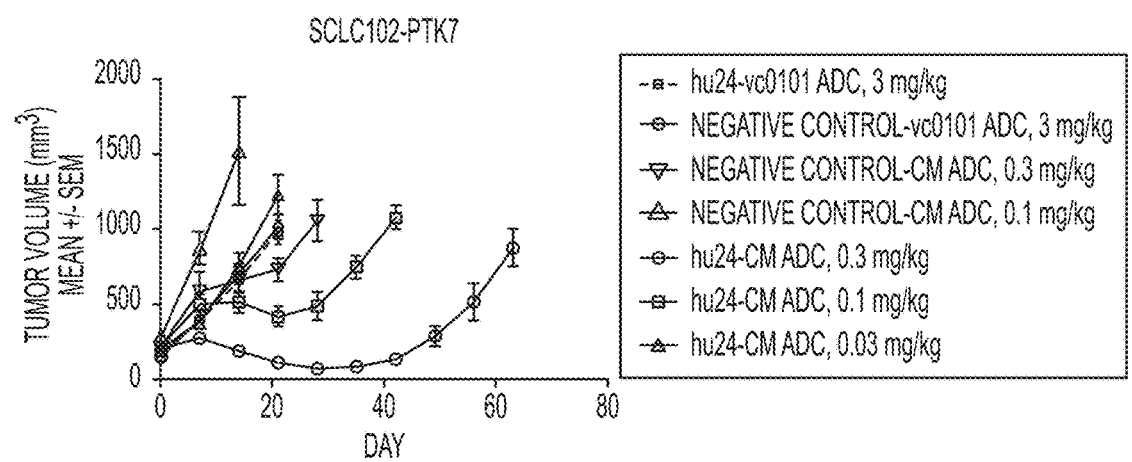

FIGS. 18A-B show the efficacy of PTK7 ADCs conjugated to either 0101 or CM in two different SCLC PDX models, a H1048 PDX model (high PTK7 expression) and SCLC 95 PDX model (high PTK7 expression), respectively FIG. 19A-B shows the efficacy of hu24-AcBut CM in two different SCLC PDX models, a SCLC 117 PDX model (moderate PTK7 expression) and a SCLC 102 PDX model (low PTK7 expression), respectively. The results demonstrate that hu24-AcButCM or hu23-AcButCM ADCs are more effective than hu24-vc0101 ADCs against SCLC. This finding is unexpected in light of the strong anti-tumor activity of hu24-vc0101 in PDX models of other tumor types such as TNBC and NSCLC. In addition, the results suggest that activity of the ADC correlates with expression of PTK7, since hu24-AcButCM ADC elicited the weakest response in SCLC102 which has low PTK7 expression.

C. Non-Small Cell Lung Cancer (NSCLC)

Figure 20:
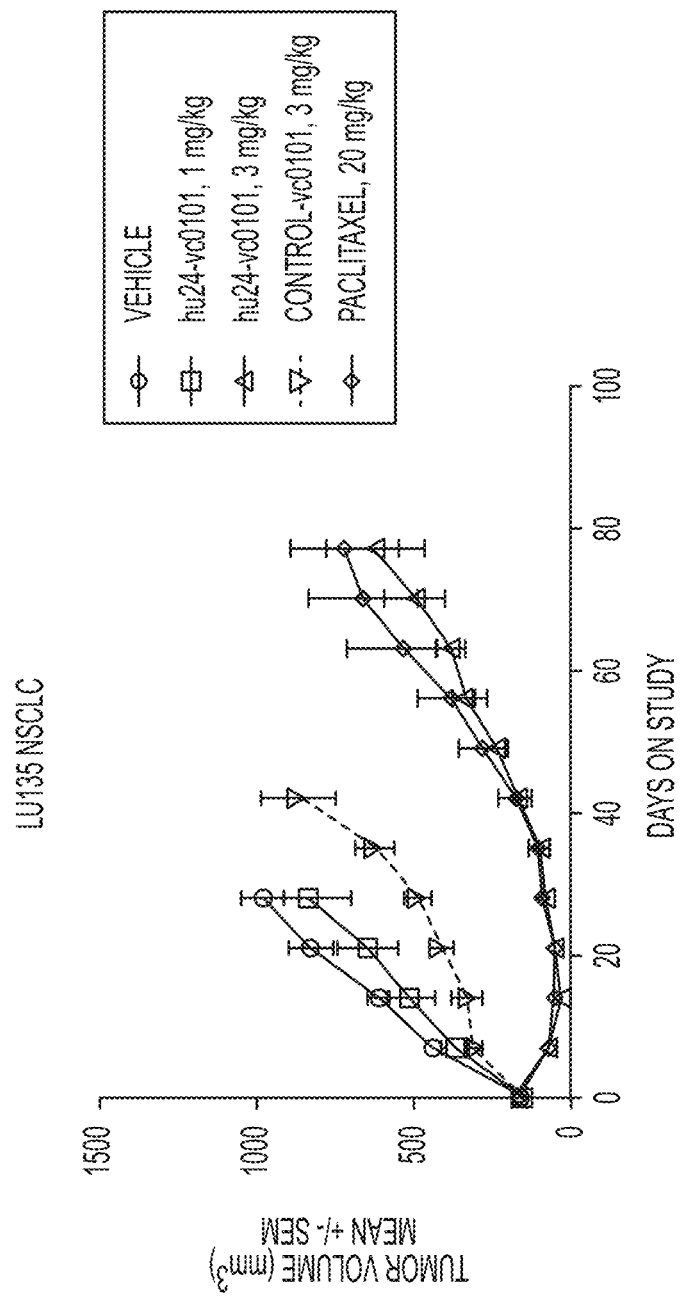
FIG. 20 is a graph showing the efficacy of hu24-vc0101 ADC in the Lung-135 (LU135) non-small cell lung cancer (NSCLC) PDX.

Table 33 and FIG. 20 show the hu24-vc0101 ADC was effective in the human non-small cell lung cancer-135 (LU135) PDX model (high PTK7 expression) compared to vehicle and drug controls. This data demonstrates the effectiveness of hu24-vc0101 in suppressing tumor growth in a NSCLC PDX. Hu24-vc0101 was more effective than paclitaxel, which is a standard of care in NSCLC.

TABLE 33

Efficacy of hu24-vc0101 in LU135 PDX.

| Day | Vehicle | 20 mg/kg Paclitaxel | 1 mg/kg Control-vc0101 | 3 mg/kg Control-vc0101 | 1 mg/kg hu24-vc0101 | 3 mg/kg hu24-vc0101 |
|---|---|---|---|---|---|---|
| 0 | 162 ± 17 | 175 ± 24 | 161 ± 15 | 168 ± 18 | 158 ± 18 | 186 ± 23 |
| 7 | 446 ± 28 | 77 ± 13 | 461 ± 19 | 329 ± 39 | 369 ± 53 | 79 ± 6 |
| 14 | 615 ± 34 | 58 ± 12 | 655 ± 39 | 337 ± 50 | 520 ± 81 | 41 ± 4 |
| 21 | 830 ± 71 | 60 ± 11 | 752 ± 46 | 414 ± 31 | 651 ± 95 | 60 ± 8 |
| 28 | 982 ± 68 | 93 ± 20 | 815 ± 101 | 488 ± 40 | 838 ± 133 | 84 ± 15 |
| 35 | GT | 110 ± 31 | GT | 627 ± 60 | GT | 104 ± 17 |
| 42 | GT | 184 ± 48 | GT | 871 ± 117 | GT | 175 ± 26 |
| 49 | GT | 284 ± 78 | GT | GT | GT | 244 ± 19 |
| 56 | GT | 384 ± 106 | GT | GT | GT | 347 ± 34 |
| 63 | GT | 538 ± 178 | GT | GT | GT | 387 ± 47 |
| 70 | GT | 667 ± 174 | GT | GT | GT | 502 ± 96 |
| 77 | GT | 724 ± 171 | GT | GT | GT | 628 ± 152 |

Figure 21:
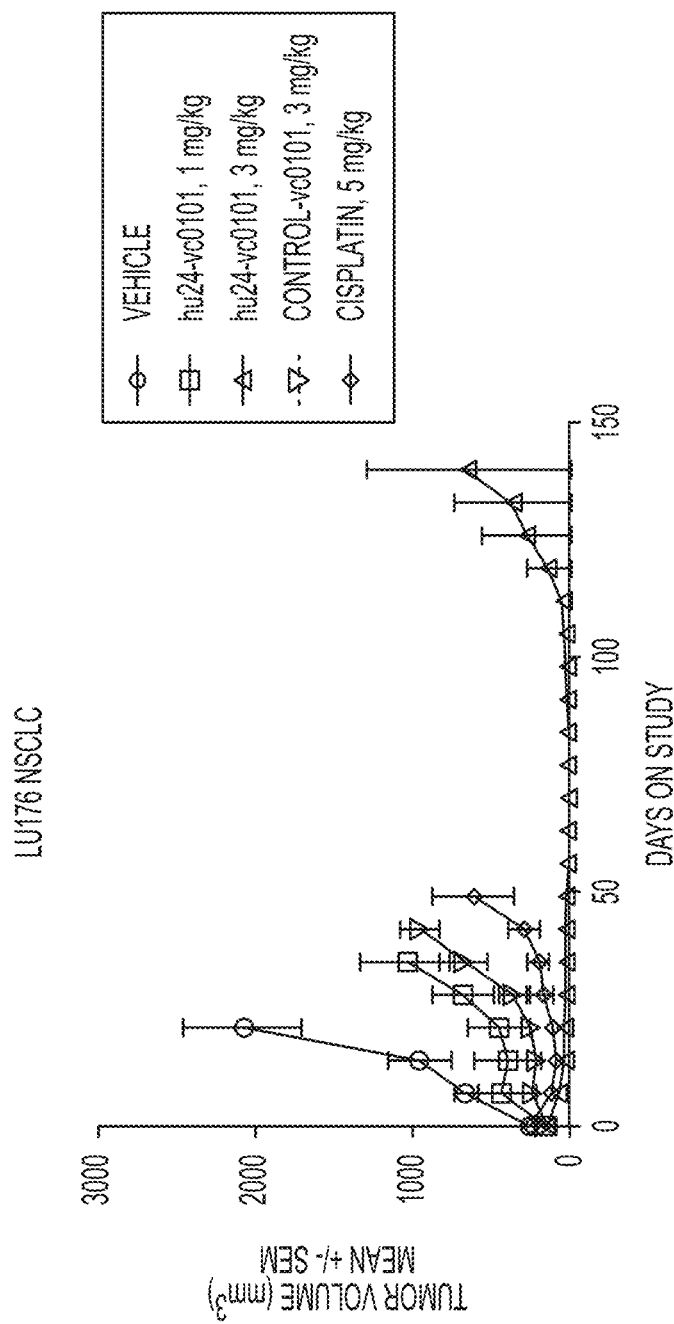
FIG. 21 is a graph showing the efficacy of hu24-vc0101 ADC in the Lung-176 (LU176) non-small cell lung cancer (NSCLC) PDX.

Table 34 and FIG. 21 show the hu24-vc0101 ADC was effective in the human non-small cell lung cancer-176 (LU176) PDX model (high PTK7 expression) compared to vehicle and drug controls. This data demonstrates the effectiveness of hu24-vc0101 in suppressing tumor growth in a NSCLC PDX. Hu24-vc0101 was more effective than cisplatin, which is a standard of care in NSCLC.

TABLE 34

Efficacy of hu24-vc0101 in LU176 PDX.

| Day | Vehicle | 5 mg/kg Cisplatin | 3 mg/kg Control-vc0101 | 1 mg/kg hu24-vc0101 | 3 mg/kg hu24-vc0101 |
|---|---|---|---|---|---|
| 0 | 262 ± 17 | 259 ± 26 | 139 ± 9 | 148 ± 12 | 138 ± 10 |
| 7 | 658 ± 71 | 124 ± 30 | 245 ± 29 | 446 ± 222 | 77 ± 21 |
| 14 | 964 ± 196 | 97 ± 22 | 208 ± 26 | 401 ± 214 | 27 ± 6 |
| 21 | 2087 ± 381 | 102 ± 24 | 244 ± 54 | 458 ± 204 | 34 ± 9 |
| 28 | GT | 179 ± 71 | 366 ± 88 | 685 ± 193 | 21 ± 3 |
| 35 | GT | 207 ± 69 | 679 ± 154 | 1046 ± 288 | 22 ± 8 |
| 42 | GT | 297 ± 97 | 955 ± 129 | GT | 20 ± 7 |
| 49 | GT | 619 ± 262 | GT | GT | 28 ± 14 |
| 56 | GT | GT | GT | GT | 14 ± 4 |
| 63 | GT | GT | GT | GT | 10 ± 4 |
| 70 | GT | GT | GT | GT | 5 ± 2 |
| 77 | GT | GT | GT | GT | 9 ± 5 |
| 84 | GT | GT | GT | GT | 8 ± 8 |
| 91 | GT | GT | GT | GT | 11 ± 11 |
| 98 | GT | GT | GT | GT | 21 ± 16 |
| 105 | GT | GT | GT | GT | 28 ± 27 |
| 112 | GT | GT | GT | GT | 46 ± 44 |
| 119 | GT | GT | GT | GT | 140 ± 140 |
| 126 | GT | GT | GT | GT | 281 ± 281 |
| 133 | GT | GT | GT | GT | 366 ± 366 |
| 140 | GT | GT | GT | GT | 649 ± 649 |

D. Ovarian Cancer (OV)

Table 35 shows the efficacy of the hu24-vc0101 and hu24-AcButCM ADCs in the ovarian-55 (OV55) PDX model (medium PTK7 expression) compared to vehicle and drug controls. This data demonstrates that a ovarian PDX model that has a moderate expression of the PTK7 target is effectively targeted by both ADCs. Surprisingly, the animals treated with hu24-vc0101 were tumor free when the experiment was terminated and the hu24-AcButCM ADC was less effective in this model.

TABLE 35

Efficacy of hu24 ADCs in OV55 PDX.

| Day | 0.1 mg/kg Control-AcButCM | 3 mg/kg Control-vc0101 | 0.1 mg/kg hu24-AcButCM | 3 mg/kg hu24-vc0101 |
| --- | --- | --- | --- | --- |
| 0 | 168 ± 7 | 167 ± 7 | 162 ± 6 | 166 ± 8 |
| 14 | 438 ± 58 | 134 ± 46 | 105 ± 15 | 33 ± 6 |
| 35 | 1204 ± 46 | 427 ± 196 | 137 ± 101 | 0 ± 0 |
| 42 | GT | 564 ± 210 | 194 ± 158 | 0 ± 0 |
| 49 | GT | 807 ± 265 | 294 ± 204 | 0 ± 0 |
| 77 | GT | GT | 895 ± 169 | 0 ± 0 |
| 84 | GT | GT | GT | 0 ± 0 |
| 133 | GT | GT | GT | 0 ± 0 |
| 168 | GT | GT | GT | 0 ± 0 |
| 182 | GT | GT | GT | 0 ± 0 |

E. Melanoma (SK)

Table 36 shows the hu24-vc0101 ADC was effective in the human melanoma-23 (SK23) PDX model (medium PTK7 expression) compared to vehicle and drug controls. This data demonstrates the effectiveness of hu24-vc0101 in a melanoma PDX model having a moderate expression of the PTK7 target, providing a potential indication for the use of the ADC.

TABLE 36

Efficacy of hu24-vc0101 in SK23 PDX.

| Day | 2 mg/kg Control-vc0101 | 4 mg/kg Control-vc0101 | 2 mg/kg hu24-vc0101 | 4 mg/kg hu24-vc0101 |
| --- | --- | --- | --- | --- |
| 0 | 183 ± 20 | 184 ± 14 | 187 ± 11 | 196 ± 17 |
| 7 | 587 ± 82 | 541 ± 54 | 432 ± 28 | 356 ± 45 |
| 14 | 871 ± 107 | 697 ± 61 | 456 ± 36 | 227 ± 45 |
| 21 | 1123 ± 86 | 910 ± 93 | 509 ± 51 | 150 ± 33 |
| 28 | GT | GT | 679 ± 65 | 135 ± 41 |
| 35 | GT | GT | 793 ± 65 | 166 ± 58 |
| 42 | GT | GT | 868 ± 63 | 178 ± 62 |
| 49 | GT | GT | GT | 228 ± 81 |
| 56 | GT | GT | GT | 250 ± 93 |
| 63 | GT | GT | GT | 295 ± 103 |
| 70 | GT | GT | GT | 398 ± 130 |
| 77 | GT | GT | GT | 568 ± 181 |
| 84 | GT | GT | GT | 688 ± 167 |

F. Tumor Growth Inhibition in Breast and NSCLC PDX Models

Animals were dosed every four days for four cycles (Q4Dx4) by intraperitoneal injection except the BR5 study which was by intravenous injection on the same schedule. Tumor measurements were recorded one or two times per week using digital calipers and tumor volume was estimated using the equation $V=(A \times B^2)/2$ where A is the long axis and B is the short axis. Animal body weights were measured and recorded at least once a week. Study groups were followed until individual mice or entire group tumor measurements reached 1200 mm$^3$ at which point sacrifice was indicated in accordance with IACUC protocol. For the BR5 study, animals were sacrificed once tumor volume approached 15% of the body weight at staging in accordance with IACUC protocol.

Tumor growth inhibition (TGI) was calculated using the equation % TGI=[1−(mean tumor volume of treated)/(mean tumor volume of vehicle)]. TGI was calculated at the latest possible time point, which was typically the last measurement before the control group was discontinued as described above. Tumor regression was defined as a reduction in mean tumor volume after dosing. In cases where tumors regressed, Time To Progression (TTP) indicates the number of days between the first does and the time at which mean tumor volume increased from the previous measurement to a statistically significant degree. If the tumor did not regrow during the course of the experiment, TTP is the number of days between the first dose and the end of the experiment.

To confirm exposure of hu24-vc0101 ADC in the efficacy studies, plasma concentrations of ADC and total antibody were determined for two PDX models, BR13 PDX and BR22 PDX. Samples were collected at three time points following the third administration of ADC and concentrations were measured by Ligand Binding Assay (LBA) (data not shown). The data indicate that drug exposures were comparable in these tumor models.

Hu24-vc0101 ADC elicited anti-tumor activity in breast cancer and NSCLC tumor models. Tumors regressed upon treatment and typically did not regrow for months after the last administration of ADC. The unconjugated hu24 mAb did not elicit anti-tumor activity in the model tested which demonstrated the auristatin-dependent mechanism of action. Results are summarized in Table 37.

TABLE 37

Summary of In Vivo Pharmacology Studies with hu24-vc0101 ADC

| Tumor Model | Target Expression by IHC | Dosing Regimen | Exposure Data | hu24-vc0101 Dose Level (mg/kg) | Regression (TTP, Days) or % TGI |
| --- | --- | --- | --- | --- | --- |
| BR13 TNBC PDX | High | Q4Dx4 ip | Yes | 1 | 37% TGI |
| | | | | 2 | Regression (35) |
| | | | | 4 | Regression (105) |
| BR22 TNBC PDX | High | Q4Dx4 ip | Yes | 0.3 | None |
| | | | | 1 | Regression (21) |
| | | | | 3 | Regression (205) |

TABLE 37-continued

Summary of In Vivo Pharmacology Studies with hu24-vc0101 ADC

| Tumor Model | Target Expression by IHC | Dosing Regimen | Exposure Data | hu24-vc0101 Dose Level (mg/kg) | Regression (TTP, Days) or % TGI |
|---|---|---|---|---|---|
| BR31 TNBC PDX | Moderate | Q4Dx4 ip | No | 3 | Regression (105) |
| BR5 TNBC PDX | High | Q4Dx4 iv | No | 3 | Regression (49) |
| | | | | hu24 mAb, 3 mg/kg | None |
| BR36 PR+ PDX | High | Q4Dx4 ip | No | 3 | Regression (103) |
| NSCLC135 PDX | High | Q4Dx4 ip | No | 1 | 15% TGI |
| | | | | 3 | Regression (32) |
| NSCLC176 PDX | High | Q4Dx4 ip | No | 1 | 78% TGI |
| | | | | 3 | Regression (98) |

% = percent;
BR = Breast Cancer;
IHC = Immunohistochemistry;
ip = Intraperitoneal;
iv = Intravenous;
mAb = Monoclonal antibody;
mg/kg = Milligram per kilogram;
NSCLC = Non-Small Cell Lung Cancer;
PDX = Patient-Derived Xenograft;
PR+ = Progesterone Receptor Positive;
Q4Dx4 = Dose Every 4 Days for 4 Cycles;
TGI = Tumor Growth Inhibition;
TNBC = Triple-Negative Breast Cancer;
TTP = Time To Progression.

Example 14

Mechanism of Action of 0101

To study the mechanism of action of the hu24-vc0101 ADC, cells were treated with the ADC and then their microtubule structure assessed. Auristatin is a fully synthetic dolastatin-based pentapeptide inhibitor of tubulin polymerization that induces G2/M cell cycle arrest and cell death at low picomolar intracellular concentrations (Sapra et al., 2011, Expert Opin Investig Drugs 20(8):1131-49 and Turner et al., 1998, Prostate 34(3):175-81).

H661 lung cancer cells were seeded onto a 4-well chamber slide system with a CC2 coated growth surface (Thermo Scientific) and treated for 48 hours with hu24-vc0101, negative control ADC, unconjugated hu24mAb at 0-4 μg/mL or free 0101 auristatin at 0.1-10 nM. The cells were then fixed in 3% paraformaldehyde, washed with PBS, permeabilized with 0.5% Triton-X® (Sigma Chemical) in PBS, washed with PBS, and incubated with blocking buffer (5% normal goat serum and 0.2% Tween-20 in PBS). Cells were incubated with the primary anti-α-tubulin antibody (Sigma NoT9026, clone DM1A) in blocking buffer for 1 hour at room temperature. Afterwards, the cells were washed with PBS and incubated for 30 minutes with an Alexa Fluor® 488-conjugated secondary antibody (Invitrogen Corp) and 4',6-diamidino-2-phenylindole (DAPI) to stain the DNA. The cells were visualized on a Zeiss LSM 510 Meta confocal microscope.

Figure 22:
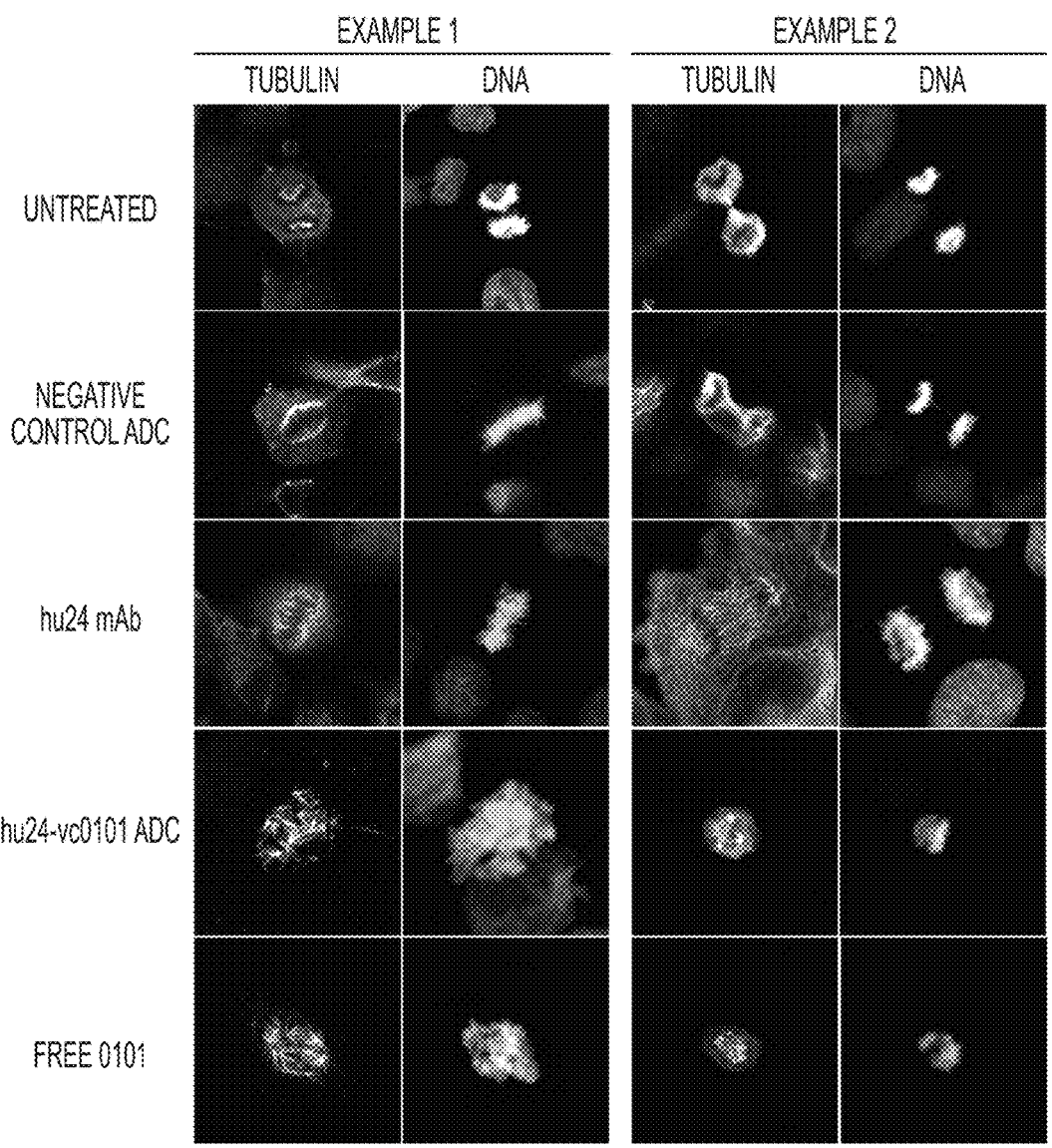
FIG. 22 shows micrographs of microtubule structure after treatment with 4 µg/mL hu24-vc0101 ADC, 4 µg/mL unconjugated hu24 mAb, 4 µg/mL negative control ADC, or 0.1 nM free 0101 auristatin. H661 cells were treated for 48 hours and then stained for anti-tubulin and DAPI to visualize the DNA.

Treatment of cells with free 0101 or hu24-vc0101 ADC disrupted microtubule structure and led to G2/M cell cycle arrest. In contrast, neither unconjugated hu24 mAb nor negative control mAb elicited these responses (FIG. 22). These results demonstrate that hu24-vc0101 ADC can elicit cytotoxicity in an antigen-dependent manner by disrupting microtubule structure and causing G2/M arrest. This mechanism is consistent with previous studies on unconjugated auristatins.

Example 15 hu24-vc0101 ADC Effect on Endothelial Cells

Figure 23:
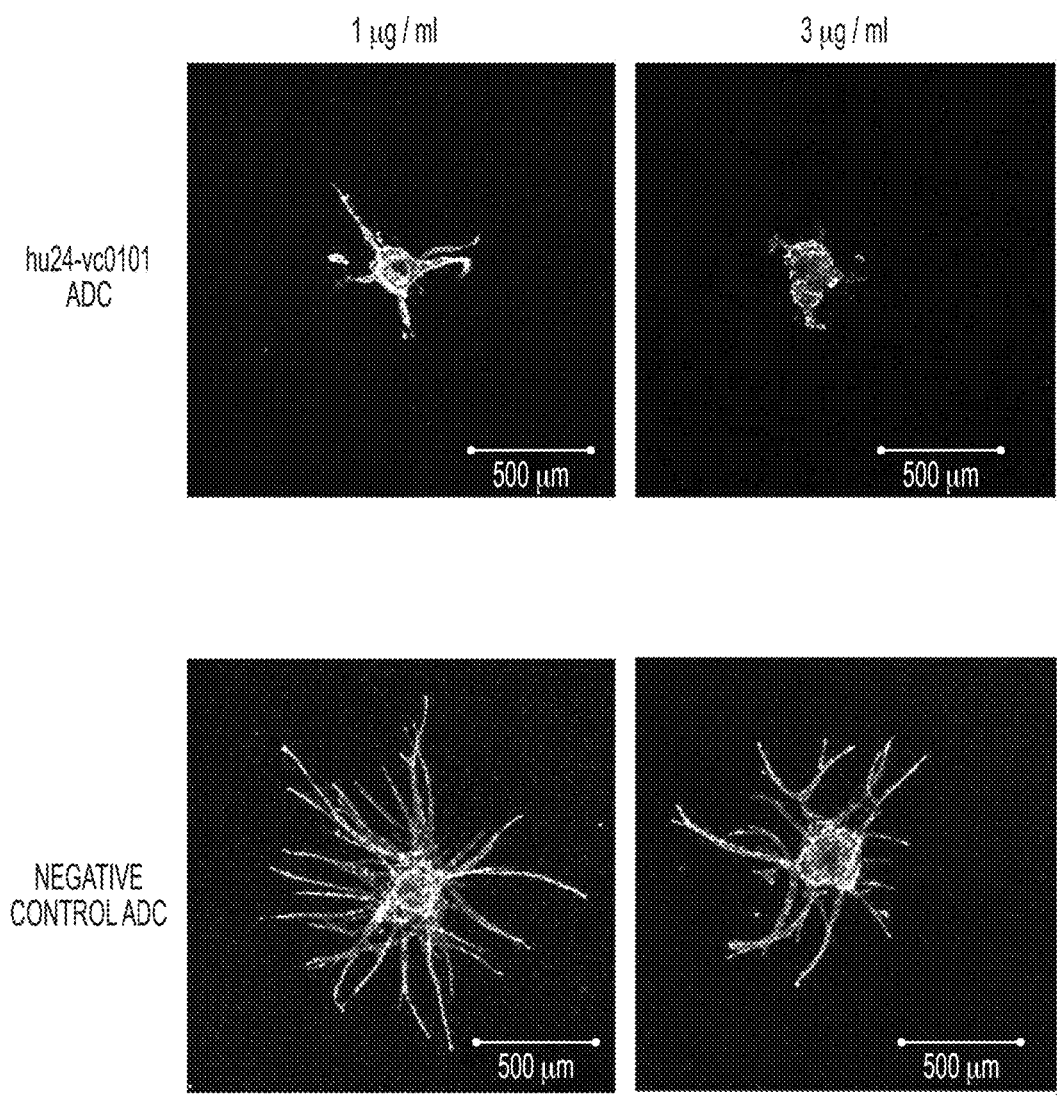
FIG. 23 shows the effect of hu24-vc0101 ADC on endothelial cells in vitro.

FIG. 23 shows that hu24-vc0101 ADC inhibits angiogenesis in a standard in vitro HUVEC sprouting assay. Briefly, HUVEC cells (Lonza—#CC-2517) were used to coat Cytodex beads (Sigma #C0646-5G) at a ratio of approximately $1 \times 10^6$ cells/2500 beads, and then placed overnight in an 37° C./5% CO2 incubator with Endothelial Cell Growth Medium (Lonza # CC-3162). The following day the beads were washed with Endothelial Cell Growth Medium, and re-suspended in a solution of a 2.0 mg/ml fibrinogen type I (filter sterilized) in DPBS and 0.15 units/ml Aprotinin. Into each well of a 24 well plate, 0.3125 units of thrombin were added prior to addition of 500 ul of the bead solution. To facilitate clotting, the plates were placed in a 37° C. incubator for 15 minutes. Lastly skin fibroblast cells (Detroit 551—ATCC #CCL-110), suspended in Endothelial Cell Growth Medium, were carefully laid on top of the formed fibrinogen clot. The cells were fed, with their respective drug treatment, every other day and grown for 8 days. The degree of HUVEC sprouting and formation of branching vessels was observed.

Hu24-vc0101 ADC inhibited sprouting angiogenesis in this assay at 1 μg/mL, while the negative control ADC did not. This result demonstrates that the anti-PTK7 ADC can inhibit angiogenesis in a target-specific manner Example 16

Reduction of Tumor-Initiating Cells (TIC)

To determine whether anti-PTK7 antibody-drug conjugate treatments reduced tumor-initiating cell (TIC) frequency in tumors, BR13 TNBC breast tumors were treated with 4 mg/kg hu24-vc0101 ADC, 4 mg/kg control IgG ADC, or 20 mg/kg docetaxel chemotherapy twice weekly for a total of 3 doses (Days 0, 3 & 7). Live, residual human tumor cells (i.e. hESA+ mCD45− mH-2Kd−) were isolated from dissociated tumors at day 10 and re-implanted into naïve animals in a limit dilution analysis (LDA). Resulting tumor incidence was monitored for up to 40 weeks post-transplant. The day of tumor harvest (day 10) and serial transplantation was chosen based on when tumors were starting to regress following hu24-vc0101 exposure. Tumors were dissociated and stained with anti-human ESA, anti-mouse CD45, and anti-mouse H-2Kd antibodies. Three tumors per treatment group were pooled, and live human tumor cells were sorted by flow cytometry. Groups of 10 mice were injected with either 293, 73, 37 or 15 tumor cells sorted from control IgG ADC treated tumors; 159, 90, 40 or 10 tumor cells sorted from hu24-vc0101 treated tumors; or 257, 33 or 15 tumor cells sorted from docetaxel-treated tumors. Tumors in recipient mice were measured weekly and tumors that exceeded 200 mm$^3$ in recipient mice were scored as positive. Using Poisson distribution statistics, via L-Calc software (Stemcell Technologies, Vancouver, BC), injected cell doses of recipients with and without tumors by 40 weeks post-transplant were used to calculate the frequency of TIC after each treatment.

The TIC frequency in hu24-vc0101 treated tumors was 5.5-fold lower than in control IgG ADC treated tumors (p=0.0013; Table 38). The TIC frequency in docetaxel-treated tumors was 2.1-fold lower than in control IgG ADC treated tumors (p=0.09; Table 38). In summary, mice injected with hu24-vc0101 treated tumor cells consistently produced less tumors than mice injected with similar number of control IgG ADC treated tumor cells, which indicated that hu24-vc0101 treatment specifically reduced TICs.

TABLE 38

Tumor-initiating cell (TIC) frequency in BR13 tumor model.

| Pre-treatment | Group | # Cells implanted per animal | # Animals with tumors | # Animals in group | TIC frequency | p-value relative to control ADC |
|---|---|---|---|---|---|---|
| Control ADC (4 mpk) | A1 | 293 | 9 | 9 | 1 in 71 | Not applicable |
|  | A2 | 73 | 6 | 8 |  |  |
|  | A3 | 37 | 3 | 8 |  |  |
|  | A4 | 15 | 0 | 8 |  |  |
| hu24-vc0101 (4 mpk) | B1 | 159 | 3 | 7 | 1 in 393 | 0.0013 |
|  | B2 | 90 | 2 | 8 |  |  |
|  | B3 | 40 | 0 | 10 |  |  |
|  | B4 | 10 | 0 | 8 |  |  |
| Docetaxel (20 mpk) | C1 | 257 | 8 | 9 | 1 in 149 | 0.09 |
|  | C2 | 33 | 1 | 8 |  |  |
|  | C3 | 15 | 0 | 6 |  |  |

What is claimed is:

1. An antibody-drug conjugate of the formula: Ab-(L-D), wherein:
   (a) Ab is an antibody that binds to human protein tyrosine kinase 7 (PTK7) comprising at least one of a heavy chain comprising an amino acid sequence set forth as SEQ ID NO: 37 and a light chain comprising an amino acid sequence set forth as SEQ ID NO: 47; and
   (b) L-D is a linker-drug moiety, wherein L is a linker, and D is an auristatin.

2. The antibody-drug conjugate of claim 1, wherein the antibody comprises a heavy chain comprising an amino acid sequence set forth as SEQ ID NO: 37 and a light chain comprising an amino acid sequence set forth as SEQ ID NO: 47.

3. The antibody-drug conjugate of claim 1, wherein the linker is selected from the group consisting of maleimidocaproyl-valine-citrulline-p-aminobenzyloxycarbonyl (vc) and maleimidocaproyl (mc).

4. The antibody-drug conjugate of claim 3, wherein the linker is maleimidocaproyl-valine-citrulline-p-aminobenzyloxycarbonyl (vc).

5. The antibody-drug conjugate of claim 3, wherein the linker is maleimidocaproyl (mc).

6. The antibody-drug conjugate of claim 1, wherein the auristatin is 0101 having the formula:

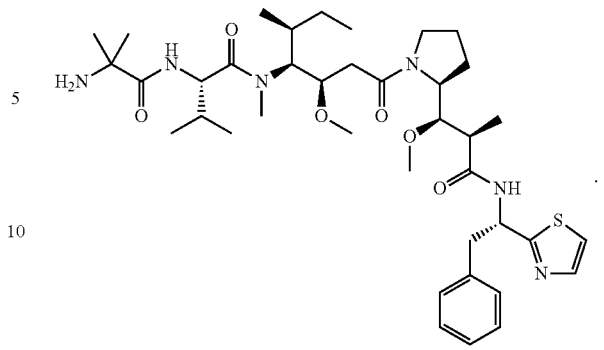

7. The antibody-drug conjugate of claim 6, wherein the linker and auristatin are vc0101 having the formula:

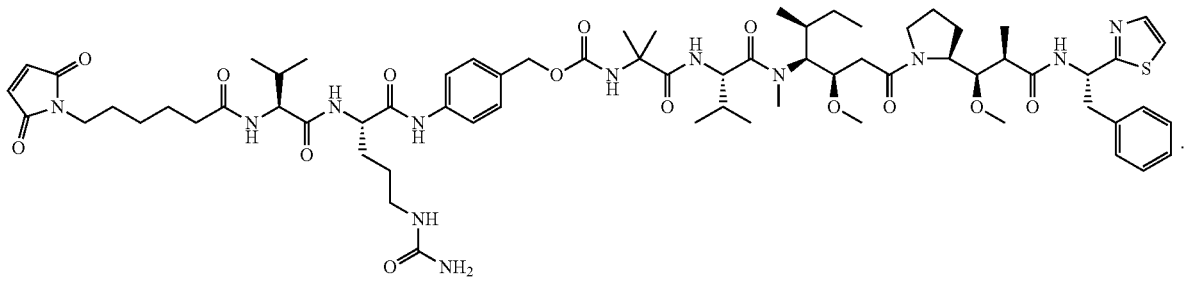 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

8. The antibody-drug conjugate of claim 1, wherein the auristatin is 8261 having the formula:

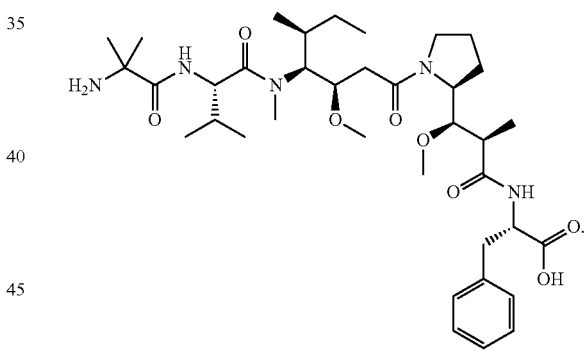

9. The antibody-drug conjugate of claim 8, wherein the linker and auristatin are mc8261 having the formula:

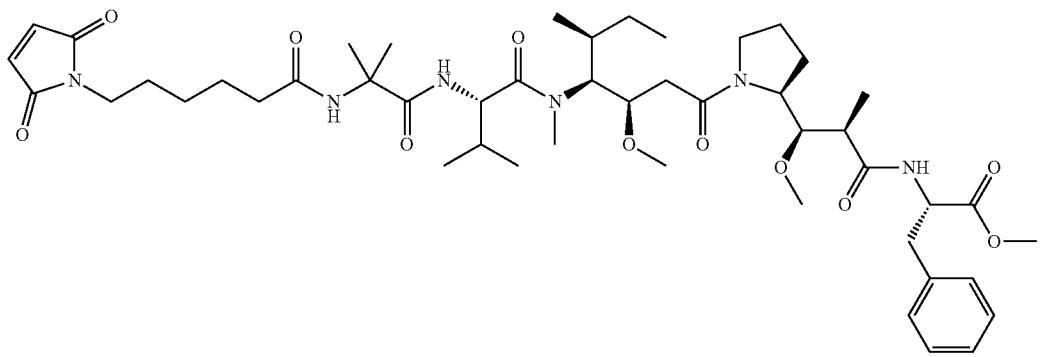

10. The antibody-drug conjugate of claim 1, wherein the antibody-drug conjugate has a DAR of 1 to 8.

11. A pharmaceutical composition comprising the antibody-drug conjugate of claim 1 and a pharmaceutically acceptable carrier.

12. A composition comprising a plurality of the antibody-drug conjugate of claim 1, and optionally a pharmaceutical carrier, wherein the composition has an average DAR within a range of 1 to 8.

13. A process for producing the antibody-drug conjugate of claim 1, comprising:
   (a) linking the linker to the drug;
   (b) conjugating the linker-drug moiety to the antibody; and
   (c) purifying the antibody-drug conjugate.

14. A method of treating a PTK7 associated disorder comprising administering a therapeutically effective amount of a composition comprising the antibody-drug conjugate of claim 1 to a subject in need thereof.

15. The method of claim 14, wherein the PTK7 associated disorder is a hyperproliferative disorder.

16. The method of claim 15, wherein the hyperproliferative disorder is a neoplastic disorder.

17. The method of claim 16, wherein the neoplastic disorder is a solid tumor.

18. The method of claim 17, wherein the solid tumor is selected from the group consisting of breast cancer, ovarian cancer, colorectal cancer, esophageal cancer, gastric cancer, melanoma, sarcoma, kidney cancer, pancreatic cancer, prostate cancer, liver cancer, and lung cancer.

19. The method of claim 16, wherein the neoplastic disorder is a hematologic malignancy.

20. The method of claim 19, wherein the hematologic malignancy is leukemia.

21. The method of claim 20, wherein the leukemia is adult myeloid leukemia (AML) or acute lymphoblastic leukemia (ALL).

22. The method of claim 18, wherein the breast cancer is selected from the group consisting of triple-negative breast cancer (TNBC), progesterone-receptor positive breast cancer (PR+), estrogen-receptor positive breast cancer (ER+) and double positive breast cancer.

23. The method of claim 18, wherein the liver cancer is hepatocellular carcinoma (HCC).

24. The method of claim 18, wherein the lung cancer is non-small cell lung cancer (NSCLC).

25. An antibody-drug conjugate of the formula: Ab-(L-D), wherein:
   (a) Ab is an antibody that binds to human protein tyrosine kinase 7 (PTK7) comprising a heavy chain comprising an amino acid sequence set forth as SEQ ID NO: 37 and a light chain comprising an amino acid sequence set forth as SEQ ID NO: 47; and
   (b) L-D is a linker-drug moiety, wherein L is a linker, and D is an auristatin, wherein the linker is maleimido-caproyl-valine-citrulline-p-aminobenzyloxycarbonyl (vc), and the auristatin is 0101 having the formula:

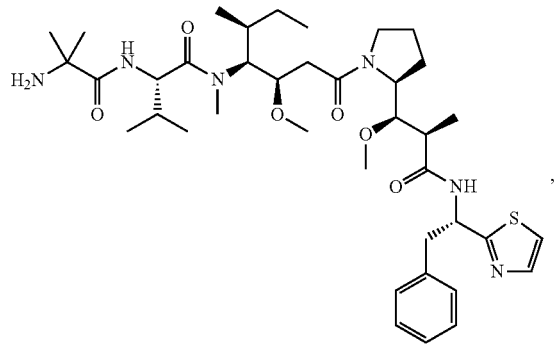 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]

wherein the antibody-drug conjugate has a drug-to-antibody ratio (DAR) of 1 to 8.

26. A pharmaceutical composition comprising the antibody-drug conjugate of claim 25 and a pharmaceutically acceptable carrier.

27. A composition comprising a plurality of the antibody-drug conjugate of claim 25, and optionally a pharmaceutical carrier, wherein the composition has an average DAR within a range of 1 to 8.

28. A process for producing the antibody-drug conjugate of claim 25, comprising:
   (a) linking the linker to the drug;
   (b) conjugating the linker-drug moiety to the antibody; and
   (c) purifying the antibody-drug conjugate.

29. A method of treating a PTK7 associated disorder comprising administering a therapeutically effective amount of a composition comprising the antibody-drug conjugate of claim 25 to a subject in need thereof.

30. The method of claim 29, wherein the PTK7 associated disorder is a hyperproliferative disorder.

31. The method of claim 30, wherein the hyperproliferative disorder is a neoplastic disorder.

32. The method of claim 31, wherein the neoplastic disorder is a solid tumor.

33. The method of claim 32, wherein the solid tumor is selected from the group consisting of breast cancer, ovarian cancer, colorectal cancer, esophageal cancer, gastric cancer, melanoma, sarcoma, kidney cancer, pancreatic cancer, prostate cancer, liver cancer, and lung cancer.

34. The method of claim 31, wherein the neoplastic disorder is a hematologic malignancy.

35. The method of claim 34, wherein the hematologic malignancy is leukemia.

36. The method of claim 35, wherein the leukemia is adult myeloid leukemia (AML) or acute lymphoblastic leukemia (ALL).

37. An antibody-drug conjugate of the formula: Ab-(L-D), wherein:
   (a) Ab is an antibody that binds to human protein tyrosine kinase 7 (PTK7) comprising at least one of a heavy chain comprising an amino acid sequence set forth as SEQ ID NO: 13 and a light chain comprising an amino acid sequence set forth as SEQ ID NO: 23; and
   (b) L-D is a linker-drug moiety, wherein L is a linker, and D is an auristatin.

38. The antibody-drug conjugate of claim 37, wherein the antibody comprises a heavy chain comprising an amino acid sequence set forth as SEQ ID NO: 13 and a light chain comprising an amino acid sequence set forth as SEQ ID NO: 23.

39. The antibody-drug conjugate of claim 37, wherein the linker is selected from the group consisting of maleimidocaproyl-valine-citrulline-p-aminobenzyloxycarbonyl (vc) and maleimidocaproyl (mc).

40. The antibody-drug conjugate of claim 39, wherein the linker is maleimidocaproyl-valine-citrulline-p-aminobenzyloxycarbonyl (vc).

41. The antibody-drug conjugate of claim 39, wherein the linker is maleimidocaproyl (mc).

42. The antibody-drug conjugate of claim 37, wherein the auristatin is 0101 having the formula:

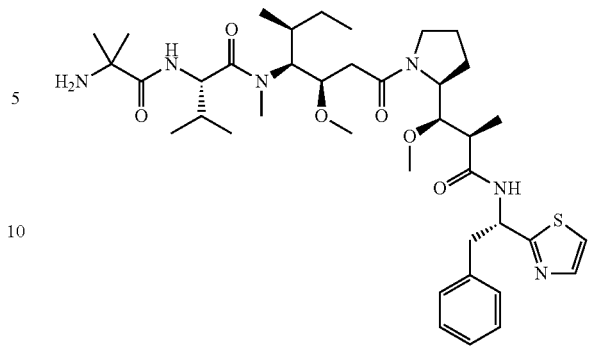

43. The antibody-drug conjugate of claim 37, wherein the linker and auristatin are vc0101 having the formula:

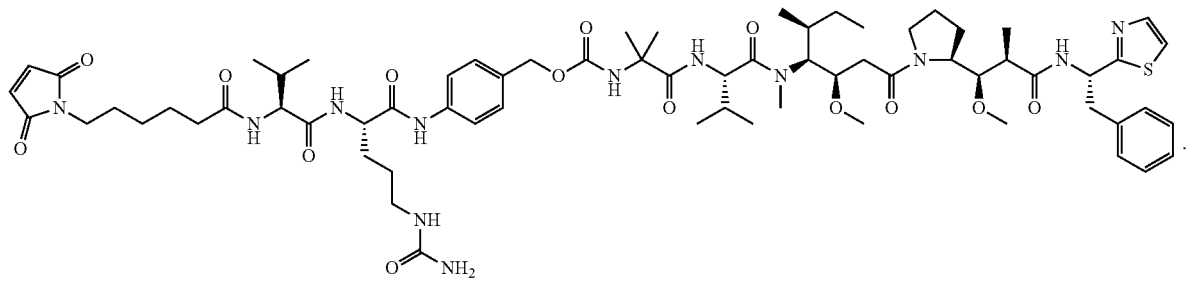 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)NC(=O)OCc1ccc(NC(=O)[C@H](CCCNC(N)=O)NC(=O)[C@@H](NC(=O)CCCCCN2C(=O)C=CC2=O)C(C)C)cc1)C(C)C]

44. The antibody-drug conjugate of claim 37, wherein the auristatin is 8261 having the formula:

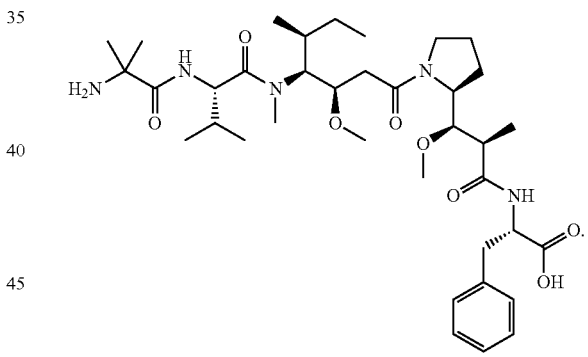

45. The antibody-drug conjugate of claim 37, wherein the linker and auristatin are mc8261 having the formula:

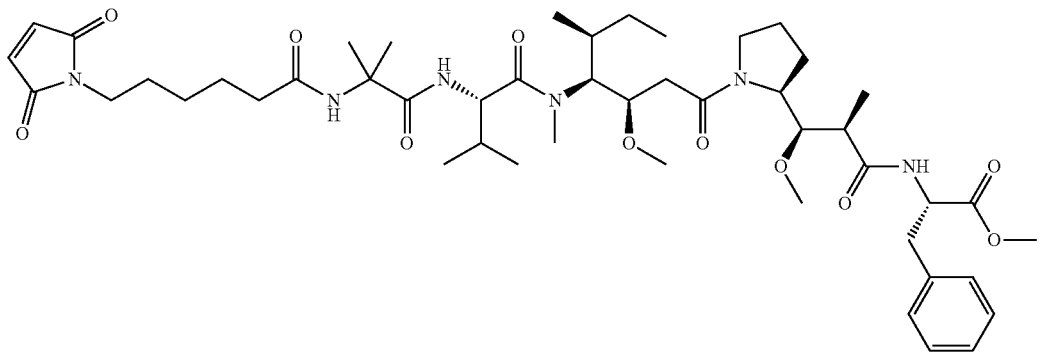

46. The antibody-drug conjugate of claim 37, wherein the antibody-drug conjugate has a DAR of 1 to 8.

47. A pharmaceutical composition comprising the antibody-drug conjugate of claim 37 and a pharmaceutically acceptable carrier.

48. A composition comprising a plurality of the antibody-drug conjugate of claim 37, and optionally a pharmaceutical carrier, wherein the composition has an average DAR within a range of 1 to 8.

49. A process for producing the antibody-drug conjugate of claim 37, comprising:
(a) linking the linker to the drug;
(b) conjugating the linker-drug moiety to the antibody; and
(c) purifying the antibody-drug conjugate.

50. A method of treating a PTK7 associated disorder comprising administering a therapeutically effective amount of a composition comprising the antibody-drug conjugate of claim 37 to a subject in need thereof.

51. The method of claim 50, wherein the PTK7 associated disorder is a hyperproliferative disorder.

52. The method of claim 51, wherein the hyperproliferative disorder is a neoplastic disorder.

53. The method of claim 52, wherein the neoplastic disorder is a solid tumor.

54. The method of claim 53, wherein the solid tumor is selected from the group consisting of breast cancer, ovarian cancer, colorectal cancer, esophageal cancer, gastric cancer, melanoma, sarcoma, kidney cancer, pancreatic cancer, prostate cancer, liver cancer, and lung cancer.

55. The method of claim 54, wherein the breast cancer is selected from the group consisting of triple-negative breast cancer (TNBC), progesterone-receptor positive breast cancer (PR+), estrogen-receptor positive breast cancer (ER+) and double positive breast cancer.

56. The method of claim 54, wherein the liver cancer is hepatocellular carcinoma (HCC).

57. The method of claim 54, wherein the lung cancer is non-small cell lung cancer (NSCLC).

58. The method of claim 52, wherein the neoplastic disorder is a hematologic malignancy.

59. The method of claim 58, wherein the hematologic malignancy is leukemia.

60. The method of claim 59, wherein the leukemia is adult myeloid leukemia (AML) or acute lymphoblastic leukemia (ALL).

* * * * *

UNITED STATES PATENT AND TRADEMARK OFFICE
CERTIFICATE OF CORRECTION

PATENT NO. : 9,777,070 B2  Page 1 of 1
APPLICATION NO. : 14/696663
DATED : October 3, 2017
INVENTOR(S) : Damelin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 81 days.

Signed and Sealed this
Twenty-fifth Day of September, 2018

Andrei Iancu
*Director of the United States Patent and Trademark Office*

SEQUENCE LISTING

<160> NUMBER OF SEQ ID NOS: 87

<210> SEQ ID NO 1
<211> LENGTH: 120
<212> TYPE: PRT
<213> ORGANISM: Artificial Sequence
<220> FEATURE:
<223> OTHER INFORMATION: Synthetic peptide sequence

<400> SEQUENCE: 1

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Asn Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Ser Asn Tyr Gly Tyr Ala Trp Phe Ala Tyr Trp Gly Gln
            100                 105                 110

Gly Thr Leu Val Thr Val Ser Ser
        115                 120
```

<210> SEQ ID NO 2
<211> LENGTH: 360
<212> TYPE: DNA
<213> ORGANISM: Artificial Sequence
<220> FEATURE:
<223> OTHER INFORMATION: Synthetic nucleotide sequence

<400> SEQUENCE: 2

```
cagatcacct tgaaggagtc tggtcctacg ctggtgaaac ccacacagac cctcacgctg      60
acctgcacct tctctgggtt ctcactcagc actagtaaca tgggtgtggg ctggatccgt     120
cagcccccag gaaaggccct ggagtggctt gcacacattt ggtgggatga tgataagtac     180
tacagcccat ctctgaagag caggctcacc atcaccaagg acacctccaa aaaccaggtg     240
gtccttacaa tgaccaacat ggaccctgtg gacacagcca catattactg tgttcgaagt     300
aactatggtt acgcctggtt tgcttactgg ggccaaggga ctctggtcac tgtctcttca     360
```

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 3

Thr Ser Asn Met Gly Val Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 4

Gly Phe Ser Leu Ser Thr Ser Asn Met
1               5

<210> SEQ ID NO 5
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 5

```
actagtaaca tgggtgtggg c                                                21
```

<210> SEQ ID NO 6
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 6

```
gggttctcac tcagcactag taacatg                                          27
```

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide sequence

```
<400> SEQUENCE: 7

His Ile Trp Trp Asp Asp Asp Lys Tyr Tyr Ser Pro Ser Leu Lys Ser
1               5                   10                  15

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 8

Trp Trp Asp Asp Asp
1               5

<210> SEQ ID NO 9
<211> LENGTH: 48
<212> TYPE: DNA
<213> ORGANISM: Artificial Sequence
<220> FEATURE:
<223> OTHER INFORMATION: Synthetic nucleotide sequence

<400> SEQUENCE: 9
cacatttggt gggatgatga taagtactac agcccatctc tgaagagc            48

<210> SEQ ID NO 10
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 10
tggtgggatg atgat                                                 15

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 11

Ser Asn Tyr Gly Tyr Ala Trp Phe Ala Tyr
1               5                   10

<210> SEQ ID NO 12
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 12
agtaactatg gttacgcctg gtttgcttac                                 30

<210> SEQ ID NO 13
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 13

Gln Ile Thr Leu Lys Glu Ser Gly Pro Thr Leu Val Lys Pro Thr Gln
```

-continued

```
  1               5                  10                 15
Thr Leu Thr Leu Thr Cys Thr Phe Ser Gly Phe Ser Leu Ser Thr Ser
                    20                 25                 30

Asn Met Gly Val Gly Trp Ile Arg Gln Pro Gly Lys Ala Leu Glu
                35                 40                 45

Trp Leu Ala His Ile Trp Trp Asp Asp Lys Tyr Tyr Ser Pro Ser
 50                 55                 60

Leu Lys Ser Arg Leu Thr Ile Thr Lys Asp Thr Ser Lys Asn Gln Val
 65                 70                 75                 80

Val Leu Thr Met Thr Asn Met Asp Pro Val Asp Thr Ala Thr Tyr Tyr
                    85                 90                 95

Cys Val Arg Ser Asn Tyr Gly Tyr Ala Trp Phe Ala Tyr Trp Gly Gln
                100                105                110

Gly Thr Leu Val Thr Val Ser Ser Ala Ser Thr Lys Gly Pro Ser Val
                115                120                125

Phe Pro Leu Ala Pro Ser Ser Lys Ser Thr Ser Gly Gly Thr Ala Ala
                130                135                140

Leu Gly Cys Leu Val Lys Asp Tyr Phe Pro Glu Pro Val Thr Val Ser
145                150                155                160

Trp Asn Ser Gly Ala Leu Thr Ser Gly Val His Thr Phe Pro Ala Val
                165                170                175

Leu Gln Ser Ser Gly Leu Tyr Ser Leu Ser Ser Val Val Thr Val Pro
                180                185                190

Ser Ser Ser Leu Gly Thr Gln Thr Tyr Ile Cys Asn Val Asn His Lys
                195                200                205

Pro Ser Asn Thr Lys Val Asp Lys Lys Val Glu Pro Lys Ser Cys Asp
                210                215                220

Lys Thr His Thr Cys Pro Pro Cys Pro Ala Pro Glu Leu Leu Gly Gly
225                230                235                240

Pro Ser Val Phe Leu Phe Pro Pro Lys Pro Lys Asp Thr Leu Met Ile
                245                250                255

Ser Arg Thr Pro Glu Val Thr Cys Val Val Val Asp Val Ser His Glu
                260                265                270

Asp Pro Glu Val Lys Phe Asn Trp Tyr Val Asp Gly Val Glu Val His
                275                280                285

Asn Ala Lys Thr Lys Pro Arg Glu Glu Gln Tyr Asn Ser Thr Tyr Arg
                290                295                300

Val Val Ser Val Leu Thr Val Leu His Gln Asp Trp Leu Asn Gly Lys
305                310                315                320

Glu Tyr Lys Cys Lys Val Ser Asn Lys Ala Leu Pro Ala Pro Ile Glu
                325                330                335

Lys Thr Ile Ser Lys Ala Lys Gly Gln Pro Arg Glu Pro Gln Val Tyr
                340                345                350

Thr Leu Pro Pro Ser Arg Asp Glu Leu Thr Lys Asn Gln Val Ser Leu
                355                360                365

Thr Cys Leu Val Lys Gly Phe Tyr Pro Ser Asp Ile Ala Val Glu Trp
                370                375                380

Glu Ser Asn Gly Gln Pro Glu Asn Asn Tyr Lys Thr Thr Pro Pro Val
385                390                395                400

Leu Asp Ser Asp Gly Ser Phe Phe Leu Tyr Ser Lys Leu Thr Val Asp
                405                410                415

Lys Ser Arg Trp Gln Gln Gly Asn Val Phe Ser Cys Ser Val Met His
                420                425                430
```

Glu Ala Leu His Asn His Tyr Thr Gln Lys Ser Leu Ser Leu Ser Pro
        435                 440                 445

Gly

<210> SEQ ID NO 14
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 14

```
cagatcacct tgaaggagtc tggtcctacg ctggtgaaac ccacacagac cctcacgctg      60
acctgcacct tctctgggtt ctcactcagc actagtaaca tgggtgtggg ctggatccgt     120
cagcccccag gaaaggccct ggagtggctt gcacacattt ggtgggatga tgataagtac     180
tacagcccat ctctgaagag caggctcacc atcaccaagg acacctccaa aaaccaggtg     240
gtccttacaa tgaccaacat ggaccctgtg acacagcca catattactg tgttcgaagt      300
aactatggtt acgcctggtt tgcttactgg ggccaaggga ctctggtcac tgtctcttca     360
gcctccacca agggcccatc ggtcttcccc ctggcaccct cgagcaagag cacctctggg     420
ggcacagcgg ccctgggctg cctggtcaag gactacttcc ccgagccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggt                                        1347
```

<210> SEQ ID NO 15
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Pro Tyr
            20                  25                  30

Leu Asn Trp Phe Gln Gln Lys Pro Gly Lys Ala Pro Lys Thr Leu Ile

```
                35                  40                  45
Tyr Arg Thr Asn Arg Leu Leu Asp Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Leu
                85                  90                  95

Thr Phe Gly Ala Gly Thr Lys Leu Glu Ile Lys
            100                 105
```

<210> SEQ ID NO 16
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 16

```
gacatccaga tgacccagtc tccatcttcc ctgtctgcat ctgtaggaga tagagtcact    60
atcacttgca aggcgagtca ggacatttat ccctatttaa actggttcca acaaaaacca   120
gggaaagctc ctaagaccct gatctatcgt acaaatagat tgctagatgg ggtcccatca   180
aggttcagtg gcagtggatc tggaacagat tttactttca ccatcagcag cctgcaacct   240
gaagatattg caacttatta ttgtctacag tatgatgagt ttccgctcac gttcggtgct   300
gggaccaagc tggaaatcaa a                                             321
```

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 17

```
Lys Ala Ser Gln Asp Ile Tyr Pro Tyr Leu Asn
1               5                   10
```

<210> SEQ ID NO 18
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 18

```
aaggcgagtc aggacattta tccctattta aac                                 33
```

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 19

```
Arg Thr Asn Arg Leu Leu Asp
1               5
```

<210> SEQ ID NO 20
<211> LENGTH: 21
<212> TYPE: DNA
<213> ORGANISM: Artificial Sequence

```
<220> FEATURE:
<223> OTHER INFORMATION: Synthetic nucleotide sequence

<400> SEQUENCE: 20
cgtacaaata gattgctaga t                                              21

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 21

Leu Gln Tyr Asp Glu Phe Pro Leu Thr
1               5

<210> SEQ ID NO 22
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 22
ctacagtatg atgagtttcc gctcacg                                        27

<210> SEQ ID NO 23
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 23
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Pro Tyr
            20                  25                  30

Leu Asn Trp Phe Gln Gln Lys Pro Gly Lys Ala Pro Lys Thr Leu Ile
        35                  40                  45

Tyr Arg Thr Asn Arg Leu Leu Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

-continued

```
             195                 200                 205
Phe Asn Arg Gly Glu Cys
    210

<210> SEQ ID NO 24
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 24
gacatccaga tgacccagtc tccatcttcc ctgtctgcat ctgtaggaga tagagtcact     60
atcacttgca aggcgagtca ggacatttat ccctatttaa actggttcca acaaaaacca    120
gggaaagctc ctaagaccct gatctatcgt acaaatagat tgctagatgg ggtcccatca    180
aggttcagtg gcagtggatc tggaacagat tttactttca ccatcagcag cctgcaacct    240
gaagatattg caacttatta ttgtctacag tatgatgagt ttccgctcac gttcggtgct    300
gggaccaagc tggaaatcaa acggactgtg gctgcaccaa gtgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                      642

<210> SEQ ID NO 25
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 25

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Val His Trp Val Arg Gln Ala Pro Gly Lys Arg Leu Glu Trp Ile
        35                  40                  45

Gly Val Ile Ser Thr Tyr Asn Asp Tyr Thr Tyr Asn Asn Gln Asp Phe
    50                  55                  60

Lys Gly Arg Val Thr Met Thr Arg Asp Thr Ser Ala Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Asn Ser Tyr Phe Tyr Ala Leu Asp Tyr Trp Gly Gln Gly
            100                 105                 110

Thr Ser Val Thr Val Ser Ser
        115

<210> SEQ ID NO 26
<211> LENGTH: 357
<212> TYPE: DNA
<213> ORGANISM: Artificial Sequence
<220> FEATURE:
<223> OTHER INFORMATION: Synthetic nucleotide sequence
```

-continued

```
<400> SEQUENCE: 26
caggtccagc ttgtgcagtc tgggcctgag gtgaagaagc ctggggcctc agtgaaggtt    60
tcctgcaagg cttctggata caccttcact gactatgctg tgcattgggt gcgccaggcc   120
cccggaaaaa ggcttgagtg gattggagtg atcagcactt acaatgatta cacatacaat   180
aaccaggact tcaagggcag agtcaccatg accagggaca catccgcgag cacagcctac   240
atggagctga gcagactgag atctgaagac acggctgtgt attactgtgc gagaggtaac   300
tcctacttct atgctttgga ctactgggt caaggaacct cagtcaccgt ctcctca       357

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 27

Asp Tyr Ala Val His
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 28

Gly Tyr Thr Phe Thr Asp Tyr
1               5

<210> SEQ ID NO 29
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 29
gactatgctg tgcat                                                     15

<210> SEQ ID NO 30
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 30
ggatacacct tcactgacta t                                              21

<210> SEQ ID NO 31
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 31

Val Ile Ser Thr Tyr Asn Asp Tyr Thr Tyr Asn Asn Gln Asp Phe Lys
1               5                   10                  15

Gly
```

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 32

Ser Thr Tyr Asn Asp Tyr
1               5

<210> SEQ ID NO 33
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 33
gtgatcagca cttacaatga ttacacatac aataaccagg acttcaaggg c        51

<210> SEQ ID NO 34
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 34
agcacttaca atgattac                                              18

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 35

Gly Asn Ser Tyr Phe Tyr Ala Leu Asp Tyr
1               5                   10

<210> SEQ ID NO 36
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 36
ggtaactcct acttctatgc tttggactac                                 30

<210> SEQ ID NO 37
<211> LENGTH: 448
<212> TYPE: PRT
<213> ORGANISM: Artificial Sequence
<220> FEATURE:
<223> OTHER INFORMATION: Synthetic peptide sequence

<400> SEQUENCE: 37

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Val His Trp Val Arg Gln Ala Pro Gly Lys Arg Leu Glu Trp Ile

Gly Val Ile Ser Thr Tyr Asn Asp Tyr Thr Tyr Asn Asn Gln Asp Phe
        35                  40                  45
 50                  55                  60

Lys Gly Arg Val Thr Met Thr Arg Asp Thr Ser Ala Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Gly Asn Ser Tyr Phe Tyr Ala Leu Asp Tyr Trp Gly Gln Gly
             100                 105                 110

Thr Ser Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 38

<211> LENGTH: 1344
<212> TYPE: DNA
<213> ORGANISM: Artificial Sequence
<220> FEATURE:
<223> OTHER INFORMATION: Synthetic nucleotide sequence

<400> SEQUENCE: 38

```
caggtccagc ttgtgcagtc tgggcctgag gtgaagaagc ctggggcctc agtgaaggtt      60
tcctgcaagg cttctggata caccttcact gactatgctg tgcattgggt gcgccaggcc     120
cccggaaaaa ggcttgagtg gattggagtg atcagcactt acaatgatta cacatacaat     180
aaccaggact tcaagggcag agtcaccatg accagggaca tccgcgagac acagcctac     240
atggagctga gcagactgag atctgaagac acggctgtgt attactgtgc gagaggtaac     300
tcctacttct atgctttgga ctactggggt caaggaacct cagtcaccgt ctcctcagcc     360
tccaccaagg gcccatcggt cttccccctg gcaccctcga gcaagagcac ctctgggggc     420
acagcggccc tgggctgcct ggtcaaggac tacttccccg agccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc ggga                                            1344
```

<210> SEQ ID NO 39
<211> LENGTH: 111
<212> TYPE: PRT
<213> ORGANISM: Artificial Sequence
<220> FEATURE:
<223> OTHER INFORMATION: Synthetic peptide sequence

<400> SEQUENCE: 39

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Tyr
            20                  25                  30

Gly Lys Ser Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80
```

Ser Leu Glu Pro Glu Asp Phe Ala Val Tyr Tyr Cys Gln Gln Ser Asn
            85                  90                  95

Glu Asp Pro Trp Thr Phe Gly Gly Gly Thr Lys Leu Glu Ile Lys
        100                 105                 110

<210> SEQ ID NO 40
<211> LENGTH: 333
<212> TYPE: DNA
<213> ORGANISM: Artificial Sequence
<220> FEATURE:
<223> OTHER INFORMATION: Synthetic nucleotide sequence

<400> SEQUENCE: 40
gaaattgtgt tgacacagtc tccagccacc ctgtctttgt ctccagggga aagagccacc    60
ctctcctgca gggccagtga gagtgttgac agctatggca aaagttttat gcactggtac   120
caacagaaac ctggccaggc tcccaggctc ctcatctata gggcatccaa cctggaatct   180
ggcatcccag ccaggttcag tggcagtggg tctgggacag acttcactct caccatcagc   240
agcctagagc ctgaagattt tgcagtttat tactgtcagc agagtaatga ggatccgtgg   300
acgttcggtg aggcaccaa gctggaaatc aaa                                  333

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 41

Arg Ala Ser Glu Ser Val Asp Ser Tyr Gly Lys Ser Phe Met His
1               5                   10                  15

<210> SEQ ID NO 42
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 42
agggccagtg agagtgttga cagctatggc aaaagtttta tgcac                    45

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 43

Arg Ala Ser Asn Leu Glu Ser
1               5

<210> SEQ ID NO 44
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 44
agggcatcca acctggaatc t                                              21

-continued

```
<210> SEQ ID NO 45
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 45

Gln Gln Ser Asn Glu Asp Pro Trp Thr
1               5

<210> SEQ ID NO 46
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 46
cagcagagta atgaggatcc gtggacg                                              27

<210> SEQ ID NO 47
<211> LENGTH: 218
<212> TYPE: PRT
<213> ORGANISM: Artificial Sequence
<220> FEATURE:
<223> OTHER INFORMATION: Synthetic peptide sequence

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Tyr
            20                  25                  30

Gly Lys Ser Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 48
<211> LENGTH: 654
```

<212> TYPE: DNA
<213> ORGANISM: Artificial Sequence
<220> FEATURE:
<223> OTHER INFORMATION: Synthetic nucleotide sequence

<400> SEQUENCE: 48

```
gaaattgtgt tgacacagtc tccagccacc ctgtctttgt ctccagggga aagagccacc      60
ctctcctgca gggccagtga gagtgttgac agctatggca aaagtttat gcactggtac     120
caacagaaac ctggccaggc tcccaggctc ctcatctata gggcatccaa cctgaatct      180
ggcatcccag ccaggttcag tggcagtggg tctgggacag acttcactct caccatcagc     240
agcctagagc ctgaagattt tgcagtttat tactgtcagc agagtaatga ggatccgtgg     300
acgttcggtg gaggcaccaa gctggaaatc aaacggactg tggctgcacc aagtgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca aagtctacgc ctgcgaagtc     600
acccatcagg gcctgagctc gcccgtcaca aagagcttca caggggaga gtgt            654
```

<210> SEQ ID NO 49
<211> LENGTH: 120
<212> TYPE: PRT
<213> ORGANISM: Artificial Sequence
<220> FEATURE:
<223> OTHER INFORMATION: Synthetic peptide sequence

<400> SEQUENCE: 49

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asp Phe Ser Arg Tyr
            20                  25                  30
Trp Met Ser Trp Val Arg Gln Ala Pro Gly Lys Gly Leu Glu Trp Ile
        35                  40                  45
Gly Asp Leu Asn Pro Asp Ser Ser Ala Ile Asn Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Thr Leu Ile Thr Thr Leu Val Pro Tyr Thr Met Asp Phe Trp Gly Gln
            100                 105                 110
Gly Thr Ser Val Thr Val Ser Ser
        115                 120
```

<210> SEQ ID NO 50
<211> LENGTH: 360
<212> TYPE: DNA
<213> ORGANISM: Artificial Sequence
<220> FEATURE:
<223> OTHER INFORMATION: Synthetic nucleotide sequence

<400> SEQUENCE: 50

```
gaggtgcagc tggtggagtc tgggggaggc ttggtccagc ctgggggtc cctgagactc       60
tcctgtgcag cctctggatt cgactttagt agatattgga tgagctgggt ccgccaggct     120
ccagggaagg ggctggagtg gatcggcgac ctaaacccag attcaagtgc gataaactat     180
```

```
gtggactctg tgaagggccg attcaccatc tccagagaca acgccaagaa ctcactgtat    240
ctgcaaatga acagcctgag agccgaggac acggctgtgt attactgtac actcattact    300
acgttagtac cctatactat ggacttctgg ggtcaaggaa cctcagtcac cgtctcctca    360
```

<210> SEQ ID NO 51
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 51

Arg Tyr Trp Met Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 52

Gly Phe Asp Phe Ser Arg Tyr
1               5

<210> SEQ ID NO 53
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 53
agatattgga tgagc                                                      15

<210> SEQ ID NO 54
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 54
ggattcgact ttagtagata t                                               21

<210> SEQ ID NO 55
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 55

Asp Leu Asn Pro Asp Ser Ser Ala Ile Asn Tyr Val Asp Ser Val Lys
1               5                   10                  15
Gly

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 56

Asn Pro Asp Ser Ser Ala
1               5

<210> SEQ ID NO 57
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 57
gacctaaacc cagattcaag tgcgataaac tatgtggact ctgtgaaggg c                    51

<210> SEQ ID NO 58
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 58
aacccagatt caagtgcg                                                         18

<210> SEQ ID NO 59
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 59

Ile Thr Thr Leu Val Pro Tyr Thr Met Asp Phe
1               5                   10

<210> SEQ ID NO 60
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 60
attactacgt tagtacccta tactatggac ttc                                        33

<210> SEQ ID NO 61
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Asp Leu Asn Pro Asp Ser Ser Ala Ile Asn Tyr Val Asp Ser Val
        50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                 85                  90                  95
Thr Leu Ile Thr Thr Leu Val Pro Tyr Thr Met Asp Phe Trp Gly Gln
            100                 105                 110
Gly Thr Ser Val Thr Val Ser Ser Ala Ser Thr Lys Gly Pro Ser Val
        115                 120                 125
Phe Pro Leu Ala Pro Ser Ser Lys Ser Thr Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 62
<211> LENGTH: 1347
<212> TYPE: DNA
<213> ORGANISM: Artificial Sequence
<220> FEATURE:
<223> OTHER INFORMATION: Synthetic nucleotide sequence
```

<400> SEQUENCE: 62

```
gaggtgcagc tggtggagtc tgggggaggc ttggtccagc ctggggggtc cctgagactc      60
tcctgtgcag cctctggatt cgactttagt agatattgga tgagctgggt ccgccaggct     120
ccagggaagg ggctggagtg gatcggcgac ctaaacccag attcaagtgc gataaactat     180
gtggactctg tgaagggccg attcaccatc tccagagaca acgccaagaa ctcactgtat     240
ctgcaaatga acagcctgag agccgaggac acggctgtgt attactgtac actcattact     300
acgttagtac cctatactat ggacttctgg ggtcaaggaa cctcagtcac cgtctcctca     360
gcctccacca agggcccatc ggtcttcccc ctggcaccct cgagcaagag cacctctggg     420
ggcacagcgg ccctgggctg cctggtcaag gactacttcc ccgagccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggt                                        1347
```

<210> SEQ ID NO 63
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 63

```
Glu Thr Thr Leu Thr Gln Ser Pro Ala Phe Met Ser Ala Thr Pro Gly
1               5                   10                  15

Asp Lys Val Asn Ile Ser Cys Ile Thr Asn Thr Asp Ile Asp Asp Asp
            20                  25                  30

Met Asn Trp Tyr Gln Gln Lys Pro Gly Glu Ala Ala Ile Leu Leu Ile
        35                  40                  45

Ser Glu Gly Asn Gly Leu Arg Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Ser Gly Thr Lys Leu Glu Ile Lys
            100                 105
```

<210> SEQ ID NO 64
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 64

```
gaaacgacac tcacgcagtc tccagcattc atgtcagcga ctccaggaga caaagtcaac    60
atctcctgca taaccaacac agacattgat gatgatatga actggtacca acagaaacca   120
ggagaagctg ctattctcct tatttcagaa ggtaatggtc tccgtcctgg aatcccacct   180
cgattcagtg gcagcgggta tggaacagat tttacccctca caattaataa catagaatct   240
gaggatgctg catattactt ctgtctacaa agtgataact tgcctctcac gttcggctcg   300
gggacaaagt tggaaataaa a                                             321
```

<210> SEQ ID NO 65
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 65

Ile Thr Asn Thr Asp Ile Asp Asp Asp Met Asn
1               5                   10

<210> SEQ ID NO 66
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 66

```
ataaccaaca cagacattga tgatgatatg aac                                 33
```

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 67

Glu Gly Asn Gly Leu Arg Pro
1               5

<210> SEQ ID NO 68
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 68

```
gaaggtaatg gtctccgtcc t                                              21
```

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 69

Leu Gln Ser Asp Asn Leu Pro Leu Thr
1               5

<210> SEQ ID NO 70
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 70
ctacaaagtg ataacttgcc tctcacg                                           27

<210> SEQ ID NO 71
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 71

Glu Thr Thr Leu Thr Gln Ser Pro Ala Phe Met Ser Ala Thr Pro Gly
1               5                   10                  15

Asp Lys Val Asn Ile Ser Cys Ile Thr Asn Thr Asp Ile Asp Asp
            20                  25                  30

Met Asn Trp Tyr Gln Gln Lys Pro Gly Glu Ala Ala Ile Leu Leu Ile
        35                  40                  45

Ser Glu Gly Asn Gly Leu Arg Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 72

-continued

```
gaaacgacac tcacgcagtc tccagcattc atgtcagcga ctccaggaga caaagtcaac      60
atctcctgca taaccaacac agacattgat gatgatatga actggtacca acagaaacca     120
ggagaagctg ctattctcct tatttcagaa ggtaatggtc tccgtcctgg aatcccacct     180
cgattcagtg gcagcgggta tggaacagat tttaccctca caattaataa catagaatct     240
gaggatgctg catattactt ctgtctacaa agtgataact tgcctctcac gttcggctcg     300
gggacaaagt tggaaataaa acggactgtg gctgcaccaa gtgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

<210> SEQ ID NO 73
<211> LENGTH: 1070
<212> TYPE: PRT
<213> ORGANISM: Homo sapiens

<400> SEQUENCE: 73

```
Met Gly Ala Ala Arg Gly Ser Pro Ala Arg Pro Arg Arg Leu Pro Leu
1               5                   10                  15

Leu Ser Val Leu Leu Pro Leu Leu Gly Gly Thr Gln Thr Ala Ile
            20                  25                  30

Val Phe Ile Lys Gln Pro Ser Ser Gln Asp Ala Leu Gln Gly Arg Arg
        35                  40                  45

Ala Leu Leu Arg Cys Glu Val Glu Ala Pro Gly Pro Val His Val Tyr
    50                  55                  60

Trp Leu Leu Asp Gly Ala Pro Val Gln Asp Thr Glu Arg Arg Phe Ala
65                  70                  75                  80

Gln Gly Ser Ser Leu Ser Phe Ala Ala Val Asp Arg Pro Gln Asp Ser
                85                  90                  95

Gly Thr Phe Gln Cys Val Ala Arg Asp Asp Val Thr Gly Glu Glu Ala
            100                 105                 110

Arg Ser Ala Asn Ala Ser Phe Asn Ile Lys Trp Ile Glu Ala Gly Pro
        115                 120                 125

Val Val Leu Lys His Pro Ala Ser Glu Ala Glu Ile Gln Pro Gln Thr
    130                 135                 140

Gln Val Thr Leu Arg Cys His Ile Asp Gly His Pro Arg Pro Thr Tyr
145                 150                 155                 160

Gln Trp Phe Arg Asp Gly Thr Pro Leu Ser Asp Gly Gln Ser Asn His
                165                 170                 175

Thr Val Ser Ser Lys Glu Arg Asn Leu Thr Leu Arg Pro Ala Gly Pro
            180                 185                 190

Glu His Ser Gly Leu Tyr Ser Cys Cys Ala His Ser Ala Phe Gly Gln
        195                 200                 205

Ala Cys Ser Ser Gln Asn Phe Thr Leu Ser Ile Ala Asp Glu Ser Phe
    210                 215                 220

Ala Arg Val Val Leu Ala Pro Gln Asp Val Val Ala Arg Tyr Glu
225                 230                 235                 240

Glu Ala Met Phe His Cys Gln Phe Ser Ala Gln Pro Pro Pro Ser Leu
                245                 250                 255
```

```
Gln Trp Leu Phe Glu Asp Glu Thr Pro Ile Thr Asn Arg Ser Arg Pro
                260                 265                 270

Pro His Leu Arg Arg Ala Thr Val Phe Ala Asn Gly Ser Leu Leu Leu
            275                 280                 285

Thr Gln Val Arg Pro Arg Asn Ala Gly Ile Tyr Arg Cys Ile Gly Gln
        290                 295                 300

Gly Gln Arg Gly Pro Pro Ile Ile Leu Glu Ala Thr Leu His Leu Ala
305                 310                 315                 320

Glu Ile Glu Asp Met Pro Leu Phe Glu Pro Arg Val Phe Thr Ala Gly
                325                 330                 335

Ser Glu Glu Arg Val Thr Cys Leu Pro Pro Lys Gly Leu Pro Glu Pro
            340                 345                 350

Ser Val Trp Trp Glu His Ala Gly Val Arg Leu Pro Thr His Gly Arg
        355                 360                 365

Val Tyr Gln Lys Gly His Glu Leu Val Leu Ala Asn Ile Ala Glu Ser
    370                 375                 380

Asp Ala Gly Val Tyr Thr Cys His Ala Ala Asn Leu Ala Gly Gln Arg
385                 390                 395                 400

Arg Gln Asp Val Asn Ile Thr Val Ala Thr Val Pro Ser Trp Leu Lys
                405                 410                 415

Lys Pro Gln Asp Ser Gln Leu Glu Glu Gly Lys Pro Gly Tyr Leu Asp
            420                 425                 430

Cys Leu Thr Gln Ala Thr Pro Lys Pro Thr Val Val Trp Tyr Arg Asn
        435                 440                 445

Gln Met Leu Ile Ser Glu Asp Ser Arg Phe Glu Val Phe Lys Asn Gly
    450                 455                 460

Thr Leu Arg Ile Asn Ser Val Glu Val Tyr Asp Gly Thr Trp Tyr Arg
465                 470                 475                 480

Cys Met Ser Ser Thr Pro Ala Gly Ser Ile Glu Ala Gln Ala Arg Val
                485                 490                 495

Gln Val Leu Glu Lys Leu Lys Phe Thr Pro Pro Pro Gln Pro Gln Gln
            500                 505                 510

Cys Met Glu Phe Asp Lys Glu Ala Thr Val Pro Cys Ser Ala Thr Gly
        515                 520                 525

Arg Glu Lys Pro Thr Ile Lys Trp Glu Arg Ala Asp Gly Ser Ser Leu
    530                 535                 540

Pro Glu Trp Val Thr Asp Asn Ala Gly Thr Leu His Phe Ala Arg Val
545                 550                 555                 560

Thr Arg Asp Asp Ala Gly Asn Tyr Thr Cys Ile Ala Ser Asn Gly Pro
                565                 570                 575

Gln Gly Gln Ile Arg Ala His Val Gln Leu Thr Val Ala Val Phe Ile
            580                 585                 590

Thr Phe Lys Val Glu Pro Glu Arg Thr Thr Val Tyr Gln Gly His Thr
        595                 600                 605

Ala Leu Leu Gln Cys Glu Ala Gln Gly Asp Pro Lys Pro Leu Ile Gln
    610                 615                 620

Trp Lys Gly Lys Asp Arg Ile Leu Asp Pro Thr Lys Leu Gly Pro Arg
625                 630                 635                 640

Met His Ile Phe Gln Asn Gly Ser Leu Val Ile His Asp Val Ala Pro
                645                 650                 655

Glu Asp Ser Gly Arg Tyr Thr Cys Ile Ala Gly Asn Ser Cys Asn Ile
            660                 665                 670

Lys His Thr Glu Ala Pro Leu Tyr Val Val Asp Lys Pro Val Pro Glu
```

```
                675                 680                 685
Glu Ser Glu Gly Pro Gly Ser Pro Pro Tyr Lys Met Ile Gln Thr
690                 695                 700

Ile Gly Leu Ser Val Gly Ala Val Ala Tyr Ile Ala Val Leu
705                 710                 715                 720

Gly Leu Met Phe Tyr Cys Lys Lys Arg Cys Lys Ala Lys Arg Leu Gln
                    725                 730                 735

Lys Gln Pro Glu Gly Glu Glu Pro Glu Met Glu Cys Leu Asn Gly Gly
            740                 745                 750

Pro Leu Gln Asn Gly Gln Pro Ser Ala Glu Ile Gln Glu Glu Val Ala
            755                 760                 765

Leu Thr Ser Leu Gly Ser Gly Pro Ala Ala Thr Asn Lys Arg His Ser
770                 775                 780

Thr Ser Asp Lys Met His Phe Pro Arg Ser Ser Leu Gln Pro Ile Thr
785                 790                 795                 800

Thr Leu Gly Lys Ser Glu Phe Gly Glu Val Phe Leu Ala Lys Ala Gln
                    805                 810                 815

Gly Leu Glu Glu Gly Val Ala Glu Thr Leu Val Leu Val Lys Ser Leu
            820                 825                 830

Gln Ser Lys Asp Glu Gln Gln Leu Asp Phe Arg Glu Leu Glu
            835                 840                 845

Met Phe Gly Lys Leu Asn His Ala Asn Val Val Arg Leu Leu Gly Leu
850                 855                 860

Cys Arg Glu Ala Glu Pro His Tyr Met Val Leu Glu Tyr Val Asp Leu
865                 870                 875                 880

Gly Asp Leu Lys Gln Phe Leu Arg Ile Ser Lys Ser Lys Asp Glu Lys
                    885                 890                 895

Leu Lys Ser Gln Pro Leu Ser Thr Lys Gln Lys Val Ala Leu Cys Thr
            900                 905                 910

Gln Val Ala Leu Gly Met Glu His Leu Ser Asn Asn Arg Phe Val His
            915                 920                 925

Lys Asp Leu Ala Ala Arg Asn Cys Leu Val Ser Ala Gln Arg Gln Val
930                 935                 940

Lys Val Ser Ala Leu Gly Leu Ser Lys Asp Val Tyr Asn Ser Glu Tyr
945                 950                 955                 960

Tyr His Phe Arg Gln Ala Trp Val Pro Leu Arg Trp Met Ser Pro Glu
                    965                 970                 975

Ala Ile Leu Glu Gly Asp Phe Ser Thr Lys Ser Asp Val Trp Ala Phe
            980                 985                 990

Gly Val Leu Met Trp Glu Val Phe Thr His Gly Glu Met Pro His Gly
            995                 1000                1005

Gly Gln Ala Asp Asp Glu Val Leu Ala Asp Leu Gln Ala Gly Lys
        1010                1015                1020

Ala Arg Leu Pro Gln Pro Glu Gly Cys Pro Ser Lys Leu Tyr Arg
        1025                1030                1035

Leu Met Gln Arg Cys Trp Ala Leu Ser Pro Lys Asp Arg Pro Ser
        1040                1045                1050

Phe Ser Glu Ile Ala Ser Ala Leu Gly Asp Ser Thr Val Asp Ser
        1055                1060                1065

Lys Pro
        1070

<210> SEQ ID NO 74
```

```
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 74

Gly Gly Leu Leu Gln Gly Gly
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 75

Leu Leu Gln Gly Ala
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 76

Gly Gly Leu Leu Gln Gly Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 77

Leu Leu Gln Gly Pro Gly Lys
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 78

Leu Leu Gln Gly Pro Gly
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 79

Leu Leu Gln Gly Pro Ala
1               5

<210> SEQ ID NO 80
<211> LENGTH: 5
```

```
<212> TYPE: PRT
<213> ORGANISM: Artificial Sequence
<220> FEATURE:
<223> OTHER INFORMATION: Synthetic peptide sequence

<400> SEQUENCE: 80

Leu Leu Gln Gly Pro
1               5

<210> SEQ ID NO 81
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 81

Leu Leu Gln Pro
1

<210> SEQ ID NO 82
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 82

Leu Leu Gln Pro Gly Lys
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 83

Leu Leu Gln Gly Ala Pro Gly Lys
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 84

Leu Leu Gln Gly Ala Pro Gly
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 85

Leu Leu Gln Gly Ala Pro
1               5

<210> SEQ ID NO 86
<211> LENGTH: 8
<212> TYPE: PRT
```

```
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (4)..(4)
<223> OTHER INFORMATION: Xaa can be G or P
<220> FEATURE:
<221> NAME/KEY: MISC_FEATURE
<222> LOCATION: (5)..(5)
<223> OTHER INFORMATION: Xaa can be A, G, P, or absent
<220> FEATURE:
<221> NAME/KEY: MISC_FEATURE
<222> LOCATION: (6)..(6)
<223> OTHER INFORMATION: Xaa can be A, G, K, P, or absent
<220> FEATURE:
<221> NAME/KEY: MISC_FEATURE
<222> LOCATION: (7)..(7)
<223> OTHER INFORMATION: Xaa can be G, K, or absent
<220> FEATURE:
<221> NAME/KEY: MISC_FEATURE
<222> LOCATION: (8)..(8)
<223> OTHER INFORMATION: Xaa can be K or absent

<400> SEQUENCE: 86

Leu Leu Gln Xaa Xaa Xaa Xaa Xaa
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
      or absent
<220> FEATURE:
<221> NAME/KEY: MISC_FEATURE
<222> LOCATION: (6)..(6)
<223> OTHER INFORMATION: Xaa can be any naturally occurring amino acid
      or absent
<220> FEATURE:
<221> NAME/KEY: MISC_FEATURE
<222> LOCATION: (7)..(7)
<223> OTHER INFORMATION: Xaa can be any naturally occurring amino acid
      or absent
<220> FEATURE:
<221> NAME/KEY: MISC_FEATURE
<222> LOCATION: (8)..(8)
<223> OTHER INFORMATION: Xaa can be any naturally occurring amino acid
      or absent

<400> SEQUENCE: 87

Leu Leu Gln Xaa Xaa Xaa Xaa Xaa
1               5
```